(12) United States Patent
Barbour et al.

(10) Patent No.: US 11,958,896 B2
(45) Date of Patent: Apr. 16, 2024

(54) ANTIBODIES RECOGNIZING TAU

(71) Applicant: Prothena Biosciences Limited, Dublin (IE)

(72) Inventors: Robin Barbour, Walnut Creek, CA (US); Svetlana Alexander, Sunnyvale, CA (US); Mark Renz, Millbrae, CA (US); Shuning Gai, Mountain View, CA (US); Tarlochan S. Nijjar, Orinda, CA (US); Philip James Dolan, III, Forster City, CA (US); Philip Payne, Turlock, CA (US)

(73) Assignee: Prothena Biosciences Limited, Dublin (IE)

( * ) Notice: Subject to any disclaimer, the term of this patent is extended or adjusted under 35 U.S.C. 154(b) by 600 days.

(21) Appl. No.: 16/500,251

(22) PCT Filed: May 2, 2018

(86) PCT No.: PCT/US2018/030739
§ 371 (c)(1),
(2) Date: Oct. 2, 2019

(87) PCT Pub. No.: WO2018/204546
PCT Pub. Date: Nov. 8, 2018

(65) Prior Publication Data
US 2022/0089702 A1 Mar. 24, 2022

Related U.S. Application Data

(60) Provisional application No. 62/580,408, filed on Nov. 1, 2017, provisional application No. 62/500,427, filed on May 2, 2017.

(51) Int. Cl.
C07K 16/18 (2006.01)

(52) U.S. Cl.
CPC .......... C07K 16/18 (2013.01); *C07K 2317/24* (2013.01); *C07K 2317/565* (2013.01);
(Continued)

(58) Field of Classification Search
None
See application file for complete search history.

(56) References Cited

U.S. PATENT DOCUMENTS

| 4,634,664 A | 1/1987 | Oestber |
| 4,634,666 A | 1/1987 | Engleman et al. |

(Continued)

FOREIGN PATENT DOCUMENTS

| CN | 104185640 | 12/2014 |
| CN | 104822389 | 8/2015 |

(Continued)

OTHER PUBLICATIONS

Stoyka, Lindsay E., et al. "Templated α-synuclein inclusion formation is independent of endogenous tau." Eneuro 8.3 (2021). (Year: 2021).*

(Continued)

*Primary Examiner* — Michael Szperka
*Assistant Examiner* — Lia E Taylor
(74) *Attorney, Agent, or Firm* — Fish & Richardson P.C.

(57) ABSTRACT

The invention provides antibodies that specifically bind tau. The antibodies inhibit or delay tau-associated pathologies and associated symptomatic deterioration.

22 Claims, 14 Drawing Sheets

Specification includes a Sequence Listing.

(52) U.S. Cl.
CPC .... *C07K 2317/567* (2013.01); *C07K 2317/76* (2013.01); *C07K 2317/92* (2013.01)

(56) References Cited

U.S. PATENT DOCUMENTS

| | | | |
|---|---|---|---|
| 5,057,540 A | 10/1991 | Kensil et al. | |
| 5,194,594 A | 3/1993 | Khawli et al. | |
| 5,208,036 A | 5/1993 | Eppstein et al. | |
| 5,225,539 A | 7/1993 | Winter et al. | |
| 5,264,618 A | 11/1993 | Felgner et al. | |
| 5,279,833 A | 1/1994 | Rose | |
| 5,283,185 A | 2/1994 | Epand et al. | |
| 5,304,489 A | 4/1994 | Rosen | |
| 5,530,101 A | 6/1996 | Queen et al. | |
| 5,545,806 A | 8/1996 | Lonberg et al. | |
| 5,565,332 A | 10/1996 | Hoogenboom et al. | |
| 5,569,825 A | 10/1996 | Lonberg et al. | |
| 5,585,089 A | 12/1996 | Queen et al. | |
| 5,624,821 A | 4/1997 | Winter et al. | |
| 5,625,126 A | 4/1997 | Lonberg et al. | |
| 5,633,425 A | 5/1997 | Lonberg et al. | |
| 5,643,576 A | 7/1997 | Johnston et al. | |
| 5,661,016 A | 8/1997 | Lonberg et al. | |
| 5,733,743 A | 3/1998 | Johnston et al. | |
| 5,736,142 A | 4/1998 | Sette et al. | |
| 5,741,957 A | 4/1998 | Deboer et al. | |
| 5,770,429 A | 6/1998 | Lonberg et al. | |
| 5,786,464 A | 7/1998 | Seed et al. | |
| 5,789,650 A | 8/1998 | Lonberg et al. | |
| 5,814,318 A | 9/1998 | Lonberg et al. | |
| 5,834,597 A | 11/1998 | Tso et al. | |
| 5,837,242 A | 11/1998 | Holliger et al. | |
| 5,849,992 A | 12/1998 | Meade et al. | |
| 5,858,657 A | 1/1999 | Winter | |
| 5,859,205 A | 1/1999 | Adair et al. | |
| 5,871,907 A | 2/1999 | Winter et al. | |
| 5,874,299 A | 2/1999 | Lonberg et al. | |
| 5,877,218 A | 3/1999 | Herzig et al. | |
| 5,877,397 A | 3/1999 | Lonberg et al. | |
| 5,888,809 A | 3/1999 | Allison | |
| 6,063,598 A | 5/2000 | Enenkel et al. | |
| 6,114,148 A | 9/2000 | Seed et al. | |
| 6,180,370 B1 * | 1/2001 | Queen .................. | C07K 16/087 435/69.6 |
| 6,407,213 B1 | 6/2002 | Carter et al. | |
| 6,624,821 B1 | 9/2003 | Shin et al. | |
| 6,881,557 B2 | 4/2005 | Foote | |
| 7,442,516 B2 | 10/2008 | Ohno et al. | |
| 7,569,339 B2 | 8/2009 | Kaufmann et al. | |
| 8,012,936 B2 | 9/2011 | Sigurdsson et al. | |
| 8,455,622 B2 | 6/2013 | Carter et al. | |
| 8,778,343 B2 | 7/2014 | Kayed | |
| 8,926,974 B2 | 1/2015 | Griswold-Prenner et al. | |
| 8,987,419 B2 | 3/2015 | Barghorn et al. | |
| 9,051,367 B2 | 6/2015 | Griswold-Prenner et al. | |
| 9,321,841 B2 | 4/2016 | Jones et al. | |
| 9,598,484 B2 * | 3/2017 | Weinreb .................. | A61P 21/02 |
| 9,605,054 B2 | 3/2017 | Brady et al. | |
| 10,196,439 B2 | 2/2019 | Pedersen et al. | |
| 10,253,100 B2 | 4/2019 | Igawa et al. | |
| 10,301,379 B2 | 5/2019 | Wadia et al. | |
| 10,478,142 B2 | 11/2019 | Pedersen et al. | |
| 10,501,531 B2 | 12/2019 | Seubert et al. | |
| 10,711,058 B2 | 7/2020 | Adolfsson et al. | |
| 10,752,679 B2 | 8/2020 | Seubert et al. | |
| 10,766,953 B2 | 9/2020 | Mercken et al. | |
| 10,829,547 B2 | 11/2020 | Roberts et al. | |
| 10,836,817 B2 | 11/2020 | Adolfsson et al. | |
| 10,889,638 B2 | 1/2021 | Barbour et al. | |
| 10,906,964 B2 | 2/2021 | Barbour et al. | |
| 10,961,302 B2 | 3/2021 | Barbour et al. | |
| 2005/0009150 A1 | 1/2005 | Basi et al. | |
| 2005/0114912 A1 | 5/2005 | Botas et al. | |
| 2005/0132424 A1 | 6/2005 | Lowe et al. | |
| 2007/0042359 A1 | 2/2007 | Throsby et al. | |
| 2008/0050383 A1 | 2/2008 | Sigurdsson et al. | |
| 2008/0076145 A1 | 3/2008 | Cummings et al. | |
| 2009/0028851 A1 | 1/2009 | Stuhmer et al. | |
| 2010/0022026 A1 | 1/2010 | Rump et al. | |
| 2010/0216703 A1 | 8/2010 | Akassoglou et al. | |
| 2010/0267927 A1 | 10/2010 | Garrett et al. | |
| 2010/0316564 A1 | 12/2010 | Sigurdsson | |
| 2011/0053264 A1 | 3/2011 | Kashmiri et al. | |
| 2011/0206702 A1 | 5/2011 | Polakis et al. | |
| 2012/0023911 A1 | 2/2012 | Liu et al. | |
| 2012/0100152 A1 | 4/2012 | Roberts et al. | |
| 2012/0142602 A1 | 6/2012 | Brady et al. | |
| 2012/0149880 A1 | 6/2012 | Cheung et al. | |
| 2012/0204275 A1 | 8/2012 | Schenk et al. | |
| 2012/0288507 A1 | 11/2012 | Qian et al. | |
| 2012/0301473 A1 | 11/2012 | Binder et al. | |
| 2012/0308480 A1 | 12/2012 | Smith et al. | |
| 2013/0189289 A1 | 7/2013 | Inoue et al. | |
| 2013/0209453 A1 | 8/2013 | Black et al. | |
| 2013/0295021 A1 | 11/2013 | Chen et al. | |
| 2014/0056901 A1 | 2/2014 | Agadjanyan et al. | |
| 2014/0086921 A1 | 3/2014 | Griswold-Prenner et al. | |
| 2014/0171373 A1 | 6/2014 | Ashe et al. | |
| 2014/0294731 A1 | 10/2014 | Pfeifer et al. | |
| 2014/0294839 A1 | 10/2014 | Kuret et al. | |
| 2015/0050215 A1 | 2/2015 | Novak et al. | |
| 2015/0050270 A1 | 2/2015 | Sanofi | |
| 2015/0056721 A1 | 2/2015 | Siman | |
| 2015/0166661 A1 | 6/2015 | Chen et al. | |
| 2015/0175682 A1 | 6/2015 | Pfeifer et al. | |
| 2015/0196663 A1 | 7/2015 | Shusta et al. | |
| 2015/0253341 A1 | 9/2015 | McAvoy et al. | |
| 2015/0266947 A1 | 9/2015 | Sierks et al. | |
| 2016/0031976 A1 | 2/2016 | Seubert et al. | |
| 2016/0196726 A1 | 7/2016 | Saito | |
| 2016/0289309 A1 | 10/2016 | Griswold-Prenner et al. | |
| 2016/0376341 A1 | 12/2016 | Adolfsson et al. | |
| 2017/0355756 A1 | 12/2017 | Julien et al. | |
| 2018/0209994 A1 | 7/2018 | Lannfelt et al. | |
| 2019/0322728 A1 | 10/2019 | Seubert et al. | |
| 2019/0330314 A1 | 10/2019 | Barbour et al. | |
| 2019/0330316 A1 | 10/2019 | Barbour et al. | |
| 2020/0030445 A1 | 1/2020 | John et al. | |
| 2020/0123239 A1 | 4/2020 | Seubert et al. | |
| 2020/0131255 A1 | 4/2020 | Kerchner et al. | |
| 2020/0181245 A1 | 6/2020 | Masliah et al. | |
| 2021/0023216 A1 | 1/2021 | Angstenberger et al. | |
| 2021/0032319 A1 | 2/2021 | Seubert et al. | |
| 2021/0130449 A1 | 5/2021 | Barbour et al. | |
| 2021/0261652 A1 | 8/2021 | Nijjar et al. | |

FOREIGN PATENT DOCUMENTS

| | | |
|---|---|---|
| EP | 0673418 B1 | 5/1998 |
| EP | 1355949 B1 | 3/2010 |
| EP | 3080611 B1 | 11/2018 |
| GB | 2220211 | 1/1990 |
| JP | 2009-056790 A | 2/2009 |
| JP | 2010-511388 A | 4/2010 |
| JP | 2011-501655 A | 1/2011 |
| JP | 2011-521623 A | 7/2011 |
| JP | 2012-500020 A | 1/2012 |
| JP | 2014-530597 A | 11/2014 |
| JP | 2015520685 A | 7/2015 |
| JP | 2015-530971 | 10/2015 |
| JP | 2016-512551 A | 4/2016 |
| SG | 11201506244 | 9/2015 |
| WO | WO 91/10741 | 7/1991 |
| WO | WO 91/17271 | 11/1991 |
| WO | WO 92/01047 | 1/1992 |
| WO | WO 93/12227 | 6/1993 |
| WO | WO 94/12629 | 6/1994 |
| WO | WO 95/07707 | 3/1995 |
| WO | WO 1996/15452 A1 | 5/1996 |
| WO | WO 96/34625 | 11/1996 |
| WO | WO 98/23635 | 6/1998 |
| WO | WO 98/40100 | 9/1998 |
| WO | WO 2000/072880 | 12/2000 |
| WO | WO 03/057838 | 7/2003 |

(56) References Cited

FOREIGN PATENT DOCUMENTS

| WO | WO 2004/050884 | | 6/2004 | |
| WO | WO 2005/019442 | | 3/2005 | |
| WO | WO 2008/012142 | | 1/2008 | |
| WO | WO 2008/081008 | | 7/2008 | |
| WO | WO 2008/103472 | | 8/2008 | |
| WO | WO 2008/107388 | | 9/2008 | |
| WO | WO 2009/027471 | | 3/2009 | |
| WO | WO 2009/134711 | A1 | 11/2009 | |
| WO | WO 2011/053565 | A2 | 5/2011 | |
| WO | WO 2011/154321 | A1 | 12/2011 | |
| WO | WO 2012/049570 | A1 | 4/2012 | |
| WO | WO 2013/004717 | A1 | 1/2013 | |
| WO | WO 2013/007839 | A1 | 1/2013 | |
| WO | WO 2013/028810 | A1 | 2/2013 | |
| WO | WO 2013/041962 | A1 | 3/2013 | |
| WO | WO 2014/008404 | A1 | 1/2014 | |
| WO | WO 2014/106000 | A2 | 6/2014 | |
| WO | WO 2014/152157 | A2 | 9/2014 | |
| WO | WO 2014/165271 | A2 | 10/2014 | |
| WO | WO 2014/165271 | A3 | 10/2014 | |
| WO | WO 2015/197823 | A3 | 12/2015 | |
| WO | WO 2016/079597 | A1 | 5/2016 | |
| WO | WO 2016/137950 | A1 | 9/2016 | |
| WO | WO 2015/200806 | A1 | 12/2016 | |
| WO | WO 2016/196726 | A1 | 12/2016 | |
| WO | WO 2016/196726 | A9 | 12/2016 | |
| WO | WO 2017/005732 | A1 | 1/2017 | |
| WO | WO-2017005732 | A1 * | 1/2017 | ............. A61P 25/28 |
| WO | WO 2017/062672 | A2 | 4/2017 | |
| WO | WO 2017/191559 | A1 | 11/2017 | |
| WO | WO 2017/191560 | A1 | 11/2017 | |
| WO | WO 2017/191561 | A1 | 11/2017 | |
| WO | WO 2018/106781 | A1 | 6/2018 | |
| WO | WO 2018/152359 | A1 | 8/2018 | |
| WO | WO 2018/156250 | A1 | 8/2018 | |
| WO | WO 2018/178077 | A1 | 10/2018 | |
| WO | WO 2018/204546 | A2 | 11/2018 | |
| WO | WO 2018/231254 | A1 | 12/2018 | |
| WO | WO 2019/094595 | A2 | 5/2019 | |
| WO | WO 2019/110571 | A1 | 6/2019 | |
| WO | WO 2019/186276 | A2 | 10/2019 | |
| WO | WO 2019/207159 | A1 | 10/2019 | |
| WO | WO 2020/096608 | A1 | 5/2020 | |
| WO | WO 2020/097561 | A1 | 5/2020 | |
| WO | WO 2020/106598 | A1 | 5/2020 | |
| WO | WO 2020/163817 | A1 | 8/2020 | |
| WO | WO 2020/180819 | A1 | 9/2020 | |
| WO | WO 2020/193520 | A1 | 10/2020 | |
| WO | WO 2021-010712 | A1 | 1/2021 | |

OTHER PUBLICATIONS

Waite, Louise M. "Treatment for Alzheimer's disease: has anything changed?." Australian prescriber vol. 38,2 (2015): 60-3. doi: 10.18773/austprescr.2015.018 (Year: 2015).*

Imbimbo, Bruno P et al. "Initial failures of anti-tau antibodies in Alzheimer's disease are reminiscent of the amyloid-β story." Neural regeneration research vol. 18,1 (2023): 117-118. doi:10.4103/1673-5374.340409 (Year: 2023).*

Kipriyanov, Sergey M., and Fabrice Le Gall. "Generation and production of engineered antibodies." Molecular biotechnology 26.1 (2004): 39-60. (Year: 2004).*

Janeway, Charles A. "Immunobiology: The Immune System in Health and Disease." 2001 (Year: 2001).*

U.S. Appl. No. 16/097,445, filed Oct. 29, 2018; now issued as U.S. Pat. No. 10,906,964 on Feb. 2, 2021.

U.S. Appl. No. 16/091,060, filed Oct. 3, 2018; now issued as U.S. Pat. No. 10,889,638 on Jan. 12, 2021.

U.S. Appl. No. 16/667,647, filed Oct. 29, 2019.

PCT/US2020/020704 filed Mar. 2, 2020.

PCT/US2020/017357 filed Feb. 7, 2020.

U.S. Appl. No. 16/933,792, filed Jul. 20, 2020.

U.S. Appl. No. 16/808,209, filed Mar. 3, 2020; now issued as U.S. Pat. No. 10,961,302 on Mar. 30, 2021.

U.S. Appl. No. 17/089,416, filed Nov. 4, 2020.

U.S. Appl. No. 17/089,599, filed Nov. 4, 2020.

U.S. Appl. No. 17/181,997, filed Feb. 22, 2021.

U.S. Appl. No. 17/291,986, filed May 6, 2021.

PCT/US2019/060616 filed Nov. 8, 2019.

U.S. Appl. No. 61/780,624, filed Mar. 13, 2013.

U.S. Appl. No. 61/800,382, filed Mar. 15, 2013.

PCT/US2014/025044 filed Mar. 12, 2014.

U.S. Appl. No. 62/330,789, filed May 2, 2016.

U.S. Appl. No. 62/330,786, filed May 2, 2016.

U.S. Appl. No. 62/330,800, filed May 2, 2016.

PCT/IB2017/052544 filed May 2, 2017.

PCT/IB2017/052543 filed May 2, 2017.

PCT/IB2017/052545 filed May 2, 2017.

U.S. Appl. No. 62/500,427, filed May 2, 2017.

U.S. Appl. No. 62/580,408, filed Nov. 1, 2017.

PCT/US2018/030739 filed May 2, 2018.

U.S. Appl. No. 62/758,421, filed Nov. 9, 2018.

U.S. Appl. No. 62/803,334, filed Feb. 8, 2019.

U.S. Appl. No. 62/855,434, filed May 31, 2019.

U.S. Appl. No. 62/813,124, filed Mar. 3, 2019.

U.S. Appl. No. 62/813,126, filed Mar. 3, 2019.

U.S. Appl. No. 62/813,137, filed Mar. 3, 2019.

U.S. Appl. No. 62/838,159, filed Apr. 24, 2019.

PCT/US2018/059895 filed Nov. 8, 2018.

PCT/US2018/059895 International Preliminary Report on Patentability dated May 11, 2021.

U.S. Appl. No. 16/667,647 Non-Final Office Action dated Jun. 28, 2021.

Ladner, "Mapping the Epitopes of Antibodies," Biotechnology and Genetic Engineering Reviews, vol. 24, 1-30, (2007).

U.S. Appl. No. 14/776,724, filed Sep. 14, 2015; now issued as U.S. Pat. No. 10,501,531 on Dec. 10, 2019.

U.S. Appl. No. 16/092,439, filed Oct. 9, 2018.

U.S. Appl. No. 16/097,445, filed Oct. 29, 2018.

U.S. Appl. No. 16/091,060, filed Oct. 3, 2018.

PCT/US2020/017357 International Preliminary Report on Patentability dated Aug. 10, 2021.

PCT/US2020/020704 International Preliminary Report on Patentability dated Aug. 25, 2021.

Yanamandra et al., "Anti-tau antibody reduces insoluble tau and decreases brain atrophy," Annals of Clinical and Translational Neurology 2, 278-288 (2015).

U.S. Appl. No. 16/933,792 Non-Final Office Action dated Dec. 15, 2021.

U.S. Appl. No. 16/092,439 Notice of Allowance and Interview Summary dated Apr. 10, 2020.

PCT/US2019/060616 International Search Report and Written Opinion dated Mar. 20, 2020.

PCT/US2020/017357 Invitation to Pay Additional Fees dated Apr. 23, 2020.

U.S. Appl. No. 16/092,439, filed Oct. 9, 2018; now issued as U.S. Pat. No. 10,752,679 on Aug. 25, 2020.

U.S. Appl. No. 16/808,209, filed Mar. 3, 2020.

Goedert, et al., "Cloning and sequencing of the cDNA encoding a core protein of the paired helical filament of Alzheimer disease: Identification as the microtubule-associated protein tau" *Proc. Natl. Acad. Sci. USA*, vol. 85, pp. 4051-4055, (Jun. 1998).

PCT/US2014/025044 International Search Report and Written Opinion dated Nov. 3, 2014.

Vigo-Pelfrey, et al., "Elevation of microtubule-associated protein tau in the cerebrospinal fluid of patients with Alzheimer's disease", *Neurology*, 45:788-793 (1995).

PCT/US2014/025044 Invitation to Pay Additional Fees and, Where Applicable, Protest Fee dated Aug. 15, 2014.

EP 14778358.2 European Supplementary Search Report completed Nov. 3, 2016.

Castillo-Carranza, et al., "Tau aggregates as immunotherapeutic targets," *Frontiers in Bioscience, Scholar*, 5, 426-438 (Jan. 1, 2013).

(56) References Cited

OTHER PUBLICATIONS

Ghoshal, et al., "Tau Conformational Changes Correspond to Impairments of Episodic Memory in Mild Cognitive Impairment and Alzheimer's Disease," *Experimental Neurology*, 177, 475-493, (2002).
Jicha, et al., "Sequence Requirements for Formation of Conformational Variants of Tau Similar to Those Found in Alzheimer's Disease," *Journal of Neuroscience Research*, 55:713-723 (1999).
Morris, "Epitope Mapping of Protein Antigens by Competition ELISA," *The Protein Protocols Handbook*, edited by J. M. Walker, Humana Press Inc., Totowa, NJ, pp. 595-600, (Jan. 1, 1996).
Dubel, "Molecular Engineering I: Humanization," *Handbook of Therapeutic Antibodies*, Chapter 6:119-144, (2007).
Yanamandra, et al., "Anti-Tau Antibodies that Block Tau Aggregate Seeding In Vitro Markedly Decrease Pathology and Improve Cognition in Vivo," *Neuron*, 80, 402-414 (Oct. 15, 2013).
PCT/US2014/025044 International Preliminary Report on Patentability completed Oct. 9, 2014.
U.S. Appl. No. 14/776,724 Restriction Requirement dated Jan. 19, 2017.
U.S. Appl. No. 14/776,724 Non-Final Office Action dated Jun. 1, 2017.
Chen, et al., "Enhancement and destruction of antibody function by somatic mutation: unequal occurrence is controlled by V gene combinatorial associations," *the EMBO Journal*, vol. 14, No. 12, pp. 2784-2794 (1995).
Kussie, et al., "A Single Engineered Amino Acid Substitution Changes Antibody Fine Specificity," *J Immunol*, 152(1):146-52 (1994).
Oddo, et al., "Reduction of Soluble Aβ and Tau, but Not Soluble Aβ Alone, Ameliorates Cognitive Decline in Transgenic Mice with Plaques and Tangles," *The Journal of Biological Chemistry*, vol. 281, No. 51, pp. 39413-39423 (Dec. 22, 2016).
Hasegawa, et al., "Characterization of Two distinct Monoclonal Antibodies to Paired Helical Filaments: Further Evidence for Fetal-Type Phosphorylation of the τ in Paired Helical Filaments", Journal of Neurochemistry, vol. 60, No. 6, (1993).
Leger, et al., "Antibody Drug Discovery Chapter 1: Humanization of Antibodies", Molecular medicine and Medicinal Chemistry, pp. 1-23 XP055119233 (Jan. 1, 2011).
Almagro, et al., "Humanization of antibodies", *Frontiers in Bioscience*, 13, 1619-1653, (Jan. 1, 2008).
Lazar, et al., "A molecular immunology approach to antibody humanization and functional optimization", *Molecular Immunology*, 44:1986-1998 (2007).
Wu, et al., "Simultaneous Humanization and Affinity Optimization of Monoclonal Antibodies", *Methods of Molecular Biology*, vol. 207: Recombinant Antibodies for Cancer Therapy: Methods and Protocols, Edited by M. Weischof and J. Krauss @ Humana Press Inc., Tolowa NJ, pp. 197-212 (Jan. 1, 2003).
PCT/IB2017/052544 Search Report and Written Opinion dated Jul. 31, 2017.
PCT/IB2017/052545 Search Report and Written Opinion dated Aug. 1, 2017.
Bacskai, et al., "Imaging of amyloid-β deposits in brains of living mice permits direct observation of clearance of plaques with immunotherapy," *Nature Medicine*, vol. 7, No. 3, pp. 369-372, (Mar. 2001).
PCT/IB2017/052544 Search Report and Written Opinion dated Jul. 19, 2017.
Agadjanyan, et al., "Humanized monoclonal antibody armanezumab specific to N-terminus of pathological tau: characterization and therapeutic potency," *Molecular Neurodegeneration*, 12:33, DOI 10.1186/s13024-017-0172-1, (2017).
Kontsekova, et al., "First-in-man tau vaccine targeting structural determinants essential for pathological tau-tau interaction reduces tau oligomerisation and neurofibrillary degeneration in an Alzheimer's disease model," *Alzheimer's Research & Therapy*, 6:44, (2014).
Rosseels, et al., "Tau Monoclonal Antibody Generation Based on Humanized Yeast Models," *Journal of Biological Chemistry*, vol. 290, No. 7, pp. 4059-4074, (Dec. 24, 2014).
PCT/IB2017/052543 International Report on Patentability dated Nov. 6, 2018.
PCT/IB2017/052544 International Report on Patentability dated Nov. 6, 2018.
PCT/IB2017/052545 International Report on Patentability dated Nov. 6, 2018.
U.S. Appl. No. 14/776,724 Final Office Action dated Oct. 31, 2018.
U.S. Appl. No. 14/776,724 Advisory Action dated Mar. 12, 2019.
U.S. Appl. No. 14/776,724 Notice of Allowance dated Apr. 10, 2019.
PCT/US2018/030739 International Search Report and Written Opinion dated Nov. 5, 2018.
PCT/US2018/059895 International Search Report and Written Opinion dated Apr. 12, 2019.
PCT/US2018/030739 International Search Report and Written Opinion dated Sep. 18, 2018.
U.S. Appl. No. 14/776,724 Notice of Allowance dated Jul. 29, 2019.
U.S. Appl. No. 16/091,060 Restriction Requirement dated Sep. 17, 2019.
U.S. Appl. No. 16/092,439 Notice of Allowance dated Oct. 16, 2019.
Pedersen, et al., "Tau immunotherapy for Alzheimer's disease," Trends in Molecular Medicine, vol. 21, No. 6, pp. 394-402, (Jun. 2015).
PCT/US2018/030739 International Preliminary Report on Patentability dated Nov. 5, 2019.
U.S. Appl. No. 16/097,445 Restriction Requirement dated Feb. 18, 2020.
U.S. Appl. No. 16/091,060 Non-Final Office Action dated Feb. 21, 2020.
U.S. Appl. No. 16/097,445 Non-Final Office Action dated May 27, 2020.
PCT/US2020/017357 International Search Report and Written Opinion dated Jun. 17, 2020.
Kawahara, et al., "The Novel Monoclonal Antibody 9F5 Reveals Expression of a Fragment of GPNMB/Osteoactivin Processed by Furin-like Protease(s) in a Subpopulation of Microglia in Neonatal Rat Brain," GLIA, vol. 64, No. 11, pp. 1938-1961, (Nov. 2016).
Strang, et al., "Generation and characterization of new monoclonal antibodies targeting the PHF1 and AT8 epitopes on human tau," Acta Neuropathologica Communications, 5:58, (2017).
Croft, et al., "Novel monoclonal antibodies targeting the microtubule-binding domain of human tau," PLoS One, 13(4): e0195211, (Apr. 2018).
PCT/US2020/020704 Invitation to Pay Additional Fees dated Jun. 3, 2020.
EP 19213368 Extended European Search Report dated Jun. 24, 2020.
Florenzano, et al., "Extracellular truncated tau causes early presynaptic dysfunction associated with Alzheimer's disease and other tauopathies," Oncotarget, vol. 8, No. 29, pp. 64745-46778, (Apr. 2017).
Gershoni, et al., "Epitope Mapping, The First Step in Developing Epitope-Based Vaccines," Biodrugs, 21:(3), p. 145-156. (2007).
PCT/US2020/020704 Search Report and Written Opinion dated Aug. 4, 2020.
U.S. Appl. No. 16/091,060 Notice of Allowance and Interview Summary dated Aug. 19, 2020.
U.S. Appl. No. 16/097,445 Corrected Notice of Allowance dated Oct. 6, 2020.
U.S. Appl. No. 16/097,445 Notice of Allowance dated Oct. 2, 2020.
EP 18795047 Extended European Search Report dated Feb. 2, 2021.
U.S. Appl. No. 16/667,647 Restriction Requirement dated Jan. 13, 2021.
U.S. Appl. No. 16/808,209 Notice of Allowance dated Dec. 31, 2020.
Alexander et al., "Development of High Potency Universal DR-Restricted Helper Epitopes by Modification of High Affinity DR-Blocking Peptides," Immunity, Dec. 1994, 1:751-761.
Andreadis et al., "Structure and novel exons of the human .tau. Gene," Biochemistry, 1992, 31:10626-1063.

(56) References Cited

OTHER PUBLICATIONS

Banner et al., "Mapping the conformational space accessible to BACE2 using surface mutants and cocrystals with Fab fragments, Fynomers and Xaperones," Acta. Crystallogr. D. Biol. Crystallogr., 2013. 69(Pt6): 1124-1137.
Bertschinger et al., "Selection of single domain binding proteins by covalent DNA display," Feb. 2007, Protein Eng. Des. Sel. 20:57-68.
Bett et al., "Packaging Capacity and Stability of Human Adenovirus Type 5 Vectors," J. Virol., 1993, 67:5911-5921.
Boris-Lawrie et al., "Recent advances in retrovirus vector technology," Current Opinion in Genetics & Development, Feb. 1993, 3(1):102-109.
Brack et al., "A bispecific HER2-targeting FynomAb with superior antitumor activity and novel mode of action." Mol. Cancer Ther., 2014, 13:2030-2039.
Chicz et al., "Specificity and promiscuity among naturally processed peptides bound to HLA-DR alleles," J. Exp. Med., Jul. 1993, 178(1):27-47.
Chothia et al., "Canonical structures for the hypervariable regions of immunoglobulins," Journal of Molecular Biology, Aug. 1987, 196(4):901-917.
Chothia et al., "Conformations of immunoglobulin hypervariable regions," Nature, Dec. 1989, 342:878-883.
Co et al., "Chimeric and humanized antibodies with specificity for the CD33 antigen," J. Immunol., Feb. 1992, 148(4): 1149-1154.
Deshpande et al., "The RCSB Protein Data Bank: a redesigned query system and relational database based on the mmCIF schema." Nucleic Acids Res., Jan. 2005, 33: D233-D237.
Dubensky et al., "Sindbis virus DNA-based expression vectors: utility for in vitro and in vivo gene transfer," J. Virol., Jan. 1996, 70(1):508-519.
Edelman et al., "The Covalent Structure of an Entire γ G Immunoglobulin Molecule," Proc. Natl. Acad. USA, May 1969, 63(1)78-85.
Falk et al., "Pool sequencing of natural HLA-DR, DQ, and DP ligands reveals detailed peptide motifs, constraints of processing, and general rules," Immunogenetics, 1994, 39:230-242.
Foote et al., "Antibody framework residues affecting the conformation of the hypervariable loops," Journal of Molecular Biology, Mar. 1992, 224(2):487-499.
Friden et al., "Anti-transferrin receptor antibody and antibody-drug conjugates cross the blood-brain barrier," Proc. Natl. Acad Sci. USA, Jun. 1991, 88(11):4771-4775.
Friden et al., "Blood-Brain Barrier Penetration and in Vivo Activity of an NGF Conjugate," Science, Jan. 1993, 259(5093):373-377.
Goedert et al., "Cloning and sequencing of the cDNA encoding an isoform of microtubule-associated protein tau containing four tandem repeats: differential expression of tau protein mRNAs in human brain," EMBO J., 1989, 8:393-399.
Goedert et al., "Multiple isoforms of human microtubule-associated protein tau: sequences and localization in neurofibrillary tangles of Alzheimer's disease," Neuron, Oct. 1989, 3:519-526.
Gonzales et al., "SDR grafting of a murine antibody using multiple human germline templates to minimize its immunogenicity," Jul. 2004, Mol. Immunol., 41: 863.
Grabulovski et al., "A novel, non-immunogenic Fyn SH3-derived binding protein with tumor vascular targeting properties," Feb. 2007, J. Biol. Chem. 282:3196-3204.
Hammer et al., "Promiscuous and allele-specific anchors in HLA-DR-binding peptides," Cell, Jul. 1993, 74:197-203.
Hazra et al., "Linking radiosilver to monoclonal antibodies reduced by ascorbic acid. Comparison of results with stable silver using gravimetric technique and silver 110-M using radiotracer technique," 1994, Cell Biophys, 24-25:1-7.
Hinton et al., "Engineered human IgG antibodies with longer serum half-lives in primates," Feb. 2004. J. Biol. Chem. 279:6213-6216.
Itner et al., "Parkinsonism and impaired axonal transport in a mouse model of frontotemporal dementia," Oct. 2008, Proc. Natl. Acad. Sci. USA, 105(41):15997-6002.

Iwahashi et al., "CDR substitutions of a humanized monoclonal antibody (CC49): contributions of individual CDRs to antigen binding and immunogenicity," Mol. Immunol., Oct. 1999, 36:1079-1091.
Jack et al., "Hypothetical model of dynamic biomarkers of the Alzheimer's pathological cascade," Lancet Neurol, Jan. 2010, 9:119-28.
Jones et al, "The INNs and outs of antibody nonproprietary names," Oct. 2015, mAbs, retrieved from URL<http://dx.doi.org/10.1080/19420862.2015.1114320>.
Junghans et al., "Anti-Tac-H, a Humanized Antibody to the Interleukin 2 Receptor with New Features for Immunotherapy in Malignant and Immune Disorders," Cancer Res., Mar. 1990, 50(5): 1495-1502.
Kanyo et al., "Antibody binding defines a structure for an epitope that participates in the PrPC—>PrPSc conformational change," Nov. 1999, J.Mol.Biol. 293: 855-863.
Kascsak, et al., "Mouse polyclonal and monoclonal antibody to scrapie-associated fibril proteins," Dec. 1987, J Virol. 61(12):3688-93.
Khlistunova et al., "Inhibition of tau aggregation in cell models of tauopathy," Dec. 2007, Current Alzheimer Research, 4:544-546.
Kostelny et al., "Formation of a bispecific antibody by the use of leucine zippers," Journal of Immunology. Mar. 1992, 148(5):1547-1553.
La Porte et al., "Structural basis of C-terminal β-amyloid peptide binding by the antibody ponezumab for the treatment of Alzheimer's disease," Aug. 2012, J.Mol.Biol, 421: 525-536.
Lantto et al., "Capturing the Natural Diversity of the Human Antibody Response against Vaccinia Virus," Journal of Virology, Feb. 2011, 85:1820-1833.
Lazar et al., "Engineered antibody Fc variants with enhanced effector function," Mar. 2005, Proc. Natl. Acad. Sci. USA 103:4005.
Lee et al., "The microtubule binding domain of tau protein," Neuron, Jun. 1989, 2(6):1615-1624.
Lefranc M.-P. et al., IMGT unique numbering for immunoglobulin and T cell receptor constant domains and Ig superfamily C-like domains, Dev. Comp. Immunol., 29, 185-203 (2005).
Lewis et al., "Neurofibrillary tangles, amyotrophy and progressive motor disturbance in mice expressing mutant (P301L) tau protein," Nature Genetics, 2000, 25:402-405.
Liu, et al., "N-terminal glutamate to pyroglutamate conversion in vivo for human IgG2 antibodies," J. Biol. Chem., Apr. 2011, 286: 11211-11217.
Martin et al., "Structural Families in Loops of Homologous Proteins: Automatic Classification, Modelling and Application to Antibodies," Journal of Molecular Biology, Nov. 1996, 263(5):800-815.
McGee et al., "The encapsulation of a model protein in poly (D, L lactide-co-glycolide) microparticles of various sizes: an evaluation of process reproducibility," 1997, J. Microenncapsul, 14(2):197-210.
Neuberger, "Generating high-avidity human Mabs in mice," Nat. Biotechnol. Jul. 1996, 14:826.
Oestberg et al., "Human X (mouse X human) hybridomas stably producing human antibodies," 1983, Hybridoma, 2:361-367.
Ohe et al., "Construction of a novel bovine papillomavirus vector without detectable transforming activity suitable for gene transfer," Human Gene Therapy, Mar. 1995, 6:325-333.
Padlan, "A possible procedure for reducing the immunogenicity of antibody variable domains while preserving their ligand-binding properties," Mal. Immunol. Apr.-May 1991, 28:489.
Pascalis et al., "Grafting of "Abbreviated" Complementarity-Determining Regions Containing Specificity-Determining Residues Essential for Ligand Contact to Engineer a Less Immunogenic Humanized Monoclonal Antibody," J Immunol., Sep. 2002, 169(6):3076.
Pietersz et al., "Novel synthesis and in vitro characterization of disulfide-linked ricin-monoclonal antibody conjugates devoid of galactose binding activity," Aug. 1988, Cancer Res. 48(16):4469-4476.
Polito et al., "The conjugate Rituximab/saporin-S6 completely inhibits clonogenic growth of CD20-expressing cells and produces a synergistic toxic effect with Fludarabine," Jul. 2004, Leukemia 18:1215-1222.

(56) References Cited

OTHER PUBLICATIONS

Poorkaj et al., "Tau is a candidate gene for chromosome 17 frontotemporal dementia," Annals of Neurology, 1998, 43(6):815-825.

Powilleit et al., "Exploiting the Yeast L-A Viral Capsid for the In Vivo Assembly of Chimeric VLPs as Platform in Vaccine Development and Foreign Protein Expression," PLoS One, May 2007, 2(5):e415.

Queen et al., "Cell-Type Specific Regulation of a K Immunoglobulin Gene by Promoter and Enhancer Elements," Immunol. Rev., Feb. 1986, 89(1):49-68.

Schiele, et al., "Structure-guided residence time optimization of a dabigatran reversal agent," 2015, MAbs. 7(5):871-80.

Schilling et al., "Glutaminyl cyclases from animals and plants: a case of functionally convergent protein evolution," Aug. 2008, Biol Chem. 389(8):983-91.

Schlatter et al., "Generation, characterization and structural data of chymase binding proteins based on the human Fyn kinase SH3 domain." Jul.-Aug. 2012, MAbs. 4:497-508.

Shriner et al., "Analysis of the young and elderly variable gene repertoire in response to pneumococcal polysaccharides using a reconstituted SCID mouse model," Nov. 2016, Vaccine. 24:7159-7166.

Sinigaglia et al., "A malaria T-cell epitope recognized in association with most mouse and human MHC class II molecules," Nature, Dec. 1988, 336:778-780.

Songsivilai et al., "Bispecific antibody: a tool for diagnosis and treatment of disease," Clin. Exp. Immunol., Mar. 1990, 79(3):315-321.

Southwood et al., "Several Common HLA-DR Types Share Largely Overlapping Peptide Binding Repertoires," J. Immunology, Apr. 1998, 160:3363-3373.

Stoute et al., "A Preliminary Evaluation of a Recombinant Circumsporozoite Protein Vaccine against Plasmodium falciparum Malaria," N. Engl. J. Med., 1997, 336:86-91.

Tamura et al., "Structural Correlates of an Anticarcinoma Antibody: Identification of Specificity-Determining Residues (SDRs) and Development of a Minimally Immunogenic Antibody Variant by Retention of SDRs Only," The Journal of Immunology, Feb. 2000, 164(3):1432-1441.

Thorpe et al., "The preparation and cytotoxic properties of antibody-toxin conjugates," 1982, Immunol. Rev., 62:119-58.

Vajdos et al., "Comprehensive functional maps of the antigen-binding site of an anti-ErbB2 antibody obtained with shotgun scanning mutagenesis," J. of Mal. Biol., Jul. 2002, 320: 415-428.

Wang et al., "Two-stage PCR protocol allowing introduction of multiple mutations, deletions and insertions using QuikChange Site-Directed Mutagenesis," Bio Techniques, Apr. 1999, 26:680-682.

WHO-INN: International nonproprietary names (INN) for biological and biotechnological substances (a review) (Internet) 2014. Available from: http://www.who.int/medicines/services/inn/BioRev2014.pdf.

Williams et al., "The human neonatal B cell response to respiratory syncytial virus uses a biased antibody variable gene repertoire that lacks somatic mutations," Dec. 2009, Mol. Immunol. 47:407-414.

Witzig, "Radioimmunotherapy for patients with relapsed B-cell non-Hodgkin lymphoma," Aug. 2001, Cancer Chemother Pharmacol., 48 Suppl 1:891-S95.

Wu et al., Generation and Characterization of a Dual Variable Domain Immunoglobulin (DVD-Ig™) Molecule, In: Antibody Engineering, Springer Berlin Heidelberg (2010).

Xiao et al., "High efficiency, long-term clinical expression of cottontail rabbit papillomavirus (CRPV) DNA in rabbit skin following particle-mediated DNA transfer," Jul. 1996, Nucleic Acids. Res. 24:2630-2622.

Ye et al., "Structural Basis for Recognition of Human Enterovirus 71 by a Bivalent Broadly Neutralizing Monoclonal Antibody," Mar. 2016, PLoS Pathog, Structural Basis for Recognition of Human Enterovirus 71 by a Bivalent Broadly Neutralizing Monoclonal Antibody.

Yu et al., "Boosting brain uptake of a therapeutic antibody by reducing its affinity for a transcytosis target," May 2011, Sci. Trans. Med. 3. 84ra44.

Zhou et al., "Adeno-associated virus 2-mediated high efficiency gene transfer into immature and mature subsets of hematopoietic progenitor cells in human umbilical cord blood," J. Exp. Med., Jun. 1994, 179:1867-75.

Zhu et al., "Antibody structure determination using a combination of homology modeling, energy-based refinement, and loop prediction," Aug. 2014, Proteins. 82(8):1646-1655.

\* cited by examiner

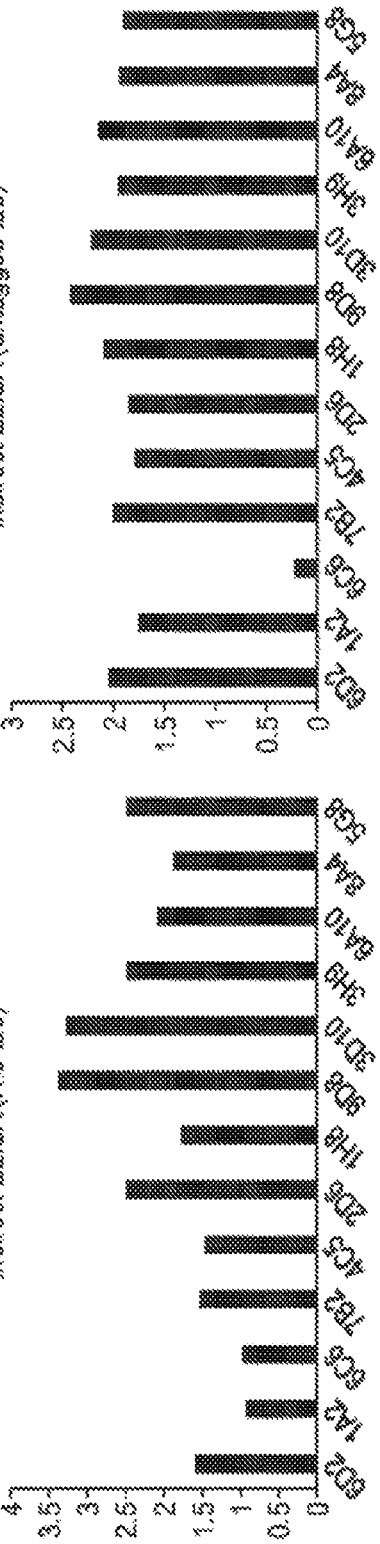
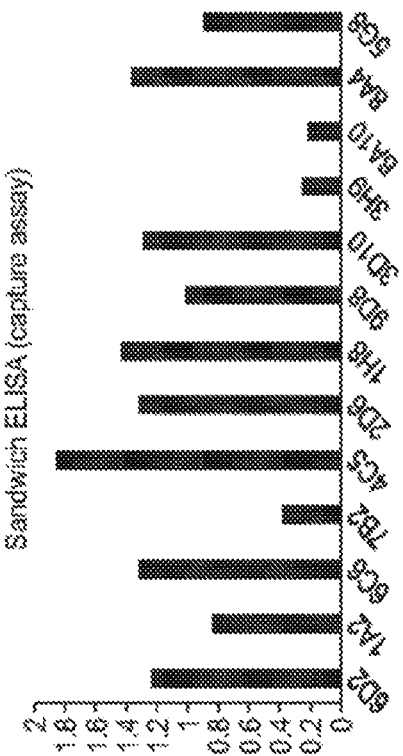

| Name | $k_a$ (M⁻¹s⁻¹) | $k_d$ (s⁻¹) | $k_D$ (nM) |
|---|---|---|---|
| 3D6 | 2.58 x 10⁶ | 1.19 x 10⁻³ | 0.46 |
| 1H6 | 5.07 x 10⁵ | 5.61 x 10⁻³ | 11.1 |
| 3H9 | 4.71 x 10⁵ | 1.41 x 10⁻³ | 3.0 |
| 5G8 | 3.75 x 10⁵ | 2.54 x 10⁻³ | 6.78 |
| 6D2 | 3.83 x 10⁵ | 3.18 x 10⁻³ | 8.29 |
| 7G6 | 5.76 x 10⁵ | 3.32 x 10⁻³ | 5.77 |
| 8A4 | 5.99 x 10⁵ | 2.27 x 10⁻³ | 3.8 |

```
5G8-VH          EVQLQQSGAELVRSGASVRLSCTAASGFNIKDYYMHWVRQR
aDabi-Fab2b-VH  QVQLVQSGAEVKKKPGASVKVSCKASGYTFTDYYMHWVRQA
hu5G8-VH_v1     QVQLVQSGAEVKKKPGASVKVSCKASGFNIKDYYMHWVRQA
hu5G8-VH_v2     QVQLVQSGAEVKKKPGASVKVSCKASGFNIKDYYMHWVRQA
hu5G8-VH_v3     EVQLVQSGAEVKKKPGASVKVSCKASGFNIKDYYMHWVRQA
hu5G8-VH_v4     EVQLVQSGAELVKKPGASVRLSCKASGFNIKDYYMHWVRQA
hu5G8-VH_v5     EVQLVQSGAELVKKPGASVKVSCKAASGFNIKDYYMHWVRQA
hu5G8-VH_v6     EVQLVQSGAELVKKPGASVKVSCKAASGFNIKDYYMHWVRQA
hu5G8-VH_v7     QVQLVQSGAEVKKKPGASVKVSCKAASGFNIKDYYMHWVRQA
hu5G8-VH_v8     EVQLVQSGAEVKKKPGASVKVSCKASGFNIKDYYMHWVRQA
                         10        20        30        40

5G8-VH          PEQGLEWIGWIDPENGDTVYAPKFQGKATMTSDTSSNTAY
aDabi-Fab2b-VH  PGQGLEWMGETNPRNGGTTYYAPKFQKKATMTRDTSTSTAY
hu5G8-VH_v1     PGQGLEWIGWIDPENGDTVYYAPKFQGKATMTSDTSTSTAY
hu5G8-VH_v2     PGQGLEWIGWIDPENGDTVYYAPKFQGKATMTSDTSTSTAY
hu5G8-VH_v3     PGQGLEWIGWIDPENGDTVYYAPKFQGKATMTSDTSTSTAY
hu5G8-VH_v4     PGQGLDWIGWIDPENGDTVYYAPKFQGKATMTSDTSTSTAY
hu5G8-VH_v5     PGQGLEWMGWIDPENGDTVYYAPKFQGKATMTSDTSTNTAY
hu5G8-VH_v6     PGQGLDWIGWIDPENGDTVYYAPKFQGRVTMTRDTSTSTVY
hu5G8-VH_v7     PGQGLEWIGWIDPENGDTVYYAPKFQGRVTMTSDTSTSTVY
hu5G8-VH_v8     PGQGLDWIGWIDPENGDTVYYAPKFQGRVTMTSDTSTSTVY
                         50        60        70        80
```

FIG. 5A

| Name | Sequence (≈85–110) | Length | SEQ ID NO |
|---|---|---|---|
| 5G8-VH | LHLSSLTSEDTAVYYCSP-------LDFWGQGTTLTVSS | 112 | (SEQ ID NO: 7) |
| aDabi-Fab2b-VH | MELSSLRSEDTAVYYCTHIGTSGYDYLDFWGQGTLVTVSS | 119 | (SEQ ID NO: 28) |
| hu5G8-VH_v1 | MELSSLRSEDTAVYYCTH-------LDFWGQGTLVTVSS | 112 | (SEQ ID NO: 33) |
| hu5G8-VH_v2 | MELSSLRSEDTAVYYCSP-------LDFWGQGTLVTVSS | 112 | (SEQ ID NO: 34) |
| hu5G8-VH_v3 | MELSSLRSEDTAVYYCSP-------LDFWGQGTLVTVSS | 112 | (SEQ ID NO: 35) |
| hu5G8-VH_v4 | MELSSLRSEDTAVYYCSP-------LDFWGQGTLVTVSS | 112 | (SEQ ID NO: 36) |
| hu5G8-VH_v5 | LELSSLRSEDTAVYYCSP-------LDFWGQGTLVTVSS | 112 | (SEQ ID NO: 37) |
| hu5G8-VH_v6 | LELSSLRSEDTAVYYCSP-------LDFWGQGTLVTVSS | 112 | (SEQ ID NO: 38) |
| hu5G8-VH_v7 | MELSSLRSEDTAVYYCAR-------LDFWGQGTLVTVSS | 112 | (SEQ ID NO: 39) |
| hu5G8-VH_v8 | MELSSLRSEDTAVYYCSP-------LDFWGQGTLVTVSS | 112 | (SEQ ID NO: 40) |

FIG. 5B

```
                         1               10              20              30              40
                         +---+---+---+---+---+---+---+---+---+---+---+---+---+---+---+---+
5G8-VL           D V V M T Q T P L T L S V T I G Q P A S I S C K S S Q S L L D S D G K T Y L N W    40
aDabi-Fab2b-VL   D I V M T Q T P L S L S V T P G Q P A S I S C R S S Q S L V H S D G K N I Y L E W  40
hu5G8-VL_v1      D I V M T Q T P L S L S V T P G Q P A S I S C K S S Q S L L D S D G K T Y L N W    40
hu5G8-VL_v2      D V V M T Q T P L S L S V T P G Q P A S I S C K S S Q S L L D S D G K T Y L N W    40
hu5G8-VL_v3      D V V M T Q T P L S L S V T P G Q P A S I S C K S S Q S L L D S D G K T Y L N W    40
hu5G8-VL_v4      D V V M T Q T P L T L S V T P G E P A S I S C K S S Q S L L D S D G K T Y L N W    40
hu5G8-VL_v5      D I V M T Q T P L S L S V T P G Q P A S I S C K S S Q S L L D S D G K T Y L N W    40
hu5G8-VL_v6      D V V M T Q T P L S L S V T P G Q P A S I S C K S S Q S L L D S D G K T Y L N W    40

41              50              60              70              80
                         +---+---+---+---+---+---+---+---+---+---+---+---+---+---+---+---+
5G8-VL           L L Q R P G Q S P K R L I Y L V S K L D S G V P D R F S G S G S G T D F T L K I    80
aDabi-Fab2b-VL   Y L Q K P G Q S P K L L I Y K V S N R F S G V P D R F S G S G S G T D F T L K I    80
hu5G8-VL_v1      Y L Q K P G Q S P K L L I Y L V S K L D S G V P D R F S G S G S G T D F T L K I    80
hu5G8-VL_v2      L L Q R P G Q S P K R L I Y L V S K L D S G V P D R F S G S G S G T D F T L K I    80
hu5G8-VL_v3      L L Q K P G Q S P K R L I Y L V S K L D S G V P D R F S G S G S G T D F T L K I    80
hu5G8-VL_v4      L L Q R P G Q S P K R L I Y L V S K L D S G V P D R F T G S G S G T D F T L K I    80
hu5G8-VL_v5      Y L Q K P G Q S P Q L L I Y L V S K L D S G V P D R F S G S G S G T D F T L K I    80
hu5G8-VL_v6      L L Q K P G Q S P Q R L I Y L V S K L D S G V P D R F S G S G S G T D F T L K I    80
```

*FIG. 6A*

| | | | | | | | |
|---|---|---|---|---|---|---|---|
| 5G8-VL | R R V E A E D L G V Y Y C W Q G T L F P Y T F G G G T K L E I K | 112 | (SEQ ID NO: 8) |
| aDabi-Fab2b-VL | S R V E A E D D V G V Y Y C C F Q Q A S H V P Y T F G G G T K L E I K | 112 | (SEQ ID NO: 31) |
| hu5G8-VL_v1 | S R V E A E D D V G V Y Y C W Q Q G T L F P Y T F G G G T K L E I K | 112 | (SEQ ID NO: 41) |
| hu5G8-VL_v2 | S R V E A E D D V G V Y Y C W Q Q G T L F P Y T F G G G T K L E I K | 112 | (SEQ ID NO: 42) |
| hu5G8-VL_v3 | S R V E A E D D V G V Y Y C W Q Q G T L F P Y T F G G G T K L E I K | 112 | (SEQ ID NO: 43) |
| hu5G8-VL_v4 | S R V E A E D D V G V Y Y C W Q Q G T L F P Y T F G G G T K L E I K | 112 | (SEQ ID NO: 44) |
| hu5G8-VL_v5 | S R V E A E D D V G V Y Y C W Q Q G T L F P Y T F G G G T K L E I K | 112 | (SEQ ID NO: 45) |
| hu5G8-VL_v6 | S R V E A E D D V G V Y Y C W Q Q G T L F P Y T F G G G T K L E I K | 112 | (SEQ ID NO: 46) |

FIG. 6B

```
6A10VH protein  ------- EVQLQQSGAELVRSGASVKLSCTAASGLNIKDYYIHWVKQR              40
ACR16112 VH     QVQLQQSGAEVKKPGASVKVSCKASGYTFTGLNIKDYYYMHWVRQA              40
hu6A10VH_v1     QVQLVQSGAEVKKPGASVKVSCKASGLNIKDYYIHWVRQA                    40
hu6A10VH_v2     QVQLVQSGAEVKKPGASVKVSCKASGLNIKDYYIHWVRQA                    40
hu6A10VH_v3     QVQLVQSGGGSVKVSCKASGLNIKDYYIHWVRQA                          40

6A10VH protein  PEQGLEWIGWIDPENDDTEYAPKFQGRATLTTDTSSNTAY                    80
ACR16112 VH     PGQGLEWMGWINPNSGDTNYAQKFQGRVTITTRDTSISTAY                   80
hu6A10VH_v1     PGQGLEWMGWIDPENDDTEYAPKFQGRVTITTRDTSISTAY                   80
hu6A10VH_v2     PGQGLEWIGWIDPENDDTEYAPKFQGRVTITTRDTSISTAY                   80
hu6A10VH_v3     PGQGLEWIGWIDPENDDTEYAPKFQGRVTITTRDTSISTAY                   80

6A10VH protein  LQLSSLTSEDTAVYYCTP--------LDYWGQGTSVTVSS                    112 (SEQ ID NO: 63)
ACR16112 VH     MELSRLRSDDDTAVYYCARLAARPLDYWGQGTLVTVSS                      117 (SEQ ID NO: 81)
hu6A10VH_v1     MELSRLRSDDDTAVYYCAR-------LDYWGQGTLVTVSS                    112 (SEQ ID NO: 85)
hu6A10VH_v2     MELSRLRSDDDTAVYYCAR-------LDYWGQGTLVTVSS                    112 (SEQ ID NO: 86)
hu6A10VH_v3     LELSRLRSDDDTAVYYCAR-------LDYWGQGTLVTVSS                    112 (SEQ ID NO: 87)
```

6A10VL protein    DVVMTQTPLTLSVTIGQPASISCKSSQSLLDSLLVYSDGKTYLNW     40
ABC66863VL        DIVMTQSPLSLPVTLGQPASISCRSSQS----LVYSDGNTYLNW      40
hu6A10VL_v1       DIVMTQSPLSLPVTLGQPASISCKSSQSLLDS-DGKTYLNW         40
hu6A10VL_v2       DIVMTQSPLSLPVTLGQPASISCKSSQSLLDS-DGKTYLNW         40
hu6A10VL_v3       DIVMTQSPLSLPVTLGEPASISCKSSQSLLDS-DGKTYLNW         40

50         60         70         80
6A10VL protein    LLQRPGQSPKRRLLIYLVSKLDSGVPDRFTGSGSGTDFTLKI        80
ABC66863VL        FQQRPGQSPRRLLIYKVSNRDSGVPDRFSGSGSGTDFTLKI         80
hu6A10VL_v1       FQQRPGQSPRRLLIYLVSKLDSGVPDRFSGSGSGTDFTLKI         80
hu6A10VL_v2       FQQRPGQSPRRLLIYLVSKLDSGVPDRFSGSGSGTDFTLKI         80
hu6A10VL_v3       FQQRPGQSPRRLLIYLVSKLDSGVPDRFSGSGSGTDFTLKI         80

90        100        110
6A10VL protein    SRVEAEDLGVYYCWQGTHFPYTFGGGTKLEIK     112 (SEQ ID NO: 64)
ABC66863VL        SRVEAEDVGVYYCMQGTHFPYTFGGGTKVEIK     112 (SEQ ID NO: 83)
hu6A10VL_v1       SRVEAEDVGVYYCWQGTHFPLTFGGGTKVEIK     112 (SEQ ID NO: 88)
hu6A10VL_v2       SRVEAEDVGVYYCWQGTHFPYTFGGGTKVEIK     112 (SEQ ID NO: 89)
hu6A10VL_v3       SRVEAEDVGVYYCWQGTHFPYTFGGGTKVEIK     112 (SEQ ID NO: 90)
```

```
                      10        20        30        40
              ----+----|----+----|----+----|----+----|
8A4-VH      : EVQLQQSGAELVRPGALVKLSCKASGFNIKDYYIHWVKQR   40
ADU57742    : QVQLVQSGAEVKKPGSSVKVSCKASGGTFSSNPVSWVRQA   40
8A4VH_v1    : QVQLVQSGAEVKKPGSSVKVSCKASGFNIKDYYIHWVRQA   40
8A4VH_v2    : QVQLVQSGAEVVKPGGSVKLSCKASGFNIKDYYIHWVRQA   40
8A4VH_v3    : QVQLVQSGAEVVKPGGSVKLSCKASGFNIKDYYIHWVRQA   40

50        60        70        80
              ----+----|----+----|----+----|----+----|
8A4-VH      : PEQGLEWIGWIDPENGDTVYDPQFQDKANITADTSSNTAY   80
ADU57742    : PGQGLEWMGGIIPIFGAQKVLGAQRVRDFQDRINITSTSTAY 80
8A4VH_v1    : PGQGLEWMGWIDPENGDTVYDPQFQDRITITADTSTSTAY   80
8A4VH_v2    : PGQGLEWMGWIDPENGDTVYDPQFQDRITITADTSTSTAY   80
8A4VH_v3    : PGQGLEWIGWIDPENGDTVYDPQFQDRITITADTSTSTAY   80

90       100       110
              ----+----|----+----|----+----|--
8A4-VH      : LQLSSLTSEGTAVYYCST---LDFWGQGTTLTVSS   112   (SEQ ID NO: 91)
ADU57742    : MELSSLRSDDDTAVYYCATGQQLYSLHYWGQGTLVTVSS  118   (SEQ ID NO: 110)
8A4VH_v1    : MELSGLRSDDTAVYYCST---LDFWGQGTLVTVSS   112   (SEQ ID NO: 113)
8A4VH_v2    : MELSEDTAVYYCST---LDFWGQGTLVTVSS       112   (SEQ ID NO: 114)
8A4VH_v3    : MELSGLRSDDTAVYYCST---LDFWGQGTLVTVSS   112   (SEQ ID NO: 115)
```

```
8A4VL_protein    DVVMTQTPLTLSVTIGQPASISCKSSQSLLDSDGKTYLNW    40
ABA26100         DIVMTQSPLSLSVTLGQPASISCRSSQSLVYSDGKTYLNW    40  (SEQ ID NO: 92)
8A4VL_v1         DIVMTQSPLSLSVTLGQPASISCKSSQSLLDSDGKTWLNW    40  (SEQ ID NO: 112)
8A4VL_v2         DIVMTQSPLSLSVTLGEPASISCKSSQSLLDSDGKTYLNW    40  (SEQ ID NO: 116)
8A4VL_v3         DVVMTQSPLSLSVTLGEPASISCKSSQSLLDSDGKTYLNW    40  (SEQ ID NO: 117)
                                                                  (SEQ ID NO: 118)

8A4VL_protein    LLQRPGQSPKRRLIYLVSKLDSGVPDRFTGSGSGTDFTLKI    80
ABA26100         FQQRPGQSPRRLIYLYDVSTRDSGVPDRFSGSGSGTDFTLKI   80
8A4VL_v1         FQQRPGQSPRRLIYLVSKLDSGVPDRFSGSGSGTDFTLKI    80
8A4VL_v2         FQQRPGQSPRRLIYLVSKLDSGVPDRFSGSGSGTDFTLKI    80
8A4VL_v3         LQQRPGQSPRRLIYLVSKLDSGVPDRFSGSGSGTDFTLKI    80

8A4VL_protein    SRVEAEDLGVYYCWQGTHFPCTFGGGTKLEIK    112
ABA26100         SRVEAEDVGVYYCMQGTHFIDWPHTFGQGTKLEIK   112
8A4VL_v1         SRVEAEDVGVYYCWQGTHFPCTFGGGQGTKLEIK    112
8A4VL_v2         SRVEAEDVGVYYCWQGTHFPCTFGGGQGTKLEIK    112
8A4VL_v3         SRVEAEDVGVYYCWQGTHFPCTFGGGQGTKLEIK    112
```

FIG. 10

```
7G6VH protein    ------EVQLQQSGAELVRPGALVKLSCKASGFNIKDYYIHWVKQR     40
3U0T VH          ------QVQLVQSGAEVKKPGASVKVSCKASGYYTEAYYIHWVRQA     40
hu7G6VHv1        ------QVQLVQSGAEVVKPGASVKLSCKASGFNIKDYYIHWVRQA     40
hu7G6VHv2        ------QVQLVQSGAEVVKPGASVKLSCKASGFNIKDYYIHWVKQA     40
                                                                       80
7G6VH protein    PEQGLEWIGWIDPENGETVYDPKFQGKASITSDTSSNTAY          80
3U0T VH          PGQGLEWMGRIDPATGNTKYAPRLQDRVTMTRDTSTSTVY          80
hu7G6VHv1        PGQGLEWMGWIDPENGETVYDPKFQGRVTITRDTSTNTAY          80
hu7G6VHv2        PGQGLEWMGWIDPENGETVYDPKFQGRVTITRDTSTNTAY          80
                                                                       110
7G6VH protein    LQLRSLTSEDTAVYYYSTSLD----FWGQGTSVTVSS             112
3U0T VH          MELSSLRSEDTAVYYCASLYSLPVYWGQGTTVTVSS              116
hu7G6VHv1        LQLSSLRSEDTAVYYYSTSLD----FWGQGTTVTVSS             112
hu7G6VHv2        LQLSSLRSEDTAVYYYSTSLD----FWGQGTTVTVSS             112
```

FIG. 11

```
                         |----+----|----+----|----+----|----+----|
                                  10        20        30        40
7GG6VL protein           DVVMTQTPLTLSVTIGQPASISCKSTQSLLDYSDGAKTYLNW  40
3U0T_VL                  DVVMTQSPLSLPVSLGDQASISCRSSQSLVHSNGNTYLHW   40
hu7G6VLv1                DVVMTQSPLSLSVTLGQPASISCKSSQSLLDSDGKTYLNW   40
hu7G6VLv2                DVVMTQSPLSLPVTLGQPASISCKSSQSLLDSDGKTYLNW   40
hu7G6VLv3                DVVMTQSPLSLSVTLGQPASISCKSTQSLLDSDGKTYLNW   40
hu7G6VLv4                DVVMTQSPLSLPVTLGQPASISCKSTQSLLDSDGKTYLNW   40
hu7G6VLv5                DVVMTQSPLSLSVTLGQPASISCKSSQSLLDSDGKTYLNW   40
hu7G6VLv6                DVVMTQSPLSLPVTLGQPASISCKSSQSLLDSDGKTYLNW   40
hu7G6VLv7                DVVMTQSPLSLSVTLGQPASISCKSTQSLLDSDGKTYLNW   40
hu7G6VLv8                DVVMTQSPLSLPVTLGQPASISCKSTQSLLDSDGKTYLNW   40

|----+----|----+----|----+----|----+----|
                                  50        60        70        80
7GG6VL protein           LLQRPGQSPKRRLIYLVSKLDSGVPDRFTGSGSGTDFTLKI  80
3U0T_VL                  FQQRPGQSPRRLIYKVSNRFSGVPDRFSGSGSGTDFTLKI   80
hu7G6VLv1                FQQRPGQSPRRLIYLVSKLDSGVPDRFSGSGSGTDFTLKI   80
hu7G6VLv2                FLQRPGQSPRRLIYLVSKLDSGVPDRFSGSGSGTDFTLKI   80
hu7G6VLv3                LLQRPGQSPKRRLIYLVSKLDSGVPDRFSGSGSGTDFTLKI   80
hu7G6VLv4                FQQRPGQSPRRLIYLVSKLDSGVPDRFSGSGSGTDFTLKI   80
hu7G6VLv5                FLQRPGQSPRRLIYLVSKLDSGVPDRFSGSGSGTDFTLKI   80
hu7G6VLv6                LLQRPGQSPKRRLIYLVSKLDSGVPDRFSGSGSGTDFTLKI   80
hu7G6VLv7                FQQRPGQSPRRLIYLVSKLDSGVPDRFSGSGSGTDFTLKI   80
hu7G6VLv8                LLQRPGQSPKRRLIYLVSKLDSGVPDRFSGSGSGTDFTLKI   80
```

*FIG. 12A*

| | | | | | | | | | | | | | | | | | | | | | | | |
|---|---|---|---|---|---|---|---|---|---|---|---|---|---|---|---|---|---|---|---|---|---|---|---|
| 7G6VL protein | S | R | V | E | A | E | D | L | G | V | Y | Y | C | W | Q | G | T | H | F | P | Y | T | F | G | G | G | T | K | L | E | I | K | | 112 (SEQ ID NO: 120) |
| 3U0T VL | S | R | V | E | A | E | D | V | G | V | Y | Y | C | W | Q | Q | T | H | Y | P | V | L | T | F | G | Q | G | T | K | L | E | I | K | R | 113 (SEQ ID NO: 138) |
| hu7G6VLv1 | S | R | V | E | A | E | D | V | G | V | Y | Y | C | W | Q | G | T | H | F | P | Y | T | F | G | Q | G | T | K | R | L | E | I | K | R | 113 (SEQ ID NO: 141) |
| hu7G6VLv2 | S | R | V | E | A | E | D | V | G | V | Y | Y | C | W | Q | G | T | H | F | P | Y | T | F | G | Q | G | T | K | K | L | E | I | K | R | 113 (SEQ ID NO: 142) |
| hu7G6VLv3 | S | R | V | E | A | E | D | V | G | V | Y | Y | C | W | Q | G | T | H | F | P | Y | T | F | G | Q | G | T | K | K | L | E | I | K | R | 113 (SEQ ID NO: 143) |
| hu7G6VLv4 | S | R | V | E | A | E | D | V | G | V | Y | Y | C | W | Q | G | T | H | F | P | Y | T | F | G | Q | G | T | K | K | L | E | I | K | R | 113 (SEQ ID NO: 144) |
| hu7G6VLv5 | S | R | V | E | A | E | D | V | G | V | Y | Y | C | W | Q | G | T | H | F | P | Y | T | F | G | Q | G | T | K | K | L | E | I | K | R | 113 (SEQ ID NO: 145) |
| hu7G6VLv6 | S | R | V | E | A | E | D | V | G | V | Y | Y | C | W | Q | G | T | H | F | P | Y | T | F | G | G | G | T | K | L | E | I | K | R | 113 (SEQ ID NO: 146) |
| hu7G6VLv7 | S | R | V | E | A | E | D | V | G | V | Y | Y | C | W | Q | G | T | H | F | P | Y | T | F | G | G | G | T | K | L | E | I | K | R | 113 (SEQ ID NO: 147) |
| hu7G6VLv8 | S | R | V | E | A | E | D | V | G | V | Y | Y | C | W | Q | G | T | H | F | P | Y | T | F | G | G | G | T | K | L | E | I | K | R | 113 (SEQ ID NO: 148) |

FIG. 12B

ANTIBODIES RECOGNIZING TAU

CROSS-REFERENCE TO RELATED APPLICATIONS

This application is a US national stage entry of PCT/US2018/030739, filed May 2, 2018, which claims the benefit under 35 USC 119(e) of U.S. Provisional Application No. 62/500,427, filed May 2, 2017 and U.S. Provisional Application No. 62/580,408, filed Nov. 1, 2017, which are incorporated by reference in their entirety for all purposes.

SEQUENCE LISTING

This application contains a Sequence Listing that has been submitted electronically as an ASCII text file named 50887-0026US1_SL_ST25.txt. The ASCII text file, updated on Aug. 21, 2023, is 110,268 bytes in size. The material in the ASCII text file is hereby incorporated by reference in its entirety.

BACKGROUND OF THE INVENTION

Tau is a well-known human protein that can exist in phosphorylated forms (see, e.g., Goedert, Proc. Natl. Acad. Sci. U.S.A. 85:4051-4055(1988); Goedert, EMBO J. 8:393-399(1989); Lee, Neuron 2:1615-1624(1989); Goedert, Neuron 3:519-526(1989); Andreadis, Biochemistry 31:10626-10633(1992). Tau has been reported to have a role in stabilizing microtubules, particularly in the central nervous system. Total tau (t-tau, i.e., phosphorylated and unphosphorylated forms) and phospho-tau (p-tau, i.e., phosphorylated tau) are released by the brain in response to neuronal injury and neurodegeneration and have been reported to occur at increased levels in the CSF of Alzheimer's patients relative to the general population (Jack et al., Lancet Neurol 9: 119-28 (2010)).

Tau is the principal constituent of neurofibrillary tangles, which together with plaques are a hallmark characteristic of Alzheimer's disease. The tangles constitute abnormal fibrils measuring 10 nm in diameter occurring in pairs wound in a helical fashion with a regular periodicity of 80 nm. The tau within neurofibrillary tangles is abnormally phosphorylated (hyperphosphorylated) with phosphate groups attached to specific sites on the molecule. Severe involvement of neurofibrillary tangles is seen in the layer II neurons of the entorhinal cortex, the CA1 and subicular regions of the hippocampus, the amygdala, and the deeper layers (layers III, V, and superficial VI) of the neocortex in Alzheimer's disease. Hyperphosphorylated tau has also been reported to interfere with microtubule assembly, which may promote neuronal network breakdown.

Tau inclusions are part of the defining neuropathology of several neurodegenerative diseases including Alzheimer's disease, frontotemporal lobar degeneration, progressive supranuclear palsy and Pick's disease.

BRIEF SUMMARY OF THE CLAIMED INVENTION

In one aspect, the invention provides an isolated monoclonal antibody that binds specifically to tau. Some such antibodies compete for binding to human tau with antibody 5G8. Some such antibodies bind to the same epitope on human tau as 5G8.

Some antibodies comprise three light chain CDRs and three heavy chain CDRs of monoclonal antibody 5G8, wherein 5G8 is a mouse antibody characterized by a heavy chain variable region having an amino acid sequence comprising SEQ ID NO: 7 and a light chain variable region having an amino acid sequence comprising SEQ ID NO:8. In some antibodies, the three heavy chain CDRs are as defined by Kabat/Chothia Composite (SEQ ID NOs: 11, 12, and 13) and the three light chain CDRs are as defined by Kabat/Chothia Composite (SEQ ID NOs: 14, 15, and 16).

For example, the antibody can be 5G8 or a chimeric, veneered, or humanized form thereof. In some such antibodies, the variable heavy chain has ≥85% identity to human sequence. In some such antibodies, the variable light chain has ≥85% identity to human sequence. In some such antibodies, each of the variable heavy chain and variable light chain has ≥85% identity to human germline sequence.

Some antibodies are humanized antibodies. Some antibodies are a humanized or chimeric 5G8 antibody that specifically binds to human tau, wherein 5G8 is a mouse antibody characterized by a mature heavy chain variable region of SEQ ID NO:7 and a mature light chain variable region of SEQ ID NO:8. Some antibodies comprise a humanized mature heavy chain variable region comprising the three heavy chain CDRs of 5G8 and a humanized mature light chain variable region comprising the three light chain CDRs of 5G8.

In some antibodies, the CDRs are of a definition selected from the group of Kabat, Chothia, Kabat/Chothia Composite, AbM and Contact. In some antibodies, the humanized mature heavy chain variable region comprises the three Kabat/Chothia Composite heavy chain CDRs of 5G8 (SEQ ID NOs: 11-13) and the humanized mature light chain variable region comprises the three Kabat/Chothia Composite light chain CDRs of 5G8 (SEQ ID NOs: 14-16). In some antibodies, the humanized mature heavy chain variable region comprises the three Kabat heavy chain CDRs of 5G8 (SEQ ID NO:17, SEQ ID NO:12, and SEQ ID NO:13) and the humanized mature light chain variable region comprises the three Kabat light chain CDRs of 5G8 (SEQ ID NOs: 14-16). In some antibodies, the humanized mature heavy chain variable region comprises the three Chothia heavy chain CDRs of 5G8 (SEQ ID NO:18, SEQ ID NO:20, and SEQ ID NO:13) and the humanized mature light chain variable region comprises the three Chothia light chain CDRs of 5G8 (SEQ ID NOs: 14-16). In some antibodies, the humanized mature heavy chain variable region comprises the three AbM heavy chain CDRs of 5G8 (SEQ ID NO:11, SEQ ID NO:21, and SEQ ID NO:13)) and the humanized mature light chain variable region comprises the three AbM light chain CDRs of 5G8 (SEQ ID NOs: 14-16). In some antibodies, the humanized mature heavy chain variable region comprises the three Contact heavy chain CDRs of 5G8 (SEQ ID NO:19, SEQ ID NO:22, and SEQ ID NO: 23)) and the humanized mature light chain variable region comprises the three Contact light chain CDRs of 5G8 (SEQ ID NO:24-26).

Some antibodies comprise a humanized mature heavy chain variable region having an amino acid sequence at least 90% identical to any one of SEQ ID NO:33-40 and a humanized mature light chain variable region having an amino acid sequence at least 90% identical to any one of SEQ ID NO: 41-46.

In some antibodies, at least one of the following positions is occupied by the amino acid as specified: H48 is occupied by I, H71 is occupied by S, H93 is occupied by S, and H94 is occupied by P. In some antibodies, positions H48, H71, H93, and H94 in the VH region are occupied by I, S, S, and P, respectively. In some antibodies, at least one of the following positions is occupied by the amino acid as specified: H1 is occupied by E, H48 is occupied by I, H71 is occupied by S, H93 is occupied by S, and H94 is occupied by P. In some antibodies, positions H1, H48, H71, H93, and H94 in the VH region are occupied by E, I, S, S, and P, respectively.

In some antibodies, at least one of the following positions is occupied by the amino acid as specified: H1 is occupied by E, H46 is occupied by D, H48 is occupied by I, H71 is occupied by S, H93 is occupied by S, and H94 is occupied by P. In some antibodies, positions H1, H46, H48, H71, H93, and H94 in the VH region are occupied by E, D, I, S, S, and P, respectively. In some antibodies, at least one of the following positions is occupied by the amino acid as specified: H1 is occupied by E, H11 is occupied by L, H12 is occupied by V, H19 is occupied by R, H20 is occupied by L, H46 is occupied by D, H48 is occupied by I, H71 is occupied by S, H76 is occupied by N, H80 is occupied by L, H93 is occupied by S, and H94 is occupied by P. In some antibodies, positions H1, H11, H12, H19, H20, H46, H48, H71, H76, H80, H93, and H94 in the VH region are occupied by E, L, V, R, L, D, I, S, N, L, S, and P, respectively.

In some antibodies, at least one of the following positions is occupied by the amino acid as specified: H66 is occupied by R, H67 is occupied by V, and H78 is occupied by V. In some antibodies, positions H66, H67, and H78 in the VH region are occupied by R, V, and V, respectively.

In some antibodies, at least one of the following positions is occupied by the amino acid as specified: H1 is occupied by Q or E, H11 is occupied by V or L, H12 is occupied by K or V, H19 is occupied by K or R, H20 is occupied by V or L, H23 is occupied by K or A, H46 is occupied E or D, H48 is occupied by M or I, H66 is occupied by K or R, H67 is occupied by A or V, H71 is occupied by R or S, H76 is occupied by S or N, H78 is occupied by A or V, H80 is occupied by M or L, H93 is occupied by T, S, or A, and H94 is occupied by I, P, or R.

In some antibodies, positions H48, H71, H93, and H94 in the VH region are occupied by I, S, S, and P, respectively. In some antibodies, positions H1, H48, H71, H93, and H94 in the VH region are occupied by E, I, S, S, and P, respectively. In some antibodies, positions H1, H46, H48, H71, H93, and H94 in the VH region are occupied by E, D, I, S, S, and P, respectively. In some antibodies, positions H1, H11, H12, H19, H20, H46, H48, H71, H76, H80, H93, and H94 in the VH region are occupied by E, L, V, R, L, D, I, S, N, L, S, and P, respectively. In some antibodies, positions H1, H11, H12, H19, H20, H23, H46, H48, H71, H76, H80, H93, and H94 in the VH region are occupied by E, L, V, R, L, A, D, I, S, N, L, S, and P, respectively. In some antibodies, positions H66, H67, H78, H93, and H94 in the VH region are occupied by R, V, V, A, and R, respectively. In some antibodies, positions H1, H46, H48, H66, H67, H71, H78, H93, and H94 in the VH region are occupied by E, D, I, R, V, S, V, S, and P, respectively.

In some antibodies, at least one of the following positions is occupied by the amino acid as specified: L2 is occupied by V, L7 is occupied by S, L17 is occupied by E, L36 is occupied by L, L45 is occupied by Q, L46 is occupied by R, and L70 is occupied by D.

In some antibodies, at least one of the following positions is occupied by the amino acid as specified: L2 is occupied by V, L36 is occupied by L, and L46 is occupied by R. In some antibodies, positions L2, L36, and L46 in the VL region are occupied by V, L, and R, respectively. In some antibodies, at least one of the following positions is occupied by the amino acid as specified: L2 is occupied by V, L36 is occupied by L, L46 is occupied by R, and L70 is occupied by D. In some antibodies, positions L2, L36, L46, and L70 in the VL region are occupied by V, L, R, and D, respectively. In some antibodies, at least one of the following positions is occupied by the amino acid as specified: L45 is occupied by Q and L70 is occupied by D. In some antibodies, positions L45 and L70 in the VL region are occupied by Q and D, respectively.

In some antibodies, at least one of the following positions is occupied by the amino acid as specified: L2 is occupied by I or V, L7 is occupied by T or S, L17 is occupied by Q or E, L36 is occupied by Y or L, L45 is occupied by K or Q, L46 is occupied by L or R, and L70 is occupied by G or D.

In some antibodies, positions L2, L36, and L46 in the VL region are occupied by V, L, and R, respectively. In some antibodies, positions L2, L36, L46, and L70 in the VL region are occupied by V, L, R, and D, respectively. In some antibodies, positions L2, L7, L17, L36, L46, and L70 in the VL region are occupied by V, S, E, L, R, and D, respectively. In some antibodies, positions L45 and L70 in the VL region are occupied by Q and D, respectively. In some antibodies, positions L2, L36, L45, L46, and L70 in the VL region are occupied by V, L, Q, R, and D, respectively.

Some antibodies comprise a mature heavy chain variable region having an amino acid sequence at least 95% identical to any one of SEQ ID NO: 33-40 and a mature light chain variable region having an amino acid sequence at least 95% identical to any one of SEQ ID NO: 41-46. Some antibodies comprise a mature heavy chain variable region having an amino acid sequence at least 98% identical to any one of SEQ ID NO: 33-40 and a mature light chain variable region having an amino acid sequence at least 98% identical to any one of SEQ ID NO: 41-46.

In some antibodies, the mature heavy chain variable region has an amino acid sequence of any of SEQ ID NO: 33-40 and the mature light chain variable region has an amino acid sequence of any one of SEQ ID NO: 41-46.

In some antibodies, the mature heavy chain variable region has an amino acid sequence of SEQ ID NO:33 and the mature light chain variable region has an amino acid sequence of SEQ ID NO:41. In some antibodies, the mature heavy chain variable region has an amino acid sequence of SEQ ID NO:33 and the mature light chain variable region has an amino acid sequence of SEQ ID NO:42. In some antibodies, the mature heavy chain variable region has an amino acid sequence of SEQ ID NO:33 and the mature light chain variable region has an amino acid sequence of SEQ ID NO:43. In some antibodies, the mature heavy chain variable region has an amino acid sequence of SEQ ID NO:33 and the mature light chain variable region has an amino acid sequence of SEQ ID NO:44. In some antibodies, the mature heavy chain variable region has an amino acid sequence of SEQ ID NO:33 and the mature light chain variable region has an amino acid sequence of SEQ ID NO:45. In some antibodies, the mature heavy chain variable region has an amino acid sequence of SEQ ID NO:33 and the mature light chain variable region has an amino acid sequence of SEQ ID NO:46.

In some antibodies, the mature heavy chain variable region has an amino acid sequence of SEQ ID NO:34 and the mature light chain variable region has an amino acid sequence of SEQ ID NO:41. In some antibodies, the mature heavy chain variable region has an amino acid sequence of SEQ ID NO:34 and the mature light chain variable region has an amino acid sequence of SEQ ID NO:42. In some antibodies, the mature heavy chain variable region has an amino acid sequence of SEQ ID NO:34 and the mature light chain variable region has an amino acid sequence of SEQ ID NO:43. In some antibodies, the mature heavy chain variable region has an amino acid sequence of SEQ ID NO:34 and the mature light chain variable region has an amino acid sequence of SEQ ID NO:44. In some antibodies, the mature heavy chain variable region has an amino acid sequence of SEQ ID NO:34 and the mature light chain variable region has an amino acid sequence of SEQ ID NO:45. In some antibodies, the mature heavy chain variable region has an amino acid sequence of SEQ ID NO:34 and the mature light chain variable region has an amino acid sequence of SEQ ID NO:46.

In some antibodies, the mature heavy chain variable region has an amino acid sequence of SEQ ID NO:35 and the mature light chain variable region has an amino acid sequence of SEQ ID NO:41. In some antibodies, the mature heavy chain variable region has an amino acid sequence of SEQ ID NO:35 and the mature light chain variable region has an amino acid sequence of SEQ ID NO:42. In some antibodies, the mature heavy chain variable region has an amino acid sequence of SEQ ID NO:35 and the mature light chain variable region has an amino acid sequence of SEQ ID NO:43. In some antibodies, the mature heavy chain variable region has an amino acid sequence of SEQ ID NO:35 and the mature light chain variable region has an amino acid sequence of SEQ ID NO:44. In some antibodies, the mature heavy chain variable region has an amino acid sequence of SEQ ID NO:35 and the mature light chain variable region has an amino acid sequence of SEQ ID NO:45. In some antibodies, the mature heavy chain variable region has an amino acid sequence of SEQ ID NO:35 and the mature light chain variable region has an amino acid sequence of SEQ ID NO:46.

In some antibodies, the mature heavy chain variable region has an amino acid sequence of SEQ ID NO:36 and the mature light chain variable region has an amino acid sequence of SEQ ID NO:41. In some antibodies, the mature heavy chain variable region has an amino acid sequence of SEQ ID NO:36 and the mature light chain variable region has an amino acid sequence of SEQ ID NO:42. In some antibodies, the mature heavy chain variable region has an amino acid sequence of SEQ ID NO:36 and the mature light chain variable region has an amino acid sequence of SEQ ID NO:43. In some antibodies, the mature heavy chain variable region has an amino acid sequence of SEQ ID NO:36 and the mature light chain variable region has an amino acid sequence of SEQ ID NO:44. In some antibodies, the mature heavy chain variable region has an amino acid sequence of SEQ ID NO:36 and the mature light chain variable region has an amino acid sequence of SEQ ID NO:45. In some antibodies, the mature heavy chain variable region has an amino acid sequence of SEQ ID NO:36 and the mature light chain variable region has an amino acid sequence of SEQ ID NO:46.

In some antibodies, the mature heavy chain variable region has an amino acid sequence of SEQ ID NO:37 and the mature light chain variable region has an amino acid sequence of SEQ ID NO:41. In some antibodies, the mature heavy chain variable region has an amino acid sequence of SEQ ID NO:37 and the mature light chain variable region has an amino acid sequence of SEQ ID NO:42. In some antibodies, the mature heavy chain variable region has an amino acid sequence of SEQ ID NO:37 and the mature light chain variable region has an amino acid sequence of SEQ ID NO:43. In some antibodies, the mature heavy chain variable region has an amino acid sequence of SEQ ID NO:37 and the mature light chain variable region has an amino acid sequence of SEQ ID NO:44. In some antibodies, the mature heavy chain variable region has an amino acid sequence of SEQ ID NO:37 and the mature light chain variable region has an amino acid sequence of SEQ ID NO:45. In some antibodies, the mature heavy chain variable region has an amino acid sequence of SEQ ID NO:37 and the mature light chain variable region has an amino acid sequence of SEQ ID NO:46.

In some antibodies, the mature heavy chain variable region has an amino acid sequence of SEQ ID NO:38 and the mature light chain variable region has an amino acid sequence of SEQ ID NO:41. In some antibodies, the mature heavy chain variable region has an amino acid sequence of SEQ ID NO:38 and the mature light chain variable region has an amino acid sequence of SEQ ID NO:42. In some antibodies, the mature heavy chain variable region has an amino acid sequence of SEQ ID NO:38 and the mature light chain variable region has an amino acid sequence of SEQ ID NO:43. In some antibodies, the mature heavy chain variable region has an amino acid sequence of SEQ ID NO:38 and the mature light chain variable region has an amino acid sequence of SEQ ID NO:44. In some antibodies, the mature heavy chain variable region has an amino acid sequence of SEQ ID NO:38 and the mature light chain variable region has an amino acid sequence of SEQ ID NO:45. In some antibodies, the mature heavy chain variable region has an amino acid sequence of SEQ ID NO:38 and the mature light chain variable region has an amino acid sequence of SEQ ID NO:46.

In some antibodies, the mature heavy chain variable region has an amino acid sequence of SEQ ID NO:39 and the mature light chain variable region has an amino acid sequence of SEQ ID NO:41. In some antibodies, the mature heavy chain variable region has an amino acid sequence of SEQ ID NO:39 and the mature light chain variable region has an amino acid sequence of SEQ ID NO:42. In some antibodies, the mature heavy chain variable region has an amino acid sequence of SEQ ID NO:39 and the mature light chain variable region has an amino acid sequence of SEQ ID NO:43. In some antibodies, the mature heavy chain variable region has an amino acid sequence of SEQ ID NO:39 and the mature light chain variable region has an amino acid sequence of SEQ ID NO:44. In some antibodies, the mature heavy chain variable region has an amino acid sequence of SEQ ID NO:39 and the mature light chain variable region has an amino acid sequence of SEQ ID NO:45. In some antibodies, the mature heavy chain variable region has an amino acid sequence of SEQ ID NO:39 and the mature light chain variable region has an amino acid sequence of SEQ ID NO:46.

In some antibodies, the mature heavy chain variable region has an amino acid sequence of SEQ ID NO:40 and the mature light chain variable region has an amino acid sequence of SEQ ID NO:41. In some antibodies, the mature heavy chain variable region has an amino acid sequence of SEQ ID NO:40 and the mature light chain variable region has an amino acid sequence of SEQ ID NO:42. In some antibodies, the mature heavy chain variable region has an amino acid sequence of SEQ ID NO:40 and the mature light chain variable region has an amino acid sequence of SEQ ID NO:43. In some antibodies, the mature heavy chain variable region has an amino acid sequence of SEQ ID NO:40 and the mature light chain variable region has an amino acid sequence of SEQ ID NO:44. In some antibodies, the mature heavy chain variable region has an amino acid sequence of SEQ ID NO:40 and the mature light chain variable region has an amino acid sequence of SEQ ID NO:45. In some antibodies, the mature heavy chain variable region has an amino acid sequence of SEQ ID NO:40 and the mature light chain variable region has an amino acid sequence of SEQ ID NO:46.

Some antibodies comprise three light chain CDRs and three heavy chain CDRs of monoclonal antibody 6A10, wherein 6A10 is a mouse antibody characterized by a heavy chain variable region having an amino acid sequence comprising SEQ ID NO: 63 and a light chain variable region having an amino acid sequence comprising SEQ ID NO:64. In some antibodies, the three heavy chain CDRs are as defined by Kabat/Chothia Composite (SEQ ID NOs: 65, 66, and 67) and the three light chain CDRs are as defined by Kabat/Chothia Composite (SEQ ID NOs: 68, 69, and 70).

For example, the antibody can be 6A10 or a chimeric, veneered, or humanized form thereof. In some such antibodies, the variable heavy chain has ≥85% identity to human sequence. In some such antibodies, the variable light chain has ≥85% identity to human sequence. In some such antibodies, each of the variable heavy chain and variable light chain has ≥85% identity to human germline sequence.

Some antibodies are humanized antibodies. Some antibodies are a humanized or chimeric 6A10 antibody that specifically binds to human tau, wherein 6A10 is a mouse antibody characterized by a mature heavy chain variable region of SEQ ID NO:63 and a mature light chain variable region of SEQ ID NO:64. Some antibodies comprises a humanized mature heavy chain variable region comprising the three heavy chain CDRs of 6A10 and a humanized mature light chain variable region comprising the three light chain CDRs of 6A10.

In some antibodies, the CDRs are of a definition selected from the group of Kabat, Chothia, Kabat/Chothia Composite, AbM and Contact. In some antibodies, the humanized mature heavy chain variable region comprises the three Kabat/Chothia Composite heavy chain CDRs of 6A10 (SEQ ID NOs: 65-67) and the humanized mature light chain variable region comprises the three Kabat/Chothia Composite light chain CDRs of 6A10 (SEQ ID NOs: 68-70). In some antibodies, the humanized mature heavy chain variable region comprises the three Kabat heavy chain CDRs of 6A10 (SEQ ID NO:71, SEQ ID NO:66, and SEQ ID NO:67) and the humanized mature light chain variable region comprises the three Kabat light chain CDRs of 6A10 (SEQ ID NOs: 68-70). In some antibodies, the humanized mature heavy chain variable region comprises the three Chothia heavy chain CDRs of 6A10 (SEQ ID NO:72, SEQ ID NO:74, and SEQ ID NO:67) and the humanized mature light chain variable region comprises the three Chothia light chain CDRs of 6A10 (SEQ ID NOs: 68-70). In some antibodies, the humanized mature heavy chain variable region comprises the three AbM heavy chain CDRs of 6A10 (SEQ ID NO:65, SEQ ID NO:75, and SEQ ID NO:67)) and the humanized mature light chain variable region comprises the three AbM light chain CDRs of 6A10 (SEQ ID NOs: 68-70). In some antibodies, the humanized mature heavy chain variable region comprises the three Contact heavy chain CDRs of 6A10 (SEQ ID NO:73, SEQ ID NO:76, and SEQ ID NO: 77)) and the humanized mature light chain variable region comprises the three Contact light chain CDRs of 6A10 (SEQ ID NO:78-80).

Some antibodies comprise a humanized mature heavy chain variable region having an amino acid sequence at least 90% identical to any one of SEQ ID NO:85-87 and a humanized mature light chain variable region having an amino acid sequence at least 90% identical to any one of SEQ ID NO: 88-90.

In some antibodies, position H48 in the VH region is occupied by I.

In some antibodies, at least one of the following positions in the VH region is occupied by the amino acid as specified: H16 is occupied by A or G, H48 is occupied by M or I, H69 is occupied by T or I, and H80 is occupied by M or L.

In some antibodies, position H48 in the VH region is occupied by I. In some antibodies, positions H16, H48, H69, and H80 in the VH region are occupied by G, I, I, and L, respectively.

In some antibodies, L46 in the VL region is occupied by L.

In some antibodies, at least one of the following positions in the VL region is occupied by the amino acid as specified: L12 is occupied by P or S, L17 is occupied by Q or E, and L46 is occupied by R or L.

In some antibodies, position L46 in the VL region is occupied by L. In some antibodies, positions L12, L17, and L46 in the VL region are occupied by S, E, and L, respectively.

Some antibodies comprise a mature heavy chain variable region having an amino acid sequence at least 95% identical to any one of SEQ ID NO: 85-87 and a mature light chain variable region having an amino acid sequence at least 95% identical to any one of SEQ ID NO: 88-90. Some antibodies comprise a mature heavy chain variable region having an amino acid sequence at least 98% identical to any one of SEQ ID NO: 85-87 and a mature light chain variable region having an amino acid sequence at least 98% identical to any one of SEQ ID NO: 88-90.

In some antibodies, the mature heavy chain variable region has an amino acid sequence of any of SEQ ID NO: 85-87 and the mature light chain variable region has an amino acid sequence of any one of SEQ ID NO: 88-90.

In some antibodies, the mature heavy chain variable region has an amino acid sequence of SEQ ID NO:85 and the mature light chain variable region has an amino acid sequence of SEQ ID NO:88. In some antibodies, the mature heavy chain variable region has an amino acid sequence of SEQ ID NO:85 and the mature light chain variable region has an amino acid sequence of SEQ ID NO:89. In some antibodies, the mature heavy chain variable region has an amino acid sequence of SEQ ID NO:85 and the mature light chain variable region has an amino acid sequence of SEQ ID NO:90.

In some antibodies, the mature heavy chain variable region has an amino acid sequence of SEQ ID NO:86 and the mature light chain variable region has an amino acid sequence of SEQ ID NO:88. In some antibodies, the mature heavy chain variable region has an amino acid sequence of SEQ ID NO:86 and the mature light chain variable region has an amino acid sequence of SEQ ID NO:89. In some antibodies, the mature heavy chain variable region has an amino acid sequence of SEQ ID NO:86 and the mature light chain variable region has an amino acid sequence of SEQ ID NO:90.

In some antibodies, the mature heavy chain variable region has an amino acid sequence of SEQ ID NO:87 and the mature light chain variable region has an amino acid sequence of SEQ ID NO:88. In some antibodies, the mature heavy chain variable region has an amino acid sequence of SEQ ID NO:87 and the mature light chain variable region has an amino acid sequence of SEQ ID NO:89. In some antibodies, the mature heavy chain variable region has an amino acid sequence of SEQ ID NO:87 and the mature light chain variable region has an amino acid sequence of SEQ ID NO:90.

Some antibodies comprise three light chain CDRs and three heavy chain CDRs of monoclonal antibody 8A4, wherein 8A4 is a mouse antibody characterized by a heavy chain variable region having an amino acid sequence comprising SEQ ID NO: 91 and a light chain variable region having an amino acid sequence comprising SEQ ID NO:92. In some antibodies, the three heavy chain CDRs are as defined by Kabat/Chothia Composite (SEQ ID NOs: 93, 94, and 95) and the three light chain CDRs are as defined by Kabat/Chothia Composite (SEQ ID NOs: 96, 97, and 98).

For example, the antibody can be 8A4 or a chimeric, veneered, or humanized form thereof. In some such antibodies, the variable heavy chain has ≥85% identity to human sequence. In some such antibodies, the variable light chain has ≥85% identity to human sequence. In some such antibodies, each of the variable heavy chain and variable light chain has ≥85% identity to human germline sequence.

Some antibodies are humanized antibodies. Some antibodies are a humanized or chimeric 8A4 antibody that specifically binds to human tau, wherein 8A4 is a mouse antibody characterized by a mature heavy chain variable region of SEQ ID NO:91 and a mature light chain variable region of SEQ ID NO:92. Some antibodies comprise a humanized mature heavy chain variable region comprising the three heavy chain CDRs of 8A4 and a humanized mature light chain variable region comprising the three light chain CDRs of 8A4.

In some antibodies, the CDRs are of a definition selected from the group of Kabat, Chothia, Kabat/Chothia Composite, AbM and Contact. In some antibodies, the humanized mature heavy chain variable region comprises the three Kabat/Chothia Composite heavy chain CDRs of 8A4 (SEQ ID NOs: 93-95) and the humanized mature light chain variable region comprises the three Kabat/Chothia Composite light chain CDRs of 8A4 (SEQ ID NOs: 96-98). In some antibodies, the humanized mature heavy chain variable region comprises the three Kabat heavy chain CDRs of 8A4 (SEQ ID NO:99, SEQ ID NO:94, and SEQ ID NO:95) and the humanized mature light chain variable region comprises the three Kabat light chain CDRs of 8A4 (SEQ ID NOs: 96-98). In some antibodies, the humanized mature heavy chain variable region comprises the three Chothia heavy chain CDRs of 8A4 (SEQ ID NO:100, SEQ ID NO:102, and SEQ ID NO:95) and the humanized mature light chain variable region comprises the three Chothia light chain CDRs of 8A4 (SEQ ID NOs: 96-98). In some antibodies, the humanized mature heavy chain variable region comprises the three AbM heavy chain CDRs of 8A4 (SEQ ID NO:93, SEQ ID NO:103, and SEQ ID NO:95)) and the humanized mature light chain variable region comprises the three AbM light chain CDRs of 8A4 (SEQ ID NOs: 96-98). In some antibodies, the humanized mature heavy chain variable region comprises the three Contact heavy chain CDRs of 8A4 (SEQ ID NO:101, SEQ ID NO:104, and SEQ ID NO: 105)) and the humanized mature light chain variable region comprises the three Contact light chain CDRs of 8A4 (SEQ ID NO:106-108).

Some antibodies comprise a humanized mature heavy chain variable region having an amino acid sequence at least 90% identical to any one of SEQ ID NO:113-115 and a humanized mature light chain variable region having an amino acid sequence at least 90% identical to any one of SEQ ID NO: 116-118.

In some antibodies, position H93 of the VH region is occupied by S.

In some antibodies, at least one of the following positions in the VH region is occupied by the amino acid as specified: H12 is occupied by V, H16 is occupied by G, H20 is occupied by L, and H68 is occupied by T. In some antibodies, positions H12, H16, H20, and H68 in the VH region are occupied by V, G, L, and T, respectively.

In some antibodies, at least one of the following positions in the VH region is occupied by the amino acid as specified: H12 is occupied by K or V, H16 is occupied by S or G, H20 is occupied by V or L, H48 is occupied by M or I, H67 is occupied by A or I, H68 is occupied by N or T, H85 is occupied by D or E, and H93 is occupied by S or A.

In some antibodies, position H93 in the VH region is occupied by S. In some antibodies, positions H12, H16, H20, H68, and H93 in the VH region are occupied by V, G, L, T, and S, respectively. In some antibodies, positions H12, H16, H20, H48, H67, H68, and H85 in the VH region are occupied by V, G, L, I, A, T, and E, respectively.

In some antibodies, position L17 in the VL region is occupied by E.

In some antibodies, at least one of the following positions in the VL region is occupied by the amino acid as specified: L2 is occupied by I or V, L17 is occupied by Q or E, and L36 is occupied by F or L.

In some antibodies, position L17 in the VL region is occupied by E. In some antibodies, positions L2, L17, and L36 in the VL region are occupied by V, E. and L.

Some antibodies comprise a mature heavy chain variable region having an amino acid sequence at least 95% identical to any one of SEQ ID NO: 113-115 and a mature light chain variable region having an amino acid sequence at least 95% identical to any one of SEQ ID NO: 116-118.

Some antibodies comprise a mature heavy chain variable region having an amino acid sequence at least 98% identical to any one of SEQ ID NO: 113-115 and a mature light chain variable region having an amino acid sequence at least 98% identical to any one of SEQ ID NO: 116-118.

In some antibodies, the mature heavy chain variable region has an amino acid sequence of any of SEQ ID NO: 113-115 and the mature light chain variable region has an amino acid sequence of any one of SEQ ID NO: 116-118.

In some antibodies, the mature heavy chain variable region has an amino acid sequence of SEQ ID NO:113 and the mature light chain variable region has an amino acid sequence of SEQ ID NO:116. In some antibodies, the mature heavy chain variable region has an amino acid sequence of SEQ ID NO:113 and the mature light chain variable region has an amino acid sequence of SEQ ID NO:117. In some antibodies, the mature heavy chain variable region has an amino acid sequence of SEQ ID NO:113 and the mature light chain variable region has an amino acid sequence of SEQ ID NO:118.

In some antibodies, the mature heavy chain variable region has an amino acid sequence of SEQ ID NO:114 and the mature light chain variable region has an amino acid sequence of SEQ ID NO:116. In some antibodies, the mature heavy chain variable region has an amino acid sequence of SEQ ID NO:114 and the mature light chain variable region has an amino acid sequence of SEQ ID NO:117. In some antibodies, the mature heavy chain variable region has an amino acid sequence of SEQ ID NO:114 and the mature light chain variable region has an amino acid sequence of SEQ ID NO:118.

In some antibodies, the mature heavy chain variable region has an amino acid sequence of SEQ ID NO:115 and the mature light chain variable region has an amino acid sequence of SEQ ID NO:116. In some antibodies, the mature heavy chain variable region has an amino acid sequence of SEQ ID NO:115 and the mature light chain variable region has an amino acid sequence of SEQ ID NO:117. In some antibodies, the mature heavy chain variable region has an amino acid sequence of SEQ ID NO:115 and the mature light chain variable region has an amino acid sequence of SEQ ID NO:118.

Some antibodies comprise three light chain CDRs and three heavy chain CDRs of monoclonal antibody 7G6, wherein 7G6 is a mouse antibody characterized by a heavy chain variable region having an amino acid sequence comprising SEQ ID NO: 119 and a light chain variable region having an amino acid sequence comprising SEQ ID NO:120. In some antibodies, the three heavy chain CDRs are as defined by Kabat/Chothia Composite (SEQ ID NOs: 121, 122, and 123) and the three light chain CDRs are as defined by Kabat/Chothia Composite (SEQ ID NOs: 124, 125, and 126).

For example, the antibody can be 7G6 or a chimeric, veneered, or humanized form thereof. In some such antibodies, the variable heavy chain has ≥85% identity to human sequence. In some such antibodies, the variable light chain has ≥85% identity to human sequence. In some such antibodies, each of the variable heavy chain and variable light chain has ≥85% identity to human germline sequence.

Some antibodies are humanized antibodies. Some antibodies are a humanized or chimeric 7G6 antibody that specifically binds to human tau, wherein 7G6 is a mouse antibody characterized by a mature heavy chain variable region of SEQ ID NO:119 and a mature light chain variable region of SEQ ID NO:120. Some antibodies comprise a humanized mature heavy chain variable region comprising the three heavy chain CDRs of 7G6 and a humanized mature light chain variable region comprising the three light chain CDRs of 7G6.

In some antibodies, the CDRs are of a definition selected from the group of Kabat, Chothia, Kabat/Chothia Composite, AbM and Contact. In some antibodies, the humanized mature heavy chain variable region comprises the three Kabat/Chothia Composite heavy chain CDRs of 7G6 (SEQ ID NOs: 121-123) and the humanized mature light chain variable region comprises the three Kabat/Chothia Composite light chain CDRs of 7G6 (SEQ ID NOs: 124-126). In some antibodies, the humanized mature heavy chain variable region comprises the three Kabat heavy chain CDRs of 7G6 (SEQ ID NO:127, SEQ ID NO:122, and SEQ ID NO:123) and the humanized mature light chain variable region comprises the three Kabat light chain CDRs of 7G6 (SEQ ID NOs: 124-126). In some antibodies, the humanized mature heavy chain variable region comprises the three Chothia heavy chain CDRs of 7G6 (SEQ ID NO:128, SEQ ID NO:130, and SEQ ID NO:123) and the humanized mature light chain variable region comprises the three Chothia light chain CDRs of 7G6 (SEQ ID NOs: 124-126). In some antibodies, the humanized mature heavy chain variable region comprises the three AbM heavy chain CDRs of 7G6 (SEQ ID NO:121, SEQ ID NO:131, and SEQ ID NO:123) and the humanized mature light chain variable region comprises the three AbM light chain CDRs of 7G6 (SEQ ID NOs: 124-126). In some antibodies, the humanized mature heavy chain variable region comprises the three Contact heavy chain CDRs of 7G6 (SEQ ID NO:129, SEQ ID NO:132, and SEQ ID NO: 133)) and the humanized mature light chain variable region comprises the three Contact light chain CDRs of 7G6 (SEQ ID NO:134, SEQ ID NO:135, and SEQ ID NO:136).

Some antibodies comprise a humanized mature heavy chain variable region having an amino acid sequence at least 90% identical to any one of SEQ ID NO:139-140 and a humanized mature light chain variable region having an amino acid sequence at least 90% identical to any one of SEQ ID NO: 141-148.

In some antibodies, at least one of the following positions in the VH region is occupied by the amino acid as specified: H12 is occupied by V, H20 is occupied by L, H69 is occupied by I, H76 is occupied by N, H78 is occupied by A, H80 is occupied by L, H81 is occupied by Q, H92 is occupied by S, and H93 is occupied by T. In some antibodies, positions H12, H20, H69, H76, H78, H80, H81, H92, H93, H101 in the VH region are occupied by V, L, I, N, A, L, Q, S, and T, respectively.

In some antibodies, at least one of the following positions in the VH region is occupied by the amino acid as specified: H12 is occupied by K or V, H20 is occupied by V or L, H38 is occupied by R or K, H69 is occupied by M or I, H76 is occupied by S or N, H78 is occupied by V or A, H80 is occupied by M or L, H81 is occupied by E or Q, H92 is occupied by C or S, and H93 is occupied by A or T.

In some antibodies, positions H12, H20, H69, H76, H78, H80, H81, H92, H93 in the VH region are occupied by V, L, I, N, A, L, Q, S, and T, respectively. In some antibodies, positions H12, H20, H38, H69, H76, H78, H80, H81, H92, H93 in the VH region are occupied by V, L, K, I, N, A, L, Q, S, and T, respectively.

In some antibodies, at least one of the following positions in the VL region is occupied by the amino acid as specified: L12 is occupied by S and L103 is occupied by K. In some antibodies, positions L12 and L103 in the VL region are occupied by S and K, respectively.

In some antibodies, at least one of the following positions in the VL region is occupied by the amino acid as specified: L12 is occupied by S, L36 is occupied by L, and L103 is occupied by K. In some antibodies, positions L12, L36, and L103 in the VL region are occupied by S, L, and K, respectively.

In some antibodies, at least one of the following positions in the VL region is occupied by the amino acid as specified: L12 is occupied by S, L37 is occupied by L, and L103 is occupied by K. In some antibodies, positions L12, L37, and L103 in the VL region are occupied by S, L, and K, respectively.

In some antibodies, at least one of the following positions in the VL region is occupied by the amino acid as specified: L12 is occupied by S, L36 is occupied by L, L37 is occupied by L, and L103 is occupied by K. In some antibodies, positions L12, L36, L37, and L103 in the VL region are occupied by S, L, L, and K, respectively.

In some antibodies, at least one of the following positions in the VL region is occupied by the amino acid as specified: L12 is occupied by S, L45 is occupied by K, and L103 is occupied by K. In some antibodies, positions L12, L45, and L103 in the VL region are occupied by S, K, and K, respectively.

In some antibodies, at least one of the following positions in the VL region is occupied by the amino acid as specified: L12 is occupied by S, L100 is occupied by G, and L103 is occupied by K. In some antibodies, positions L12, L100, and L103 in the VL region are occupied by S, G, and K, respectively.

In some antibodies, at least one of the following positions in the VL region is occupied by the amino acid as specified:

L36 is occupied by F or L, L37 is occupied by Q or L, L45 is occupied by R or K, L100 is occupied by Q or G.

In some antibodies, positions L12 and L103 in the VL region are occupied by S and K, respectively. In some antibodies, positions L12, L37, and L103 in the VL region are occupied by S, L, and K, respectively. In some antibodies, positions L12, L36, and L103 in the VL region are occupied by S, L, and K, respectively. In some antibodies, positions L12, L36, L37, and L103 in the VL region are occupied by S, L, L, and K, respectively. In some antibodies, positions L12, L45, and L103 in the VL region are occupied by S, K, and K, respectively. In some antibodies, positions L12, L36, L37, L45, and L103 in the VL region are occupied by S, L, L, K, and K, respectively. In some antibodies, positions L12, L100, and L103 in the VL region are occupied by S, G, and K, respectively, as in hu7G6-VL_v7. In some antibodies, positions L12, L36, L37, L100, and L103 in the VL region are occupied by S, L, L, G, and K, respectively.

Some antibodies comprise a mature heavy chain variable region having an amino acid sequence at least 95% identical to any one of SEQ ID NO: 139-140 and a mature light chain variable region having an amino acid sequence at least 95% identical to any one of SEQ ID NO: 141-148. Some antibodies comprise a mature heavy chain variable region having an amino acid sequence at least 98% identical to any one of SEQ ID NO: 139-140 and a mature light chain variable region having an amino acid sequence at least 98% identical to any one of SEQ ID NO: 141-148.

In some antibodies, the mature heavy chain variable region has an amino acid sequence of any of SEQ ID NO: 139-140 and the mature light chain variable region has an amino acid sequence of any one of SEQ ID NO: 141-148.

In some antibodies, the mature heavy chain variable region has an amino acid sequence of SEQ ID NO:139 and the mature light chain variable region has an amino acid sequence of SEQ ID NO:141. In some antibodies, the mature heavy chain variable region has an amino acid sequence of SEQ ID NO: 139 and the mature light chain variable region has an amino acid sequence of SEQ ID NO: 142. In some antibodies, the mature heavy chain variable region has an amino acid sequence of SEQ ID NO:139 and the mature light chain variable region has an amino acid sequence of SEQ ID NO:143. In some antibodies, the mature heavy chain variable region has an amino acid sequence of SEQ ID NO:139 and the mature light chain variable region has an amino acid sequence of SEQ ID NO:144. In some antibodies, the mature heavy chain variable region has an amino acid sequence of SEQ ID NO:139 and the mature light chain variable region has an amino acid sequence of SEQ ID NO:145. In some antibodies, the mature heavy chain variable region has an amino acid sequence of SEQ ID NO:139 and the mature light chain variable region has an amino acid sequence of SEQ ID NO: 146. In some antibodies, the mature heavy chain variable region has an amino acid sequence of SEQ ID NO:139 and the mature light chain variable region has an amino acid sequence of SEQ ID NO:147. In some antibodies, the mature heavy chain variable region has an amino acid sequence of SEQ ID NO:139 and the mature light chain variable region has an amino acid sequence of SEQ ID NO:148.

In some antibodies, the mature heavy chain variable region has an amino acid sequence of SEQ ID NO:140 and the mature light chain variable region has an amino acid sequence of SEQ ID NO:141. In some antibodies, the mature heavy chain variable region has an amino acid sequence of SEQ ID NO: 140 and the mature light chain variable region has an amino acid sequence of SEQ ID NO:142. In some antibodies, the mature heavy chain variable region has an amino acid sequence of SEQ ID NO:140 and the mature light chain variable region has an amino acid sequence of SEQ ID NO:143. In some antibodies, the mature heavy chain variable region has an amino acid sequence of SEQ ID NO: 140 and the mature light chain variable region has an amino acid sequence of SEQ ID NO:144. In some antibodies, the mature heavy chain variable region has an amino acid sequence of SEQ ID NO:140 and the mature light chain variable region has an amino acid sequence of SEQ ID NO:145. In some antibodies, the mature heavy chain variable region has an amino acid sequence of SEQ ID NO:140 and the mature light chain variable region has an amino acid sequence of SEQ ID NO:146. In some antibodies, the mature heavy chain variable region has an amino acid sequence of SEQ ID NO:140 and the mature light chain variable region has an amino acid sequence of SEQ ID NO: 147. In some antibodies, the mature heavy chain variable region has an amino acid sequence of SEQ ID NO:140 and the mature light chain variable region has an amino acid sequence of SEQ ID NO: 148.

For example, the antibody can be a chimeric antibody. For example, the antibody can be a veneered antibody. The antibody can be an intact antibody. The antibody can be a binding fragment. In an embodiment, the binding fragment is a single-chain antibody, Fab, or Fab'2 fragment. The antibody can be a Fab fragment, or single chain Fv. Some of the antibodies have a human IgG1 isotype, while others may have a human IgG2 or IgG4 isotype.

Some antibodies have the mature light chain variable region fused to a light chain constant region and the mature heavy chain variable region fused to a heavy chain constant region. The heavy chain constant region of some antibodies is a mutant form of a natural human heavy chain constant region which has reduced binding to a Fcγ receptor relative to the natural human heavy chain constant region. In some antibodies, the heavy chain constant region is of IgG1 isotype.

Some antibodies may have at least one mutation in the constant region, such as a mutation that reduces complement fixation or activation by the constant region, for example a mutation at one or more of positions 241, 264, 265, 270, 296, 297, 318, 320, 322, 329 and 331 by EU numbering. Some antibodies have an alanine at positions 318, 320 and 322.

Some antibodies can be at least 95% w/w pure. The antibody can be conjugated to a therapeutic, cytotoxic, cytostatic, neurotrophic, or neuroprotective agent.

In another aspect, the invention provides a pharmaceutical composition comprising any of the antibodies disclosed herein and a pharmaceutically-acceptable carrier.

In another aspect, the invention provides a nucleic acid encoding the heavy chain and/or light chain of any of the antibodies disclosed herein, a recombinant expression vector comprising the nucleic acid and a host cell transformed with the recombinant expression vector.

In yet another aspect, the invention provides methods of humanizing any non-human antibody described herein, for example, mouse antibody 5G8, wherein 5G8 is characterized by a mature heavy chain variable region of SEQ ID NO: 7 and a mature light chain variable region of SEQ ID NO:8. In yet another aspect, the invention provides methods of humanizing any non-human antibody described herein, for example, mouse antibody 6A10, wherein 6A10 is characterized by a mature heavy chain variable region of SEQ ID NO: 63 and a mature light chain variable region of SEQ ID NO:64. In yet another aspect, the invention provides methods of humanizing any non-human antibody described herein, for example, mouse antibody 8A4, wherein 8A4 is characterized by a mature heavy chain variable region of SEQ ID NO: 91 and a mature light chain variable region of SEQ ID NO:92. In yet another aspect, the invention provides methods of humanizing any non-human antibody described herein, for example, mouse antibody 7G6, wherein 7G6 is characterized by a mature heavy chain variable region of SEQ ID NO: 119 and a mature light chain variable region of SEQ ID NO:120. Such methods can involve selecting one or more acceptor antibodies, identifying the amino acid residues of the mouse antibody to be retained; synthesizing a nucleic acid encoding a humanized heavy chain comprising CDRs of the mouse heavy chain and a nucleic acid encoding a humanized light chain comprising CDRs of the mouse antibody light chain, and expressing the nucleic acids in a host cell to produce a humanized antibody.

Methods of producing antibodies, such as a humanized, chimeric or veneered antibody, for example humanized, chimeric or veneered forms of 5G8, 6A10, 8A4, or 7G6, are also provided. In such methods, cells transformed with nucleic acids encoding the heavy and light chains of the antibody are cultured so that the cells secrete the antibody. The antibody can then be purified from the cell culture media.

Cell lines producing any of the antibodies disclosed herein can be produced by introducing a vector encoding heavy and light chains of the antibody and a selectable marker into cells, propagating the cells under conditions to select for cells having increased copy number of the vector, isolating single cells from the selected cells; and banking cells cloned from a single cell selected based on yield of antibody.

Some cells can be propagated under selective conditions and screened for cell lines naturally expressing and secreting at least 100 mg/L/$10^6$ cells/24 hours. Single cells can be isolated from the selected cells. Cells cloned from a single cell can then be banked. Single cells can be selected based on desirable properties, such as the yield of the antibody. Exemplary cell lines are cell lines expressing 5G8.

The invention also provides methods of inhibiting or reducing aggregation of tau in a subject having or at risk of developing a tau-mediated amyloidosis, comprising administering to the subject an effective regime of an antibody disclosed herein, thereby inhibiting or reducing aggregation of tau in the subject. Exemplary antibodies include humanized versions of 5G8, 6A10, 8A4, or 7G6.

Also provided are methods of treating or effecting prophylaxis of a tau-related disease in a subject, comprising administering an effective regime of an antibody disclosed herein and thereby treating or effecting prophylaxis of the disease. Examples of such a disease are Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP). In some methods, the tau-related disease is Alzheimer's disease. In some methods, the patient is an ApoE4 carrier.

Also provided are methods of reducing aberrant transmission of tau comprising administering an effective regime of an antibody disclosed herein and thereby reducing transmission of tau.

Also provided are methods of inducing phagocytosis of tau comprising administering an effective regime of an antibody disclosed herein and thereby inducing phagocytosis of tau.

Also provided are methods of inhibiting tau aggregation or deposition comprising administering an effective regime of an antibody disclosed herein thereby inhibiting tau aggregation or deposition.

Also provided are methods of inhibiting formation of tau tangles comprising administering an effective regime of an antibody disclosed herein.

The invention also provides a method of detecting tau protein deposits in a subject having or at risk of a disease associated with tau aggregation or deposition, comprising administering to a subject an antibody disclosed herein, and detecting the antibody bound to tau in the subject. Examples of such a disease are Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP).

In some embodiments the antibody is administered by intravenous injection into the body of the subject. In some embodiments the antibody is administered directly to the brain of the subject by intracranial injection or by drilling a hole through the skull of the subject. In some embodiments the antibody is labeled. In some embodiments the antibody is labeled with a fluorescent label, a paramagnetic label, or a radioactive label. In some embodiments the radioactive label is detected using positron emission tomography (PET) or single-photon emission computed tomography (SPECT).

The invention also provides a method of measuring efficacy of treatment in a subject being treated for a disease associated with tau aggregation or deposition, comprising measuring a first level of tau protein deposits in the subject prior to treatment by administering to a subject an antibody disclosed herein, and detecting a first amount of the antibody bound to tau in the subject, administering the treatment to the subject, measuring a second level of tau protein deposits in the in subject after treatment by administering to a subject the antibody, and detecting the antibody bound to tau in the subject, wherein a decrease in the level of tau protein deposits indicates a positive response to treatment.

The invention also provides a method of measuring efficacy of treatment in a subject being treated for a disease associated with tau aggregation or deposition, comprising measuring a first level of tau protein deposits in the subject prior to treatment by administering to a subject an antibody disclosed herein, and detecting a first amount of antibody bound to tau in the subject, administering the treatment to the subject, measuring a second level of tau protein deposits in the in subject after treatment by administering to a subject the antibody, and detecting a second amount of antibody bound to tau in the subject, wherein no change in the level of tau protein deposits or a small increase in tau protein deposits indicates a positive response to treatment.

In one aspect, the invention provides an isolated monoclonal antibody that specifically binds to a peptide consisting of residues 199-213 of SEQ ID NO:3.

In one aspect, the invention provides an isolated monoclonal antibody that specifically binds to a peptide consisting of residues 262-276 of SEQ ID NO:3.

Some antibodies specifically bind to both the peptide consisting of residues 199-213 of SEQ ID NO:3 and a peptide consisting of residues 262-276 of SEQ ID NO:3.

In one aspect, the invention provides an isolated monoclonal antibody that specifically binds to the polypeptide of SEQ ID NO:3 at an epitope including at least one residue within 199-213 of SEQ ID NO:3.

Some antibodies bind to an epitope within residues 199-213 of SEQ ID NO:3.

In one aspect, the invention provides an isolated monoclonal antibody that specifically binds to the polypeptide of SEQ ID NO:3 at an epitope including at least one residue within 262-276 of SEQ ID NO:3.

Some antibodies bind to an epitope within residues 262-276 of SEQ ID NO:3.

Some antibodies specifically bind to an epitope including at least one residue from both 199-213 and 262-276 of SEQ ID NO:3.

The invention also provides a method of treating or effecting prophylaxis of a tau-related disease in a subject comprising administering an immunogen comprising a tau peptide of up to 20 contiguous amino acids of SEQ ID NO:3 to which antibody 5G8 specifically binds, wherein the peptide induces formation of antibodies specifically binding to tau in the subject. The invention also provides a method of treating or effecting prophylaxis of a tau-related disease in a subject comprising administering an immunogen comprising a tau peptide of up to 20 contiguous amino acids of SEQ ID NO:3 to which antibody 6A10 specifically binds, wherein the peptide induces formation of antibodies specifically binding to tau in the subject. The invention also provides a method of treating or effecting prophylaxis of a tau-related disease in a subject comprising administering an immunogen comprising a tau peptide of up to 20 contiguous amino acids of SEQ ID NO:3 to which antibody 8A4 specifically binds, wherein the peptide induces formation of antibodies specifically binding to tau in the subject. The invention also provides a method of treating or effecting prophylaxis of a tau-related disease in a subject comprising administering an immunogen comprising a tau peptide of up to 20 contiguous amino acids of SEQ ID NO:3 to which antibody 7G6 specifically binds, wherein the peptide induces formation of antibodies specifically binding to tau in the subject. The invention also provides a method of treating or effecting prophylaxis of a tau-related disease in a subject comprising administering an immunogen comprising a tau peptide of up to 20 contiguous amino acids of SEQ ID NO:3 to which antibody 3D6 specifically binds, wherein the peptide induces formation of antibodies specifically binding to tau in the subject.

In some such methods, at least two of antibodies 5G8, 6A10, 8A4, 7G6, and 3D6 specifically bind to the tau peptide.

In some such methods, the tau peptide epitope consists of 4-11 contiguous amino acids from residues 199-213 of SEQ ID NO:3 or from residues 262-276 of SEQ ID NO:3. In some such methods, the tau peptide epitope consists of two contiguous segments of amino acids, one segment from residues 199-213 of SEQ ID NO:3, the other from residues 262-276 of SEQ ID NO:3, wherein the two contiguous segments together consist of 4-11 amino acids.

BRIEF DESCRIPTION OF THE DRAWINGS

FIGS. 1A, 1, and 1C depict results of ELISA screening assays for selected mouse monoclonal anti-tau antibodies.

FIGS. 5A and 5B depict an alignment of heavy chain variable regions of the mouse 5G8 antibody, human acceptor aDabi-Fab2b-VH, and humanized versions of the 5G8 antibody (hu5G8_VH-v1, hu5G8_VH-v2, hu5G8_VH-v3, hu5G8_VH-v4, hu5G8_VH-v5, hu5G8_VH-v6, hu5G8_VH-v7, hu5G8_VH-v8).

FIGS. 6A and 6B depict an alignment of light chain variable regions of the mouse 5G8 antibody, human acceptor aDabi-Fab2b-VL, and humanized versions of the 5G8 antibody (hu5G8-VL-v1, hu5G8-VL-v2, hu5G8-VL-v3, hu5G8-VL-v4, hu5G8-VL-v5, and hu5G8-VL-v6).

FIG. 7 depicts an alignment of heavy chain variable regions of the mouse 6A10 antibody, human acceptor ACR16112 VH, and humanized versions of the 6A10 antibody (hu6A10_VH-v1, hu6A10_VH-v2, and hu6A10_VH-v 3).

FIG. 8 depicts an alignment of light chain variable regions of the mouse 6A10 antibody, human acceptor ABC66863 VL, and humanized versions of the 6A10 antibody (hu6A10VL-v1, hu6A10-VL-v2, and hu6A10-VL-v3).

FIG. 9 depicts an alignment of heavy chain variable regions of the mouse 8A4 antibody, human acceptor ADU57742 VH, and humanized versions of the 8A4 antibody (hu8A4_VH-v1, hu8A4_VH-v2, and hu8A4_VH-v 3).

FIG. 10 depicts an alignment of light chain variable regions of the mouse 8A4 antibody, human acceptor ABA26100 VL, and humanized versions of the 8A4 antibody (hu8A4-VL-v1, hu8A4-VL-v2, and hu8A4-VL-v3).

FIG. 11 depicts an alignment of heavy chain variable regions of the mouse 7G6 antibody, human acceptor 3U0T_VH, and humanized versions of the 7G6 antibody (hu7G6_VH-v1 and hu7G6_VH-v2).

FIGS. 12A and 12B depict an alignment of light chain variable regions of the mouse 7G6 antibody, human acceptor 3U0T_VL, and humanized versions of the 7G6 antibody (hu7G6-VL-v1, hu7G6-VL-v2, hu7G6-VL-v3, hu7G6-VL-v4, hu7G6-VL-v5, hu7G6-VL-v6, hu7G6-VL-7, and hu7G6-VL-8).

BRIEF DESCRIPTION OF THE SEQUENCES

Figures 2, 3:
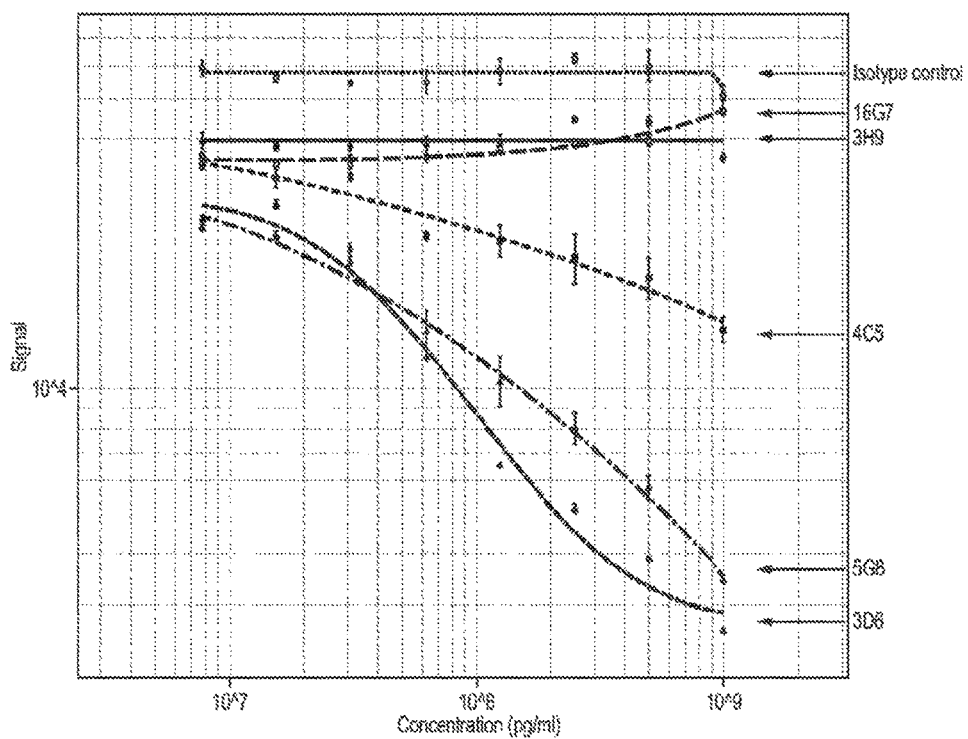
FIG. 2 depicts binding kinetics for selected mouse monoclonal anti-tau antibodies to recombinant human tau.
FIG. 3 depicts results of functional blocking assays for selected mouse monoclonal anti-tau antibodies.

SEQ ID NO:1 sets forth the amino acid sequence of an isoform of human tau (Swiss-Prot P10636-8).

SEQ ID NO:2 sets forth the amino acid sequence of an isoform of human tau (Swiss-Prot P10636-7).

SEQ ID NO:3 sets forth the amino acid sequence of an isoform of human tau (Swiss-Prot P10636-6), (4R0N human tau).

SEQ ID NO:4 sets forth the amino acid sequence of an isoform of human tau (Swiss-Prot P10636-5).

SEQ ID NO:5 sets forth the amino acid sequence of an isoform of human tau (Swiss-Prot P10636-4).

SEQ ID NO:6 sets forth the amino acid sequence of an isoform of human tau (Swiss-Prot P10636-2).

SEQ ID NO: 7 sets forth the amino acid sequence of the heavy chain variable region of the mouse 5G8 antibody.

SEQ ID NO: 8 sets forth the amino acid sequence of the light chain variable region of the mouse 5G8 antibody.

SEQ ID NO: 9 sets forth a nucleic acid sequence encoding the heavy chain variable region of the mouse 5G8 antibody with signal peptide.

SEQ ID NO: 10 sets forth a nucleic acid sequence encoding the light chain variable region of the mouse 5G8 antibody with signal peptide.

SEQ ID NO: 11 sets forth the amino acid sequence of Kabat/Chothia composite CDR-H1 of the mouse 5G8 antibody.

SEQ ID NO:12 sets forth the amino acid sequence of Kabat CDR-H2 of the mouse 5G8 antibody.

SEQ ID NO: 13 sets forth the amino acid sequence of Kabat CDR-H3 of the mouse 5G8 antibody.

SEQ ID NO: 14 sets forth the amino acid sequence of Kabat CDR-L1 of the mouse 5G8 antibody.

SEQ ID NO: 15 sets forth the amino acid sequence of Kabat CDR-L2 of the mouse 5G8 antibody.

SEQ ID NO: 16 sets forth the amino acid sequence of Kabat CDR-L3 of the mouse 5G8 antibody.

SEQ ID NO: 17 sets forth the amino acid sequence of Kabat CDR-H1 of the mouse 5G8 antibody.

SEQ ID NO: 18 sets forth the amino acid sequence of Chothia CDR-H1 of the mouse 5G8 antibody.

SEQ ID NO: 19 sets forth the amino acid sequence of Contact CDR-H1 of the mouse 5G8 antibody.

SEQ ID NO:20 sets forth the amino acid sequence of Chothia CDR-H2 of the mouse 5G8 antibody.

SEQ ID NO:21 sets forth the amino acid sequence of AbM CDR-H2 of the mouse 5G8 antibody.

SEQ ID NO:22 sets forth the amino acid sequence of Contact CDR-H2 of the mouse 5G8 antibody.

SEQ ID NO:23 sets forth the amino acid sequence of Contact CDR-H3 of the mouse 5G8 antibody.

SEQ ID NO: 24 sets forth the amino acid sequence of Contact CDR-L1 of the mouse 5G8 antibody.

SEQ ID NO: 25 sets forth the amino acid sequence of Contact CDR-L2 of the mouse 5G8 antibody.

SEQ ID NO: 26 sets forth the amino acid sequence of Contact CDR-L3 of the mouse 5G8 antibody.

SEQ ID NO:27 sets forth the amino acid sequence of model sequence murine anti-prion antibody 3F4 heavy chain variable region Acc. #1CR9_H.

SEQ ID NO:28 sets forth the amino acid sequence of acceptor sequence humanized anti-dabigatran Fab aDabi-Fab2b-VH Acc. #4YHM_H.

SEQ ID NO:29 sets forth the amino acid sequence of human germline sequence IGHV1-46 Acc. #P01743.2.

SEQ ID NO:30 sets forth the amino acid sequence of model sequence model sequence murine anti-prion antibody 3F4 light chain variable region Acc. #1CR9_L.

SEQ ID NO:31 sets forth the amino acid sequence of human acceptor sequence humanized anti-dabigatran Fab aDabi-Fab2b-VL Acc. #4YHM_L.

SEQ ID NO:32 sets forth the amino acid sequence of human germline gene IGKV2-29 Acc. #A2NJV5.2.

SEQ ID NO:33 sets forth the amino acid sequence of heavy chain variable region of the humanized 5G8 antibody hu5G8-VH_1.

SEQ ID NO:34 sets forth the amino acid sequence of heavy chain variable region of the humanized 5G8 antibody hu5G8-VH_2.

SEQ ID NO:35 sets forth the amino acid sequence of heavy chain variable region of the humanized 5G8 antibody hu5G8-VH_3.

SEQ ID NO:36 sets forth the amino acid sequence of heavy chain variable region of the humanized 5G8 antibody hu5G8-VH_4.

SEQ ID NO:37 sets forth the amino acid sequence of heavy chain variable region of the humanized 5G8 antibody hu5G8-VH_5.

SEQ ID NO:38 sets forth the amino acid sequence of heavy chain variable region of the humanized 5G8 antibody hu5G8-VH_6.

SEQ ID NO:39 sets forth the amino acid sequence of heavy chain variable region of the humanized 5G8 antibody hu5G8-VH_7.

SEQ ID NO:40 sets forth the amino acid sequence of heavy chain variable region of the humanized 5G8 antibody hu5G8-VH_8.

SEQ ID NO:41 sets forth the amino acid sequence of light chain variable region of the humanized 5G8 antibody hu5G8-VL_1.

SEQ ID NO:42 sets forth the amino acid sequence of light chain variable region of the humanized 5G8 antibody hu5G8-VL_2.

SEQ ID NO:43 sets forth the amino acid sequence of light chain variable region of the humanized 5G8 antibody hu5G8-VL_3.

SEQ ID NO:44 sets forth the amino acid sequence of light chain variable region of the humanized 5G8 antibody hu5G8-VL_4.

SEQ ID NO:45 sets forth the amino acid sequence of light chain variable region of the humanized 5G8 antibody hu5G8-VL_5.

SEQ ID NO:46 sets forth the amino acid sequence of light chain variable region of the humanized 5G8 antibody hu5G8-VL_6.

SEQ ID NO: 47 sets forth the amino acid sequence of the heavy chain variable region of the mouse 5G8 antibody with signal peptide.

SEQ ID NO: 48 sets forth the amino acid sequence of the light chain variable region of the mouse 5G8 antibody with signal peptide.

SEQ ID NO 49 sets forth the amino acid sequence of the heavy chain variable region of the mouse 6A10 antibody with signal peptide.

SEQ ID NO: 50 sets forth the amino acid sequence of the light chain variable region of the mouse 6A10 mouse antibody with signal peptide.

SEQ ID NO: 51 sets forth the amino acid sequence of the heavy chain variable region of the mouse 7G6 antibody with signal peptide.

SEQ ID NO:52 sets forth the amino acid sequence of the light chain variable region of the mouse 7G6 antibody with signal peptide.

SEQ ID NO: 53 sets forth the amino acid sequence of the heavy chain variable region of the mouse 8A4 antibody with signal peptide.

SEQ ID NO:54 sets forth the amino acid sequence of the light chain variable region of the mouse 8A4 antibody with signal peptide.

SEQ ID NO: 55 sets forth the amino acid sequence of the mature heavy chain variable region of the mouse 3D6 antibody.

SEQ ID NO:56 sets forth the amino acid sequence of Kabat/Chothia composite CDR-H1 of the mouse 3D6 antibody.

SEQ ID NO:57 sets forth the amino acid sequence of Kabat CDR-H2 of the mouse 3D6 antibody.

SEQ ID NO: 58 sets forth the amino acid sequence of Kabat CDR-H3 of the mouse 3D6 antibody.

SEQ ID NO:59 sets forth the amino acid sequence of the mature light chain variable region of the mouse 3D6 antibody.
SEQ ID NO: 60 sets forth the amino acid sequence of Kabat CDR-L1 of the mouse 3D6 antibody.
SEQ ID NO: 61 sets forth the amino acid sequence of Kabat CDR-L2 of the mouse 3D6 antibody.
SEQ ID NO: 62 sets forth the amino acid sequence of Kabat CDR-L3 of the mouse 3D6 antibody.
SEQ ID NO 63 sets forth the amino acid sequence of the mature heavy chain variable region of the mouse 6A10 antibody.
SEQ ID NO: 64 sets forth the amino acid sequence of the mature light chain variable region of the mouse 6A10 antibody.
SEQ ID NO: 65 sets forth the amino acid sequence of Kabat/Chothia composite CDR-H1 of the mouse 6A10 antibody.
SEQ ID NO:66 sets forth the amino acid sequence of Kabat CDR-H2 of the mouse 6A10 antibody.
SEQ ID NO: 67 sets forth the amino acid sequence of Kabat CDR-H3 of the mouse 6A10 antibody.
SEQ ID NO: 68 sets forth the amino acid sequence of Kabat CDR-L1 of the mouse 6A10 antibody.
SEQ ID NO: 69 sets forth the amino acid sequence of Kabat CDR-L2 of the mouse 6A10 antibody.
SEQ ID NO: 70 sets forth the amino acid sequence of Kabat CDR-L3 of the mouse 6A10 antibody.
SEQ ID NO: 71 sets forth the amino acid sequence of Kabat CDR-H1 of the mouse 6A10 antibody.
SEQ ID NO: 72 sets forth the amino acid sequence of Chothia CDR-H1 of the mouse 6A10 antibody.
SEQ ID NO: 73 sets forth the amino acid sequence of Contact CDR-H1 of the mouse 6A10 antibody.
SEQ ID NO:74 sets forth the amino acid sequence of Chothia CDR-H2 of the mouse 6A10 antibody.
SEQ ID NO:75 sets forth the amino acid sequence of AbM CDR-H2 of the mouse 6A10 antibody.
SEQ ID NO:76 sets forth the amino acid sequence of Contact CDR-H2 of the mouse 6A10 antibody.
SEQ ID NO:77 sets forth the amino acid sequence of Contact CDR-H3 of the mouse 6A10 antibody.
SEQ ID NO: 78 sets forth the amino acid sequence of Contact CDR-L1 of the mouse 6A10 antibody.
SEQ ID NO: 79 sets forth the amino acid sequence of Contact CDR-L2 of the mouse 6A10 antibody.
SEQ ID NO: 80 sets forth the amino acid sequence of Contact CDR-L3 of the mouse 6A10 antibody.
SEQ ID NO:81 sets forth the amino acid sequence of acceptor sequence human heavy chain variable region, accession #ACR16112.
SEQ ID NO:82 sets forth the amino acid sequence of human germline sequence IGHV1-2*02.
SEQ ID NO:83 sets forth the amino acid sequence of human acceptor sequence human kappa light chain variable region, accession #ABC66863.
SEQ ID NO:84 sets forth the amino acid sequence of human germline sequence IGKV2-30*02.
SEQ ID NO:85 sets forth the amino acid sequence of heavy chain variable region of the humanized 6A10 antibody hu6A10-VH_1.
SEQ ID NO:86 sets forth the amino acid sequence of heavy chain variable region of the humanized 6A10 antibody hu6A10-VH_2.
SEQ ID NO:87 sets forth the amino acid sequence of heavy chain variable region of the humanized 6A10 antibody hu6A10-VH_3.
SEQ ID NO:88 sets forth the amino acid sequence of light chain variable region of the humanized 6A10 antibody hu6A10-VL_1.
SEQ ID NO:89 sets forth the amino acid sequence of light chain variable region of the humanized 6A10 antibody hu6A10-VL_2.
SEQ ID NO:90 sets forth the amino acid sequence of light chain variable region of the humanized 6A10 antibody hu6A10-VL_3.
SEQ ID NO 91 sets forth the amino acid sequence of the mature heavy chain variable region of the mouse 8A4 antibody.
SEQ ID NO: 92 sets forth the amino acid sequence of the mature light chain variable region of the mouse 8A4 antibody.
SEQ ID NO: 93 sets forth the amino acid sequence of Kabat/Chothia composite CDR-H1 of the mouse 8A4 antibody.
SEQ ID NO:94 sets forth the amino acid sequence of Kabat CDR-H2 of the mouse 8A4 antibody.
SEQ ID NO: 95 sets forth the amino acid sequence of Kabat CDR-H3 of the mouse 8A4 antibody.
SEQ ID NO: 96 sets forth the amino acid sequence of Kabat CDR-L1 of the mouse 8A4 antibody.
SEQ ID NO: 97 sets forth the amino acid sequence of Kabat CDR-L2 of the mouse 8A4 antibody.
SEQ ID NO: 98 sets forth the amino acid sequence of Kabat CDR-L3 of the mouse 8A4 antibody.
SEQ ID NO: 99 sets forth the amino acid sequence of Kabat CDR-H1 of the mouse 8A4 antibody.
SEQ ID NO: 100 sets forth the amino acid sequence of Chothia CDR-H1 of the mouse 8A4 antibody.
SEQ ID NO: 101 sets forth the amino acid sequence of Contact CDR-H1 of the mouse 8A4 antibody.
SEQ ID NO:102 sets forth the amino acid sequence of Chothia CDR-H2 of the mouse 8A4 antibody.
SEQ ID NO:103 sets forth the amino acid sequence of AbM CDR-H2 of the mouse 8A4 antibody.
SEQ ID NO:104 sets forth the amino acid sequence of Contact CDR-H2 of the mouse 8A4 antibody.
SEQ ID NO:105 sets forth the amino acid sequence of Contact CDR-H3 of the mouse 8A4 antibody.
SEQ ID NO: 106 sets forth the amino acid sequence of Contact CDR-L1 of the mouse 8A4 antibody.
SEQ ID NO: 107 sets forth the amino acid sequence of Contact CDR-L2 of the mouse 8A4 antibody.
SEQ ID NO: 108 sets forth the amino acid sequence of Contact CDR-L3 of the mouse 8A4 antibody.
SEQ ID NO:109 sets forth the amino acid sequence of model sequence 3JAUVH.
SEQ ID NO:110 sets forth the amino acid sequence of acceptor sequence human heavy chain variable region, accession #ADU57742.
SEQ ID NO:111 sets forth the amino acid sequence of model sequence 3JAUVL.
SEQ ID NO: 112 sets forth the amino acid sequence of human acceptor sequence human kappa light chain variable region, accession #ABA26100.
SEQ ID NO:113 sets forth the amino acid sequence of heavy chain variable region of the humanized 8A4 antibody hu8A4-VH_1.
SEQ ID NO:114 sets forth the amino acid sequence of heavy chain variable region of the humanized 8A4 antibody hu8A4-VH_2.
SEQ ID NO:115 sets forth the amino acid sequence of heavy chain variable region of the humanized 8A4 antibody hu8A4-VH_3.

SEQ ID NO:116 sets forth the amino acid sequence of light chain variable region of the humanized 8A4 antibody hu8A4-VL_1.

SEQ ID NO:117 sets forth the amino acid sequence of light chain variable region of the humanized 8A4 antibody hu8A4-VL_2.

SEQ ID NO:118 sets forth the amino acid sequence of light chain variable region of the humanized 8A4 antibody hu8A4-VL_3.

SEQ ID NO 119 sets forth the amino acid sequence of the mature heavy chain variable region of the mouse 7G6 antibody.

SEQ ID NO: 120 sets forth the amino acid sequence of the mature light chain variable region of the mouse 7G6 antibody.

SEQ ID NO: 121 sets forth the amino acid sequence of Kabat/Chothia composite CDR-H1 of the mouse 7G6 antibody.

SEQ ID NO: 122 sets forth the amino acid sequence of Kabat CDR-H2 of the mouse 7G6 antibody.

SEQ ID NO: 123 sets forth the amino acid sequence of Kabat CDR-H3 of the mouse 7G6 antibody.

SEQ ID NO: 124 sets forth the amino acid sequence of Kabat CDR-L1 of the mouse 7G6 antibody.

SEQ ID NO: 125 sets forth the amino acid sequence of Kabat CDR-L2 of the mouse 7G6 antibody.

SEQ ID NO: 126 sets forth the amino acid sequence of Kabat CDR-L3 of the mouse 7G6 antibody.

SEQ ID NO: 127 sets forth the amino acid sequence of Kabat CDR-H1 of the mouse 7G6 antibody.

SEQ ID NO: 128 sets forth the amino acid sequence of Chothia CDR-H1 of the mouse 7G6 antibody.

SEQ ID NO: 129 sets forth the amino acid sequence of Contact CDR-H1 of the mouse 7G6 antibody.

SEQ ID NO:130 sets forth the amino acid sequence of Chothia CDR-H2 of the mouse 7G6 antibody.

SEQ ID NO:131 sets forth the amino acid sequence of AbM CDR-H2 of the mouse 7G6 antibody.

SEQ ID NO:132 sets forth the amino acid sequence of Contact CDR-H2 of the mouse 7G6 antibody.

SEQ ID NO:133 sets forth the amino acid sequence of Contact CDR-H3 of the mouse 7G6 antibody.

SEQ ID NO: 134 sets forth the amino acid sequence of Contact CDR-L1 of the mouse 7G6 antibody.

SEQ ID NO: 135 sets forth the amino acid sequence of Contact CDR-L2 of the mouse 7G6 antibody.

SEQ ID NO: 136 sets forth the amino acid sequence of Contact CDR-L3 of the mouse 7G6 antibody.

SEQ ID NO:137 sets forth the amino acid sequence of acceptor sequence human heavy chain variable region, accession #PDB 3U0T_VH.

SEQ ID NO: 138 sets forth the amino acid sequence of human acceptor sequence human kappa light chain variable region, accession #PDB 3U0T_VL SEQ ID NO:139 sets forth the amino acid sequence of heavy chain variable region of the humanized 7G6 antibody hu7G6-VH_1.

SEQ ID NO:140 sets forth the amino acid sequence of heavy chain variable region of the humanized 7G6 antibody hu7G6-VH_2.

SEQ ID NO:141 sets forth the amino acid sequence of light chain variable region of the humanized 7G6 antibody hu7G6-VL_1.

SEQ ID NO:142 sets forth the amino acid sequence of light chain variable region of the humanized 7G6 antibody hu7G6-VL_2.

SEQ ID NO:143 sets forth the amino acid sequence of light chain variable region of the humanized 7G6 antibody hu7G6-VL_3.

SEQ ID NO:144 sets forth the amino acid sequence of light chain variable region of the humanized 7G6 antibody hu7G6-VL_4.

SEQ ID NO:145 sets forth the amino acid sequence of light chain variable region of the humanized 7G6 antibody hu7G6-VL_5.

SEQ ID NO:146 sets forth the amino acid sequence of light chain variable region of the humanized 7G6 antibody hu7G6-VL_6

SEQ ID NO:147 sets forth the amino acid sequence of light chain variable region of the humanized 7G6 antibody hu7G6-VL_7.

SEQ ID NO:148 sets forth the amino acid sequence of light chain variable region of the humanized 7G6 antibody hu7G6-VL_8.

SEQ ID NO: 149 sets forth the amino acid sequence of human germline sequence IGHV1-69-2*01.

Definitions

Monoclonal antibodies or other biological entities are typically provided in isolated form. This means that an antibody or other biologically entity is typically at least 50% w/w pure of interfering proteins and other contaminants arising from its production or purification but does not exclude the possibility that the monoclonal antibody is combined with an excess of pharmaceutically acceptable carrier(s) or other vehicle intended to facilitate its use. Sometimes monoclonal antibodies are at least 60%, 70%, 80%, 90%, 95% or 99% w/w pure of interfering proteins and contaminants from production or purification. Often an isolated monoclonal antibody or other biological entity is the predominant macromolecular species remaining after its purification.

Specific binding of an antibody to its target antigen means an affinity and/or avidity of at least $10^6$, $10^7$, $10^8$, $10^9$, $10^{10}$, $10^{11}$, or $10^{12}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not however necessarily imply that an antibody binds one and only one target.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. See generally, *Fundamental Immunology, Paul, W., ed.,* 2nd ed. Raven Press, N.Y., 1989, Ch. 7 (incorporated by reference in its entirety for all purposes).

CDRs contain Kabat CDR residues and no other CDR residues, and an antibody in which CDR H1 is a composite Chothia-Kabat CDR H1 and other CDRs contain Kabat CDR residues and no additional CDR residues based on other definitions.

TABLE 1

Conventional Definitions of CDRs Using Kabat Numbering

| Loop | Kabat | Chothia | Composite of Chothia & Kabat | AbM | Contact |
|------|-------|---------|------------------------------|-----|---------|
| L1 | L24--L34 | L24--L34 | L24--L34 | L24--L34 | L30--L36 |
| L2 | L50--L56 | L50--L56 | L50--L56 | L50--L56 | L46--L55 |
| L3 | L89--L97 | L89--L97 | L89--L97 | L89--L97 | L89--L96 |
| H1 | H31--H35B | H26--H32 ... H34* | H26--H35B* | H26--H35B | H30--H35B |
| H2 | H50--H65 | H52--H56 | H50--H65 | H50--H58 | H47--H58 |
| H3 | H95--H102 | H95--H102 | H95--H102 | H95--H102 | H93--H101 |

*CDR-H1 by Chothia can end at H32, H33, or H34 (depending on the length of the loop). This is because the Kabat numbering scheme places insertions of extra residues at 35A and 35B, whereas Chothia numbering places them at 31A and 31B. If neither H35A nor H35B (Kabat numbering) is present, the Chothia CDR-H1 loop ends at H32. If only H35A is present, it ends at H33. If both H35A and H35B are present, it ends at H34.

An immunoglobulin light or heavy chain variable region (also referred to herein as a "light chain variable domain" ("VL domain") or "heavy chain variable domain" ("VH domain"), respectively) consists of a "framework" region interrupted by three "complementarity determining regions" or "CDRs." The framework regions serve to align the CDRs for specific binding to an epitope of an antigen. The CDRs include the amino acid residues of an antibody that are primarily responsible for antigen binding. From amino-terminus to carboxyl-terminus, both VL and VH domains comprise the following framework (FR) and CDR regions: FR1, CDR1, FR2, CDR2, FR3, CDR3, and FR4. CDRs 1, 2, and 3 of a VL domain are also referred to herein, respectively, as CDR-L1, CDR-L2, and CDR-L3; CDRs 1, 2, and 3 of a VH domain are also referred to herein, respectively, as CDR-H1, CDR-H2, and CDR-H3. When the application discloses a VL sequence with R as the C-terminal residue, the R can alternatively be considered as being the N-terminal residue of the light chain constant region. Thus, the application should also be understood as disclosing the VL sequence without the C-terminal R.

The assignment of amino acids to each VL and VH domain is in accordance with any conventional definition of CDRs. Conventional definitions include, the Kabat definition (Kabat, *Sequences of Proteins of Immunological Interest* (National Institutes of Health, Bethesda, MD, 1987 and 1991), the Chothia definition (Chothia & Lesk, *J. Mol. Biol.* 196:901-917, 1987; Chothia et al., *Nature* 342:878-883, 1989); a composite of Chothia Kabat CDR in which CDR-H1 is a composite of Chothia and Kabat CDRs; the AbM definition used by Oxford Molecular's antibody modelling software; and, the contact definition of Martin et al (bioinfo.org.uk/abs) (see Table 1). Kabat provides a widely used numbering convention (Kabat numbering) in which corresponding residues between different heavy chains or between different light chains are assigned the same number. When an antibody is said to comprise CDRs by a certain definition of CDRs (e.g., Kabat) that definition specifies the minimum number of CDR residues present in the antibody (i.e., the Kabat CDRs). It does not exclude that other residues falling within another conventional CDR definition but outside the specified definition are also present. For example, an antibody comprising CDRs defined by Kabat includes among other possibilities, an antibody in which the The term "antibody" includes intact antibodies and binding fragments thereof. Typically, fragments compete with the intact antibody from which they were derived for specific binding to the target including separate heavy chains, light chains Fab, Fab', F(ab')$_2$, F(ab)c, Dabs, nanobodies, and Fv. Fragments can be produced by recombinant DNA techniques, or by enzymatic or chemical separation of intact immunoglobulins. The term "antibody" also includes a bispecific antibody and/or a humanized antibody. A bispecific or bifunctional antibody is an artificial hybrid antibody having two different heavy/light chain pairs and two different binding sites (see, e.g., Songsivilai and Lachmann, *Clin. Exp. Immunol.,* 79:315-321 (1990); Kostelny et al., *J. Immunol.,* 148:1547-53 (1992)). In some bispecific antibodies, the two different heavy/light chain pairs include a humanized 5G8, 6A10, 8A4, or 7G6 heavy chain/light chain pair and a heavy chain/light chain pair specific for a different epitope on tau than that bound by 5G8, 6A10, 8A4, or 7G6.

In some bispecific antibodies, one heavy chain/light chain pair is a humanized 5G8 antibody, humanized 6A10 antibody, humanized 8A4 antibody, or humanized 7G6 antibody as further disclosed below and the other heavy chain/light chain pair is from an antibody that binds to a receptor expressed on the blood brain barrier, such as an insulin receptor, an insulin-like growth factor (IGF) receptor, a leptin receptor, or a lipoprotein receptor, or a transferrin receptor (Friden et al., *Proc. Natl. Acad. Sci. USA* 88:4771-4775, 1991; Friden et al., *Science* 259:373-377, 1993). Such a bispecific antibody can be transferred cross the blood brain barrier by receptor-mediated transcytosis. Brain uptake of the bispecific antibody can be further enhanced by engineering the bi-specific antibody to reduce its affinity to the blood brain barrier receptor. Reduced affinity for the receptor resulted in a broader distribution in the brain (see, e.g., Atwal et al., *Sci. Trans. Med.* 3, 84ra43, 2011; Yu et al., *Sci. Trans. Med.* 3, 84ra44, 2011).

Exemplary bispecific antibodies can also be: (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so-called "dock and lock" molecule, based on the "dimerization and docking domain" in Protein Kinase A, which, when applied to Fabs, can yield a trivalent bispecific binding protein consisting of two identical Fab fragments linked to a different Fab fragment; or (5) a so-called Scorpion molecule, comprising, e.g., two scFvs fused to both termini of a human Fc-region. Examples of platforms useful for preparing bispecific antibodies include BiTE (Micromet), DART (MacroGenics), Fcab and Mab2 (F-star), Fc-engineered IgG1 (Xencor) or DuoBody (based on Fab arm exchange, Genmab).

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., *Cancer Res.* 50:1495, 1990). A test antibody competes with a reference antibody if an excess of a test antibody (e.g., at least 2×, 5×, 10×, 20× or 100×) inhibits binding of the reference antibody by at least 50% as measured in a competitive binding assay. Some test antibodies inhibit binding of the references antibody by at least 75%, 90% or 99%. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

The term "pharmaceutically acceptable" means that the carrier, diluent, excipient, or auxiliary is compatible with the other ingredients of the formulation and not substantially deleterious to the recipient thereof.

The term "patient" includes human and other mammalian subjects that receive either prophylactic or therapeutic treatment.

An individual is at increased risk of a disease if the subject has at least one known risk-factor (e.g., genetic, biochemical, family history, and situational exposure) placing individuals with that risk factor at a statistically significant greater risk of developing the disease than individuals without the risk factor.

The term "biological sample" refers to a sample of biological material within or obtainable from a biological source, for example a human or mammalian subject. Such samples can be organs, organelles, tissues, sections of tissues, bodily fluids, peripheral blood, blood plasma, blood serum, cells, molecules such as proteins and peptides, and any parts or combinations derived therefrom. The term biological sample can also encompass any material derived by processing the sample. Derived material can include cells or their progeny. Processing of the biological sample may involve one or more of filtration, distillation, extraction, concentration, fixation, inactivation of interfering components, and the like.

The term "control sample" refers to a biological sample not known or suspected to include tau-related disease-affected regions, or at least not known or suspect to include diseased regions of a given type. Control samples can be obtained from individuals not afflicted with the tau-related disease. Alternatively, control samples can be obtained from patients afflicted with the tau-related disease. Such samples can be obtained at the same time as a biological sample thought to comprise the tau-related disease or on a different occasion. A biological sample and a control sample can both be obtained from the same tissue. Preferably, control samples consist essentially or entirely of normal, healthy regions and can be used in comparison to a biological sample thought to comprise tau-related disease-affected regions. Preferably, the tissue in the control sample is the same type as the tissue in the biological sample. Preferably, the tau-related disease-affected cells thought to be in the biological sample arise from the same cell type (e.g., neurons or glia) as the type of cells in the control sample.

The term "disease" refers to any abnormal condition that impairs physiological function. The term is used broadly to encompass any disorder, illness, abnormality, pathology, sickness, condition, or syndrome in which physiological function is impaired, irrespective of the nature of the etiology.

The term "symptom" refers to a subjective evidence of a disease, such as altered gait, as perceived by the subject. A "sign" refers to objective evidence of a disease as observed by a physician.

The term "positive response to treatment" refers to a more favorable response in an individual patient or average response in a population of patients relative to an average response in a control population not receiving treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" or "including" one or more recited elements may include other elements not specifically recited. For example, a composition that "comprises" or "includes" an antibody may contain the antibody alone or in combination with other ingredients.

Designation of a range of values includes all integers within or defining the range, and all subranges defined by integers within the range.

Unless otherwise apparent from the context, the term "about" encompasses insubstantial variations, such as values within a standard margin of error of measurement (e.g., SEM) of a stated value.

Statistical significance means p≤0.05.

The singular forms of the articles "a," "an," and "the" include plural references unless the context clearly dictates otherwise. For example, the term "a compound" or "at least one compound" can include a plurality of compounds, including mixtures thereof.

DETAILED DESCRIPTION

I. General

The invention provides antibodies that specifically bind to tau. Some exemplary binding specificities of antibodies of the invention are characterized by specific binding to a peptide consisting of residues 199-213 or a peptide consisting of residues 262-276 of SEQ ID NO:3 (corresponding to residues 257-271 or 320-334, respectively, of SEQ ID NO:1), or to both peptides. Exemplary antibodies of the invention are 5G8, 6A10, 8A4, and 7G6. Some antibodies bind to an epitope including at least one residue from residues 199-213 or at least one residue from residues 262-276 of SEQ ID NO:3 or both. Some antibodies bind to an epitope in which all residues of the epitope are within residues 119-213 or residues 262-276 of SEQ ID NO:3 or both. Some antibodies bind to an epitope formed from amino acids within both residues 199-213 and 262-276 of SEQ ID NO:3. Some antibodies bind to an epitope within residues 199-213 of SEQ ID NO:3 or with residues 262-276 of SEQ ID NO:3. Some antibodies bind to tau irrespective of phosphorylation state. Some antibodies inhibit or delay tau-associated pathologies and associated symptomatic deterioration. Although an understanding of mechanism is not required for practice of the invention, a reduction in toxicity may occur as a result of the antibody inducing phagocytosis of tau, inhibiting tau from inter or intramolecular aggregation, or from binding to other molecules, by stabilizing a non-toxic conformation, by inhibiting intercellular or intracellular transmission of pathogenic tau forms, by blockade of tau phosphorylation, by preventing binding of tau to cells, or by inducing proteolytic cleavage of tau, among other mechanisms. The antibodies of the invention or agents that induce such antibodies can be used in methods of treating or effecting prophylaxis of Alzheimer's and other diseases associated with tau.

II. Target Molecules

Unless otherwise apparent from the context, reference to tau means a natural human form of tau including all isoforms irrespective of whether posttranslational modification (e.g., phosphorylation, glycation, or acetylation) is present. There are six major isoforms (splice variants) of tau occurring in the human brain. The longest of these variants has 441 amino acids, of which the initial met residue is cleaved. Residues are numbered according to the 441 isoform. Thus, for example, reference to a phosphorylation at position 404 means position 404 of the 441 isoform, or corresponding position of any other isoform when maximally aligned with the 441 isoform. The amino acid sequences of the isoforms and Swiss-Prot numbers are indicated below.

```
P10636-8
                                                          (SEQ ID NO: 1)
         10         20         30         40         50         60
MAEPRQEFEV MEDHAGTYGL GDRKDQGGYT MHQDQEGDTD AGLKESPLQT PIEDGSEEPG 70         80         90        100        110        120
SETSDAKSTP TAEDVTAPLV DEGAPGKQAA AQPHTEIPEG TTAEEAGIGD TPSLEDEAAG 130        140        150        160        170        180
HVTQARMVSK SKDGTGSDDK KAKGADGKTK IATPRGAAPP GQKGQANATR IPAKTPPAPK 190        200        210        220        230        240
TPPSSGEPPK SGDRSGYSSP GSPGTPGSRS RTPSLPTPPT REPKKVAVVR TPPKSPSSAK 250        260        270        280        290        300
SRLQTAPVPM PDLKNVKSKI GSTENLKHQP GGGKVQIINK KLDLSNVQSK CGSKDNIKHV 310        320        330        340        350        360
PGGGSVQIVY KPVDLSKVTS KCGSLGNIHH KPGGGQVEVK SEKLDFKDRV QSKIGSLDNI 370        380        390        400        410        420
THVPGGGNKK IETHKLTFRE NAKAKTDHGA EIVYKSPVVS GDTSPRHLSN VSSTGSIDMV 430        440
DSPQLATLAD EVSASLAKQG L

P10636-7
                                                          (SEQ ID NO: 2)
         10         20         30         40         50         60
MAEPRQEFEV MEDHAGTYGL GDRKDQGGYT MHQDQEGDTD AGLKESPLQT PIEDGSEEPG 70         80         90        100        110        120
SETSDAKSTP TAEAEEAGIG DTPSLEDEAA GHVTQARMVS KSKDGTGSDD KKAKGADGKT
```

```
            130        140        150        160        170        180
KIATPRGAAP PGQKGQANAT RIPAKTPPAP KTPPSSGEPP KSGDRSGYSS PGSPGTPGSR 190        200        210        220        230        240
SRTPSLPTPP TREPKKVAVV RTPPKSPSSA KSRLQTAPVP MPDLKNVKSK IGSTENLKHQ 250        260        270        280        290        300
PGGGKVQIIN KKLDLSNVQS KCGSKDNIKH VPGGGSVQIV YKPVDLSKVT SKCGSLGNIH 310        320        330        340        350        360
HKPGGGQVEV KSEKLDFKDR VQSKIGSLDN ITHVPGGGNK KIETHKLTFR ENAKAKTDHG 370        380        390        400        410
AEIVYKSPVV SGDTSPRHLS NVSSTGSIDM VDSPQLATLA DEVSASLAKQ GL

P10636-6 (4R0N human tau)
                                                          (SEQ ID NO: 3)
            10         20         30         40         50         60
MAEPRQEFEV MEDHAGTYGL GDRKDQGGYT MHQDQEGDTD AGLKAEEEAGI GDTPSLEDEA 70         80         90         100        110        120
AGHVTQARMV SKSKDGTGSD DKKAKGADGK TKIATPRGAA PPGQKGQANA TRIPAKTPPA 130        140        150        160        170        180
PKTPPSSGEP PKSGDRSGYS SPGSPGTPGS RSRTPSLPTP PTREPKKVAV VRTPPKSPSS 190        200        210        220        230        240
AKSRLQTAPV PMPDLKNVKS KIGSTENLKH QPGGGKVQII NKKLDLSNVQ SKCGSKDNIK 250        260        270        280        290        300
HVPGGGSVQI VYKPVDLSKV TSKCGSLGNI HHKPGGGQVE VKSEKLDFKD RVQSKIGSLD 310        320        330        340        350        360
NITHVPGGGN KKIETHKLTF RENAKAKTDH GAEIVYKSPV VSGDTSPRHL SNVSSTGSID 370        380
MVDSPQLATL ADEVSASLAK QGL P10636-5
                                                          (SEQ ID NO: 4)
            10         20         30         40         50         60
MAEPRQEFEV MEDHAGTYGL GDRKDQGGYT MHQDQEGDTD AGLKESPLQT P1EDGSEEPG 70         80         90         100        110        120
SETSDAKSTP TAEDVTAPLV DEGAPGKQAA AQPHTEIPEG TTAEEAGIGD TPSLEDEAAG 130        140        150        160        170        180
HVTQARMVSK SKDGTGSDDK KAKGADGKTK IATPRGAAPP GQKGQANATR IPAKTPPAPK 190        200        210        220        230        240
TPPSSGEPPK SGDRSGYSSP GSPGTPGSRS RTPSLPTPPT REPKKVAVVR TPPKSPSSAK 250        260        270        280        290        300
SRLQTAPVPM PDLKNVKSKI GSTENLKHQP GGGKVQIVYK PVDLSKVTSK CGSLGNIHHK 310        320        330        340        350        360
PGGGQVEVKS EKLDFKDRVQ SKIGSLDNIT HVPGGGNKKI ETHKLTFREN AKAKTDHGAE 370        380        390        400        410
IVYKSPVVSG DTSPRHLSNV SSTGSIDMVD SPQLATLADE VSASLAKQGL P10636-4
                                                          (SEQ ID NO: 5)
            10         20         30         40         50         60
MAEPRQEFEV MEDHAGTYGL GDRKDQGGYT MHQDQEGDTD AGLKESPLQT P1EDGSEEPG 70         80         90         100        110        120
SETSDAKSTP TAEAEEAGIG DTPSLEDEAA GHVTQARMVS KSKDGTGSDD KKAKGADGKT 130        140        150        160        170        180
KIATPRGAAP PGQKGQANAT RIPAKTPPAP KTPPSSGEPP KSGDRSGYSS PGSPGTPGSR 190        200        210        220        230        240
SRTPSLPTPP TREPKKVAVV RTPPKSPSSA KSRLQTAPVP MPDLKNVKSK IGSTENLKHQ 250        260        270        280        290        300
PGGGKVQIY KPVDLSKVTS KCGSLGNIHH KPGGGQVEVK SEKLDFKDRV QSKIGSLDNI 310        320        330        340        350        360
THVPGGGNKK IETHKLTFRE NAKAKTDHGA EIVYKSPVVS GDTSPRHLSN VSSTGSIDMV
```

-continued

P10636-2
(SEQ ID NO: 6)

```
         10         20         30         40         50         60
MAEPRQEFEV MEDHAGTYGL GDRKDQGGYT MHQDQEGDTD AGLKAEEAGI GDTPSLEDEA 70         80         90        100        110        120
AGHVTQARMV SKSKDGTGSD DKKAKGADGK TKIATPRGAA PPGQKGQANA TRIPAKTPPA 130        140        150        160        170        180
PKTPPSSGEP PKSGDRSGYS SPGSPGTPGS RSRTPSLPTP PTREPKKVAV VRTPPKSPSS 190        200        210        220        230        240
AKSRLQTAPV PMPDLKNVKS KIGSTENLKH QPGGGKVQIV YKPVDLSKVT SKCGSLGNIH 250        260        270        280        290        300
HKPGGGQVEV KSEKLDFKDR VQSKIGSLDN ITHVPGGGNK KIETHKLTFR ENAKAKTDHG 310        320        330        340        350
AEIVYKSPVV SGDTSPRHLS NVSSTGSIDM VDSPQLATLA DEVSASLAKQ GL
```

Reference to tau includes known natural variations about 30 of which are listed in the Swiss-Prot database and permutations thereof, as well as mutations associated with tau pathologies, such as dementia, Pick's disease, supranuclear palsy, among others (see, e.g., Swiss-Prot database and Poorkaj, et al. Ann Neurol. 43:815-825 (1998)). Some examples of tau mutations numbered by the 441 isoform are a lysine to threonine mutation at amino acid residue 257 (K257T), an isoleucine to valine mutation at amino acid position 260 (I260V); a glycine to valine mutation at amino acid position 272 (G272V); an asparagine to lysine mutation at amino acid position 279 (N279K); an asparagine to histidine mutation at amino acid position 296 (N296H); a proline to serine mutation at amino acid position 301 (P301S); a proline to leucine mutation at amino acid 301 (P301L); a glycine to valine mutation at amino acid position 303 (G303V); a serine to asparagine mutation at position 305 (S305N); a glycine to serine mutation at amino acid position 335 (G335S); a valine to methionine mutation at position 337 (V337M); a glutamic acid to valine mutation at position 342 (E342V); a lysine to isoleucine mutation at amino acid position 369 (K369I); a glycine to arginine mutation at amino acid position 389 (G389R); and an arginine to tryptophan mutation at amino acid position 406 (R406W).

Tau can be phosphorylated at one or more amino acid residues including tyrosine at amino acid positions 18, 29, 97, 310, and 394, serine at amino acid positions 184, 185, 198, 199, 202, 208, 214, 235, 237, 238, 262, 293, 324, 356, 396, 400, 404, 409, 412, 413, and 422; and threonine at amino acids positions 175, 181, 205, 212, 217, 231, and 403. Unless otherwise apparent from context, reference to tau, or their fragments includes the natural human amino acid sequences including isoforms, mutants, and allelic variants thereof.

III. Antibodies

A. Binding Specificity and Functional Properties

The invention provides antibodies that bind to tau. Some antibodies bind to tau irrespective of phosphorylation state. Some antibodies bind to an epitope not including a residue subject to phosphorylation. These antibodies can be obtained by immunizing with a tau polypeptide purified from a natural source or recombinantly expressed. Antibodies can be screened for binding tau in unphosphorylated form as well as a form in which one or more residues susceptible to phosphorylation are phosphorylated. Such antibodies preferably bind with indistinguishable affinities or at least within a factor of 1.5, 2 or 3-fold to phosphorylated tau compared to non-phosphorylated tau (i.e., are "pan-specific"). 5G8, 6A10, 8A4, and 7G6 are examples of pan-specific monoclonal antibodies. The invention also provides antibodies binding to the same or to an overlapping epitope as that of 5G8, 6A10, 8A4, or 7G6. Also included are antibodies competing for binding to tau with 5G8, 6A10, 8A4, or 7G6.

The above-mentioned antibodies can be generated de novo by immunizing with a full length tau polypeptide or peptide fragment thereof Such peptides are preferably attached to a heterologous conjugate molecule that helps elicit an antibody response to the peptide. Attachment can be direct or via a spacer peptide or amino acid. Cysteine is used as a spacer amino acid because its free SH group facilitates attachment of a carrier molecule. A polyglycine linker (e.g., 2-6 glycines), with or without a cysteine residue between the glycines and the peptide can also be used. The carrier molecule serves to provide a T-cell epitope that helps elicit an antibody response against the peptide. Several carriers are commonly used particularly keyhole limpet hemocyanin (KLH), ovalbumin and bovine serum albumin (BSA). Peptide spacers can be added to peptide immunogen as part of solid phase peptide synthesis. Carriers are typically added by chemical cross-linking. Some examples of chemical crosslinkers that can be used include cross-N-maleimido-6-aminocaproyl ester or m-maleimidobenzoyl-N-hydroxysuccinimide ester (MBS) (see for example, Harlow, E. et al., Antibodies: A Laboratory Manual, Cold Spring Harbor Laboratory Press, Cold Spring Harbor, N.Y. 1988; Sinigaglia et al., Nature, 336:778-780 (1988); Chicz et al., J. Exp. Med., 178:27-47 (1993); Hammer et al., Cell 74:197-203 (1993); Falk K. et al., Immunogenetics, 39:230-242 (1994); WO 98/23635; and, Southwood et al. J. Immunology, 160: 3363-3373 (1998)). The carrier and spacer if present can be attached to either end of the immunogen.

A peptide with optional spacer and carrier can be used to immunize laboratory animals or B-cells as described in more detail below. Hybridoma supernatants can be tested for ability to bind phosphorylated and non-phosphorylated forms of tau, such as, for example, a full-length isoform of tau with position 404 in phosphorylated form. The peptide can be attached to a carrier or other tag to facilitate the screening assay. In this case, the carrier or tag is preferentially different than the combination of spacer and carrier molecule used for immunization to eliminate antibodies specific for the spacer or carrier rather than the tau peptide. Any of the tau isoforms can be used.

The invention provides monoclonal antibodies binding to epitopes within tau. An antibody designated 5G8 is one such exemplary mouse antibody. Unless otherwise apparent from the context, reference to 5G8 should be understood as referring to any of the mouse, chimeric, veneered, and humanized forms of this antibody. This antibody is further characterized by its ability to bind both phosphorylated and unphosphorylated tau, both non-pathological and pathological forms and conformations of tau, and misfolded/aggregated forms of tau.

Additional antibodies that compete with 5G8 for binding to tau and/or bind the same or overlapping epitope as 5G8 have been isolated designated 6A10, 8A4, 7G6, and 3D6 and produced by hybridomas of the same names. 6A10 has variable heavy and light regions characterized by SEQ ID NO:49 and SEQ ID NO:50 respectively and are of mouse isotypes IgG1/kappa. 6A10 has mature variable heavy and light regions (after cleavage of signal peptide) characterized by SEQ ID NO:63 and SEQ ID NO:64 respectively. Unless otherwise apparent from the context, reference to 6A10 should be understood as referring to any of the mouse, chimeric, veneered, and humanized forms of this antibody. 6A10 is further characterized by its ability to bind both phosphorylated and unphosphorylated tau, both non-pathological and pathological forms and conformations of tau, and misfolded/aggregated forms of tau.

7G6 has variable heavy and light regions characterized by SEQ ID NO:51 and SEQ ID NO:52, respectively and are of mouse isotypes IgG2b/kappa. 7G6 has mature variable heavy and light regions (after cleavage of signal peptide) characterized by SEQ ID NO:119 and SEQ ID NO:120 respectively. Unless otherwise apparent from the context, reference to 7G6 should be understood as referring to any of the mouse, chimeric, veneered, and humanized forms of this antibody. 7G6 is further characterized by its ability to bind both phosphorylated and unphosphorylated tau, both non-pathological and pathological forms and conformations of tau, and misfolded/aggregated forms of tau.

8A4 has variable heavy and light regions characterized by SEQ ID NO:53 and SEQ ID NO: 54, respectively and are of mouse isotypes IgG1/kappa. 8A4 has mature variable heavy and light regions (after cleavage of signal peptide) characterized by SEQ ID NO:91 and SEQ ID NO:92 respectively. Unless otherwise apparent from the context, reference to 8A4 should be understood as referring to any of the mouse, chimeric, veneered, and humanized forms of this antibody. 8A4 is further characterized by its ability to bind both phosphorylated and unphosphorylated tau, both non-pathological and pathological forms and conformations of tau, and misfolded/aggregated forms of tau.

3D6 has mature variable heavy and light regions characterized by SEQ ID NO: 55 and SEQ ID NO:59, respectively and are of mouse isotypes IgG1 kappa. For 3D6, the three heavy chain CDRs are as defined by Kabat/Chothia Composite (SEQ ID NOs: 56, 57, and 58) and the three light chain CDRs are as defined by Kabat (SEQ ID NOs: 60, 61, and 62). For 3D6 and humanized variants thereof, see PCT/IB2017/052544, which is incorporated by reference in its entirety for all purposes. Unless otherwise apparent from the context, reference to 3D6 should be understood as referring to any of the mouse, chimeric, veneered, and humanized forms of this antibody. 3D6 is further characterized by its ability to bind both phosphorylated and unphosphorylated tau, both non-pathological and pathological forms and conformations of tau, and misfolded/aggregated forms of tau.

Optionally, the antibodies of the invention do not include a 6A10 antibody as disclosed in PCT/IB2017/052544. Optionally, the antibodies of the invention do not include an 8A4 antibody. Optionally, the antibodies of the invention do not include a 7G6 antibody. Optionally, the antibodies of the invention do not include a 3D6 antibody as disclosed in PCT/IB2017/052544.

Some antibodies of the invention bind to the same or overlapping epitope as an antibody designated 5G8, 6A10, 8A4, 7G6, or 3D6. The sequences of the heavy and light chain mature variable regions of 5G8 are designated SEQ ID NOs: 7 and 8 respectively. The sequences of the heavy and light chain mature variable regions of 6A10 are designated SEQ ID NOs: 63 and 64 respectively. The sequences of the heavy and light chain mature variable regions of 8A4 are designated SEQ ID NOs: 91 and 92 respectively. The sequences of the heavy and light chain mature variable regions of 7G6 are designated SEQ ID NOs: 119 and 120 respectively. The sequences of the heavy and light chain mature variable regions of 3D6 are designated SEQ ID NOs: 55 and 59 respectively. Other antibodies having such a binding specificity can be produced by immunizing mice with tau or a portion thereof including the desired epitope and screening resulting antibodies for binding to tau optionally in competition with an antibody having the variable regions of mouse 5G8, 6A10, 8A4, 7G6, or 3D6 (IgG1 kappa). Fragments of tau including the desired epitope can be linked to a carrier that helps elicit an antibody response to the fragment and/or be combined with an adjuvant the helps elicit such a response. Such antibodies can be screened for differential binding to tau or a fragment thereof compared with mutants of specified residues. Screening against such mutants more precisely defines the binding specificity to allow identification of antibodies whose binding is inhibited by mutagenesis of particular residues and which are likely to share the functional properties of other exemplified antibodies. The mutations can be systematic replacement substitution with alanine (or serine if an alanine is present already) one residue at a time, or more broadly spaced intervals, throughout the target or throughout a section thereof in which an epitope is known to reside. If the same set of mutations significantly reduces the binding of two antibodies, the two antibodies bind the same epitope.

Antibodies having the binding specificity of a selected murine antibody (e.g., 5G8, 6A10, 8A4, 7G6, or 3D6) can also be produced using a variant of the phage display method. See Winter, WO 92/20791. This method is particularly suitable for producing human antibodies. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions can for example be obtained from a library of rearranged human heavy chain variable regions. A phage showing strong specific binding for tau or a fragment thereof (e.g., at least $10^8$ and preferably at least $10^9$ M$^{-1}$) is selected. The heavy chain variable region from this phage then serves as a starting material for constructing a further phage library. In this library, each phage displays the same heavy chain variable region (i.e., the region identified from the first display library) and a different light chain variable region. The light chain variable regions can be obtained for example from a library of rearranged human variable light chain regions. Again, phage showing strong specific binding for tau or a fragment thereof are selected. The resulting antibodies usually have the same or similar epitope specificity as the murine starting material.

Kabat/Chothia Composite CDRs of the heavy chain of 5G8 are designated SEQ ID NOs: 11, 12, and 13, respectively, and Kabat CDRs of the light chain of 5G8 are designated SEQ ID NOs: 14, 15, and 16, respectively.

Table 2 indicates the 5G8 CDRs as defined by Kabat, Chothia, Composite of Chothia and Kabat (also referred to herein as "Kabat/Chothia Composite"), AbM, and Contact.

TABLE 2

5G8 CDRs as defined by Kabat, Chothia, Composite of Chothia and Kabat, AbM, and Contact

| Loop | Kabat | Chothia | Composite of Chothia & Kabat | AbM | Contact |
|---|---|---|---|---|---|
| L1 | L24--L34 | L24--L34 | L24--L34 | L24--L34 | L30--L36 |
|  | SEQ ID NO: 14 | SEQ ID NO: 14 | SEQ ID NO: 14 | SEQ ID NO: 14 | SEQ ID NO: 24 |
| L2 | L50--L56 | L50--L56 | L50--L56 | L50--L56 | L46--L55 |
|  | SEQ ID NO: 15 | SEQ ID NO: 15 | SEQ ID NO: 15 | SEQ ID NO: 15 | SEQ ID NO: 25 |
| L3 | L89--L97 | L89--L97 | L89--L97 | L89--L97 | L89--L96 |
|  | SEQ ID NO: 16 | SEQ ID NO: 16 | SEQ ID NO: 16 | SEQ ID NO: 16 | SEQ ID NO: 26 |
| H1 | H31--H35B | H26--H32 | H26--H35B | H26--H35B | H30--H35B |
|  | SEQ ID NO: 17 | SEQ ID NO: 18 | SEQ ID NO: 11 | SEQ ID NO: 11 | SEQ ID NO: 19 |
| H2 | H50--H65 | H52--H56 | H50--H65 | H50--H58 | H47--H58 |
|  | SEQ ID NO: 12 | SEQ ID NO: 20 | SEQ ID NO: 12 | SEQ ID NO: 21 | SEQ ID NO: 22 |
| H3 | H95--H102 | H95--H102 | H95--H102 | H95--H102 | H93--H101 |
|  | SEQ ID NO: 13 | SEQ ID NO: 13 | SEQ ID NO: 13 | SEQ ID NO: 13 | SEQ ID NO: 23 |

Kabat/Chothia Composite CDRs of the heavy chain of 6A10 are designated SEQ TD NOs: 65-67, respectively, and Kabat CDRs of the light chain of 6A10 are designated SEQ TD NOs: 68-70, respectively.

Table 3 indicates the 6A10 CDRs as defined by Kabat, Chothia, Composite of Chothia and Kabat (also referred to herein as "Kabat/Chothia Composite"), AbM, and Contact.

TABLE 3

6A10 CDRs as defined by Kabat, Chothia, Composite of Chothia and Kabat, AbM, and Contact

| Loop | Kabat | Chothia | Composite of Chothia & Kabat | AbM | Contact |
|---|---|---|---|---|---|
| L1 | L24--L34 | L24--L34 | L24--L34 | L24--L34 | L30--L36 |
|  | SEQ ID NO: 68 | SEQ ID NO: 68 | SEQ ID NO: 68 | SEQ ID NO: 68 | SEQ ID NO: 78 |
| L2 | L50--L56 | L50--L56 | L50--L56 | L50--L56 | L46--L55 |
|  | SEQ ID NO: 69 | SEQ ID NO: 69 | SEQ ID NO: 69 | SEQ ID NO: 69 | SEQ ID NO: 79 |
| L3 | L89--L97 | L89--L97 | L89--L97 | L89--L97 | L89--L96 |
|  | SEQ ID NO: 70 | SEQ ID NO: 70 | SEQ ID NO: 70 | SEQ ID NO: 70 | SEQ ID NO: 80 |
| H1 | H31--H35B | H26--H32 . . . H34* | H26--H35B* | H26--H35B | H30--H35B |
|  | SEQ ID NO: 71 | SEQ ID NO: 72 | SEQ ID NO: 65 | SEQ ID NO: 65 | SEQ ID NO: 73 |
| H2 | H50--H65 | H52--H56 | H50--H65 | H50--H58 | H47--H58 |
|  | SEQ ID NO: 66 | SEQ ID NO: 74 | SEQ ID NO: 66 | SEQ ID NO: 75 | SEQ ID NO: 76 |
| H3 | H95--H102 | H95--H102 | H95--H102 | H95--H102 | H93--H101 |
|  | SEQ ID NO: 67 | SEQ ID NO: 67 | SEQ ID NO: 67 | SEQ ID NO: 67 | SEQ ID NO: 77 |

Kabat/Chothia Composite CDRs of the heavy chain of 8A4 are designated SEQ ID NOs: 93-95, respectively, and Kabat CDRs of the light chain of 8A4 are designated SEQ ID NOs: 96-98, respectively.

Table 4 indicates the 8A4 CDRs as defined by Kabat, Chothia, Composite of Chothia and Kabat (also referred to herein as "Kabat/Chothia Composite"), AbM, and Contact.

TABLE 4

8A4 CDRs as defined by Kabat, Chothia, Composite of Chothia and Kabat, AbM, and Contact

| Loop | Kabat | Chothia | Composite of Chothia & Kabat | AbM | Contact |
|---|---|---|---|---|---|
| L1 | L24--L34 | L24--L34 | L24--L34 | L24--L34 | L30--L36 |
|  | SEQ ID NO: 96 | SEQ ID NO: 96 | SEQ ID NO: 96 | SEQ ID NO: 96 | SEQ ID NO: 106 |
| L2 | L50--L56 | L50--L56 | L50--L56 | L50--L56 | L46--L55 |
|  | SEQ ID NO: 97 | SEQ ID NO: 97 | SEQ ID NO: 97 | SEQ ID NO: 97 | SEQ ID NO: 107 |

TABLE 4-continued

8A4 CDRs as defined by Kabat, Chothia, Composite of Chothia and Kabat, AbM, and Contact

| Loop | Kabat | Chothia | Composite of Chothia & Kabat | AbM | Contact |
|---|---|---|---|---|---|
| L3 | L89--L97 | L89--L97 | L89--L97 | L89--L97 | L89--L96 |
|  | SEQ ID NO: 98 | SEQ ID NO: 98 | SEQ ID NO: 98 | SEQ ID NO: 98 | SEQ ID NO: 108 |
| H1 | H31--H35B | H26--H32 ... H34* | H26--H35B* | H26--H35B | H30--H35B |
|  | SEQ ID NO: 99 | SEQ ID NO: 100 | SEQ ID NO: 93 | SEQ ID NO: 93 | SEQ ID NO: 101 |
| H2 | H50--H65 | H52--H56 | H50--H65 | H50--H58 | H47--H58 |
|  | SEQ ID NO: 94 | SEQ ID NO: 102 | SEQ ID NO: 94 | SEQ ID NO: 103 | SEQ ID NO: 104 |
| H3 | H95--H102 | H95--H102 | H95--H102 | H95--H102 | H93--H101 |
|  | SEQ ID NO: 95 | SEQ ID NO: 95 | SEQ ID NO: 95 | SEQ ID NO: 95 | SEQ ID NO: 105 |

Kabat/Chothia Composite CDRs of the heavy chain of 7G6 are designated SEQ ID NOs: 121-123, respectively, and Kabat CDRs of the light chain of 7G6 are designated SEQ ID NOs: 124-126, respectively.

Table 5 indicates the 7G6 CDRs as defined by Kabat, Chothia, Composite of Chothia and Kabat (also referred to herein as "Kabat/Chothia Composite"), AbM, and Contact.

TABLE 5

7G6 CDRs as defined by Kabat, Chothia, Composite of Chothia and Kabat, AbM, and Contact

| Loop | Kabat | Chothia | Composite of Chothia & Kabat | AbM | Contact |
|---|---|---|---|---|---|
| L1 | L24--L34 | L24--L34 | L24--L34 | L24--L34 | L30--L36 |
|  | SEQ ID NO: 124 | SEQ ID NO: 124 | SEQ ID NO: 124 | SEQ ID NO: 124 | SEQ ID NO: 134 |
| L2 | L50--L56 | L50--L56 | L50--L56 | L50--L56 | L46--L55 |
|  | SEQ ID NO: 125 | SEQ ID NO: 125 | SEQ ID NO: 125 | SEQ ID NO: 125 | SEQ ID NO: 135 |
| L3 | L89--L97 | L89--L97 | L89--L97 | L89--L97 | L89--L96 |
|  | SEQ ID NO: 126 | SEQ ID NO: 126 | SEQ ID NO: 126 | SEQ ID NO: 126 | SEQ ID NO: 136 |
| H1 | H31--H35B | H26--H32 ... H34* | H26--H35B* | H26--H35B | H30--H35B |
|  | SEQ ID NO: 127 | SEQ ID NO: 128 | SEQ ID NO: 121 | SEQ ID NO: 121 | SEQ ID NO: 129 |
| H2 | H50--H65 | H52--H56 | H50--H65 | H50--H58 | H47--H58 |
|  | SEQ ID NO: 122 | SEQ ID NO: 130 | SEQ ID NO: 122 | SEQ ID NO: 131 | SEQ ID NO: 132 |
| H3 | H95--H102 | H95--H102 | H95--H102 | H95--H102 | H93--H101 |
|  | SEQ ID NO: 123 | SEQ ID NO: 123 | SEQ ID NO: 123 | SEQ ID NO: 123 | SEQ ID NO: 133 |

Other antibodies can be obtained by mutagenesis of cDNA encoding the heavy and light chains of an exemplary antibody, such as 5G8, 6A10, 8A4, 7G6, or 3D6. Monoclonal antibodies that are at least 70%, 80%, 90%, 95%, 96%, 97%, 98%, or 99% identical to 5G8, 6A10, 8A4, or 7G6 in amino acid sequence of the mature heavy and/or light chain variable regions and maintain its functional properties, and/or which differ from the respective antibody by a small number of functionally inconsequential amino acid substitutions (e.g., conservative substitutions), deletions, or insertions are also included in the invention. Monoclonal antibodies having at least one or all six CDR(s) as defined by any conventional definition, but preferably Kabat, that are 90%, 95%, 99% or 100% identical to corresponding CDRs of 5G8, 6A10, 8A4, or 7G6 are also included.

The invention also provides antibodies having some or all (e.g., 3, 4, 5, and 6) CDRs entirely or substantially from 5G8, 6A10, 8A4, or 7G6. Such antibodies can include a heavy chain variable region that has at least two, and usually all three, CDRs entirely or substantially from the heavy chain variable region of 5G8, 6A10, 8A4, or 7G6 and/or a light chain variable region having at least two, and usually all three, CDRs entirely or substantially from the light chain variable region of 5G8, 6A10, 8A4, or 7G6. The antibodies can include both heavy and light chains. A CDR is substantially from a corresponding 5G8, 6A10, 8A4, or 7G6 CDR when it contains no more than 4, 3, 2, or 1 substitutions, insertions, or deletions, except that CDR-H2 (when defined by Kabat) can have no more than 6, 5, 4, 3, 2, or 1 substitutions, insertions, or deletions. Such antibodies can have at least 70%, 80%, 90%, 95%, 96%, 97%, 98%, or 99% identity to 5G8, 6A10, 8A4, or 7G6 in the amino acid sequence of the mature heavy and/or light chain variable regions and maintain their functional properties, and/or differ from 5G8 by a small number of functionally inconsequential amino acid substitutions (e.g., conservative substitutions), deletions, or insertions.

Some antibodies identified by such assays can bind to monomeric, misfolded, aggregated, phosphorylated, or unphosphorylated forms of tau or otherwise. Likewise, some antibodies are immunoreactive on non-pathological and pathological forms and conformations of tau.

B. Non-Human Antibodies

The production of other non-human antibodies, e.g., murine, guinea pig, primate, rabbit or rat, against tau or a fragment thereof can be accomplished by, for example, immunizing the animal with tau or a fragment thereof. See Harlow & Lane, *Antibodies, A Laboratory Manual* (CSHP NY, 1988) (incorporated by reference for all purposes). Such an immunogen can be obtained from a natural source, by peptide synthesis, or by recombinant expression. Optionally, the immunogen can be administered fused or otherwise complexed with a carrier protein. Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Mice are typically used for making monoclonal antibodies. Antibodies are screened for specific binding to tau or an epitope within tau. Such screening can be accomplished by determining binding of an antibody to a collection of tau variants, and determining which tau variants bind to the antibody. Binding can be assessed, for example, by Western blot, FACS or ELISA.

C. Humanized Antibodies

A humanized antibody is a genetically engineered antibody in which CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having at least three, four, five or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by any conventional definition but preferably defined by Kabat) are identical between the respective CDRs. The variable region framework sequences of an antibody chain or the constant region of an antibody chain are substantially from a human variable region framework sequence or human constant region respectively when at least 85%, 90%, 95% or 100% of corresponding residues defined by Kabat are identical. To be classified as humanized under the 2014 World Health Organization (WHO) International non-proprietary names (INN) definition of humanized antibodies, an antibody must have at least 85% identity to human germline antibody sequences (i.e., prior to somatic hypermutation). Mixed antibodies are antibodies for which one antibody chain (e.g., heavy chain) meets the threshold but the other chain (e.g., light chain) does not meet the threshold. An antibody is classified as chimeric if neither chain meets the threshold, even though the variable framework regions for both chains were substantially human with some murine backmutations. See, Jones et al. (2016) The INNs and outs of antibody nonproprietary names, mAbs 8:1, 1-9, DOI: 10.1080/19420862.2015.1114320. See also "WHO-INN: International nonproprietary names (INN) for biological and biotechnological substances (a review)" (Internet) 2014. Available from World Health Organization website, incorporated herein by reference. For the avoidance of doubt, the term "humanized" as used herein is not intended to be limited to the 2014 WHO INN definition of humanized antibodies. Some of the humanized antibodies provided herein have at least 85% sequence identity to human germline sequences and some of the humanized antibodies provided herein have less than 85% sequence identity to human germline sequences. Some of the heavy chains of the humanized antibodies provided herein have from about 60% to 100% sequence identity to human germ line sequences, such as, for example, in the range of about 60% to 69%, 70% to 79%, 80% to 84%, or 85% to 89%. Some heavy chains fall below the 2014 WHO INN definition and have, for example, about 64%, 65%, 66%, 67%, 68%, 69%, 70%, 71%, 72%, 73%, 74%, 75%, 76%, 77%, 78%, 79%, 80%, 81%, or 82%, 83%, or 84% sequence identity to human germ line sequences, while other heavy chains meet the 2014 WHO INN definition and have about 85%, 86%, 87%, 88%, 89% or greater sequence identity to human germ line sequences. Some of the light chains of the humanized antibodies provided herein have from about 60% to 100% sequence identity to human germ line sequences, such as, for example, in the range of about 80% to 84% or 85% to 89%. Some light chains fall below the 2014 WHO INN definition and have, for example, about 81%, 82%, 83% or 84% sequence identity to human germ line sequences, while other light chains meet the 2014 WHO INN definition and have about 85%, 86%, 87%, 88%, 89% or greater sequence identity to human germ line sequences. Some humanized antibodies provided herein that are "chimeric" under the 2014 WHO INN definition have heavy chains with less than 85% identity to human germ line sequences paired with light chains having less than 85% identity to human germ line sequences. Some humanized antibodies provided herein are "mixed" under the 2014 WHO INN definition, for example, having a heavy chain with at least 85% sequence identity to human germ line sequences paired with a light chain having less than 85% sequence identity to human germ line sequences, or vice versa. Some humanized antibodies provided herein meet the 2014 WHO INN definition of "humanized" and have a heavy chain with at least 85% sequence identity to human germ line sequences paired with a light chain having at least 85% sequence identity to human germ line sequences. Exemplary 5G8 antibodies that meet the 2014 WHO INN definition of "humanized" include antibodies having a mature heavy chain with the amino acid sequence of SEQ ID NO:39 paired with a mature light chain sequence having an amino acid sequence of SEQ ID NO:41, SEQ ID NO:42, SEQ ID NO:43, SEQ ID NO:45, or SEQ ID NO:46. Additional humanized 5G8 antibodies of the invention include antibodies having a mature heavy chain having an amino acid sequence of any of SEQ ID NOs: 33-40 paired with a mature light chain having an amino acid sequence of any of SEQ ID NOs: 41-46. Humanized 6A10 antibodies of the invention include antibodies having a mature heavy chain having an amino acid sequence of any of SEQ ID NOs: 85-87 paired with a mature light chain having an amino acid sequence of any of SEQ ID NOs: 88-90. Humanized 8A4 antibodies of the invention include antibodies having a mature heavy chain having an amino acid sequence of any of SEQ ID NOs: 113-115 paired with a mature light chain having an amino acid sequence of any of SEQ ID NOs: 116-118. Humanized 7G6 antibodies of the invention include antibodies having a mature heavy chain having an amino acid sequence of any of SEQ ID NOs: 139-140 paired with a mature light chain having an amino acid sequence of any of SEQ ID NOs: 141-148.

Although humanized antibodies often incorporate all six CDRs (defined by any conventional definition but preferably as defined by Kabat) from a mouse antibody, they can also be made with less than all CDRs (e.g., at least 3, 4, or 5 CDRs) from a mouse antibody (e.g., Pascalis et al., *J. Immunol.* 169:3076, 2002; Vajdos et al., *J. of Mol. Biol.,* 320: 415-428, 2002; Iwahashi et al., *Mol. Immunol.* 36:1079-1091, 1999; Tamura et al, *J. Immunol.,* 164:1432-1441, 2000).

In some antibodies only part of the CDRs, namely the subset of CDR residues required for binding, termed the SDRs, are needed to retain binding in a humanized antibody. CDR residues not contacting antigen and not in the SDRs can be identified based on previous studies (for example residues H60-H65 in CDR H2 are often not required), from regions of Kabat CDRs lying outside Chothia hypervariable loops (Chothia, *J. Mol. Biol.* 196:901, 1987), by molecular modeling and/or empirically, or as described in Gonzales et al., *Mol. Immunol.* 41: 863, 2004. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity and/or for meeting the WHO INN definition of "humanized". However, substitutions can also cause changes of affinity, and significant reductions in affinity are preferably avoided. Positions for substitution within CDRs and amino acids to substitute can also be selected empirically.

The human acceptor antibody sequences can optionally be selected from among the many known human antibody sequences to provide a high degree of sequence identity (e.g., 65-85% identity) between a human acceptor sequence variable region frameworks and corresponding variable region frameworks of a donor antibody chain.

An example of an acceptor sequence for the 5G8 heavy chain is the humanized anti-dabigatran aDabi-Fab2b-VH with NCBI accession code 4YHM_H (SEQ ID NO:28). Another example of an acceptor sequence for the 5G8 heavy chain is the human germline gene IGHV1-46 with NCBI accession code P01743.2 (SEQ ID NO:29). An example of an acceptor sequence for the 5G8 light chain is the humanized anti-dabigatran aDabi-Fab2b-VL with NCBI accession code 4YHM_L (SEQ ID NO:31). Another example of an acceptor sequence for the 5G8 light chain is the human germline gene IGKV2-29 with NCBI accession code A2NJV5.2 (SEQ ID NO:32).

An example of an acceptor sequence for the 6A10 heavy chain is the human heavy chain variable region with accession #ACR16112 (SEQ ID NO:81). An example of an acceptor sequence for the 6A10 light chain is the human kappa light chain variable region with accession #ABC66863 (SEQ ID NO:83).

An example of an acceptor sequence for the 8A4 heavy chain is the human heavy chain variable region with accession #ADU57742 (SEQ ID NO:110). An example of an acceptor sequence for the 8A4 light chain is the human kappa light chain variable region with accession #ABA26100 (SEQ ID NO:112).

An example of an acceptor sequence for the 7G6 heavy chain is the VH region of a human antibody with accession #PDB 3U0T_VH (SEQ ID NO:137). An example of an acceptor sequence for the 7G6 light chain is the VL region of a human antibody with accession #PDB 3U0T_VL (SEQ ID NO:138).

If more than one human acceptor antibody sequence is selected, a composite or hybrid of those acceptors can be used, and the amino acids used at different positions in the humanized light chain and heavy chain variable regions can be taken from any of the human acceptor antibody sequences used.

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly;
(2) is adjacent to a CDR region or within a CDR as defined by Chothia but not Kabat;
(3) otherwise interacts with a CDR region (e.g., is within about 6 Å of a CDR region), (e.g., identified by modeling the light or heavy chain on the solved structure of a homologous known immunoglobulin chain); or
(4) is a residue participating in the VL-VH interface.

The invention provides humanized forms of the murine 5G8 antibody including 8 exemplified humanized heavy chain mature variable regions (hu5G8-VH_v1 (SEQ ID NO:33), hu5G8-VH_v2 (SEQ ID NO:34), hu5G8-VH v3 (SEQ ID NO:35), hu5G8-VH v4 (SEQ ID NO:36), hu5G8-VH v5 (SEQ ID NO:37), hu5G8-VH_v6 (SEQ ID NO:38), hu5G8-VH_v7 (SEQ ID NO:39), and hu5G8-VH_v8 (SEQ ID NO:40)), and 6 exemplified humanized light chain mature variable regions (hu5G8-VL_v1 (SEQ ID NO:41, hu5G8-VL v2 (SEQ ID NO:42), hu5G8-VL_v3 (SEQ ID NO:43), hu5G8-VL v4 (SEQ ID NO:44), hu5G8-VL v5 (SEQ ID NO:45), and hu5G8-VL_v6 (SEQ ID NO:46)).

The invention provides humanized forms of the murine 6A10 antibody including 3 exemplified humanized heavy chain mature variable regions (hu6A10-VH_v1 (SEQ ID NO:85), hu6A10-VH_v2 (SEQ ID NO:86), and hu6A10-VH_v3 (SEQ ID NO:87)), and 3 exemplified humanized light chain mature variable regions (hu6A10-VL v1 (SEQ ID NO:88), hu6A10-VL_v2 (SEQ ID NO:89), and hu6A10-VL_v3 (SEQ ID NO:90)).

The invention provides humanized forms of the murine 8A4 antibody including 3 exemplified humanized heavy chain mature variable regions (hu8A4-VH_v1 (SEQ ID NO:113), hu8A4-VH_v2 (SEQ ID NO:114), and hu8A4-VH_v3 (SEQ ID NO:115)), and 3 exemplified humanized light chain mature variable regions (hu8A4-VL v1 (SEQ ID NO:116), hu8A4-VL_v2 (SEQ ID NO: 117), and hu8A4-VL_v3 (SEQ ID NO: 118)).

The invention provides humanized forms of the murine 7G6 antibody including 2 exemplified humanized heavy chain mature variable regions (hu7G6-VH_v1 (SEQ ID NO:139) and hu7G6-VH v2 (SEQ ID NO:140), and 8 exemplified humanized light chain mature variable regions (hu7G6-VL v1 (SEQ ID NO:141), hu7G6-VL v2 (SEQ ID NO:142), hu7G6-VL_v3 (SEQ ID NO:143), hu7G6-VL_v4

(SEQ ID NO:144), hu7G6-VL v5 (SEQ ID NO:145), hu7G6-VL_v6 (SEQ ID NO:146), hu7G6-VL v7 (SEQ ID NO:147), and hu7G6-VL v8 (SEQ ID NO:148)).

In an embodiment, humanized sequences are generated using a two-stage PCR protocol that allows introduction of multiple mutations, deletions, and insertions using QuikChange site-directed mutagenesis [Wang, W. and Malcolm, B. A. (1999) BioTechniques 26:680-682)].

Framework residues from classes (1) through (3) as defined by Queen, U.S. Pat. No. 5,530,101, are sometimes alternately referred to as canonical and vernier residues. Framework residues that help define the conformation of a CDR loop are sometimes referred to as canonical residues (Chothia & Lesk, J. Mol. Biol. 196:901-917 (1987); Thornton & Martin, J. Mol. Biol. 263:800-815 (1996)). Framework residues that support antigen-binding loop conformations and play a role in fine-tuning the fit of an antibody to antigen are sometimes referred to as vernier residues (Foote & Winter, J. Mol. Biol 224:487-499 (1992)).

Other framework residues that are candidates for substitution are residues creating a potential glycosylation site. Still other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins.

Other framework residues that are candidates for substitution are N-terminal glutamine residues (Q) that may be replaced with glutamic acid (E) to minimize potential for pyroglutamate conversion [Y. Diana Liu, et al., 2011, J. Biol. Chem., 286: 11211-11217]. Glutamic acid (E) conversion to pyroglutamate (pE) occurs more slowly than from glutamine (Q). Because of the loss of a primary amine in the glutamine to pE conversion, antibodies become more acidic. Incomplete conversion produces heterogeneity in the antibody that can be observed as multiple peaks using charge-based analytical methods. Heterogeneity differences may indicate a lack of process control. Exemplary humanized antibodies with N-terminal glutamine to glutamate substitutions are SEQ ID NO:35 (hu5G8-VH v3), SEQ ID NO:36 (hu5G8-VH v4), SEQ ID NO:37 (hu5G8-VH v5), SEQ ID NO:38 (hu5G8-VH_v6), and SEQ ID NO:40 (hu5G8-VH_v8).

Exemplary humanized antibodies are humanized forms of the mouse 5G8, designated Hu5G8.

The mouse antibody 5G8 comprises mature heavy and light chain variable regions having amino acid sequences comprising SEQ ID NO: 7 and SEQ ID NO:8, respectively. The invention provides 8 exemplified humanized mature heavy chain variable regions: hu5G8-VH_v1, hu5G8-VH_v2, hu5G8-VH_v3, hu5G8-VH_v4, hu5G8-VH_v5, hu5G8-VH_v6, hu5G8-VH_v7, and hu5G8-VH_v8. The invention further provides 6 exemplified human mature light chain variable regions: hu5G8-VL v1, hu5G8-VL_v2, hu5G8-VL_v3, hu5G8-VL_v4, hu5G8-VL_v5, and hu5G8-VL_v6. Alignments of the murine 5G8 and various humanized antibodies are shown for the light chain variable regions (Table 6 and FIGS. 6A and 6B), and heavy chain variable regions (Table 7 and FIGS. 5A and 5B).

For reasons such as possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, getting aggregation potential, and other reasons, the following 23 variable region framework positions of 5G8 were considered as candidates for substitutions in the 6 exemplified human mature light chain variable regions and the 8 exemplified human mature heavy chain variable regions, as further specified in Example 6: L2 (I2V), L7 (T7S), L17 (Q17E), L36 (Y36L), L45 (K45Q), L46 (G46R), L70 (G70D), H1 (Q1E), H11 (V11L), H12 (K12V), H19 (K19R), H20 (V20L), H23 (K23A), H46 (E46D), H48 (M48I), H66 (K66R), H67 (A67V), H71 (R71S), H76 (S76N), H78 (A78V), H80 (M80L), H93 (T93S or T93A), H94 (194P or 194R).

Here, as elsewhere, the first-mentioned residue is the residue of a humanized antibody formed by grafting Kabat CDRs or a composite Chothia-Kabat CDR in the case of CDR-H1 into a human acceptor framework, and the second-mentioned residue is a residue being considered for replacing such residue. Thus, within variable region frameworks, the first mentioned residue is human, and within CDRs, the first mentioned residue is mouse.

Exemplified antibodies include any permutations or combinations of the exemplified mature heavy and light chain variable regions of 5G8 e.g., hu5G8VH_v1/hu5G8VL_v1, hu5G8VH_v1/hu5G8VL_v2, hu5G8VH_v1/hu5G8VL_v3, hu5G8VH_v1/hu5G8VL_v4, hu5G8VH v1/hu5G8VL v5, hu5G8VH v1/hu5G8VL v6, hu5G8VH v2/hu5G8VL v1, hu5G8VH_v2/hu5G8VL_v2, hu5G8VH_v2/hu5G8VL_v3, hu5G8VH_v2/hu5G8VL_v4, hu5G8VH_v2/hu5G8VL_v5, hu5G8VH_v2/hu5G8VL_v6, hu5G8VH_v3/hu5G8VL_v1, hu5G8VH_v3/hu5G8VL_v2, hu5G8VH_v3/hu5G8VL_v3, hu5G8VH_v3/hu5G8VL_v4, hu5G8VH v3/hu5G8VL v5, hu5G8VH v3/hu5G8VL v6, hu5G8VH v4/hu5G8VL v1, hu5G8VH_v4/hu5G8VL_v2, hu5G8VH_v4/hu5G8VL_v3, hu5G8VH_v4/hu5G8VL_v4, hu5G8VH_v4/hu5G8VL_v5, hu5G8VH_v4/hu5G8VL_v6, hu5G8VH_v5/hu5G8VL_v1, hu5G8VH_v5/hu5G8VL_v2, hu5G8VH_v5/hu5G8VL_v3, hu5G8VH_v5/hu5G8VL_v4, hu5G8VH v5/hu5G8VL v5, hu5G8VH v5/hu5G8VL v6, hu5G8VH v6/hu5G8VL_v1, hu5G8VH_v6/hu5G8VL_v2, hu5G8VH_v6/hu5G8VL_v3, hu5G8VH_v6/hu5G8VL_v4, hu5G8VH_v6/hu5G8VL_v5, hu5G8VH_v6/hu5G8VL_v6, hu5G8VH_v7/hu5G8VL_v1, hu5G8VH_v7/hu5G8VL_v2, hu5G8VH_v7/hu5G8VL_v3, hu5G8VH_v7/hu5G8VL_v4, hu5G8VH v7/hu5G8VL v5, hu5G8VH v7/hu5G8VL v6, hu5G8VH v8/hu5G8VL v1, hu5G8VH_v8/hu5G8VL_v2, hu5G8VH_v8/hu5G8VL_v3, hu5G8VH_v8/hu5G8VL_v4, hu5G8VH_v8/hu5G8VL_v5, or hu5G8VH_v8/hu5G8VL_v6.

The invention provides variants of the 5G8 humanized antibody in which the humanized mature heavy chain variable region shows at least 90%, 95%, 96%, 97%, 98%, or 99% identity to hu5G8-VH_v1, hu5G8-VH_v2, hu5G8-VH_v3, hu5G8-VH_v4, hu5G8-VH_v5, hu5G8-VH_v6, hu5G8-VH_v7, and hu5G8-VH_v8. (SEQ ID NOs: 33-40) and the humanized mature light chain variable region shows at least 90%, 95%, 96%, 97%, 98%, or 99% identity to hu5G8-VL_v1, hu5G8-VL_v2, hu5G8-VL_v3, hu5G8-VL_v4, hu5G8-VL_v5, and hu5G8-VL v6 (SEQ ID NO: 41-46). In some such antibodies at least 1, 2, 3, 4, 5, 6, 7, 8, 9, 10, 11, 12, 13, 14, 15, 16, 17, 18, 19, 20, 21, 22, or all 23 of the backmutations or other mutations found in SEQ ID NOs:33-40 and SEQ ID NOs:41-46 are retained.

In some humanized 5G8 antibodies, at least one of the following positions is occupied by the amino acid as specified: H48 is occupied by I, H71 is occupied by S, H93 is occupied by S, and H94 is occupied by P. In some humanized 5G8 antibodies, positions H48, H71, H93, and H94 in the VH region are occupied by I, S, S, and P, respectively.

In some humanized 5G8 antibodies, at least one of the following positions is occupied by the amino acid as specified: H1 is occupied by E, H48 is occupied by I, H71 is occupied by S, H93 is occupied by S, and H94 is occupied by P. In some humanized 5G8 antibodies, positions H1, H48, H71, H93, and H94 in the VH region are occupied by E, I, S, S, and P, respectively.

In some humanized 5G8 antibodies, at least one of the following positions is occupied by the amino acid as specified: H1 is occupied by E, H46 is occupied by D, H48 is occupied by I, H71 is occupied by S, H93 is occupied by S, and H94 is occupied by P. In some humanized 5G8 antibodies, positions H1, H46, H48, H71, H93, and H94 in the VH region are occupied by E, D, I, S, S, and P, respectively.

In some humanized 5G8 antibodies, at least one of the following positions is occupied by the amino acid as specified: H1 is occupied by E, H11 is occupied by L, H12 is occupied by V, H19 is occupied by R, H20 is occupied by L, H46 is occupied by D, H48 is occupied by I, H71 is occupied by S, H76 is occupied by N, H80 is occupied by L, H93 is occupied by S, and H94 is occupied by P. In some humanized 5G8 antibodies, positions H1, H11, H12, H19, H20, H46, H48, H71, H76, H80, H93, and H94 in the VH region are occupied by E, L, V, R, L, D, I, S, N, L, S, and P, respectively.

In some humanized 5G8 antibodies, at least one of the following positions is occupied by the amino acid as specified: H66 is occupied by R, H67 is occupied by V, and H78 is occupied by V. In some humanized 5G8 antibodies, positions H66, H67, and H78 in the VH region are occupied by R, V, and V, respectively.

In some humanized 5G8 antibodies, at least one of the following positions is occupied by the amino acid as specified: H1 is occupied by Q or E, H11 is occupied by V or L, H12 is occupied by K or V, H19 is occupied by K or R, H20 is occupied by V or L, H23 is occupied by K or A, H46 is occupied E or D, H48 is occupied by M or I, H66 is occupied by K or R, H67 is occupied by A or V, H71 is occupied by R or S, H76 is occupied by S or N, H78 is occupied by A or V, H80 is occupied by M or L, H93 is occupied by T, S, or A, and H94 is occupied by I, P, or R.

In some humanized 5G8 antibodies, positions H48, H71, H93, and H94 in the VH region are occupied by I, S, S, and P, respectively, as in hu5G8-VH_v2. In some humanized 5G8 antibodies, positions H1, H48, H71, H93, and H94 in the VH region are occupied by E, I, S, S, and P, respectively, as in hu5G8-VH_v3. In some humanized 5G8 antibodies, positions H1, H46, H48, H71, H93, and H94 in the VH region are occupied by E, D, I, S, S, and P, respectively, as in hu5G8-VH_v4. In some humanized 5G8 antibodies, positions H1, H11, H12, H19, H20, H46, H48, H71, H76, H80, H93, and H94 in the VH region are occupied by E, L, V, R, L, D, I, S, N, L, S, and P, respectively, as in hu5G8-VH_v5. In some humanized 5G8 antibodies, positions H1, H11, H12, H19, H20, H23, H46, H48, H71, H76, H80, H93, and H94 in the VH region are occupied by E, L, V, R, L, A, D, I, S, N, L, S, and P, respectively, as in hu5G8-VH_v6. In some humanized 5G8 antibodies, positions H66, H67, H78, H93, and H94 in the VH region are occupied by R, V, V, A, and R, respectively, as in hu5G8-VH_v7. In some humanized 5G8 antibodies, positions H1, H46, H48, H66, H67, H71, H78, H93, and H94 in the VH region are occupied by E, D, I, R, V, S, V, S, and P, respectively, as in hu5G8-VH_v8.

In some humanized 5G8 antibodies, at least one of the following positions is occupied by the amino acid as specified: L2 is occupied by V, L36 is occupied by L, and L46 is occupied by R. In some humanized 5G8 antibodies, positions L2, L36, and L46 in the VL region are occupied by V, L, and R, respectively.

In some humanized 5G8 antibodies, at least one of the following positions is occupied by the amino acid as specified: L2 is occupied by V, L36 is occupied by L, L46 is occupied by R, and L70 is occupied by D. In some humanized 5G8 antibodies, positions L2, L36, L46, and L70 in the VL region are occupied by V, L, R, and D, respectively.

In some humanized 5G8 antibodies, at least one of the following positions is occupied by the amino acid as specified: L45 is occupied by Q and L70 is occupied by D. In some humanized 5G8 antibodies, positions L45 and L70 in the VL region are occupied by Q and D, respectively.

In some humanized 5G8 antibodies, at least one of the following positions is occupied by the amino acid as specified: L2 is occupied by I or V, L7 is occupied by T or S, L17 is occupied by Q or E, L36 is occupied by Y or L, L45 is occupied by K or Q, L46 is occupied by L or R, and L70 is occupied by G or D.

In some humanized 5G8 antibodies, provided positions L2, L36, L46 in the VL region are occupied by V, L, and R, respectively, as in hu5G8-VL_v2. In some humanized 5G8 antibodies, positions L2, L36, L46, and L70 in the VL region are occupied by V, L, R, and D, respectively, as in hu5G8-VL_v3. In some humanized 5G8 antibodies, positions L2, L7, L17, L36, L46, and L70 in the VL region are occupied by V, S, E, L, R, and D, respectively, as in hu5G8-VL_v4. In some humanized 5G8 antibodies, positions L45 and L70 in the VL region are occupied by Q and D, respectively, as in hu5G8-VL_v5. In some humanized 5G8 antibodies, positions L2, L36, L45, L46, L70 in the VL region are occupied by V, L, Q, R, and D, respectively, as in hu5G8-VL_v6.

Exemplary humanized antibodies are humanized forms of the mouse 6A10, designated Hu6A10.

The mouse antibody 6A10 comprises mature heavy and light chain variable regions having amino acid sequences comprising SEQ ID NO: 63 and SEQ ID NO:64 respectively. The invention provides 3 exemplified humanized 6A10 mature heavy chain variable regions: hu6A10-VH_v1, hu6A10-VH_v2, and hu6A10-VH_v3. The invention further provides 3 exemplified human 6A10 mature light chain variable regions: hu6A10-VL v1, hu6A10-VL_v2, and hu6A10-VL_v3. Alignments of the murine 6A10 and various humanized antibodies are shown for the light chain variable regions (Tables 12 and FIG. 8), and heavy chain variable regions (Table 13 and FIG. 7).

For reasons such as possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, getting aggregation potential, and other reasons, the following 7 variable region framework positions were considered as candidates for substitutions in the 3 exemplified human mature light chain variable regions and the 3 exemplified human mature heavy chain variable regions, as further specified in Example 7: L12 (P12S), L17 (Q17E), L46 (R46L), H16 (A16G), H48 (M48I), H69 (T69I), and H80 (M80L).

Here, as elsewhere, the first-mentioned residue is the residue of a humanized antibody formed by grafting Kabat CDRs or a composite Chothia-Kabat CDR in the case of CDR-H1 into a human acceptor framework, and the second-mentioned residue is a residue being considered for replacing such residue. Thus, within variable region frameworks, the first mentioned residue is human, and within CDRs, the first mentioned residue is mouse.

Exemplified 6A10 antibodies include any permutations or combinations of the exemplified mature heavy and light chain variable regions e.g., hu6A10VH_v1/hu6A10VL_v1, hu6A10VH_v1/hu6A10VL_v2, hu6A10VH_v1/hu6A10-VL_v3, hu6A10VH_v2/hu6A10VL_v1, hu6A10VH_v2/hu6A10VL_v2, hu6A10VH_v2/hu6A10VL_v3, hu6A10-VH_v3/hu6A10VL_v1, hu6A10VH_v3/hu6A10VL_v2, or hu6A10VH_v3/hu6A10VL_v3.

The invention provides variants of the 6A10 humanized antibody in which the humanized mature heavy chain variable region shows at least 90%, 95%, 96%, 97%, 98%, or 99% identity to hu6A10-VH v1, hu6A10-VH_v2, and hu6A10-VH_v3, (SEQ ID NOs: 85-87) and the humanized mature light chain variable region shows at least 90%, 95%, 96%, 97%, 98%, or 99% identity to hu6A10-VL_v1, hu6A10-VL_v2, hu6A10-VL_v3 (SEQ ID NO: 88-90). In some such antibodies at least 1, 2, 3, 4, 5, 6, or all 7 of the backmutations or other mutations found in SEQ ID NOs: 85-87 and SEQ ID NOs:88-90 are retained.

In some humanized 6A10 antibodies, position H48 in the VH region is occupied by I.

In some humanized 6A10 antibodies, at least one of the following positions in the VH region is occupied by the amino acid as specified: H16 is occupied by A or G, H48 is occupied by M or I, H69 is occupied by T or I, and H80 is occupied by M or L.

In some humanized 6A10 antibodies, position H48 in the VH region is occupied by I as in hu6A10-VH_v2. In some humanized 6A10 antibodies, positions H16, H48, H69, and H80 in the VH region are occupied by G, I, I, and L, respectively, as in hu6A10-VH_v3.

In some humanized 6A10 antibodies, position L46 in the VL region is occupied by L.

In some humanized 6A10 antibodies, at least one of the following positions in the VL region is occupied by the amino acid as specified: L12 is occupied by P or S, L17 is occupied by Q or E, and L46 is occupied by R or L.

In some humanized 6A10 antibodies, position L46 in the VL region are occupied by L, as in hu6A10-VL_v2. In some humanized 6A10 antibodies, positions L12, L17, and L46 in the VL region are occupied by S, E, and L, respectively, as in hu6A10-VL_v3.

Exemplary humanized antibodies are humanized forms of the mouse 8A4, designated Hu8A4.

The mouse antibody 8A4 comprises mature heavy and light chain variable regions having amino acid sequences comprising SEQ ID NO:91 and SEQ ID NO:92 respectively. The invention provides 3 exemplified humanized mature heavy chain variable regions: hu8A4-VH_v1, hu8A4-VH_v2, and hu8A4-VH_v3. The invention further provides 3 exemplified human mature light chain variable regions: hu8A4-VL v1, hu8A4-VL_v2, and hu8A4-VL_v3. Alignments of the murine 8A4 and various humanized antibodies are shown for the light chain variable regions (Table 18 and FIG. 10), and heavy chain variable regions (Table 19 and FIG. 9).

For reasons such as possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, getting aggregation potential, and other reasons, the following 11 variable region framework positions of 8A4 were considered as candidates for substitutions in the 3 exemplified human mature light chain variable regions and the 3 exemplified human mature heavy chain variable regions, as further specified in Example 8: L2 (I2V), L17 (Q17E), L36 (F36L), H12 (K12V), H16 (S16G), H20 (V20L), H48 (M48I), H67 (I67A), H68 (N68T), H85 (D85E), and H93 (A93S).

Here, as elsewhere, the first-mentioned residue is the residue of a humanized antibody formed by grafting Kabat CDRs or a composite Chothia-Kabat CDR in the case of CDR-H1 into a human acceptor framework, and the second-mentioned residue is a residue being considered for replacing such residue. Thus, within variable region frameworks, the first mentioned residue is human, and within CDRs, the first mentioned residue is mouse.

Exemplified 8A4 antibodies include any permutations or combinations of the exemplified mature heavy and light chain variable regions e.g., hu8A4VH_v1/hu8A4VL v1, hu8A4VH_v1/hu8A4VL_v2, hu8A4VH_v1/hu8A4VL v3, hu8A4VH_v2/hu8A4VL_v1, hu8A4VH_v2/hu8A4VL_v2, hu8A4VH_v2/hu8A4VL_v3, hu8A4VH_v3/hu8A4VL_v1, hu8A4VH_v3/hu8A4VL_v2, or hu8A4VH_v3/hu8A4VL_v3.

The invention provides variants of the 8A4 humanized antibody in which the humanized mature heavy chain variable region shows at least 90%, 95%, 96%, 97%, 98%, or 99% identity to hu8A4-VH_v1, hu8A4-VH_v2, and hu8A4-VH_v3, (SEQ ID NOs: 113-115) and the humanized mature light chain variable region shows at least 90%, 95%, 96%, 97%, 98%, or 99% identity to hu8A4-VL_v1, hu8A4-VL_v2, hu8A4-VL_v3 (SEQ ID NO: 116-118). In some such antibodies at least 1, 2, 3, 4, 5, 6, 7, 8, 9, 10, or 11 of the backmutations or other mutations found in SEQ ID NOs:113-115 and SEQ ID NOs:116-118 are retained.

In some humanized 8A4 antibodies, position H93 in the VH region is occupied by S.

In some humanized 8A4 antibodies, at least one of the following positions in the VH region is occupied by the amino acid as specified: H12 is occupied by V, H16 is occupied by G, H20 is occupied by L, and H68 is occupied by T. In some humanized 8A4 antibodies, positions H12, H16, H20, and H68 in the VH region are occupied by V, G, L, and T, respectively.

In some humanized 8A4 antibodies, at least one of the following positions in the VH region is occupied by the amino acid as specified: H12 is occupied by K or V, H16 is occupied by S or G, H20 is occupied by V or L, H48 is occupied by M or I, H67 is occupied by A or I, H68 is occupied by N or T, H85 is occupied by D or E, and H93 is occupied by S or A.

In some humanized 8A4 antibodies, position H93 in the VH region is occupied by S, as in hu8A4VH_v1. In some humanized 8A4 antibodies, position H12, positions H16, H20, H68, and H93 in the VH region are occupied by V, G, L, T, and S, respectively, as in hu8A4VH_v2. In some humanized 8A4 antibodies, positions H12, H16, H20, H48, H67, H68, and H85 in the VH region are occupied by V, G, L, I, A, T, and E, respectively, as in hu8A4VH_v3.

In some humanized 8A4 antibodies, position L17 in the VL region is occupied by E.

In some humanized 8A4 antibodies, at least one of the following positions in the VL region is occupied by the amino acid as specified: L2 is occupied by I or V, L17 is occupied by Q or E, and L36 is occupied by F or L.

In some humanized 8A4 antibodies, position L17 in the VL region is occupied by E, as in hu8A4-VL_v2. In some humanized 8A4 antibodies, positions L2, L17, and L36 in the VL region are occupied by V, E. and L, respectively, as in hu8A4-VL_v3.

Exemplary humanized antibodies are humanized forms of the mouse 7G6, designated Hu7G6.

The mouse antibody 7G6 comprises mature heavy and light chain variable regions having amino acid sequences comprising SEQ ID NO: 119 and SEQ ID NO:120 respectively. The invention provides 2 exemplified humanized mature heavy chain variable regions: hu7G6-VH_v1 and hu7G6-VH_v2. The invention further provides 8 exemplified human mature light chain variable regions: hu7G6-VL_v1, hu7G6-VL_v2, hu7G6-VL_v3, hu7G6-VL_v4, hu7G6-VL_v5, hu7G6-VL_v6, hu7G6-VL_v7, and hu7G6-VL_v8. Alignments of the murine 7G6 and various humanized antibodies are shown for the light chain variable regions (Table 25 and FIGS. 12A and 12B), and heavy chain variable regions (Table 26 and FIG. 11).

For reasons such as possible influence on CDR conformation and/or binding to antigen, mediating interaction between heavy and light chains, interaction with the constant region, being a site for desired or undesired post-translational modification, being an unusual residue for its position in a human variable region sequence and therefore potentially immunogenic, getting aggregation potential, and other reasons, the following 16 variable region framework positions of 7G6 were considered as candidates for substitutions in the 8 exemplified human mature light chain variable regions and the 2 exemplified human mature heavy chain variable regions, as further specified in Example 9: L12 (P12S), L36 (F36L), L37 (Q37L), L45 (R45K), L100 (Q100G), L103 (R103K), H12 (K12V), H20 (V20L), H38 (R39K), H69 (M69I), H76 (S76N), H78 (V78A), H80 (M80L), H81 (E81Q), H92 (C92S), and H93 (A93T).

Here, as elsewhere, the first-mentioned residue is the residue of a humanized antibody formed by grafting Kabat CDRs or a composite Chothia-Kabat CDR in the case of CDR-H1 into a human acceptor framework, and the second-mentioned residue is a residue being considered for replacing such residue. Thus, within variable region frameworks, the first mentioned residue is human, and within CDRs, the first mentioned residue is mouse.

Exemplified 7G6 antibodies include any permutations or combinations of the exemplified mature heavy and light chain variable regions e.g., hu7G6VH_v1/hu7G6VL v1, hu7G6VH_v1/hu7G6VL_v2, hu7G6VH_v1/hu7G6VL_v3, hu7G6VH_v1/hu7G6VL_v4, hu7G6VH_v1/hu7G6VL_v5, hu7G6VH_v1/hu7G6VL v6, hu7G6VH_v1/hu7G6VL_v7, hu7G6VH_v1/hu7G6VL_v8, hu7G6VH_v2/hu7G6VL v1, hu7G6VH_v2/hu7G6VL_v2, hu7G6VH_v2/hu7G6VL_v3, hu7G6VH_v2/hu7G6VL_v4, hu7G6VH_v2/hu7G6VL_v5, hu7G6VH_v2/hu7G6VL_v6, hu7G6VH_v2/hu7G6VL_v7, or hu7G6VH_v2/hu7G6VL_v8.

The invention provides variants of the 7G6 humanized antibody in which the humanized mature heavy chain variable region shows at least 90%, 95%, 96%, 97%, 98%, or 99% identity to hu7G6-VH_v1, and hu7G6-VH_v2, (SEQ ID NOs: 139-140) and the humanized mature light chain variable region shows at least 90%, 95%, 96%, 97%, 98%, or 99% identity to hu7G6-VL_v1, hu7G6-VL_v2, hu7G6-VL_v3, hu7G6-VL_v4, hu7G6-VL_v5, hu7G6-VL_v6, hu7G6-VL_v7, and hu7G6-VL_v8 (SEQ ID NO: 141-148). In some such antibodies at least 1, 2, 3, 4, 5, 6, 7, 8, 9, 10, 11, 12, 13, 14, 15, 16, or all 17 of the backmutations or other mutations found in SEQ ID NOs:139-140 and SEQ ID NOs:141-148 are retained.

In some humanized 7G6 antibodies, at least one of the following positions in the VH region is occupied by the amino acid as specified: H12 is occupied by V, H20 is occupied by L, H69 is occupied by I, H76 is occupied by N, H78 is occupied by A, H80 is occupied by L, H81 is occupied by Q, H92 is occupied by S, and H93 is occupied by T. In some humanized 7G6 antibodies, positions H12, H20, H69, H76, H78, H80, H81, H92, H93 in the VH region are occupied by V, L, I, N, A, L, Q, S, and T, respectively.

In some humanized 7G6 antibodies, at least one of the following positions in the VH region is occupied by the amino acid as specified: H12 is occupied by K or V, H20 is occupied by V or L, H38 is occupied by R or K, H69 is occupied by M or I, H76 is occupied by S or N, H78 is occupied by V or A, H80 is occupied by M or L, H81 is occupied by E or Q, H92 is occupied by C or S, and H93 is occupied by A or T.

In some humanized 7G6 antibodies, positions H12, H20, H69, H76, H78, H80, H81, H92, H93 in the VH region are occupied by V, L, I, N, A, L, Q, S, and T, respectively, as in hu7G6-VH_v1. In some humanized 7G6 antibodies, positions H12, H20, H38, H69, H76, H78, H80, H81, H92, H93 in the VH region are occupied by V, L, K, I, N, A, L, Q, S, and T, respectively, as in hu7G6-VH_v2.

In some humanized 7G6 antibodies, at least one of the following positions in the VL region is occupied by the amino acid as specified: L12 is occupied by S and L103 is occupied by K. In some humanized 7G6 antibodies, positions L12 and L103 in the VL region are occupied by S and K, respectively.

In some humanized 7G6 antibodies, at least one of the following positions in the VL region is occupied by the amino acid as specified: L12 is occupied by S, L36 is occupied by L, and L103 is occupied by K. In some humanized 7G6 antibodies, positions L12, L36, and L103 in the VL region are occupied by S, L, and K, respectively.

In some humanized 7G6 antibodies, at least one of the following positions in the VL region is occupied by the amino acid as specified: L12 is occupied by S, L37 is occupied by L, and L103 is occupied by K. In some humanized 7G6 antibodies, positions L12, L37, and L103 in the VL region are occupied by S, L, and K, respectively.

In some humanized 7G6 antibodies, at least one of the following positions in the VL region is occupied by the amino acid as specified: L12 is occupied by S, L36 is occupied by L, L37 is occupied by L, and L103 is occupied by K. In some humanized 7G6 antibodies, positions L12, L36, L37, and L103 in the VL region are occupied by S, L, L, and K, respectively.

In some humanized 7G6 antibodies, at least one of the following positions in the VL region is occupied by the amino acid as specified: L12 is occupied by S, L45 is occupied by K, and L103 is occupied by K. In some humanized 7G6 antibodies, positions L12, L45, and L103 in the VL region are occupied by S, K, and K, respectively.

In some humanized 7G6 antibodies, at least one of the following positions in the VL region is occupied by the amino acid as specified: L12 is occupied by S, L100 is occupied by G, and L103 is occupied by K. In some humanized 7G6 antibodies, positions L12, L100, and L103 in the VL region are occupied by S, G, and K, respectively.

In some humanized 7G6 antibodies, at least one of the following positions in the VL region is occupied by the amino acid as specified: L36 is occupied by F or L, L37 is occupied by Q or L, L45 is occupied by R or K, or L100 is occupied by Q or G.

In some humanized 7G6 antibodies, positions L12 and L103 in the VL region are occupied by S and K, respectively, as in hu7G6-VL_v1. In some humanized 7G6 antibodies, positions L12, L37, and L103 in the VL region are occupied by S, L, and K, respectively, as in hu7G6-VL_v2. In some humanized 7G6 antibodies, positions L12, L36, and L103 in the VL region are occupied by S, L, and K, respectively, as in hu7G6-VL_v3. In some humanized 7G6 antibodies, positions L12, L36, L37, and L103 in the VL region are occupied by S, L, L, and K, respectively, as in hu7G6-VL_v4. In some humanized 7G6 antibodies, positions L12, L45, and L103 in the VL region are occupied by S, K, and K, respectively, as in hu7G6-VL_v5. In some humanized 7G6 antibodies, positions L12, L36, L37, L45, and L103 in the VL region are occupied by S, L, L, K, and K, respectively, as in hu7G6-VL_v6. In some humanized 7G6 antibodies, positions L12, L100, and L103 in the VL region are occupied by S, G, and K, respectively, as in hu7G6-VL_v7. In some humanized 7G6 antibodies, positions L12, L36, L37, L100, and L103 in the VL region are occupied by S, L, L, G, and K, respectively, as in hu7G6-VL_v8.

In some humanized 5G8, 6A10, 8A4, and 7G6 antibodies, the variable heavy chain has ≥85% identity to human sequence. In some humanized 5G8, 6A10, 8A4, and 7G6 antibodies, the variable light chain has ≥85% identity to human sequence. In some humanized 5G8, 6A10, 8A4, and 7G6 antibodies, each of the variable heavy chain and variable light chain has ≥85% identity to human germline sequence.

The CDR regions of such humanized 5G8, 6A10, 8A4, and 7G6 antibodies can be identical or substantially identical to the CDR regions of 5G8, 6A10, 8A4, or 7G6, respectively, The CDR regions can be defined by any conventional definition (e.g., Chothia, or composite of Chothia and Kabat) but are preferably as defined by Kabat.

Variable regions framework positions are in accordance with Kabat numbering unless otherwise stated. Other such variants typically differ from the sequences of the exemplified Hu5G8, Hu6A10, Hu8A4, or Hu7G6 heavy and light chains by a small number (e.g., typically no more than 1, 2, 3, 5, 10, or 15) of replacements, deletions or insertions.

A possibility for additional variation in humanized 5G8, 6A10, 8A4, and 7G6, variants is additional backmutations in the variable region frameworks. Many of the framework residues not in contact with the CDRs in the humanized mAb can accommodate substitutions of amino acids from the corresponding positions of the donor mouse mAb or other mouse or human antibodies, and even many potential CDR-contact residues are also amenable to substitution. Even amino acids within the CDRs may be altered, for example, with residues found at the corresponding position of the human acceptor sequence used to supply variable region frameworks. In addition, alternate human acceptor sequences can be used, for example, for the heavy and/or light chain. If different acceptor sequences are used, one or more of the backmutations recommended above may not be performed because the corresponding donor and acceptor residues are already the same without backmutations.

Preferably, replacements or backmutations in humanized 5G8, 6A10, 8A4, and 7G6 variants (whether or not conservative) have no substantial effect on the binding affinity or potency of the humanized mAb, that is, its ability to bind to tau.

The humanized 5G8, 6A10, 8A4, and 7G6 antibodies are further characterized by their ability to bind any or all of phosphorylated tau, unphosphorylated tau, and misfolded/aggregated forms of tau. The humanized 5G8, 6A10, 8A4, and 7G6 antibodies are further characterized by their ability to compete with murine 5G8, 6A10, 8A4, or 7G6 for binding to any or all of phosphorylated tau, unphosphorylated tau, and misfolded/aggregated forms of tau.

D. Chimeric and Veneered Antibodies

The invention further provides chimeric and veneered forms of non-human antibodies, particularly the 5G8, 6A10, 8A4, or 7G6 antibodies of the examples.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of the 5G8, 6A10, 8A4, and 7G6 antibodies are included in the invention.

E. Human Antibodies

Human antibodies against tau or a fragment thereof are provided by a variety of techniques described below. Some human antibodies are selected by competitive binding experiments, by the phage display method of Winter, above, or otherwise, to have the same epitope specificity as a particular mouse antibody, such as one of the mouse monoclonal antibodies described in the examples. Human antibodies can also be screened for a particular epitope specificity by using only a fragment of tau as the target antigen, and/or by screening antibodies against a collection of tau variants.

Methods for producing human antibodies include the trioma method of Oestberg et al., *Hybridoma* 2:361-367 (1983); Oestberg, U.S. Pat. No. 4,634,664; and Engleman et al., U.S. Pat. No. 4,634,666, use of transgenic mice including human immunoglobulin genes (see, e.g., Lonberg et al., WO93/12227 (1993); U.S. Pat. Nos. 5,877,397; 5,874,299; 5,814,318; 5,789,650; 5,770,429; 5,661,016; 5,633,425; 5,625,126; 5,569,825; 5,545,806; Neuberger, Nat. Biotechnol. 14:826 (1996); and Kucherlapati, WO 91/10741 (1991)) phage display methods (see, e.g., Dower et al., WO 91/17271; McCafferty et al., WO 92/01047; U.S. Pat. Nos. 5,877,218; 5,871,907; 5,858,657; 5,837,242; 5,733,743; and 5,565,332); and methods described in WO 2008/081008 (e.g., immortalizing memory B cells isolated from humans, e.g., with EBV, screening for desired properties, and cloning and expressing recombinant forms).

F. Selection of Constant Region

The heavy and light chain variable regions of chimeric, veneered or humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have complement-dependent cytotoxicity and human isotypes IgG2 and IgG4 do not. Human IgG1 and IgG3 also induce stronger cell mediated effector functions than human IgG2 and IgG4. Light chain constant regions can be lambda or kappa. Numbering conventions for constant regions include EU numbering (Edelman, G. M. et al., Proc. Natl. Acad. USA, 63, 78-85 (1969)), Kabat numbering (Kabat, *Sequences of Proteins of Immunological Interest* (National Institutes of Health, Bethesda, M D, 1991, IMGT unique numbering (Lefranc M.-P. et al., IMGT unique numbering for immunoglobulin and T cell receptor constant domains and Ig superfamily C-like domains, Dev. Comp. Immunol., 29, 185-203 (2005), and IMGT exon numbering (Lefranc, supra).

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduce affinity for Fc7 receptors, particularly FcTRI receptor (see, e.g., U.S. Pat. No. 6,624,821). An alanine substitution at positions 234, 235, and 237 of human IgG1 can be used for reducing effector functions. Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624, 821). In some antibodies, a mutation at one or more of positions 241, 264, 265, 270, 296, 297, 322, 329, and 331 by EU numbering of human IgG1 is used. In some antibodies, a mutation at one or more of positions 318, 320, and 322 by EU numbering of human IgG1 is used. In some antibodies, positions 234 and/or 235 are substituted with alanine and/or position 329 is substituted with glycine. In some antibodies, positions 234 and 235 are substituted with alanine. In some antibodies, the isotype is human IgG2 or IgG4.

Antibodies can be expressed as tetramers containing two light and two heavy chains, as separate heavy chains, light chains, as Fab, Fab', F(ab')2, and Fv, or as single chain antibodies in which heavy and light chain mature variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Thus, for example, another heavy chain constant region is of IgG1 Glm3 with or without the C-terminal lysine. Reference to a human constant region includes a constant region with any natural allotype or any permutation of residues occupying positions in natural allotypes.

G. Expression of Recombinant Antibodies

A number of methods are known for producing chimeric and humanized antibodies using an antibody-expressing cell line (e.g., hybridoma). For example, the immunoglobulin variable regions of antibodies can be cloned and sequenced using well known methods. In one method, the heavy chain variable VH region is cloned by RT-PCR using mRNA prepared from hybridoma cells. Consensus primers are employed to the VH region leader peptide encompassing the translation initiation codon as the 5' primer and a g2b constant regions specific 3' primer. Exemplary primers are described in U.S. patent publication US 2005/0009150 by Schenk et al. (hereinafter "Schenk"). The sequences from multiple, independently derived clones can be compared to ensure no changes are introduced during amplification. The sequence of the VH region can also be determined or confirmed by sequencing a VH fragment obtained by 5' RACE RT-PCR methodology and the 3' g2b specific primer.

The light chain variable VL region can be cloned in an analogous manner. In one approach, a consensus primer set is designed for amplification of VL regions using a 5' primer designed to hybridize to the VL region encompassing the translation initiation codon and a 3' primer specific for the Ck region downstream of the V-J joining region. In a second approach, 5'RACE RT-PCR methodology is employed to clone a VL encoding cDNA. Exemplary primers are described in Schenk, supra. The cloned sequences are then combined with sequences encoding human (or other non-human species) constant regions.

In one approach, the heavy and light chain variable regions are re-engineered to encode splice donor sequences downstream of the respective VDJ or VJ junctions and are cloned into a mammalian expression vector, such as pCMV-hγ1 for the heavy chain and pCMV-Mcl for the light chain. These vectors encode human γ1 and Ck constant regions as exonic fragments downstream of the inserted variable region cassette. Following sequence verification, the heavy chain and light chain expression vectors can be co-transfected into CHO cells to produce chimeric antibodies. Conditioned media is collected 48 hours post-transfection and assayed by western blot analysis for antibody production or ELISA for antigen binding. The chimeric antibodies are humanized as described above.

Chimeric, veneered, humanized, and human antibodies are typically produced by recombinant expression. Recombinant polynucleotide constructs typically include an expression control sequence operably linked to the coding sequences of antibody chains, including naturally associated or heterologous expression control elements, such as a promoter. The expression control sequences can be promoter systems in vectors capable of transforming or transfecting eukaryotic or prokaryotic host cells. Once the vector has been incorporated into the appropriate host, the host is maintained under conditions suitable for high level expression of the nucleotide sequences and the collection and purification of the crossreacting antibodies.

These expression vectors are typically replicable in the host organisms either as episomes or as an integral part of the host chromosomal DNA. Commonly, expression vectors contain selection markers, e.g., ampicillin resistance or hygromycin resistance, to permit detection of those cells transformed with the desired DNA sequences.

*E. coli* is one prokaryotic host useful for expressing antibodies, particularly antibody fragments. Microbes, such as yeast, are also useful for expression. *Saccharomyces* is a yeast host with suitable vectors having expression control sequences, an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells can be used for expressing nucleotide segments encoding immunoglobulins or fragments thereof. See Winnacker, From Genes to Clones, (VCH Publishers, N Y, 1987). A number of suitable host cell lines capable of secreting intact heterologous proteins have been developed, and include CHO cell lines, various COS cell lines, HeLa cells, HEK293 cells, L cells, and non-antibody-producing myelomas including Sp2/0 and NS0. The cells can be nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Expression control sequences can include promoters derived from endogenous genes, cytomegalovirus, SV40, adenovirus, bovine papillomavirus, and the like. See Co et al., *J. Immunol.* 148:1149 (1992).

Alternatively, antibody coding sequences can be incorporated in transgenes for introduction into the genome of a transgenic animal and subsequent expression in the milk of the transgenic animal (see, e.g., U.S. Pat. Nos. 5,741,957; 5,304,489; and 5,849,992). Suitable transgenes include coding sequences for light and/or heavy chains operably linked with a promoter and enhancer from a mammary gland specific gene, such as casein or beta lactoglobulin.

The vectors containing the DNA segments of interest can be transferred into the host cell by methods depending on the type of cellular host. For example, calcium chloride transfection is commonly utilized for prokaryotic cells, whereas calcium phosphate treatment, electroporation, lipofection, biolistics, or viral-based transfection can be used for other cellular hosts. Other methods used to transform mammalian cells include the use of polybrene, protoplast fusion, liposomes, electroporation, and microinjection. For production of transgenic animals, transgenes can be microinjected into fertilized oocytes or can be incorporated into the genome of embryonic stem cells, and the nuclei of such cells transferred into enucleated oocytes.

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be used. Antibodies produced by single cell clones can also be tested for turbidity, filtration properties, PAGE, IEF, UV scan, HP-SEC, carbohydrate-oligosaccharide mapping, mass spectrometry, and binding assay, such as ELISA or Biacore. A selected clone can then be banked in multiple vials and stored frozen for subsequent use.

Once expressed, antibodies can be purified according to standard procedures of the art, including protein A capture, HPLC purification, column chromatography, gel electrophoresis and the like (see generally, Scopes, *Protein Purification* (Springer-Verlag, NY, 1982)).

Methodology for commercial production of antibodies can be employed, including codon optimization, selection of promoters, selection of transcription elements, selection of terminators, serum-free single cell cloning, cell banking, use of selection markers for amplification of copy number, CHO terminator, or improvement of protein titers (see, e.g., U.S. Pat. Nos. 5,786,464; 6,114,148; 6,063,598; 7,569,339; WO2004/050884; WO2008/012142; WO2008/012142; WO2005/019442; WO2008/107388; WO2009/027471; and U.S. Pat. No. 5,888,809).

IV. Active Immunogens

The invention also provides methods for treating or effecting prophylaxis of a tau-related disease in a subject, comprising administering an agent inducing an immune response against tau. Such an agent used for active immunization serves to induce in a patient the same types of antibody described in connection with passive immunization above. Some such methods include administering to a subject an immunogen comprising an epitope to which antibody 5G8 specifically binds in a regime effective to generate antibodies to tau. In some methods, an immunogen comprises a tau peptide of up to 20 contiguous amino acids of SEQ ID NO:3 to which antibody 5G8 specifically binds. In other methods, an immunogen comprising an epitope to which antibody 6A10 specifically binds is administered. In some methods, an immunogen comprises a tau peptide of up to 20 contiguous amino acids of SEQ ID NO:3 to which antibody 6A10 specifically binds. In some methods, an immunogen comprising an epitope to which antibody 8A4 specifically binds is administered. In some methods, an immunogen comprises a tau peptide of up to 20 contiguous amino acids of SEQ ID NO:3 to which antibody 8A4 specifically binds. In other methods, an immunogen comprising an epitope to which antibody 7G6 specifically binds is administered. In some methods, an immunogen comprising an epitope to which antibody 3D6 specifically binds is administered. In some methods, an immunogen comprises a tau peptide of up to 20 contiguous amino acids of SEQ ID NO:3 to which antibody 3D6 specifically binds. In some methods, an immunogen comprises a tau peptide of up to 20 contiguous amino acids of SEQ ID NO:3 is administered, wherein at least two of antibodies 5G8, 6A10, 8A4, 7G6, and 3D6 specifically bind to the tau peptide. In some methods, an immunogen comprising an epitope to which more than one of the afore-mentioned antibodies specifically bind, which epitope consists of a peptide of 4-11 contiguous amino acids from residues 199-213 of SEQ ID NO:3 or residues 262-276 of SEQ ID NO:3, or 4-11 contiguous amino acids from residues 199-213 of SEQ ID NO:3 and residues 262-276 of SEQ ID NO:3. In some methods, the tau peptide epitope consists of 4-11 contiguous amino acids from residues 199-213 of SEQ ID NO:3 or from residues 262-276 of SEQ ID NO:3. In other methods, the tau peptide epitope consists of two contiguous segments of amino acids, one segment from residues 199-213 of SEQ ID NO:3, the other from residues 262-276 of SEQ ID NO:3, wherein the two contiguous segments together consist of 4-11 amino acids.

For inducing antibodies binding to the same or overlapping epitope as 5G8, 6A10, 8A4, 7G6 or 3D6, the epitope specificity of these antibodies can be mapped (e.g., by testing binding to a series of overlapping peptides spanning tau). A fragment of tau consisting of or including or overlapping the epitope can then be used as an immunogen. Such fragments are typically used in unphosphorylated form.

The heterologous carrier and adjuvant, if used may be the same as used for generating monoclonal antibody, but may also be selected for better pharmaceutical suitability for use in humans. Suitable carriers include serum albumins, keyhole limpet hemocyanin, immunoglobulin molecules, thyroglobulin, ovalbumin, tetanus toxoid, or a toxoid from other pathogenic bacteria, such as diphtheria (e.g., CRM197), *E. coli*, cholera, or *H. pylori*, or an attenuated toxin derivative. T cell epitopes are also suitable carrier molecules. Some conjugates can be formed by linking agents of the invention to an immunostimulatory polymer molecule (e.g., tripalmitoyl-S-glycerine cysteine (Pam$_3$Cys), mannan (a mannose polymer), or glucan (a β1→2 polymer)), cytokines (e.g., IL-1, IL-1 alpha and β peptides, IL-2, γ-INF, IL-10, GM-CSF), and chemokines (e.g., MIP1-α and β, and RANTES). Immunogens may be linked to the carriers with or without spacers amino acids (e.g., gly-gly). Additional carriers include virus-like particles. Virus-like particles (VLPs), also called pseudovirions or virus-derived particles, represent subunit structures composed of multiple copies of a viral capsid and/or envelope protein capable of self-assembly into VLPs of defined spherical symmetry in vivo. (Powilleit, et al., (2007) PLoS ONE 2(5):e415.) Alternatively, peptide immunogens can be linked to at least one artificial T-cell epitope capable of binding a large proportion of MHC Class II molecules. such as the pan DR epitope ("PADRE"). PADRE is described in U.S. Pat. No. 5,736,142, WO 95/07707, and Alexander J et al, Immunity, 1:751-761 (1994). Active immunogens can be presented in multimeric form in which multiple copies of an immunogen and/or its carrier are presented as a single covalent molecule.

Fragments are often administered with pharmaceutically acceptable adjuvants. The adjuvant increases the titer of induced antibodies and/or the binding affinity of induced antibodies relative to the situation if the peptide were used alone. A variety of adjuvants can be used in combination with an immunogenic fragment of tau to elicit an immune response. Preferred adjuvants augment the intrinsic response to an immunogen without causing conformational changes in the immunogen that affect the qualitative form of the response. Preferred adjuvants include aluminum salts, such as aluminum hydroxide and aluminum phosphate, 3 De-O-acylated monophosphoryl lipid A (MPL™) (see GB 2220211 (RIBI ImmunoChem Research Inc., Hamilton, Montana, now part of Corixa). Stimulon™ QS-21 is a triterpene glycoside or saponin isolated from the bark of the *Quillaja Saponaria* Molina tree found in South America (see Kensil et al., in *Vaccine Design: The Subunit and Adjuvant Approach* (eds. Powell & Newman, Plenum Press, N Y, 1995); U.S. Pat. No. 5,057,540), (Aquila BioPharmaceuticals, Framingham, MA; now Antigenics, Inc., New York, NY). Other adjuvants are oil in water emulsions (such as squalene or peanut oil), optionally in combination with immune stimulants, such as monophosphoryl lipid A (see Stoute et al., *N. Engl. J. Med.* 336, 86-91 (1997)), pluronic polymers, and killed mycobacteria. Ribi adjuvants are oil-in-water emulsions. Ribi contains a metabolizable oil (squalene) emulsified with saline containing Tween 80. Ribi also contains refined mycobacterial products which act as immunostimulants and bacterial monophosphoryl lipid A. Another adjuvant is CpG (WO 98/40100). Adjuvants can be administered as a component of a therapeutic composition with an active agent or can be administered separately, before, concurrently with, or after administration of the therapeutic agent.

Analogs of natural fragments of tau that induce antibodies against tau can also be used. For example, one or more or all L-amino acids can be substituted with D amino acids in such peptides. Also the order of amino acids can be reversed (retro peptide). Optionally a peptide includes all D-amino acids in reverse order (retro-inverso peptide). Peptides and other compounds that do not necessarily have a significant amino acid sequence similarity with tau peptides but nevertheless serve as mimetics of tau peptides and induce a similar immune response. Anti-idiotypic antibodies against monoclonal antibodies to tau as described above can also be used. Such anti-Id antibodies mimic the antigen and generate an immune response to it (see Essential Immunology, Roit ed., Blackwell Scientific Publications, Palo Alto, CA 6th ed., p. 181).

Peptides (and optionally a carrier fused to the peptide) can also be administered in the form of a nucleic acid encoding the peptide and expressed in situ in a patient. A nucleic acid segment encoding an immunogen is typically linked to regulatory elements, such as a promoter and enhancer that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. Antibodies can also be administered in the form of nucleic acids encoding the antibody heavy and/or light chains. If both heavy and light chains are present, the chains are preferably linked as a single chain antibody. Antibodies for passive administration can also be prepared e.g., by affinity chromatography from sera of patients treated with peptide immunogens.

The DNA can be delivered in naked form (i.e., without colloidal or encapsulating materials). Alternatively a number of viral vector systems can be used including retroviral systems (see, e.g., Lawrie and Tumin, Cur. Opin. Genet. Develop. 3, 102-109 (1993)); adenoviral vectors {see, e.g., Bett et al, J. Virol. 67, 591 1 (1993)); adeno-associated virus vectors {see, e.g., Zhou et al., J. Exp. Med. 179, 1867 (1994)), viral vectors from the pox family including vaccinia virus and the avian pox viruses, viral vectors from the alpha virus genus such as those derived from Sindbis and Semliki Forest Viruses (see, e.g., Dubensky et al., J. Virol. 70, 508-519 (1996)), Venezuelan equine encephalitis virus (see U.S. Pat. No. 5,643,576) and rhabdoviruses, such as vesicular stomatitis virus (see WO 96/34625) and papillomaviruses (Ohe et al., Human Gene Therapy 6, 325-333 (1995); Woo et al, WO 94/12629 and Xiao & Brandsma, Nucleic Acids. Res. 24, 2630-2622 (1996)).

DNA encoding an immunogen, or a vector containing the same, can be packaged into liposomes. Suitable lipids and related analogs are described by U.S. Pat. Nos. 5,208,036, 5,264,618, 5,279,833, and 5,283,185. Vectors and DNA encoding an immunogen can also be adsorbed to or associated with particulate carriers, examples of which include polymethyl methacrylate polymers and polylactides and poly(lactide-co-glycolides), (see, e.g., McGee et al., J. Micro Encap. 1996).

H. Antibody Screening Assays

Antibodies can be initially screened for the intended binding specificity as described above. Active immunogens can likewise be screened for capacity to induce antibodies with such binding specificity. In this case, an active immunogen is used to immunize a laboratory animal and the resulting sera tested for the appropriate binding specificity.

Antibodies having the desired binding specificity can then be tested in cellular and animal models. The cells used for such screening are preferentially neuronal cells. A cellular model of tau pathology has been reported in which neuroblastoma cells are transfected with a four-repeat domain of tau, optionally with a mutation associated with tau pathology (e.g., delta K280, see Khlistunova, Current Alzheimer Research 4, 544-546 (2007)). In another model, tau is induced in the neuroblastoma N2a cell line by the addition of doxycyclin. The cell models enable one to study the toxicity of tau to cells in the soluble or aggregated state, the appearance of tau aggregates after switching on tau gene expression, the dissolution of tau aggregates after switching the gene expression off again, and the efficiency of antibodies in inhibiting formation of tau aggregates or disaggregating them.

Antibodies or active immunogens can also be screened in transgenic animal models of diseases associated with tau. Such transgenic animals can include a tau transgene (e.g., any of the human isoforms) and optionally a human APP transgene among others, such as a kinase that phosphorylates tau, ApoE, presenilin or alpha synuclein. Such transgenic animals are disposed to develop at least one sign or symptom of a disease associated with tau.

An exemplary transgenic animal is the K3 line of mice (Itner et al., Proc. Natl. Acad. Sci. USA 105(41):15997-6002 (2008)). These mice have a human tau transgene with a K 369 I mutation (the mutation is associated with Pick's disease) and a Thy 1.2 promoter. This model shows a rapid course of neurodegeneration, motor deficit and degeneration of afferent fibers and cerebellar granule cells. Another exemplary animal is the JNPL3 line of mice. These mice have a human tau transgene with a P301L mutation (the mutation is associated with frontotemporal dementia) and a Thy 1.2 promoter (Taconic, Germantown, N.Y., Lewis, et al., Nat Genet. 25:402-405 (2000)). These mice have a more gradual course of neurodegeneration. The mice develop neurofibrillary tangles in several brain regions and spinal cord, which is hereby incorporated by reference in its entirety). This is an excellent model to study the consequences of tangle development and for screening therapy that may inhibit the generation of these aggregates. Another advantage of these animals is the relatively early onset of pathology. In the homozygous line, behavioral abnormalities associated with tau pathology can be observed at least as early as 3 months, but the animals remain relatively healthy at least until 8 months of age. In other words, at 8 months, the animals ambulate, feed themselves, and can perform the behavioral tasks sufficiently well to allow the treatment effect to be monitored. Active immunization of these mice for 6-13 months with—AI wI KLH-PHF-1 generated titers of about 1,000 and showed fewer neurofibrillary tangles, less pSer422, and reduced weight loss relative to untreated control ice.

The activity of antibodies or active agents can be assessed by various criteria including reduction in amount of total tau or phosphorylated tau, reduction in other pathological characteristics, such as amyloid deposits of A3, and inhibition or delay or behavioral deficits. Active immunogens can also be tested for induction of antibodies in the sera. Both passive and active immunogens can be tested for passage of antibodies across the blood brain barrier into the brain of a transgenic animal. Antibodies or fragments inducing an antibody can also be tested in non-human primates that naturally or through induction develop symptoms of diseases characterized by tau. Tests on an antibody or active agent are usually performed in conjunction with a control in which a parallel experiment is conduct except that the antibody or active agent is absent (e.g., replaced by vehicle). Reduction, delay or inhibition of signs or symptoms disease attributable to an antibody or active agent under test can then be assessed relative to the control.

V. Patients Amenable to Treatment

The presence of neurofibrillary tangles has been found in several diseases including Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), and progressive supranuclear palsy (PSP). The present regimes can also be used in treatment or prophylaxis of any of these diseases. Because of the widespread association between neurological diseases and conditions and tau, the present regimes can be used in treatment or prophylaxis of any subject showing elevated levels of tau or phosphorylated tau (e.g., in the CSF) compared with a mean value in individuals without neurological disease. The present regimes can also be used in treatment or prophylaxis of neurological disease in individuals having a mutation in tau associated with neurological disease. The present methods are particularly suitable for treatment or prophylaxis of Alzheimer's disease, and especially in patients.

Patients amenable to treatment include individuals at risk of disease but not showing symptoms, as well as patients presently showing symptoms. Patients at risk of disease include those having a known genetic risk of disease. Such individuals include those having relatives who have experienced this disease, and those whose risk is determined by analysis of genetic or biochemical markers. Genetic markers of risk include mutations in tau, such as those discussed above, as well as mutations in other genes associated with neurological disease. For example, the ApoE4 allele in heterozygous and even more so in homozygous form is associated with risk of Alzheimer's disease. Other markers of risk of Alzheimer's disease include mutations in the APP gene, particularly mutations at position 717 and positions 670 and 671 referred to as the Hardy and Swedish mutations respectively, mutations in the presenilin genes, PS1 and PS2, a family history of AD, hypercholesterolemia or atherosclerosis. Individuals presently suffering from Alzheimer's disease can be recognized by PET imaging, from characteristic dementia, as well as the presence of risk factors described above. In addition, a number of diagnostic tests are available for identifying individuals who have AD. These include measurement of CSF tau or phospho-tau and Aβ42 levels. Elevated tau or phospho-tau and decreased Aβ42 levels signify the presence of AD. Some mutations associated with Parkinson's disease. Ala30Pro or Ala53, or mutations in other genes associated with Parkinson's disease such as leucine-rich repeat kinase, PARK8. Individuals can also be diagnosed with any of the neurological diseases mentioned above by the criteria of the DSM IV TR.

In asymptomatic patients, treatment can begin at any age (e.g., 10, 20, 30). Usually, however, it is not necessary to begin treatment until a patient reaches 40, 50, 60 or 70 years of age. Treatment typically entails multiple dosages over a period of time. Treatment can be monitored by assaying antibody levels over time. If the response falls, a booster dosage is indicated. In the case of potential Down's syndrome patients, treatment can begin antenatally by administering therapeutic agent to the mother or shortly after birth.

I. Nucleic Acids

The invention further provides nucleic acids encoding any of the heavy and light chains described above (e.g., SEQ ID NOs: 7-8, 47-48, 49-50, 51-52, 53-54, 55, 59). For example SEQ ID NO: 9 encodes the amino acid sequence of murine 5G8 heavy chain variable region SEQ ID NO:47, and SEQ ID NO:10 encodes the amino acid sequence of murine 5G8 light chain variable region SEQ ID NO:48. Optionally, such nucleic acids further encode a signal peptide and can be expressed with the signal peptide linked to the constant region. Coding sequences of nucleic acids can be operably linked with regulatory sequences to ensure expression of the coding sequences, such as a promoter, enhancer, ribosome binding site, transcription termination signal, and the like. The nucleic acids encoding heavy and light chains can occur in isolated form or can be cloned into one or more vectors. The nucleic acids can be synthesized by, for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

J. Conjugated Antibodies

Conjugated antibodies that specifically bind to antigens, such as tau, are useful in detecting the presence of tau; monitoring and evaluating the efficacy of therapeutic agents being used to treat patients diagnosed with Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP); inhibiting or reducing aggregation of tau; inhibiting or reducing tau fibril formation; reducing or clearing tau deposits; stabilizing non-toxic conformations of tau; or treating or effecting prophylaxis of Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP) in a patient. For example, such antibodies can be conjugated with other therapeutic moieties, other proteins, other antibodies, and/or detectable labels. See WO 03/057838; U.S. Pat. No. 8,455,622. Such therapeutic moieties can be any agent that can be used to treat, combat, ameliorate, prevent, or improve an unwanted condition or disease in a patient, such as Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP).

Conjugated therapeutic moieties can include cytotoxic agents, cytostatic agents, neurotrophic agents, neuroprotective agents, radiotherapeutic agents, immunomodulators, or any biologically active agents that facilitate or enhance the activity of the antibody. A cytotoxic agent can be any agent that is toxic to a cell. A cytostatic agent can be any agent that inhibits cell proliferation. A neurotrophic agent can be any agent, including chemical or proteinaceous agents, that promotes neuron maintenance, growth, or differentiation. A neuroprotective agent can be agent, including chemical or proteinaceous agents, that protects neurons from acute insult or degenerative processes. An immunomodulator can be any agent that stimulates or inhibits the development or maintenance of an immunologic response. A radiotherapeutic agent can be any molecule or compound that emits radiation. If such therapeutic moieties are coupled to a tau-specific antibody, such as the antibodies described herein, the coupled therapeutic moieties will have a specific affinity for tau-related disease-affected cells over normal cells. Consequently, administration of the conjugated antibodies directly targets cancer cells with minimal damage to surrounding normal, healthy tissue. This can be particularly useful for therapeutic moieties that are too toxic to be administered on their own. In addition, smaller quantities of the therapeutic moieties can be used.

Some such antibodies can be modified to act as immunotoxins. See, e.g., U.S. Pat. No. 5,194,594. For example, ricin, a cellular toxin derived from plants, can be coupled to antibodies by using the bifunctional reagents S-acetylmercaptosuccinic anhydride for the antibody and succinimidyl 3-(2-pyridyldithio)propionate for ricin. See Pietersz et al., Cancer Res. 48(16):4469-4476 (1998). The coupling results in loss of B-chain binding activity of ricin, while impairing neither the toxic potential of the A-chain of ricin nor the activity of the antibody. Similarly, saporin, an inhibitor of ribosomal assembly, can be coupled to antibodies via a disulfide bond between chemically inserted sulfhydryl groups. See Polito et al., Leukemia 18:1215-1222 (2004).

Some such antibodies can be linked to radioisotopes. Examples of radioisotopes include, for example, yttrium$^{90}$ (90Y), indium$^{11}$ (111In), $^{131}$I, $^{99}$mTc, radiosilver-111, radiosilver-199, and Bismuth$^{213}$. Linkage of radioisotopes to antibodies may be performed with conventional bifunction chelates. For radiosilver-111 and radiosilver-199 linkage, sulfur-based linkers may be used. See Hazra et al., Cell Biophys. 24-25:1-7 (1994). Linkage of silver radioisotopes may involve reducing the immunoglobulin with ascorbic acid. For radioisotopes such as 11 In and 90Y, ibritumomab tiuxetan can be used and will react with such isotopes to form 11 In-ibritumomab tiuxetan and 90Y-ibritumomab tiuxetan, respectively. See Witzig, Cancer Chemother. Pharmacol., 48 Suppl 1:S91-S95 (2001).

Some such antibodies can be linked to other therapeutic moieties. Such therapeutic moieties can be, for example, cytotoxic, cytostatic, neurotrophic, or neuroprotective. For example, antibodies can be conjugated with toxic chemotherapeutic drugs such as maytansine, geldanamycin, tubulin inhibitors such as tubulin binding agents (e.g., auristatins), or minor groove binding agents such as calicheamicin. Other representative therapeutic moieties include agents known to be useful for treatment, management, or amelioration of Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP).

Antibodies can also be coupled with other proteins. For example, antibodies can be coupled with Fynomers. Fynomers are small binding proteins (e.g., 7 kDa) derived from the human Fyn SH3 domain. They can be stable and soluble, and they can lack cysteine residues and disulfide bonds. Fynomers can be engineered to bind to target molecules with the same affinity and specificity as antibodies. They are suitable for creating multi-specific fusion proteins based on antibodies. For example, Fynomers can be fused to N-terminal and/or C-terminal ends of antibodies to create bi- and tri-specific FynomAbs with different architectures. Fynomers can be selected using Fynomer libraries through screening technologies using FACS, Biacore, and cell-based assays that allow efficient selection of Fynomers with optimal properties. Examples of Fynomers are disclosed in Grabulovski et al., *J. Biol. Chem.* 282:3196-3204 (2007); Bertschinger et al., *Protein Eng. Des. Sel.* 20:57-68 (2007); Schlatter et al., *MAbs.* 4:497-508 (2011); Banner et al., *Acta. Crystallogr. D. Biol. Crystallogr.* 69(Pt6):1124-1137 (2013); and Brack et al., *Mol. Cancer Ther.* 13:2030-2039 (2014).

The antibodies disclosed herein can also be coupled or conjugated to one or more other antibodies (e.g., to form antibody heteroconjugates). Such other antibodies can bind to different epitopes within tau or can bind to a different target antigen.

Antibodies can also be coupled with a detectable label. Such antibodies can be used, for example, for diagnosing Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP), and/or for assessing efficacy of treatment. Such antibodies are particularly useful for performing such determinations in subjects having or being susceptible to Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP), or in appropriate biological samples obtained from such subjects. Representative detectable labels that may be coupled or linked to an antibody include various enzymes, such as horseradish peroxidase, alkaline phosphatase, beta-galactosidase, or acetylcholinesterase; prosthetic groups, such streptavidin/biotin and avidin/biotin; fluorescent materials, such as umbelliferone, fluorescein, fluorescein isothiocyanate, rhodamine, dichlorotriazinylamine fluorescein, dansyl chloride or phycoerythrin; luminescent materials, such as luminol; bioluminescent materials, such as luciferase, luciferin, and aequorin; radioactive materials, such as radiosilver-111, radiosilver-199, Bismuth$^{213}$, iodine ($^{131}$I, $^{125}$I, $^{123}$I, $^{121}$I), carbon ($^{14}$C), sulfur ($^{5}$S), tritium ($^{3}$H), indium ($^{115}$In, $^{113}$In, $^{112}$In, $^{111}$In), technetium ($^{99}$Tc), thallium ($^{201}$Ti), gallium ($^{68}$Ga $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, 175Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies; non- radioactive paramagnetic metal ions; and molecules that are radiolabelled or conjugated to specific radioisotopes.

Linkage of radioisotopes to antibodies may be performed with conventional bifunction chelates. For radiosilver-111 and radiosilver-199 linkage, sulfur-based linkers may be used. See Hazra et al., *Cell Biophys.* 24-25:1-7 (1994). Linkage of silver radioisotopes may involve reducing the immunoglobulin with ascorbic acid. For radioisotopes such as 111In and 90Y, ibritumomab tiuxetan can be used and will react with such isotopes to form 111In-ibritumomab tiuxetan and 90Y-ibritumomab tiuxetan, respectively. See Witzig, *Cancer Chemother. Pharmacol.*, 48 Suppl 1:S91-S95 (2001).

Therapeutic moieties, other proteins, other antibodies, and/or detectable labels may be coupled or conjugated, directly or indirectly through an intermediate (e.g., a linker), to an antibody of the invention. See e.g., Amon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery," in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985); and Thorpe et al., *Immunol. Rev.*, 62:119-58 (1982). Suitable linkers include, for example, cleavable and non-cleavable linkers. Different linkers that release the coupled therapeutic moieties, proteins, antibodies, and/or detectable labels under acidic or reducing conditions, on exposure to specific proteases, or under other defined conditions can be employed.

VI. Pharmaceutical Compositions and Methods of Use

In prophylactic applications, an antibody or agent for inducing an antibody or a pharmaceutical composition the same is administered to a patient susceptible to, or otherwise at risk of a disease (e.g., Alzheimer's disease) in regime (dose, frequency and route of administration) effective to reduce the risk, lessen the severity, or delay the onset of at least one sign or symptom of the disease. In particular, the regime is preferably effective to inhibit or delay tau or phospho-tau and paired filaments formed from it in the brain, and/or inhibit or delay its toxic effects and/or inhibit/ or delay development of behavioral deficits. In therapeutic applications, an antibody or agent to induce an antibody is administered to a patient suspected of, or already suffering from a disease (e.g., Alzheimer's disease) in a regime (dose, frequency and route of administration) effective to ameliorate or at least inhibit further deterioration of at least one sign or symptom of the disease. In particular, the regime is preferably effective to reduce or at least inhibit further increase of levels of tau, phosphor-tau, or paired filaments formed from it, associated toxicities and/or behavioral deficits.

A regime is considered therapeutically or prophylactically effective if an individual treated patient achieves an outcome more favorable than the mean outcome in a control population of comparable patients not treated by methods of the invention, or if a more favorable outcome is demonstrated in treated patients versus control patients in a controlled clinical trial (e.g., a phase II, phase II/III or phase III trial) at the p<0.05 or 0.01 or even 0.001 level.

Effective doses of vary depending on many different factors, such as means of administration, target site, physiological state of the patient, whether the patient is an ApoE carrier, whether the patient is human or an animal, other medications administered, and whether treatment is prophylactic or therapeutic.

Exemplary dosage ranges for antibodies are from about 0.01 to 60 mg/kg, or from about 0.1 to 3 mg/kg or 0.15-2 mg/kg or 0.15-1.5 mg/kg, of patient body weight. Antibody can be administered such doses daily, on alternative days, weekly, fortnightly, monthly, quarterly, or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months.

The amount of an agent for active administration varies from 0.1-500 µg per patient and more usually from 1-100 or 1-10 µg per injection for human administration. The timing of injections can vary significantly from once a day, to once a year, to once a decade. A typical regimen consists of an immunization followed by booster injections at time intervals, such as 6 week intervals or two months. Another regimen consists of an immunization followed by booster injections 1, 2 and 12 months later. Another regimen entails an injection every two months for life. Alternatively, booster injections can be on an irregular basis as indicated by monitoring of immune response.

Antibodies or agents for inducing antibodies are preferably administered via a peripheral route (i.e., one in which an administered or induced antibody crosses the blood brain barrier to reach an intended site in the brain. Routes of administration include topical, intravenous, oral, subcutaneous, intraarterial, intracranial, intrathecal, intraperitoneal, intranasal, intraocular, or intramuscular. Preferred routes for administration of antibodies are intravenous and subcutaneous. Preferred routes for active immunization are subcutaneous and intramuscular. This type of injection is most typically performed in the arm or leg muscles. In some methods, agents are injected directly into a particular tissue where deposits have accumulated, for example intracranial injection.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

The present regimes can be administered in combination with another agent effective in treatment or prophylaxis of the disease being treated. For example, in the case of Alzheimer's disease, the present regimes can be combined with immunotherapy against Aβ (WO/2000/072880), cholinesterase inhibitors or memantine or in the case of Parkinson's disease immunotherapy against alpha synuclein WO/2008/103472, Levodopa, dopamine agonists, COMT inhibitors, MAO-B inhibitors, Amantadine, or anticholinergic agents.

Antibodies are administered in an effective regime meaning a dosage, route of administration and frequency of administration that delays the onset, reduces the severity, inhibits further deterioration, and/or ameliorates at least one sign or symptom of a disorder being treated. If a patient is already suffering from a disorder, the regime can be referred to as a therapeutically effective regime. If the patient is at elevated risk of the disorder relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for an antibody are 0.1-60 mg/kg (e.g., 0.5, 3, 10, 30, or 60 mg/kg), or 0.5-5 mg/kg body weight (e.g., 0.5, 1, 2, 3, 4 or 5 mg/kg) or 10-4000 mg or 10-1500 mg as a fixed dosage. The dosage depends on the condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Some antibodies can be administered into the systemic circulation by intravenous or subcutaneous administration. Intravenous administration can be, for example, by infusion over a period such as 30-90 min.

The frequency of administration depends on the half-life of the antibody in the circulation, the condition of the patient and the route of administration among other factors. The frequency can be daily, weekly, monthly, quarterly, or at irregular intervals in response to changes in the patient's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of a chronic disorder, between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

A. Diagnostics and Monitoring Methods

In Vivo Imaging, Diagnostic Methods, and Optimizing Immunotherapy

The invention provides methods of in vivo imaging tau protein deposits (e.g., neurofibrillary tangles and tau inclusions) in a patient. The methods work by administering a reagent, such as antibody that binds tau (e.g., a mouse, humanized, chimeric or veneered 5G8, 6A10, 8A4, or 7G6 antibody), to the patient and then detecting the agent after it has bound. A clearing response to the administered antibodies can be avoided or reduced by using antibody fragments lacking a full-length constant region, such as Fabs. In some methods, the same antibody can serve as both a treatment and diagnostic reagent.

Diagnostic reagents can be administered by intravenous injection into the body of the patient, or directly into the brain by intracranial injection or by drilling a hole through the skull. The dosage of reagent should be within the same ranges as for treatment methods. Typically, the reagent is labeled, although in some methods, the primary reagent with affinity for tau is unlabeled and a secondary labeling agent is used to bind to the primary reagent. The choice of label depends on the means of detection. For example, a fluorescent label is suitable for optical detection. Use of paramagnetic labels is suitable for tomographic detection without surgical intervention. Radioactive labels can also be detected using positron emission tomography (PET) or single-photon emission computed tomography (SPECT).

The methods of in vivo imaging of tau protein deposits are useful to diagnose or confirm diagnosis of a tauopathy, such as Alzheimer's disease, frontotemporal lobar degeneration, progressive supranuclear palsy and Pick's disease, or susceptibility to such a disease. For example, the methods can be used on a patient presenting with symptoms of dementia. If the patient has abnormal neurofibrillary tangles, then the patient is likely suffering from Alzheimer's disease. Alternatively, if the patient has abnormal tau inclusions, then depending on the location of the inclusions, the patient may be suffering from frontotemporal lobar degeneration. The methods can also be used on asymptomatic patients. Presence of abnormal tau protein deposits indicates susceptibility to future symptomatic disease. The methods are also useful for monitoring disease progression and/or response to treatment in patients who have been previously diagnosed with a tau-related disease.

Diagnosis can be performed by comparing the number, size, and/or intensity of labeled loci, to corresponding baseline values. The base line values can represent the mean levels in a population of undiseased individuals. Baseline values can also represent previous levels determined in the same patient. For example, baseline values can be determined in a patient before beginning tau immunotherapy treatment, and measured values thereafter compared with the baseline values. A decrease in values relative to baseline signals a positive response to treatment.

In some patients, diagnosis of a tauopathy may be aided by performing a PET scan. A PET scan can be performed using, for example, a conventional PET imager and auxiliary equipment. The scan typically includes one or more regions of the brain known in general to be associated with tau protein deposits and one or more regions in which few if any deposits are generally present to serve as controls.

The signal detected in a PET scan can be represented as a multidimensional image. The multidimensional image can be in two dimensions representing a cross-section through the brain, in three dimensions, representing the three dimensional brain, or in four dimensions representing changes in the three dimensional brain over time. A color scale can be used with different colors indicating different amounts of label and, inferentially, tau protein deposit detected. The results of the scan can also be presented numerically, with numbers relating to the amount of label detected and consequently amount of tau protein deposits. The label present in a region of the brain known to be associated with deposits for a particular tauopathy (e.g., Alzheimer's disease) can be compared with the label present in a region known not to be associated with deposits to provide a ratio indicative of the extent of deposits within the former region. For the same radiolabeled ligand, such ratios provide a comparable measure of tau protein deposits and changes thereof between different patients.

In some methods, a PET scan is performed concurrent with or in the same patient visit as an MRI or CAT scan. An MRI or CAT scan provides more anatomical detail of the brain than a PET scan. However, the image from a PET scan can be superimposed on an MRI or CAT scan image more precisely indicating the location of PET ligand and inferentially tau deposits relative to anatomical structures in the brain. Some machines can perform both PET scanning and MRI or CAT scanning without the patient changing positions between the scans facilitating superimposition of images.

Suitable PET ligands include radiolabeled antibodies of the invention (e.g., a mouse, humanized, chimeric or veneered 5G8, 6A10, 8A4, or 7G6 antibody). The radioisotope used can be, for example, $C^{11}$, $N^{13}$, $O^{15}$, $F^{18}$, or $I^{123}$. The interval between administering the PET ligand and performing the scan can depend on the PET ligand and particularly its rate of uptake and clearing into the brain, and the half-life of its radiolabel.

PET scans can also be performed as a prophylactic measure in asymptomatic patients or in patients who have symptoms of mild cognitive impairment but have not yet been diagnosed with a tauopathy but are at elevated risk of developing a tauopathy. For asymptomatic patients, scans are particularly useful for individuals considered at elevated risk of tauopathy because of a family history, genetic or biochemical risk factors, or mature age. Prophylactic scans can commence for example, at a patient age between 45 and 75 years. In some patients, a first scan is performed at age 50 years.

Prophylactic scans can be performed at intervals of for example, between six months and ten years, preferably between 1-5 years. In some patients, prophylactic scans are performed annually. If a PET scan performed as a prophylactic measure indicates abnormally high levels of tau protein deposits, immunotherapy can be commenced and subsequent PET scans performed as in patients diagnosed with a tauopathy. If a PET scanned performed as a prophylactic measure indicates levels of tau protein deposits within normal levels, further PET scans can performed at intervals of between six months and 10 years, and preferably 1-5 years, as before, or in response to appearance of signs and symptoms of a tauopathy or mild cognitive impairment. By combining prophylactic scans with administration of tau-directed immunotherapy if and when an above normal level of tau protein deposits is detected, levels of tau protein deposits can be reduced to, or closer to, normal levels, or at least inhibited from increasing further, and the patient can remain free of the tauopathy for a longer period than if not receiving prophylactic scans and tau-directed immunotherapy (e.g., at least 5, 10, 15 or 20 years, or for the rest of the patient's life).

Normal levels of tau protein deposits can be determined by the amount of neurofibrillary tangles or tau inclusions in the brains of a representative sample of individuals in the general population who have not been diagnosed with a particular tauopathy (e.g., Alzheimer's disease) and are not considered at elevated risk of developing such disease (e.g., a representative sample of disease-free individuals under 50 years of age). Alternatively, a normal level can be recognized in an individual patient if the PET signal according to the present methods in a region of the brain in which tau protein deposits are known to develop is not different (within the accuracy of measurement) from the signal from a region of the brain in which it is known that such deposits do not normally develop. An elevated level in an individual can be recognized by comparison to the normal levels (e.g., outside mean and variance of a standard deviation) or simply from an elevated signal beyond experimental error in a region of the brain associated with tau protein deposits compared with a region not known to be associated with deposits. For purposes of comparing the levels of tau protein deposits in an individual and population, the tau protein deposits should preferably be determined in the same region(s) of the brain, these regions including at least one region in which tau protein deposits associated with a particular tauopathy (e.g., Alzheimer's disease) are known to form. A patient having an elevated level of tau protein deposits is a candidate for commencing immunotherapy.

After commencing immunotherapy, a decrease in the level of tau protein deposits can be first seen as an indication that the treatment is having the desired effect. The observed decrease can be, for example, in the range of 1-100%, 1-50%, or 1-25% of the baseline value. Such effects can be measured in one or more regions of the brain in which deposits are known to form or can be measured from an average of such regions. The total effect of treatment can be approximated by adding the percentage reduction relative to baseline to the increase in tau protein deposits that would otherwise occur in an average untreated patient.

Maintenance of tau protein deposits at an approximately constant level or even a small increase in tau protein deposits can also be an indication of response to treatment albeit a suboptimal response. Such responses can be compared with a time course of levels of tau protein deposits in patients with a particular tauopathy (e.g., Alzheimer's disease) that did not receive treatment, to determine whether the immunotherapy is having an effect in inhibiting further increases of tau protein deposits.

Monitoring of changes in tau protein deposits allows adjustment of the immunotherapy or other treatment regime in response to the treatment. PET monitoring provides an indication of the nature and extent of response to treatment. Then a determination can be made whether to adjust treatment and if desired treatment can be adjusted in response to the PET monitoring. PET monitoring thus allows for tau-directed immunotherapy or other treatment regime to be adjusted before other biomarkers, MRI or cognitive measures have detectably responded. A significant change means that comparison of the value of a parameter after treatment relative to basement provides some evidence that treatment has or has not resulted in a beneficial effect. In some instances, a change of values of a parameter in a patient itself provides evidence that treatment has or has not resulted in a beneficial effect. In other instances, the change of values, if any, in a patient, is compared with the change of values, if any, in a representative control population of patients not undergoing immunotherapy. A difference in response in a particular patient from the normal response in the control patient (e.g., mean plus variance of a standard deviation) can also provide evidence that an immunotherapy regime is or is not achieving a beneficial effect in a patient.

In some patients, monitoring indicates a detectable decline in tau protein deposits but that the level of tau protein deposits remains above normal. In such patients, if there are no unacceptable side effects, the treatment regime can be continued as is or even increased in frequency of administration and/or dose if not already at the maximum recommended dose.

If the monitoring indicates levels of tau protein deposits in a patient have already been reduced to normal, or near-normal, levels of tau protein deposits, the immunotherapy regime can be adjusted from one of induction (i.e., that reduces the level of tau protein deposits) to one of maintenance (i.e., that maintains tau protein deposits at an approximately constant level). Such a regime can be affected by reducing the dose and or frequency of administering immunotherapy.

In other patients, monitoring can indicate that immunotherapy is having some beneficial effect but a suboptimal effect. An optimal effect can be defined as a percentage reduction in the level of tau protein deposits within the top half or quartile of the change in tau protein deposits (measured or calculated over the whole brain or representative region(s) thereof in which tau protein deposits are known to form) experienced by a representative sample of tauopathy patients undergoing immunotherapy at a given time point after commencing therapy. A patient experiencing a smaller decline or a patient whose tau protein deposits remains constant or even increases, but to a lesser extent than expected in the absence of immunotherapy (e.g., as inferred from a control group of patients not administered immunotherapy) can be classified as experiencing a positive but suboptimal response. Such patients can optionally be subject to an adjustment of regime in which the dose and or frequency of administration of an agent is increased.

In some patients, tau protein deposits may increase in similar or greater fashion to tau deposits in patients not receiving immunotherapy. If such increases persist over a period of time, such as 18 months or 2 years, even after any increase in the frequency or dose of agents, immunotherapy can if desired be discontinued in favor of other treatments.

The foregoing description of diagnosing, monitoring, and adjusting treatment for tauopathies has been largely focused on using PET scans. However, any other technique for visualizing and/or measuring tau protein deposits that is amenable to the use of tau antibodies of the invention (e.g., a mouse, humanized, chimeric or veneered 5G8, 6A10, 8A4, or 7G6 antibody) can be used in place of PET scans to perform such methods.

Also provided are methods of detecting an immune response against tau in a patient suffering from or susceptible to diseases associated with tau. The methods can be used to monitor a course of therapeutic and prophylactic treatment with the agents provided herein. The antibody profile following passive immunization typically shows an immediate peak in antibody concentration followed by an exponential decay. Without a further dose, the decay approaches pretreatment levels within a period of days to months depending on the half-life of the antibody administered. For example, the half-life of some human antibodies is of the order of 20 days.

In some methods, a baseline measurement of antibody to tau in the subject is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dose of antibody is administered. In some methods, peak or subsequent measured levels less background are compared with reference levels previously determined to constitute a beneficial prophylactic or therapeutic treatment regime in other subjects. If the measured antibody level is significantly less than a reference level (e.g., less than the mean minus one or, preferably, two standard deviations of the reference value in a population of subjects benefiting from treatment) administration of an additional dose of antibody is indicated.

Also provided are methods of detecting tau in a subject, for example, by measuring tau in a sample from a subject or by in vivo imaging of tau in a subject. Such methods are useful to diagnose or confirm diagnosis of diseases associated with tau, or susceptibility thereto. The methods can also be used on asymptomatic subjects. The presence of tau indicates susceptibility to future symptomatic disease. The methods are also useful for monitoring disease progression and/or response to treatment in subjects who have been previously diagnosed with Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP).

Biological samples obtained from a subject having, suspected of having, or at risk of having Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP) can be contacted with the antibodies disclosed herein to assess the presence of tau. For example, levels of tau in such subjects may be compared to those present in healthy subjects. Alternatively, levels of tau in such subjects receiving treatment for the disease may be compared to those of subjects who have not been treated for Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP). Some such tests involve a biopsy of tissue obtained from such subjects. ELISA assays may also be useful methods, for example, for assessing tau in fluid samples.

VII. Kits

The invention further provides kits (e.g., containers) comprising an antibody disclosed herein and related materials, such as instructions for use (e.g., package insert). The instructions for use may contain, for example, instructions for administration of the antibody and optionally one or more additional agents. The containers of antibody may be unit doses, bulk packages (e.g., multi-dose packages), or sub-unit doses.

Package insert refers to instructions customarily included in commercial packages of therapeutic products that contain information about the indications, usage, dosage, administration, contraindications and/or warnings concerning the use of such therapeutic products.

Kits can also include a second container comprising a pharmaceutically-acceptable buffer, such as bacteriostatic water for injection (BWFI), phosphate-buffered saline, Ringer's solution and dextrose solution. It can also include other materials desirable from a commercial and user standpoint, including other buffers, diluents, filters, needles, and syringes.

VIII. Other Applications

The antibodies can be used for detecting tau, or fragments thereof, in the context of clinical diagnosis or treatment or in research. For example, the antibodies can be used to detect the presence of tau in a biological sample as an indication that the biological sample comprises tau deposits. Binding of the antibodies to the biological sample can be compared to binding of the antibodies to a control sample. The control sample and the biological sample can comprise cells of the same tissue origin. Control samples and biological samples can be obtained from the same individual or different individuals and on the same occasion or on different occasions. If desired, multiple biological samples and multiple control samples are evaluated on multiple occasions to protect against random variation independent of the differences between the samples. A direct comparison can then be made between the biological sample(s) and the control sample(s) to determine whether antibody binding (i.e., the presence of tau) to the biological sample(s) is increased, decreased, or the same relative to antibody binding to the control sample(s). Increased binding of the antibody to the biological sample(s) relative to the control sample(s) indicates the presence of tau in the biological sample(s). In some instances, the increased antibody binding is statistically significant. Optionally, antibody binding to the biological sample is at least 1.5-fold, 2-fold, 3-fold, 4-fold, 5-fold, 10-fold, 20-fold, or 100-fold higher than antibody binding to the control sample.

In addition, the antibodies can be used to detect the presence of the tau in a biological sample to monitor and evaluate the efficacy of a therapeutic agent being used to treat a patient diagnosed with Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP). A biological sample from a patient diagnosed with Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP) is evaluated to establish a baseline for the binding of the antibodies to the sample (i.e., a baseline for the presence of the tau in the sample) before commencing therapy with the therapeutic agent. In some instances, multiple biological samples from the patient are evaluated on multiple occasions to establish both a baseline and measure of random variation independent of treatment. A therapeutic agent is then administered in a regime. The regime may include multiple administrations of the agent over a period of time. Optionally, binding of the antibodies (i.e., presence of tau) is evaluated on multiple occasions in multiple biological samples from the patient, both to establish a measure of random variation and to show a trend in response to immunotherapy. The various assessments of antibody binding to the biological samples are then compared. If only two assessments are made, a direct comparison can be made between the two assessments to determine whether antibody binding (i.e., presence of tau) has increased, decreased, or remained the same between the two assessments. If more than two measurements are made, the measurements can be analyzed as a time course starting before treatment with the therapeutic agent and proceeding through the course of therapy. In patients for whom antibody binding to biological samples has decreased (i.e., the presence of tau), it can be concluded that the therapeutic agent was effective in treating the Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP) in the patient. The decrease in antibody binding can be statistically significant. Optionally, binding decreases by at least 1%, 2%, 3%, 4%, 5%0, 1, 15%, 20%, 30%, 40%, 50%, 60%, 70%, 80%, 90%, or 100%. Assessment of antibody binding can be made in conjunction with assessing other signs and symptoms of Alzheimer's disease, Down's syndrome, mild cognitive impairment, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer disease (LBVAD), or progressive supranuclear palsy (PSP).

The antibodies can also be used as research reagents for laboratory research in detecting tau, or fragments thereof. In such uses, antibodies can be labeled with fluorescent molecules, spin-labeled molecules, enzymes, or radioisotopes, and can be provided in the form of kit with all the necessary reagents to perform the detection assay. The antibodies can also be used to purify tau, or binding partners of tau, e.g., by affinity chromatography.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1. Identification of Tau Monoclonal Antibodies

Monoclonal antibodies against tau were generated as follows. Immunizations were performed with either recombinant N-terminally His-tagged 383 a.a. human tau (4R0N), containing a P301S mutation [immunogen A] or recombinant 383 a.a. human tau (4R0N), containing a P301S mutation, lacking an N-terminal His-tag [immunogen B]. Immunogens were emulsified in RIBI adjuvant.

Five week old female Balb/c mice were intraperitoneally immunized with 25 µg of immunogen A on day 0, and 10 µg of immunogen A each on days 7, 14, 21, 27, 34, 48, 55, and 62. Mice were immunized with 10 µg of immunogen B on days 76 and 90. On days 43 and 98, mice were bled and titered against immunogen A; on day 101 the animals with highest titers were boosted with a terminal immunization of 50 µg immunogen B, which was delivered ½ intraperitoneally and 12 intravenously. Fused hybridomas were screened via ELISA against both immunogens).

Example 2. Mouse Monoclonal Antibodies Bind Tau in ELISA Assays

Methods: Indirect ELISA: 96-well polystyrene plates were coated with capture antibodies anti-6×His (FIG. 1A) or polyclonal anti-tau (Dako #A0024, FIG. 1B) suspended in 1×PBS for 2 hr at RT or 16 hr at 4° C. Coating was removed, and plates were blocked for 1 hr with 1% BSA in 1×PBS, followed by incubation with human recombinant tau, either with (FIG. 1A) or without (FIG. 1B) a polyhistidine tag at the N-terminus of the protein. After washing, plates were incubated with indicated antibodies, washed, and incubated with HRP-conjugated goat anti-mouse secondary antibody. Plates were developed with TMB, and $A_{450}$ was measured with a plate reader.

Sandwich ELISA: 96-well polystyrene plates were coated with anti-mouse antibodies in 1×PBS for 2 hr at RT or 16 hr at 4° C. Coating was removed, and plates were blocked for 1 hr with 1% BSA in 1×PBS. The plate was next incubated with the Indicated antibodies at identical concentrations, diluted in 0.1% BSA in 1×PBS. Plates were successively treated with human tau, polyclonal rabbit anti-tau (Dako #A0024), and HRP-conjugated goat anti-rabbit antibody, all diluted in 0.1% BSA in PBS with washes occurring between each step. Streptavidin-RP was added, plates were developed with TMB, and $A_{450}$ was measured with a plate reader. See FIG. 1C.

Results: A panel of hybridoma-produced antibodies were assayed for binding to tau via a number of different ELISA formats. Detection of tau was confirmed using an indirect format, using tau protein immobilized by its N-terminally fused polyhistidine tag (FIG. 1A). Binding to the native, untagged protein was also confirmed (FIG. 1). To assess the solution affinity of the various antibodies, a sandwich ELISA format was used in which tested hybridoma antibodies were used as capture reagents (FIG. 1C).

Example 3. Affinity of Mouse Monoclonal Antibodies to Tau

Methods: SPR analysis was performed using a Biacore T200 to determine the binding kinetics of murine antibodies to recombinant human tau. To prepare a sensor surface, anti-mouse antibody (GE Life Sciences) was immobilized on sensor chip CM5 via amine coupling, and antibody was captured at a level to ensure maximum binding of 50 RU. Various concentrations of recombinant tau ranging from 10-0.14 nM were passed over the captured ligand at a flow rate of 50 µL/min in running buffer (HBS+0.05% P-20, 1 mg/mL BSA), for 180 sec association and 900 sec dissociation. Data were double-referenced to both an irrelevant sensor not containing antibody ligand, and 0 nM analyte concentration to account for the dissociation of ligand from the capture moiety. Data was then analyzed using a global 1:1 fit.

Results: Multiple murine antibodies were selected based on their performance in a battery of ELISA assays, and their binding affinities were assessed via SPR. Antibodies were tested in parallel sets, and their binding association and dissociation rates were measured. Binding affinities are shown in FIG. 2.

Example 4. Mouse Monoclonal Antibodies Prevent Binding of Human Tau to the Surface of Immortalized Neuronal Cells Methods: Inhibition of Tau Binding to B103 Neuroblastoma Cells with anti-Tau Monoclonal Antibodies
1. Resuspend B103 cells in PBS at $5 \times 10^5$ cells/mL. Plate 50 µL of cell suspension per well in a MSD High Bind plate. This results in 25K cells/well. Cover the plate and allow cells to attach at 37° C., 5% $CO_2$, for 2 hrs.
2. Following cell attachment, remove PBS from wells by inverting plate and gently tapping to remove excess buffer. Add 50 µL of 3% MSD Blocker A in PBS or other suitable blocking buffer to each well and incubate plate at RT for 1 hr without shaking.
3. During the plate blocking step co-incubate Tau and anti-Tau antibodies as follows:
   a. Start with anti-Tau antibody at 2 mg/mL and serial dilute in PBS, 1:2, for 7 additional dilutions.
   b. Dilute Tau to 20 nM in PBS. The Tau concentration will be constant in each well.
   c. Mix the Tau and anti-Tau antibody, 1:1, for a final Tau concentration of 10 nM and a starting concentration of anti-Tau of 1 mg/mL.
   d. Incubate the mixture for approximately 1 hr at RT with shaking (600 rpm).
4. After plate blocking, step 2, remove blocking buffer from wells by inverting plate and gently tapping and wash plate 2× with PBS using a multichannel pipette. Ensure excess buffer is completely removed. Cool the plated cells to 4° C. prior to adding the Tau: anti-Tau complexes.
5. Add 50 µL of cooled complex, step 3, to the plated cells and incubate on ice for 30 minutes.
6. Wash plate 2× with chilled PBS as previously described.
7. Add 50 µL per well of the 16B5.SULFO-TAG for detection of cell surface bound Tau. Incubate for 30 minutes on ice.
8. Wash plate 2× with chilled PBS again as previously described.
9. Add 150 µL per well of 1×Read Buffer T Without Surfactant (diluted in $H_2O$) and read immediately on the MSD SECTOR™ 600 instrument. Avoid introducing bubbles when adding read buffer.
10. Report the MSD signals vs. concentration of anti-Tau.

Antibodies tested were anti-tau antibodies 3D6, 16G7, 3H9, 4C5, 5G8, and isotype control.

Results:
Decreasing SulfoTag anti-tau signal occurring with increasing test antibody indicates functional blocking of the binding of tau to neuronal cell surfaces. No blocking was observed with isotype control, 16G7, or 3H9. Increasing amounts of functional blocking activity were observed with 4C5, 5G8, and 3D6. See FIG. 3.

Example 5. 3D6 and 5G8 Immunocapture Tau from Human Disease Tissue

Methods: High-salt soluble protein fractions were prepared to 1 mg/ml. For each immunoprecipitation, 200 µg of sample was used. 10 µg of the indicated antibody (either an isotype control, anti-tau antibody 3D6, or 5G8) was added to the high-salt sample preparations, and incubated for 2 hr. Protein G magnetic beads were then added to the mixtures, and incubated for a further hour to capture antibody/antigen complexes. Samples were thoroughly washed with 1×PBS, and beads were boiled in reducing/denaturing sample buffer to release captured proteins. Resulting samples were resolved by SDS-PAGE and Western blotting was performed using a polyclonal anti-tau antibody (Dako, #A0024).

Figure 4:
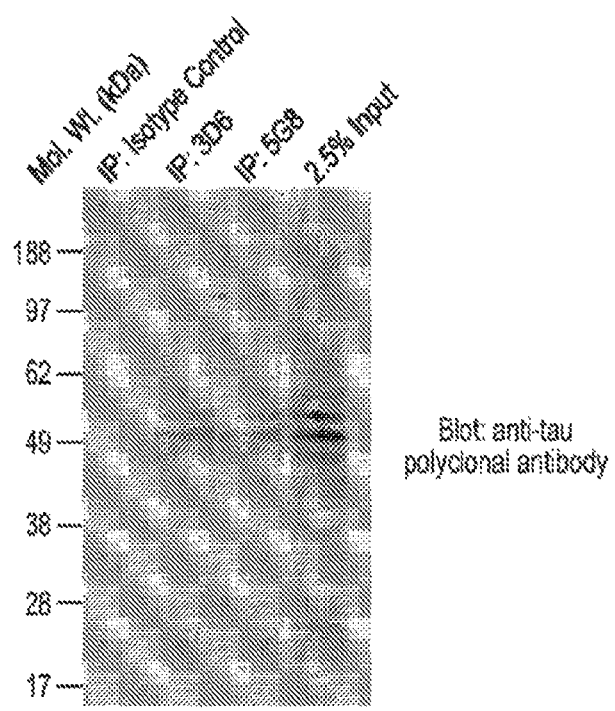
FIG. 4 depicts results of experiments showing that 5G8 immunocaptures tau from human Alzheimer's disease tissue.

Results: As shown in FIG. 4, anti-tau antibodies 3D6 and 5G8 immunoprecipitated tau from Alzheimer disease tissue. High-salt soluble fractions were immunoprecipitated with the indicated antibody, and detected with a polyclonal anti-tau antibody directed towards a separate region of the tau molecule from the binding sites for 3D6 and 5G8. Both 5G8 and 3D6 captured tau from this fraction. The input (high-salt soluble sample) is shown at right.

Example 6. Design of Humanized 5G8 Antibodies

The starting point or donor antibody for humanization was the mouse antibody 5G8. The heavy chain variable amino acid sequence of mature m5G8 is provided as SEQ ID NO:9. The light chain variable amino acid sequence of mature m5G8 is provided as SEQ ID NO:10. The heavy chain Kabat/Chothia Composite CDR1, CDR2, and CDR3 amino acid sequences are provided as SEQ ID NOs:11-13, respectively. The light chain Kabat CDR1, CDR2, and CDR3 amino acid sequences are provided as SEQ ID NOs:14-16 respectively. Kabat numbering is used throughout.

The CDRs of 5G8 VH and VL were identified using Martin's sequence-based CDR-identification rules (Martin A C R. (2010). In: Kontermann R and Dübel S (eds).

*Antibody Engineering*. Heidelberg, Germany: Springer International Publishing AG). The variable kappa (Vk) of 5G8 belongs to mouse Vk subgroup 2, which corresponds to human Vk subgroup 2 and the variable heavy (Vh) to mouse VH subgroup 2c, which corresponds to human VH subgroup 1 [Kabat E. A., et al., (1991), Sequences of Proteins of Immunological Interest, Fifth Edition. NIH Publication No. 91-3242]. 16 residue Kabat CDR-L1 is similar to Chothia canonical class 4, 7 residue Kabat CDR-L2 is of Chothia canonical class 1, 9 residue Kabat CDR-L3 is similar to Chothia canonical class 1 in Vk [Martin A. C, and Thornton J. M. (1996) J. Mol. Biol. 263:800-15.]. 10 residue Kabat/Chothia Composite CDR-H1 is similar to Chothia canonical class 1, 17 residue Kabat/Chothia Composite CDR-H2 and is similar to Chothia canonical class 2 [Martin & Thornton, 1996]. Kabat/Chothia Composite CDR-H3 has no canonical classes.

The sequences of 5G8 VH and VL were used to query the curated antibody database of BioLuminate software (Schrödinger, LLC; Zhu K, et al., (2014) *Proteins*. 82(8): 1646-1655) for proteins with similar amino acid sequences and known structures. The structure of the highly similar murine anti-prion antibody 3F4 (PDB ID: 1CR9; 1CR9_H; SEQ ID NO:27 and 1CR9_L; SEQ ID NO:30), discovered by Kascsak, et al. ((1987) *J Virol*. 61(12):3688-93) and sequenced by Kanyo, et al. ((1999). *J Mol Biol*. 293(4):855-63), with a resolution of 2.9 Å, was chosen to serve as a template for building a model of 5G8 in BioLuminate. A further query of the BioLuminate database for antibodies of human origin found the frameworks of 5G8 VH and VL to share a high degree of sequence similarity with the corresponding regions of the VH and VL regions of humanized anti-dabigatran Fab aDabi-Fab2b (VH Accession No. 4YHM_H); VL Accession No. 4YHM_L), designed by Schiele, et al. ((2015) *MAbs*. 7(5):871-80). The variable domains of 5G8 and aDabi-Fab2b also share identical lengths for the CDR-H1, H2, L1, L2, and L3 loops. Accordingly, the framework regions of aDabi-Fab2b VH (acc. no 4YHM_H; SEQ ID NO:28) and VL (acc. no. 4YHM_L; SEQ ID NO:31) were chosen as the acceptor sequences for the CDRs of 5G8.

Heavy and light chain variant sequences resulting from antibody humanization process were further aligned to human germ line sequences using IMGT Domain GapAlign tool to assess the humanness of the heavy and light chain as outlined by WHO INN committee guidelines. (WHO-INN: International nonproprietary names (INN) for biological and biotechnological substances (a review) (Internet) 2014. Available from the World Health Organization website. Residues were changed to align with corresponding human germ line sequence, where possible, to enhance humanness. For humanized VL_v5 and VL_v6 variants, mutations were introduced to render the sequences more similar to human germline gene IGKV2-29 (acc. No. A2NJV5.2; SEQ ID NO:32) For humanized VH_v7 and VH_v8 variants, mutations were introduced to render the sequences more similar to human germline gene IGHV1-46 (acc. No. P01743.2; SEQ ID NO:29)

The amino acid sequences consisting of aDabi-Fab2b frameworks and 5G8 CDRs are designated hu5G8-VH_v1 and hu5G8-VL_v1. Additional versions of hu5G8-VH and hu5G8-VL were designed to enable assessment of various framework residues for their contributions to antigen binding and immunogenicity. The positions considered for mutation include those that:

- define the canonical CDR conformations (summarized in Martin 2010)
- are within the Vernier zone (Foote J and Winter G. (1992) Antibody framework residues affecting the conformation of the hypervariable loops. *J Mol Biol*. 224(2): 487-99),
- localize to the VH/VL domain interface (summarized in Léger O J P and Saldanha J. (2000) Preparation of recombinant antibodies from immune rodent spleens and the design of their humanization by CDR grafting. In: Shepherd P and Dean C (eds). *Monoclonal Antibodies: a Practical Approach*. Oxford, UK: Oxford University Press),
- are susceptible to post-translational modifications, such as glycosylation or pyroglutamination,
- are occupied by residues that are predicted to clash with CDRs, according to the model of 5G8 CDRs grafted onto aDabi-Fab2b frameworks, or
- are occupied by residues that are rare among sequenced human antibodies, where either the parental mouse 5G8 residue or some other residue is much more prevalent.

8 humanized heavy chain variable region variants and 6 humanized light chain variable region variants were constructed containing different permutations of substitutions 8 exemplified humanized mature heavy chain variable regions: hu5G8-VH_v1, hu5G8-VH_v2, hu5G8-VH_v3, hu5G8-VH_v4, hu5G8-VH_v5, hu5G8-VH_v6, hu5G8-VH_v7, and hu5G8-VH_v8 (SEQ ID NOs: 33-40, respectively) and hu5G8-VL_v1, hu5G8-VL_v2, hu5G8-VL_v3, hu5G8-VL_v4, hu5G8-VL_v5, and hu5G8-VL v6 (SEQ ID NOs: 41-46, respectively). (Tables 4 and 3). The exemplary humanized Vk and Vh designs, with backmutations and other mutations based on selected human frameworks, are shown in Tables 6 and 7, respectively. The bolded areas in Tables 6 and 7 indicate the CDRs as defined by Kabat/Chothia Composite. A "." in the columns in Table 6 for hu5G8-VL_v2, hu5G8-VL_v3, hu5G8-VL_v4, hu5G8-VL_v5, and hu5G8-VL_v6 indicates that the amino acid at the indicated position is the same as that in hu5G8-VL_v1. A "." in the columns in Table 7 for hu5G8-VH_v2, hu5G8-VH_v3, hu5G8-VH_v4, hu5G8-VH v5, hu5G8-VH v6, hu5G8-VH_v7, and hu5G8-VH_v8 indicates that the amino acid at the indicated position is the same as that in hu5G8-VH_v1. A "-" in the columns in Tables 6 and 7 indicates no residue at the indicated position. SEQ ID NOs: 33-40 and SEQ ID NOs: 41-46 contain backmutations and other mutations as shown in Table 8. The amino acids at positions in hu5G8-VH_v1, hu5G8-VH_v2, hu5G8-VH_v3, hu5G8-VH_v4, hu5G8-VH_v5, hu5G8-VH_v6, hu5G8-VH_v7, and hu5G8-VH_v8 are listed in Table 9. The amino acids at positions in hu5G8-VL_v1, hu5G8-VL_v2, hu5G8-VL_v3, hu5G8-VL_v4, hu5G8-VL_v5, and hu5G8-VL_v6 are listed in Table 10. The percentage humanness for humanized VH chains hu5G8-VH_v1, hu5G8-VH_v2, hu5G8-VH_v3, hu5G8-VH_v4, hu5G8-VH_v5, hu5G8-VH_v6, hu5G8-VH_v7, and hu5G8-VH_v8 (SEQ ID NOs: 33-40, respectively) with respect to the most similar human germline gene IGHV1-46, and for humanized VL chains hu5G8-VL_v1, hu5G8-VL_v2, hu5G8-VL_v3, hu5G8-VL_v4, hu5G8-VL_v5, and hu5G8-VL_v6 (SEQ ID NOs:41-46, respectively) with respect to the most similar human germline gene IGKV2-29, is shown in Table 11.

TABLE 6

| Linear residue # | Kabat residue # | FR or CDR | Murine 5G8 VL (SEQ ID NO: 8) | Germline IGKV2-29 Acc. # A2NJV5.2 (SEQ ID NO: 32) | Accentor aDabi-Fab2b-VL Acc. # 4YHM_L (SEQ ID NO: 31) | hu5G8-VL_v1 (SEQ ID NO: 41) | hu5G8-VL_v2 (SEQ ID NO: 42) | hu5G8-VL_v3 (SEQ ID NO: 43) | hu5G8-VL_v4 (SEQ ID NO: 44) | hu5G8-VL_v5 (SEQ ID NO: 45) | hu5G8-VL_v6 (SEQ ID NO: 46) |
|---|---|---|---|---|---|---|---|---|---|---|---|
| 1 | 1 | Fr1 | D | D | D | D | . | . | . | . | . |
| 2 | 2 | Fr1 | V | I | I | I | V | V | V | . | V |
| 3 | 3 | Fr1 | V | V | V | V | . | . | . | . | . |
| 4 | 4 | Fr1 | M | M | M | M | . | . | . | . | . |
| 5 | 5 | Fr1 | T | T | T | T | . | . | . | . | . |
| 6 | 6 | Fr1 | Q | Q | Q | Q | . | . | . | . | . |
| 7 | 7 | Fr1 | T | T | T | T | . | . | S | . | . |
| 8 | 8 | Fr1 | P | P | P | P | . | . | . | . | . |
| 9 | 9 | Fr1 | L | L | L | L | . | . | . | . | . |
| 10 | 10 | Fr1 | T | S | S | S | . | . | . | . | . |
| 11 | 11 | Fr1 | L | L | L | L | . | . | . | . | . |
| 12 | 12 | Fr1 | S | S | S | S | . | . | . | . | . |
| 13 | 13 | Fr1 | V | V | V | V | . | . | . | . | . |
| 14 | 14 | Fr1 | T | T | T | T | . | . | . | . | . |
| 15 | 15 | Fr1 | I | P | P | P | . | . | . | . | . |
| 16 | 16 | Fr1 | G | G | G | G | . | . | . | . | . |
| 17 | 17 | Fr1 | Q | Q | Q | Q | . | . | E | . | . |
| 18 | 18 | Fr1 | P | P | P | P | . | . | . | . | . |
| 19 | 19 | Fr1 | A | A | A | A | . | . | . | . | . |
| 20 | 20 | Fr1 | S | S | S | S | . | . | . | . | . |
| 21 | 21 | Fr1 | I | I | I | I | . | . | . | . | . |
| 22 | 22 | Fr1 | S | S | S | S | . | . | . | . | . |
| 23 | 23 | Fr1 | C | C | C | C | . | . | . | . | . |
| 24 | 24 | CDR-L1 | K | K | R | K | . | . | . | . | . |
| 25 | 25 | CDR-L1 | S | S | S | S | . | . | . | . | . |
| 26 | 26 | CDR-L1 | S | S | S | S | . | . | . | . | . |
| 27 | 27 | CDR-L1 | Q | Q | Q | Q | . | . | . | . | . |
| 28 | 27A | CDR-L1 | S | S | S | S | . | . | . | . | . |
| 29 | 27B | CDR-L1 | L | L | I | L | . | . | . | . | . |
| 30 | 27C | CDR-L1 | L | L | V | L | . | . | . | . | . |
| 31 | 27D | CDR-L1 | D | H | H | D | . | . | . | . | . |
| 32 | 27E | CDR-L1 | S | S | S | S | . | . | . | . | . |
| 33 | 27F | CDR-L1 | — | — | — | — | — | — | — | — | — |
| 34 | 28 | CDR-L1 | D | D | D | D | . | . | . | . | . |
| 35 | 29 | CDR-L1 | G | G | G | G | . | . | . | . | . |
| 36 | 30 | CDR-L1 | K | K | N | K | . | . | . | . | . |
| 37 | 31 | CDR-L1 | T | T | I | T | . | . | . | . | . |
| 38 | 32 | CDR-L1 | Y | Y | Y | Y | . | . | . | . | . |
| 39 | 33 | CDR-L1 | L | L | L | L | . | . | . | . | . |
| 40 | 34 | CDR-L1 | N | Y | E | N | . | . | . | . | . |
| 41 | 35 | Fr2 | W | W | W | W | . | . | . | . | . |
| 42 | 36 | Fr2 | L | Y | Y | Y | L | L | L | . | L |
| 43 | 37 | Fr2 | L | L | L | L | . | . | . | . | . |
| 44 | 38 | Fr2 | Q | Q | Q | Q | . | . | . | . | . |
| 45 | 39 | Fr2 | R | K | K | K | . | . | . | . | . |
| 46 | 40 | Fr2 | P | P | P | P | . | . | . | . | . |
| 47 | 41 | Fr2 | G | G | G | G | . | . | . | . | . |
| 48 | 42 | Fr2 | Q | Q | Q | Q | . | . | . | . | . |
| 49 | 43 | Fr2 | S | S | S | S | . | . | . | . | . |
| 50 | 44 | Fr2 | P | P | P | P | . | . | . | . | . |
| 51 | 45 | Fr2 | K | Q | K | K | . | . | . | Q | Q |
| 52 | 46 | Fr2 | R | L | L | L | R | R | R | . | R |
| 53 | 47 | Fr2 | L | L | L | L | . | . | . | . | . |
| 54 | 48 | Fr2 | I | I | I | I | . | . | . | . | . |
| 55 | 49 | Fr2 | Y | Y | Y | Y | . | . | . | . | . |
| 56 | 50 | CDR-L2 | L | E | K | L | . | . | . | . | . |
| 57 | 51 | CDR-L2 | V | V | V | V | . | . | . | . | . |
| 58 | 52 | CDR-L2 | S | S | S | S | . | . | . | . | . |
| 59 | 53 | CDR-L2 | K | S | Y | K | . | . | . | . | . |
| 60 | 54 | CDR-L2 | L | R | R | L | . | . | . | . | . |
| 61 | 55 | CDR-L2 | D | F | F | D | . | . | . | . | . |
| 62 | 56 | CDR-L2 | S | S | S | S | . | . | . | . | . |
| 63 | 57 | Fr3 | G | G | G | G | . | . | . | . | . |
| 64 | 58 | Fr3 | V | V | V | V | . | . | . | . | . |
| 65 | 59 | Fr3 | P | P | P | P | . | . | . | . | . |
| 66 | 60 | Fr3 | D | D | D | D | . | . | . | . | . |
| 67 | 61 | Fr3 | R | R | R | R | . | . | . | . | . |
| 68 | 62 | Fr3 | F | F | F | F | . | . | . | . | . |
| 69 | 63 | Fr3 | T | S | S | S | . | . | . | . | . |
| 70 | 64 | Fr3 | G | G | G | G | . | . | . | . | . |
| 71 | 65 | Fr3 | S | S | S | S | . | . | . | . | . |
| 72 | 66 | Fr3 | G | G | G | G | . | . | . | . | . |

TABLE 6-continued

| Linear residue # | Kabat residue # | FR or CDR | Murine 5G8 VL (SEQ ID NO: 8) | Germline IGKV2-29 Acc. # A2NJV5.2 (SEQ ID NO: 32) | Accentor aDabi-Fab2b-VL Acc. # 4YHM_L (SEQ ID NO: 31) | hu5G8-VL_v1 (SEQ ID NO: 41) | hu5G8-VL_v2 (SEQ ID NO: 42) | hu5G8-VL_v3 (SEQ ID NO: 43) | hu5G8-VL_v4 (SEQ ID NO: 44) | hu5G8-VL_v5 (SEQ ID NO: 45) | hu5G8-VL_v6 (SEQ ID NO: 46) |
|---|---|---|---|---|---|---|---|---|---|---|---|
| 73 | 67 | Fr3 | S | S | S | S | . | . | . | . | . |
| 74 | 68 | Fr3 | G | G | G | G | . | . | . | . | . |
| 75 | 69 | Fr3 | T | T | T | T | . | . | . | . | . |
| 76 | 70 | Fr3 | D | D | G | G | . | D | D | D | D |
| 77 | 71 | Fr3 | F | F | F | F | . | . | . | . | . |
| 78 | 72 | Fr3 | T | T | T | T | . | . | . | . | . |
| 79 | 73 | Fr3 | L | L | L | L | . | . | . | . | . |
| 80 | 74 | Fr3 | K | K | K | K | . | . | . | . | . |
| 81 | 75 | Fr3 | I | I | I | I | . | . | . | . | . |
| 82 | 76 | Fr3 | R | S | S | S | . | . | . | . | . |
| 83 | 77 | Fr3 | R | R | R | R | . | . | . | . | . |
| 84 | 78 | Fr3 | V | V | V | V | . | . | . | . | . |
| 85 | 79 | Fr3 | E | E | E | E | . | . | . | . | . |
| 86 | 80 | Fr3 | A | A | A | A | . | . | . | . | . |
| 87 | 81 | Fr3 | E | E | E | E | . | . | . | . | . |
| 88 | 82 | Fr3 | D | D | D | D | . | . | . | . | . |
| 89 | 83 | Fr3 | L | V | V | V | . | . | . | . | . |
| 90 | 84 | Fr3 | G | G | G | G | . | . | . | . | . |
| 91 | 85 | Fr3 | V | V | V | V | . | . | . | . | . |
| 92 | 86 | Fr3 | Y | Y | Y | Y | . | . | . | . | . |
| 93 | 87 | Fr3 | Y | Y | Y | Y | . | . | . | . | . |
| 94 | 88 | Fr3 | C | C | C | C | . | . | . | . | . |
| 95 | 89 | CDR-L3 | W | M | F | W | . | . | . | . | . |
| 96 | 90 | CDR-L3 | Q | Q | Q | Q | . | . | . | . | . |
| 97 | 91 | CDR-L3 | G | — | A | G | . | . | . | . | . |
| 98 | 92 | CDR-L3 | T | — | S | T | . | . | . | . | . |
| 99 | 93 | CDR-L3 | L | — | H | L | . | . | . | . | . |
| 100 | 94 | CDR-L3 | F | — | V | F | . | . | . | . | . |
| 101 | 95 | CDR-L3 | P | — | P | P | . | . | . | . | . |
| 102 | 95A | CDR-L3 | — | — | — | — | — | — | — | — | — |
| 103 | 95B | CDR-L3 | — | — | — | — | — | — | — | — | — |
| 104 | 95C | CDR-L3 | — | — | — | — | — | — | — | — | — |
| 105 | 95D | CDR-L3 | — | — | — | — | — | — | — | — | — |
| 106 | 95E | CDR-L3 | — | — | — | — | — | — | — | — | — |
| 107 | 95F | CDR-L3 | — | — | — | — | — | — | — | — | — |
| 108 | 96 | CDR-L3 | Y | G | Y | Y | . | . | . | . | . |
| 109 | 97 | CDR-L3 | T | I | T | T | . | . | . | . | . |
| 110 | 98 | Fr4 | F | H | F | F | . | . | . | . | . |
| 111 | 99 | Fr4 | G | L | G | G | . | . | . | . | . |
| 112 | 100 | Fr4 | G | P | G | G | . | . | . | . | . |
| 113 | 101 | Fr4 | G | | G | G | . | . | . | . | . |
| 114 | 102 | Fr4 | T | | T | T | . | . | . | . | . |
| 115 | 103 | Fr4 | K | | K | K | . | . | . | . | . |
| 116 | 104 | Fr4 | L | | L | L | . | . | . | . | . |
| 117 | 105 | Fr4 | E | | E | E | . | . | . | . | . |
| 118 | 106 | Fr4 | I | | I | I | . | . | . | . | . |
| 119 | 106A | Fr4 | — | | — | — | — | — | — | — | — |
| 120 | 107 | Fr4 | K | | K | K | . | . | . | . | . |

TABLE 7

| Linear residue | Kabat residue | FR or CDR | Murine 5G8 VH (SEQ ID NO: 7) | Germline IGHV1-46 Acc. # P01743.2 (SEQ ID NO: 29) | Accentor Acc. # 4YHM_H aDabi-Fab2b-VH (SEQ ID NO: 28) | hu5G8-VH_v1 (SEQ ID NO: 33) | hu5G8-VH_v2 (SEQ ID NO: 34) |
|---|---|---|---|---|---|---|---|
| 1 | 1 | Fr1 | E | Q | Q | Q | . |
| 2 | 2 | Fr1 | V | V | V | V | . |
| 3 | 3 | Fr1 | Q | Q | Q | Q | . |
| 4 | 4 | Fr1 | L | L | L | L | . |
| 5 | 5 | Fr1 | Q | V | V | V | . |
| 6 | 6 | Fr1 | Q | Q | Q | Q | . |
| 7 | 7 | Fr1 | S | S | S | S | . |
| 8 | 8 | Fr1 | G | G | G | G | . |
| 9 | 9 | Fr1 | A | A | A | A | . |
| 10 | 10 | Fr1 | E | E | E | E | . |

TABLE 7-continued

| | | | | | | | |
|---|---|---|---|---|---|---|---|
| 11 | 11 | Fr1 | L | V | V | V | . |
| 12 | 12 | Fr1 | V | K | K | K | . |
| 13 | 13 | Fr1 | R | K | K | K | . |
| 14 | 14 | Fr1 | S | P | P | P | . |
| 15 | 15 | Fr1 | G | G | G | G | . |
| 16 | 16 | Fr1 | A | A | A | A | . |
| 17 | 17 | Fr1 | S | S | S | S | . |
| 18 | 18 | Fr1 | V | V | V | V | . |
| 19 | 19 | Fr1 | R | K | K | K | . |
| 20 | 20 | Fr1 | L | V | V | V | . |
| 21 | 21 | Fr1 | S | S | S | S | . |
| 22 | 22 | Fr1 | C | C | C | C | . |
| 23 | 23 | Fr1 | T | K | K | K | . |
| 24 | 24 | Fr1 | A | A | A | A | . |
| 25 | 25 | Fr1 | S | S | S | S | . |
| 26 | 26 | CDR-H1 | G | G | G | G | . |
| 27 | 27 | CDR-H1 | F | Y | Y | F | . |
| 28 | 28 | CDR-H1 | N | T | T | N | . |
| 29 | 29 | CDR-H1 | I | F | F | I | . |
| 30 | 30 | CDR-H1 | K | T | T | K | . |
| 31 | 31 | CDR-H1 | D | S | D | D | . |
| 32 | 32 | CDR-H1 | Y | Y | Y | Y | . |
| 33 | 33 | CDR-H1 | Y | Y | Y | Y | . |
| 34 | 34 | CDR-H1 | M | M | M | M | . |
| 35 | 35 | CDR-H1 | H | H | H | H | . |
| 36 | 35A | CDR-H1 | — | — | — | — | — |
| 37 | 35B | CDR-H1 | — | — | — | — | — |
| 38 | 36 | Fr2 | W | W | W | W | . |
| 39 | 37 | Fr2 | V | V | V | V | . |
| 40 | 38 | Fr2 | R | R | R | R | . |
| 41 | 39 | Fr2 | Q | Q | Q | Q | . |
| 42 | 40 | Fr2 | R | A | A | A | . |
| 43 | 41 | Fr2 | P | P | P | P | . |
| 44 | 42 | Fr2 | E | G | G | G | . |
| 45 | 43 | Fr2 | Q | Q | Q | Q | . |
| 46 | 44 | Fr2 | G | G | G | G | . |
| 47 | 45 | Fr2 | L | L | L | L | . |
| 48 | 46 | Fr2 | E | E | E | E | . |
| 49 | 47 | Fr2 | W | W | W | W | . |
| 50 | 48 | Fr2 | I | M | M | M | I |
| 51 | 49 | Fr2 | G | G | G | G | . |
| 52 | 50 | CDR-H2 | W | I | E | W | . |
| 53 | 51 | CDR-H2 | I | I | T | I | . |
| 54 | 52 | CDR-H2 | D | N | N | D | . |
| 55 | 52A | CDR-H2 | P | P | P | P | . |
| 56 | 52B | CDR-H2 | — | — | — | — | — |
| 57 | 52C | CDR-H2 | — | — | — | — | — |
| 58 | 53 | CDR-H2 | E | S | R | E | . |
| 59 | 54 | CDR-H2 | N | G | N | N | . |
| 60 | 55 | CDR-H2 | G | G | G | G | . |
| 61 | 56 | CDR-H2 | D | S | G | D | . |
| 62 | 57 | CDR-H2 | T | T | T | T | . |
| 63 | 58 | CDR-H2 | V | S | T | V | . |
| 64 | 59 | CDR-H2 | Y | Y | Y | Y | . |
| 65 | 60 | CDR-H2 | A | A | N | A | . |
| 66 | 61 | CDR-H2 | P | Q | E | P | . |
| 67 | 62 | CDR-H2 | K | K | K | K | . |
| 68 | 63 | CDR-H2 | F | F | F | F | . |
| 69 | 64 | CDR-H2 | Q | Q | K | Q | . |
| 70 | 65 | CDR-H2 | G | G | G | G | . |
| 71 | 66 | Fr3 | K | R | K | K | . |
| 72 | 67 | Fr3 | A | V | A | A | . |
| 73 | 68 | Fr3 | T | T | T | T | . |
| 74 | 69 | Fr3 | M | M | M | M | . |
| 75 | 70 | Fr3 | T | T | T | T | . |
| 76 | 71 | Fr3 | S | R | R | R | S |
| 77 | 72 | Fr3 | D | D | D | D | . |
| 78 | 73 | Fr3 | T | T | T | T | . |
| 79 | 74 | Fr3 | S | S | S | S | . |
| 80 | 75 | Fr3 | S | T | T | T | . |
| 81 | 76 | Fr3 | N | S | S | S | . |
| 82 | 77 | Fr3 | T | T | T | T | . |
| 83 | 78 | Fr3 | A | V | A | A | . |
| 84 | 79 | Fr3 | Y | Y | Y | Y | . |
| 85 | 80 | Fr3 | L | M | M | M | . |
| 86 | 81 | Fr3 | H | E | E | E | . |
| 87 | 82 | Fr3 | L | L | L | L | . |
| 88 | 82A | Fr3 | S | S | S | S | . |
| 89 | 82B | Fr3 | S | S | S | S | . |
| 90 | 82C | Fr3 | L | L | L | L | . |

TABLE 7-continued

| | | | | | | | |
|---|---|---|---|---|---|---|---|
| 91 | 83 | Fr3 | T | R | R | R | . |
| 92 | 84 | Fr3 | S | S | S | S | . |
| 93 | 85 | Fr3 | E | E | E | E | . |
| 94 | 86 | Fr3 | D | D | D | D | . |
| 95 | 87 | Fr3 | T | T | T | T | . |
| 96 | 88 | Fr3 | A | A | A | A | . |
| 97 | 89 | Fr3 | V | V | V | V | . |
| 98 | 90 | Fr3 | Y | Y | Y | Y | . |
| 99 | 91 | Fr3 | Y | Y | Y | Y | . |
| 100 | 92 | Fr3 | C | C | C | C | . |
| 101 | 93 | Fr3 | S | A | T | T | S |
| 102 | 94 | Fr3 | P | R | I | I | P |
| 103 | 95 | CDR-H3 | L | | G | L | . |
| 104 | 96 | CDR-H3 | — | | T | — | — |
| 105 | 97 | CDR-H3 | — | | S | — | — |
| 106 | 98 | CDR-H3 | — | | G | — | — |
| 107 | 99 | CDR-H3 | — | | Y | — | — |
| 108 | 100 | CDR-H3 | — | | D | — | — |
| 109 | 100A | CDR-H3 | — | | Y | — | — |
| 110 | 100B | CDR-H3 | — | | F | — | — |
| 111 | 100C | CDR-H3 | — | | | — | — |
| 112 | 100D | CDR-H3 | — | | | — | — |
| 113 | 100E | CDR-H3 | — | | | — | — |
| 114 | 100F | CDR-H3 | — | | | — | — |
| 115 | 100G | CDR-H3 | — | | | — | — |
| 116 | 100H | CDR-H3 | — | | | — | — |
| 117 | 100I | CDR-H3 | — | | | — | — |
| 118 | 100J | CDR-H3 | — | | | — | — |
| 119 | 100K | CDR-H3 | — | | | — | — |
| 120 | 101 | CDR-H3 | D | | D | D | . |
| 121 | 102 | CDR-H3 | F | | Y | F | . |
| 122 | 103 | Fr4 | W | | W | W | . |
| 123 | 104 | Fr4 | G | | G | G | . |
| 124 | 105 | Fr4 | Q | | Q | Q | . |
| 125 | 106 | Fr4 | G | | G | G | . |
| 126 | 107 | Fr4 | T | | T | T | . |
| 127 | 108 | Fr4 | T | | L | L | . |
| 128 | 109 | Fr4 | L | | V | V | . |
| 129 | 110 | Fr4 | T | | T | T | . |
| 130 | 111 | Fr4 | V | | V | V | . |
| 131 | 112 | Fr4 | S | | S | S | . |
| 132 | 113 | Fr4 | S | | S | S | . |

| Linear residue | hu5G8-VH_v3 (SEQ ID NO: 35) | hu5G8-VH_v4 (SEQ ID NO: 36) | hu5G8-VH_v5 (SEQ ID NO: 37) | hu5G8-VH_v6 (SEQ ID NO: 38) | hu5G8-VH_v7 (SEQ ID NO: 39) | hu5G8-VH_v8 (SEQ ID NO: 40) |
|---|---|---|---|---|---|---|
| 1 | E | E | E | E | . | E |
| 2 | . | . | . | . | . | . |
| 3 | . | . | . | . | . | . |
| 4 | . | . | . | . | . | . |
| 5 | . | . | . | . | . | . |
| 6 | . | . | . | . | . | . |
| 7 | . | . | . | . | . | . |
| 8 | . | . | . | . | . | . |
| 9 | . | . | . | . | . | . |
| 10 | . | . | . | . | . | . |
| 11 | . | . | L | L | . | . |
| 12 | . | . | V | V | . | . |
| 13 | . | . | . | . | . | . |
| 14 | . | . | . | . | . | . |
| 15 | . | . | . | . | . | . |
| 16 | . | . | . | . | . | . |
| 17 | . | . | . | . | . | . |
| 18 | . | . | . | . | . | . |
| 19 | . | . | R | R | . | . |
| 20 | . | . | L | L | . | . |
| 21 | . | . | . | . | . | . |
| 22 | . | . | . | . | . | . |
| 23 | . | . | . | A | . | . |
| 24 | . | . | . | . | . | . |
| 25 | . | . | . | . | . | . |
| 26 | . | . | . | . | . | . |
| 27 | . | . | . | . | . | . |
| 28 | . | . | . | . | . | . |
| 29 | . | . | . | . | . | . |
| 30 | . | . | . | . | . | . |
| 31 | . | . | . | . | . | . |
| 32 | . | . | . | . | . | . |

TABLE 7-continued

| | | | | | | |
|---|---|---|---|---|---|---|
| 33 | . | . | . | . | . | . |
| 34 | . | . | . | . | . | . |
| 35 | . | . | . | . | . | . |
| 36 | — | — | — | — | — | — |
| 37 | — | — | — | — | — | — |
| 38 | . | . | . | . | . | . |
| 39 | . | . | . | . | . | . |
| 40 | . | . | . | . | . | . |
| 41 | . | . | . | . | . | . |
| 42 | . | . | . | . | . | . |
| 43 | . | . | . | . | . | . |
| 44 | . | . | . | . | . | . |
| 45 | . | . | . | . | . | . |
| 46 | . | . | . | . | . | . |
| 47 | . | . | . | . | . | . |
| 48 | . | D | D | D | . | D |
| 49 | . | . | . | . | . | . |
| 50 | I | I | I | I | . | I |
| 51 | . | . | . | . | . | . |
| 52 | . | . | . | . | . | . |
| 53 | . | . | . | . | . | . |
| 54 | . | . | . | . | . | . |
| 55 | . | . | . | . | . | . |
| 56 | — | — | — | — | — | — |
| 57 | — | — | — | — | — | — |
| 58 | . | . | . | . | . | . |
| 59 | . | . | . | . | . | . |
| 60 | . | . | . | . | . | . |
| 61 | . | . | . | . | . | . |
| 62 | . | . | . | . | . | . |
| 63 | . | . | . | . | . | . |
| 64 | . | . | . | . | . | . |
| 65 | . | . | . | . | . | . |
| 66 | . | . | . | . | . | . |
| 67 | . | . | . | . | . | . |
| 68 | . | . | . | . | . | . |
| 69 | . | . | . | . | . | . |
| 70 | . | . | . | . | . | . |
| 71 | . | . | . | . | R | R |
| 72 | . | . | . | . | V | V |
| 73 | . | . | . | . | . | . |
| 74 | . | . | . | . | . | . |
| 75 | . | . | . | . | . | . |
| 76 | S | S | S | S | . | S |
| 77 | . | . | . | . | . | . |
| 78 | . | . | . | . | . | . |
| 79 | . | . | . | . | . | . |
| 80 | . | . | . | . | . | . |
| 81 | . | . | N | N | . | . |
| 82 | . | . | . | . | . | . |
| 83 | . | . | . | . | V | V |
| 84 | . | . | . | . | . | . |
| 85 | . | . | L | L | . | . |
| 86 | . | . | . | . | . | . |
| 87 | . | . | . | . | . | . |
| 88 | . | . | . | . | . | . |
| 89 | . | . | . | . | . | . |
| 90 | . | . | . | . | . | . |
| 91 | . | . | . | . | . | . |
| 92 | . | . | . | . | . | . |
| 93 | . | . | . | . | . | . |
| 94 | . | . | . | . | . | . |
| 95 | . | . | . | . | . | . |
| 96 | . | . | . | . | . | . |
| 97 | . | . | . | . | . | . |
| 98 | . | . | . | . | . | . |
| 99 | . | . | . | . | . | . |
| 100 | . | . | . | . | . | . |
| 101 | S | S | S | S | A | S |
| 102 | P | P | P | P | R | P |
| 103 | . | . | . | . | . | . |
| 104 | — | — | — | — | — | — |
| 105 | — | — | — | — | — | — |
| 106 | — | — | — | — | — | — |
| 107 | — | — | — | — | — | — |
| 108 | — | — | — | — | — | — |
| 109 | — | — | — | — | — | — |
| 110 | — | — | — | — | — | — |
| 111 | — | — | — | — | — | — |
| 112 | — | — | — | — | — | — |

TABLE 7-continued

| | | | | | |
|---|---|---|---|---|---|
| 113 | — | — | — | — | — | — |
| 114 | — | — | — | — | — | — |
| 115 | — | — | — | — | — | — |
| 116 | — | — | — | — | — | — |
| 117 | — | — | — | — | — | — |
| 118 | — | — | — | — | — | — |
| 119 | — | — | — | — | — | — |
| 120 | . | . | . | . | . | . |
| 121 | . | . | . | . | . | . |
| 122 | . | . | . | . | . | . |
| 123 | . | . | . | . | . | . |
| 124 | . | . | . | . | . | . |
| 125 | . | . | . | . | . | . |
| 126 | . | . | . | . | . | . |
| 127 | . | . | . | . | . | . |
| 128 | . | . | . | . | . | . |
| 129 | . | . | . | . | . | . |
| 130 | . | . | . | . | . | . |
| 131 | . | . | . | . | . | . |
| 132 | . | . | . | . | . | . |

TABLE 8

$V_H$, $V_L$ Backmutations and Other Mutations for Humanized 5G8

| $V_H$ or $V_L$ Variant | $V_H$ or $V_L$ Exon Acceptor Sequence | Changes from Acceptor Framework Residues (based on Kabat/Chothia Composite CDRs) |
|---|---|---|
| hu5G8-VH_v1 (SEQ ID NO: 33) | Acceptor Acc. # 4YHM_H aDabi-Fab2b-VH (SEQ ID NO: 28) | None |
| hu5G8-VH_v2 (SEQ ID NO: 34) | Acceptor Acc. # 4YHM_H aDabi-Fab2b-VH (SEQ ID NO: 28) | H48, H71, H93, H94 |
| hu5G8-VH_v3 (SEQ ID NO: 35) | Acceptor Acc. # 4YHM_H aDabi-Fab2b-VH (SEQ ID NO: 28) | H1, H48, H71, H93, H94 |
| hu5G8-VH_v4 (SEQ ID NO: 36) | Acceptor Acc. # 4YHM_H aDabi-Fab2b-VH (SEQ ID NO: 28) | H1, H46, H48, H71, H93, H94 |
| hu5G8-VH_v5 (SEQ ID NO: 37) | Acceptor Acc. # 4YHM_H aDabi-Fab2b-VH (SEQ ID NO: 28) | H1, H11, H12, H19, H20, H46, H48, H71, H76, H80, H93, H94 |
| hu5G8-VH_v6 (SEQ ID NO: 38) | Acceptor Acc. # 4YHM_H aDabi-Fab2b-VH (SEQ ID NO: 28) | H1, H11, H12, H19, H20, H23, H46, H48, H71, H76, H80, H93, H94 |
| hu5G8-VH_v7 (SEQ ID NO: 39) | Acceptor Acc. # 4YHM_H aDabi-Fab2b-VH (SEQ ID NO: 28) | H66, H67, H78, H93, H94 |
| hu5G8-VH_v8 (SEQ ID NO: 40) | Acceptor Acc. # 4YHM_H aDabi-Fab2b-VH (SEQ ID NO: 28) | H1, H46, H48, H66, H67, H71, H78, H93, H94 |
| hu5G8-VL_v1 (SEQ ID NO: 41) | Acceptor aDabi-Fab2b-VL Acc. # 4YHM_L (SEQ ID NO: 31) | none |
| hu5G8-VL_v2 (SEQ ID NO: 42) | Acceptor aDabi-Fab2b-VL Acc. # 4YHM_L (SEQ ID NO: 31) | L2, L36, L46 |
| hu5G8-VL_v3 (SEQ ID NO: 43) | Acceptor aDabi-Fab2b-VL Acc. #4YHM_L (SEQ ID NO: 31) | L2, L36, L46, L70 |
| hu5G8-VL_v4 (SEQ ID NO: 44) | Acceptor aDabi-Fab2b-VL Acc. # 4YHM_L (SEQ ID NO: 31) | L2, L7, L17, L36, L46, L70 |
| hu5G8-VL_v5 (SEQ ID NO: 45) | Acceptor aDabi-Fab2b-VL Acc. # 4YHM_L (SEQ ID NO: 31) | L45, L70 |
| hu5G8-VL_v6 (SEQ ID NO: 46) | Acceptor aDabi-Fab2b-VL Acc. # 4YHM_L (SEQ ID NO: 31) | L2, L36, L45, L46, L70 |

TABLE 9

Kabat Numbering of Framework Residues (based on Kabat/Chothia Composite CDRs) for Backmutations and Other Mutations in Heavy Chains of Humanized 5G8 Antibodies

| Kabat Residue # | Accentor Acc. # 4YHM_H aDabi-Fab2b-VH (SEQ ID NO: 28) | Murine 5G8 VH (SEQ ID NO: 7) | hu5G8-VH_v1 (SEQ ID NO: 33) | hu5G8-VH_v2 (SEQ ID NO: 34) | hu5G8-VH_v3 (SEQ ID NO: 35) | hu5G8-VH_v4 (SEQ ID NO: 36) | hu5G8-VH_v5 (SEQ ID NO: 37) | hu5G8-VH_v6 (SEQ ID NO: 38) | hu5G8-VH_v7 (SEQ ID NO: 39) | hu5G8-VH_v8 (SEQ ID NO: 40) |
|---|---|---|---|---|---|---|---|---|---|---|
| H1  | Q | E | Q | Q | E | E | E | E | Q | E |
| H11 | V | L | V | V | V | V | L | L | V | V |
| H12 | K | V | K | K | K | K | V | V | K | K |
| H19 | K | R | K | K | K | K | R | R | K | K |
| H20 | V | L | V | V | V | V | L | L | V | V |
| H23 | K | T | K | K | K | K | K | A | K | K |
| H46 | E | E | E | E | E | D | D | D | E | D |
| H48 | M | I | M | I | I | I | I | I | M | I |
| H66 | K | K | K | K | K | K | K | K | R | R |
| H67 | A | A | A | A | A | A | A | A | V | V |
| H71 | R | S | R | S | S | S | S | S | R | S |
| H76 | S | N | S | S | S | S | N | N | S | S |
| H78 | A | A | A | A | A | A | A | A | V | V |
| H80 | M | L | M | M | M | M | L | L | M | M |
| H93 | T | S | T | S | S | S | S | S | A | S |
| H94 | I | P | I | P | P | P | P | P | R | P |

TABLE 10

Kabat Numbering of Framework Residues (based on Kabat/Chothia Composite CDRs) for Backmutations and Other Mutations in Light Chains of Humanized 5G8 Antibodies

| Kabat Residue # | Accentor aDabi-Fab2b-VL Acc. # 4YHM_L (SEQ ID NO: 31) | Murine 5G8 VL (SEQ ID NO: 8) | hu5G8-VL_v1 (SEQ ID NO: 41) | hu5G8-VL_v2 (SEQ ID NO: 42) | hu5G8-VL_v3 (SEQ ID NO: 43) | hu5G8-VL_v4 (SEQ ID NO: 44) | hu5G8-VL_v5 (SEQ ID NO: 45) | hu5G8-VL_v6 (SEQ ID NO: 46) |
|---|---|---|---|---|---|---|---|---|
| L2  | I | V | I | V | V | V | I | V |
| L7  | T | T | T | T | T | S | T | T |
| L17 | Q | Q | Q | Q | Q | E | Q | Q |
| L36 | Y | L | Y | L | L | L | Y | L |
| L45 | K | K | K | K | K | K | Q | Q |
| L46 | L | R | L | R | R | R | L | R |
| L70 | G | D | G | G | D | D | D | D |

TABLE 11

Percentage Humanness of Heavy and Light Chains of Humanized 5G8 Antibodies

| $V_H$ or $V_L$ Variant | % Humanness |
|---|---|
| hu5G8-VH_v1 (SEQ ID NO: 33) | 84.4% |
| hu5G8-VH_v2 (SEQ ID NO: 34) | 81.4% |
| hu5G8-VH_v3 (SEQ ID NO: 35) | 80.4% |
| hu5G8-VH_v4 (SEQ ID NO: 36) | 79.4% |
| hu5G8-VH_v5 (SEQ ID NO: 37) | 73.2% |
| hu5G8-VH_v6 (SEQ ID NO: 38) | 72.2% |
| hu5G8-VH_v7 (SEQ ID NO: 39) | 87.8% |
| hu5G8-VH_v8 (SEQ ID NO: 40) | 82.5% |
| hu5G8-VL_v1 (SEQ ID NO: 41) | 88.0% |
| hu5G8-VL_v2 (SEQ ID NO: 42) | 85.0% |
| hu5G8-VL_v3 (SEQ ID NO: 43) | 86.0% |
| hu5G8-VL_v4 (SEQ ID NO: 44) | 84.0% |
| hu5G8-VL_v5 (SEQ ID NO: 45) | 90.0% |
| hu5G8-VL_v6 (SEQ ID NO: 46) | 87.0% |

Positions at which Chothia class canonical, vernier, or interface/packing residues differ between mouse and human acceptor sequences are candidates for substitution Examples of Chothia class canonical residues include Kabat residues L2, L27B, L27C, L34, L94, H29, H71, and H94 in Tables 3 and 4. Examples of vernier residues include Kabat residues L2, L36, L46, H27, H28, H29, H30, H48, H71, H78, H93, and H94 in Tables 3 and 4. Examples of interface/packing (VH+VL) residues include Kabat residues L34, L36, L46, L89, L91, H93, and H95, in Tables 3 and 4.

The rationales for selection of the positions indicated in Table 6 in the light chain variable region as candidates for substitution are as follows.

L2 (I2V) is a backmutation of a residue of a canonical and vernier residue.

L7 (T2S) is a mutation from a residue (T) that is rare in humans at this position to one that is most common (S).

L17 (Q17E) is a mutation from a residue (Q) that is rare in humans at this position to one that is most common (E).

L36 (Y36L) is a backmutation of a vernier and interface residue.

L45 (K45Q) is a mutation to germline IGKV2-29 residue.

L46 (G46R) is a backmutation of a vernier and interface residue.

L70 (G70D) is a backmutation and is a mutation to the germline IGKV2-29 residue. D is frequent in humans at this position.

The rationales for humanized variants as indicated in Table 6 in the light chain variable region are as follows.

Hu5G8-VL_v1 consists of the CDR-L1, L2, and L3 loops of 5G8-VL grafted onto the framework of aDabi-Fab2b-VL.

Hu5G8-VL_v2 reverts all framework substitutions at positions that are key for defining the Chothia canonical classes, are part of the Vernier zone, or locate to the VH/VL domain interface. Kabat position 2 defines the Chothia canonical conformation of CDR-L1; Kabat positions 2, 36, and 46 are part of the Vernier zone; and Kabat positions 36 and 46 also localize to the VH/VL interface. hu5G8-VL_v2 incorporates backmutations I2V, Y36L, and L46R, to enable assessment of these positions' contributions to antigen-binding affinity and immunogenicity.

Hu5G8-VL_v3 is the same as hu5G8-VL-v2, and additionally reverts all framework substitutions at positions where the parental mouse 5G8-VL amino acid is of higher prevalence in sequenced human antibodies compared to the aDabi-Fab2b-VL residue. At Kabat position 70, the 5G8-VL residue is more common in human antibodies than the aDabi-Fab2b-VL residue. Hu5G8-VL_v3 incorporates the backmutation G70D, which restores a parental 5G8-VL framework residue while increasing the human-ness of the sequence.

Hu5G8-VL_v4 is the same as hu5G8-VL-v3, but additionally incorporates substitutions at framework positions where the residue of neither aDabi-Fab2b-VL nor 5G8-VL is the most common among sequenced human antibodies. At Kabat position 7, the most common residue is S, which is not present in aDabi-Fab2b-VL (T) or 5G8-VL (T); and at Kabat position 17, the most common residue is E, which is not present in aDabi-Fab2b-VL (Q) or 5G8-VL (Q). Hu5G8-VL_v4 incorporates the mutations T7S and Q17E, to increase the human-ness of the sequence.

Hu5G8-VL_v5 consists of the CDR-L1, L2, and L3 loops of 5G8-VL grafted onto the framework of aDabi-Fab2b-VL, as hu5G8-VL_v1, and additionally incorporates framework mutations that render the sequence more similar to a particular human immunoglobulin kappa variable germline gene. The framework of aDabi-Fab2b-VL, and therefore that of hu5G8-VL_v1, shares a high degree of sequence similarity with the human germline gene IGKV2-29, with differences at Kabat positions 45 and 70. Hu5G8-VL_v5 contains the mutations K45Q and G70D, as another strategy to increase the human-ness of the sequence.

Hu5G8-VL_v6 contains the mutations of hu5G8-VL-v5, and additionally incorporates mutations introduced in hu5G8-VL-v2, namely reverting all framework substitutions at positions that are key for defining the Chothia canonical classes, are part of the Vernier zone, or locate to the VH/VL domain interface (backmutations I2V, Y36L, and L46R).

The rationales for selection of the positions indicated in Table 7 in the heavy chain variable region as candidates for substitution are as follows.

H1 (Q1E) is a backmutation and is a stability enhancing mutation to mitigate pyroglutamate formation potential. (Liu, 2011, supra).S H11 (V11L) is a backmutation. L is frequent in humans at this position.

H12 (K12V) is a backmutation. V is frequent in humans at this position.

H19 (K19R) is a backmutation. R is frequent in human at this position.

H20 (V20L) is a backmutation. L is frequent in human at this position.

H23 (K23A) is mutation to a residue which is frequent in humans at this position.

H46 (E46D) is a conservative mutation. E46 is predicted to clash with K62 of CDR-H2.

H48 (M48I) is a backmutation in the vernier zone. I is frequent in human at this position.

H66 (K66R) is a mutation to IGHV1-46 germline residue. K is rare in human at this position. R is most common at this position.

H67 (A67V) is a mutation to IGHV1-46 germline residue. A is rare in human at this position. V is most common at this position.

H71 (R71S) is a backmutation of a canonical and vernier residue.

H76 (S76N) is a backmutation. N is frequent in human at this position.

H78 (A78V) is a mutation to IGHV1-46 germline residue.

H80 (M80L) is a backmutation. L is frequent in human at this position.

H93 (T93S or T93A) T93S is a backmutation of a vernier and interface residue. T93A is a mutation to IGHV1-46 germline residue. T and S are rare at this position in human. A is most common at this position in human.

H94 (I94P or I94R) I94P is a backmutation of a canonical and vernier residue. I94R is a mutation to IGHV1-46 germline residue. I and P are rare in human at this position. P is most common at this position in human.

The rationales for humanized variants as indicated in Table 7 in the heavy chain variable region are as follows.

Hu5G8-VH_v1 consists of the CDR-H1, H2, and H3 loops of 5G8-VH grafted onto the framework of aDabi-Fab2b-VH.

Hu5G8-VH_v2 reverts all framework substitutions at positions that are key for defining the Chothia canonical classes, are part of the Vernier zone, or localize to the VH/VL domain interface. Kabat positions 71 and 94 define the Chothia canonical conformation of CDR-H2 and CDR-H1, respectively; Kabat positions 48, 71, 93, and 94 are part of the Vernier zone; and Kabat position 93 localizes to the VH/VL domain interface. Hu5G8-VH_v2 incorporates backmutations M48I, R71S, T93S, and I94P, to enable assessment of these positions' contributions to antigen-binding affinity and immunogenicity.

Hu5G8-VH_v3 contains the backmutations of hu5G8-VH-v2, and additionally reverts the framework substitution at Kabat position 1. At the N-terminus of proteins, both E and Q are known to cyclize spontaneously to form pyroglutamate; however, the conversion from E occurs more slowly than from Q (Liu Y D, et al., (2011) *J Biol Chem.* 286(13): 11211-7; Schilling S, et al., (2008) *Biol Chem.* 389(8):983-91). Hu5G8-VH_v3 incorporates the backmutation Q1E, to reduce pyroglutamination.

Hu5G8-VH_v4 contains the backmutations of hu5G8-VH-v3, and additionally incorporates mutations of framework residues that are predicted by BioLuminate to clash with CDRs. Based on van der Waals interactions, E at Kabat position 46 is predicted to clash with K at Kabat position 62 of CDR-H2. Hu5G8-VH_v4 incorporates the conservative mutation E46D.

Hu5G8-VH_v5 contains the mutations of hu5G8-VH-v4, and additionally reverts all framework substitutions at positions where the parental mouse 5G8-VH amino acid is of higher prevalence in sequenced human antibodies compared to the aDabi-Fab2b-VH residue. At Kabat positions 11, 12, 19, 20, 76, and 80, the 5G8-VH residue is more common in human antibodies than the aDabi-Fab2b-VH residue. Hu5G8-VH_v5 incorporates the backmutations V1 IL, K12V, K19R, V20L, S76N, and M80L, which restore parental 5G8-VH framework residues while increasing the human-ness of the sequence.

Hu5G8-VH_v6 contains the mutations of hu5G8-VH-v5, and additionally incorporates substitutions at framework positions where the residue of neither aDabi-Fab2b-VH nor 5G8-VH is the most common among sequenced human antibodies. At Kabat position 23, the most common residue is A, which is not present in aDabi-Fab2b-VH (K) or 5G8-VH (T). Hu5G8-VH_v6 incorporates the mutation K23A, to increase the human-ness of the sequence. In hu5G8-VH_v6, the following Kabat positions were not mutated to the most common residue due to their location in or near the interface or the Vernier zone:

position 66: R is most common; aDabi-Fab2b-VH (K) and 5G8-VH (K);
position 67: V is most common; aDabi-Fab2b-VH (A) and 5G8-VH (A);
position 93: A is most common; aDabi-Fab2b-VH (T) and 5G8-VH (S); and
position 94: R is most common; aDabi-Fab2b-VH (I) and 5G8-VH (P).

Hu5G8-VH_v7 consists of the CDR-H1, H2, and H3 loops of 5G8-VH grafted onto the framework of aDabi-Fab2b-VH, as hu5G8-VH_v1, and additionally incorporates framework mutations that render the sequence more similar to a particular human immunoglobulin variable heavy germline gene. The framework of aDabi-Fab2b-VH, and therefore that of hu5G8-VH_v1, shares a high degree of sequence similarity with the human germline gene IGHV1-46, with differences at Kabat positions 66, 67, 78, 93, and 94. Hu5G8-VH_v7 contains the mutations K66R, A67V, A78V, T93A, and I94R, as another strategy to increase the human-ness of the sequence.

Hu5G8-VH_v8 contains the mutations of hu5G8-VH-v7, and additionally incorporates mutations introduced in hu5G8-VH-v2, 3, and 4, namely . . .

reverting all framework substitutions at positions that are key for defining the Chothia canonical classes, are part of the Vernier zone, or localize to the VH/VL domain interface (backmutations M48I, R71S, A93S, and R94P),
reverting the framework substitution at Kabat position 1 to reduce pyroglutamination (backmutation Q1E), and
incorporating mutations of framework residues that are predicted by BioLuminate to clash with CDRs (conservative mutation E46D).

Humanized sequences are generated using a two-stage PCR protocol that allows introduction of multiple mutations, deletions, and insertions using QuikChange site-directed mutagenesis [Wang, W. and Malcolm, B. A. (1999) Bio-Techniques 26:680-682).

```
Heavy chain variable regions
>5G8-VH
                                                    (SEQ ID NO: 7)
EVQLQQSGAELVRSGASVRLSCTASGFNIKDYYMHWVRQRPEQGLEWIGWIDPENGDT
VYAPKFQGKATMTSDTSSNTAYLHLSSLTSEDTAVYYCSPLDFWGQGTTLTVSS >3F4-VH Accession No. 1CR9_H
                                                    (SEQ ID NO: 27)
KVKLQQSGAELVRSGASVKLSCTASGFNIKDYYIQWVKQRPEQGLEWIGWIDPENGNSE
YAPRFQGKATMTADTLSNTAYLQLSSLTSEDTAVYYCNADLHDYWGQGTTLTVSS >aDabi-Fab2b-VH Accession No. 4YHM_H
                                                    (SEQ ID NO: 28)
QVQLVQSGAEVKKPGASVKVSCKASGYTFTDYYMHWVRQAPGQGLEWMGETNPRNG
GTTYNEKFKGKATMTRDTSTSTAYMELSSLRSEDTAVYYCTIGTSGYDYFDYWGQGTL
VTVSS >IGHV1-46 Accession No. P01743.2
                                                    (SEQ ID NO: 29)
QVQLVQSGAEVKKPGASVKVSCKASGYTFTSYYMHWVRQAPGQGLEWMGIINPSGGS
TSYAQKFQGRVTMTRDTSTSTVYMELSSLRSEDTAVYYCAR >hu5G8-VH_v1
                                                    (SEQ ID NO: 33)
QVQLVQSGAEVKKPGASVKVSCKASGFNIKDYYMHWVRQAPGQGLEWMGWIDPENG
DTVYAPKFQGKATMTRDTSTSTAYMELSSLRSEDTAVYYCTILDFWGQGTLVTVSS >hu5G8-VH_v2
                                                    (SEQ ID NO: 34)
QVQLVQSGAEVKKPGASVKVSCKASGFNIKDYYMHWVRQAPGQGLEWIGWIDPENGD
TVYAPKFQGKATMTSDTSTSTAYMELSSLRSEDTAVYYCSPLDFWGQGTLVTVSS >hu5G8-VH_v3
                                                    (SEQ ID NO: 35)
EVQLVQSGAEVKKPGASVKVSCKASGFNIKDYYMHWVRQAPGQGLEWIGWIDPENGD
TVYAPKFQGKATMTSDTSTSTAYMELSSLRSEDTAVYYCSPLDFWGQGTLVTVSS >hu5G8-VH_v4
                                                    (SEQ ID NO: 36)
EVQLVQSGAEVKKPGASVKVSCKASGFNIKDYYMHWVRQAPGQGLDWIGWIDPENGD
TVYAPKFQGKATMTSDTSTSTAYMELSSLRSEDTAVYYCSPLDFWGQGTLVTVSS >hu5G8-VH_v5
                                                    (SEQ ID NO: 37)
EVQLVQSGAELVKPGASVRLSCKASGFNIKDYYMHWVRQAPGQGLDWIGWIDPENGD
TVYAPKFQGKATMTSDTSTNTAYLELSSLRSEDTAVYYCSPLDFWGQGTLVTVSS
```

-continued

\>hu5G8-VH_v6
(SEQ ID NO: 38)
EVQLVQSGAELVKPGASVRLSCAASGFNIKDYYMHWVRQAPGQGLDWIGWIDPENGD
TVYAPKFQGKATMTSDTSTNTAYLELSSLRSEDTAVYYCSPLDFWGQGTLVTVSS

\>hu5G8-VH_v7
(SEQ ID NO: 39)
QVQLVQSGAEVKKPGASVKVSCKASGFNIKDYYMHWVRQAPGQGLEWMGWIDPENG
DTVYAPKFQGRVTMTRDTSTSTVYMELSSLRSEDTAVYYCARLDFWGQGTLVTVSS

\>hu5G8-VH_v8
(SEQ ID NO: 40)
EVQLVQSGAEVKKPGASVKVSCKASGFNIKDYYMHWVRQAPGQGLDWIGWIDPENGD
TVYAPKFQGRVTMTSDTSTSTVYMELSSLRSEDTAVYYCSPLDFWGQGTLVTVSS

Kappa light chain variable regions
\>5G8-VL
(SEQ ID NO: 8)
DVVMTQTPLTLSVTIGQPASISCKSSQSLLDSDGKTYLNWLLQRPGQSPKRLIYLVSKLD
SGVPDRFTGSGSGTDFTLKIRRVEAEDLGVYYCWQGTLFPYTFGGGTKLEIK \>3F4-VL Accession No. 1CR9_L
(SEQ ID NO: 30)
DVVMTQTPLSLSVTIGQPASISCKSSQSLLDSDGKTYLIWVFQRPGQSPKRLIFLVSKRDS
GVPDRFTGSGSGTDFTLKISRVEAEDVGVYYCWQGTHFPHTVGGGTKLEIA \>aDabi-Fab2b-VL Accession No. 4YHM_L
(SEQ ID NO: 31)
DIVMTQTPLSLSVTPGQPASISCRSSQSIVHSDGNIYLEWYLQKPGQSPKLLIYKVSYRFS
GVPDRFSGSGSGTGFTLKISRVEAEDVGVYYCFQASHVPYTFGGGTKLEIK \>IGKV2-29 Accession No. A2NJV5.2
(SEQ ID NO: 32)
DIVMTQTPLSLSVTPGQPASISCKSSQSLLHSDGKTYLYWYLQKPGQSPQLLIYEVSSRFS
GVPDRFSGSGSGTDFTLKISRVEAEDVGVYYCMQGIHLP \>hu5G8-VL_v1
(SEQ ID NO: 41)
DIVMTQTPLSLSVTPGQPASISCKSSQSLLDSDGKTYLNWYLQKPGQSPKWYLVSKLD
SGVPDRFSGSGSGTGFTLKISRVEAEDVGVYYCWQGTLFPYTFGGGTKLEIK \>hu5G8-VL_v2
(SEQ ID NO: 42)
DVVMTQTPLSLSVTPGQPASISCKSSQSLLDSDGKTYLNWLLQKPGQSPKRLIYLVSKLD
SGVPDRFSGSGSGTGFTLKISRVEAEDVGVYYCWQGTLFPYTFGGGTKLEIK \>hu5G8-VL_v3
(SEQ ID NO: 43)
DVVMTQTPLSLSVTPGQPASISCKSSQSLLDSDGKTYLNWLLQKPGQSPKRLIYLVSKLD
SGVPDRFSGSGSGTDFTLKISRVEAEDVGVYYCWQGTLFPYTFGGGTKLEIK \>hu5G8-VL_v4
(SEQ ID NO: 44)
DVVMTQSPLSLSVTPGEPASISCKSSQSLLDSDGKTYLNWLLQKPGQSPKRLIYLVSKLD
SGVPDRFSGSGSGTDFTLKISRVEAEDVGVYYCWQGTLFPYTFGGGTKLEIK
\>hu5G8-VL_v5
(SEQ ID NO: 45)
DIVMTQTPLSLSVTPGQPASISCKSSQSLLDSDGKTYLNWYLQKPGQSPQLLIYLVSKLD
SGVPDRFSGSGSGTDFTLKISRVEAEDVGVYYCWQGTLFPYTFGGGTKLEIK \>hu5G8-VL_v6
(SEQ ID NO: 46)
DVVMTQTPLSLSVTPGQPASISCKSSQSLLDSDGKTYLNWLLQKPGQSPQRLIYLVSKLD
SGVPDRFSGSGSGTDFTLKISRVEAEDVGVYYCWQGTLFPYTFGGGTKLEIK Example 7. Design of Humanized 6A10 Antibodies The starting point for monoclonal antibody 6A10 humanization is murine antibody 6A10. The heavy chain variable amino acid sequence of mature 6A10 is provided as SEQ ID NO:63. The light chain variable amino acid sequence of mature 6A10 is provided as SEQ ID NO:64. The heavy chain Kabat/Chothia Composite CDR1, CDR2, and CDR3 amino acid sequences are provided as SEQ ID NOs:65-67, respectively. The light chain Kabat CDR1, CDR2, and CDR3 amino acid sequences are provided as SEQ ID NOs:68-70 respectively. Kabat numbering is used throughout.

The variable kappa (Vk) of 6A10 belongs to mouse Kabat subgroup 2 which corresponds to human Kabat subgroup 3 and variable heavy (Vh) to mouse Kabat subgroup 2c which corresponds to human Kabat subgroup 1 [Kabat E. A., et al, (1991) Sequences of Proteins of Immunological Interest, Fifth Edition. NIH Publication No. 91-3242.]. 16 residue CDR-L1 belongs to canonical class 4, 7 residue CDR-L2 to class 1, 9 residue CDR-L3 to class 1 in Vk [Martin A. C. and Thornton J. M. (1996) J. Mol. Biol. 263:800-815.]. 10 residue CDR-H1 belongs to class 1, 17 residue CDR-H2 to class 1 [Martin & Thornton, 1996]. CDR-H3 has no canonical classes.

The residues at the interface between the Vk and Vh domains are the ones commonly found, except that 93T in the heavy chain is typically an alanine; therefore, this residue is analyzed as a target for back-mutation. Similarly, 36L in Vk is typically Y or F and 46R is typically L therefore, these residues are also analyzed for back-mutations.

A search was made over the protein sequences in the PDB database [Deshpande N. et al., (2005) Nucleic Acids Res. 33: D233-D237.] to find structures, which would provide a rough structural model of 6A10. The crystal structure of antibody fab [pdb code 1CR9; SEQ ID NO;30] [Kanyo Z. F. et al., (1999) J. Mol. Biol. 293:855-863.] was used for the Vk structure since it had good resolution (2.0 A) and overall sequence similarity to 6A10 Vk, retaining the same canonical structures for the loops. Same structure [pdb code 1CR9; SEQ ID NO:27] was used for the Vh structure since it had good overall sequence similarity and reasonably good resolution (2.0 Å). In addition, CDRs-H1 and H2 had the same canonical structures as 6A10 Vh. Bioluminate software was used to model a rough structure of 6A10. This software was licensed from Schrodinger Inc.

A search of the non-redundant protein sequence database from NCBI allowed selection of suitable human frameworks into which to graft the murine CDRs. For Vk, a human kappa light chain variable region with accession #ABC66863 [SEQ ID NO:83; Shriner, A. K., et al., (2016) 24:7159-7166] was chosen. This has the same canonical classes for CDR-L1 and L2. It is a member of Kabat human kappa subgroup 3. For Vh, human heavy chain variable region with accession #ACR16112 [SEQ ID NO: 81; Williams, J. V et al., (2009) Mol. Immunol. 47:407-414] was chosen, it has same canonical classes. It is a member of Kabat human heavy subgroup 1.

3 humanized heavy chain variable region variants and 3 humanized light chain variable region variants were constructed containing different permutations of substitutions, hu6A10-VH_v1, hu6A10-VH_v2, and hu6A10-VH_v3, (SEQ ID NOs: 85-87, respectively) and hu6A10-VL_v1, hu6A10-VL_v2, and hu6A10-VL_v3, (SEQ ID NOs: 88-90, respectively). (Tables 12 and 13). The exemplary humanized VL and VH designs, with backmutations and other mutations based on selected human frameworks, are shown in Tables 12 and 13, respectively. The bolded areas in Tables 12 and 13 indicate the CDRs as defined by Kabat/Chothia Composite. A "-" in the columns in Tables 12 and 13 indicates no residue at the indicated position. SEQ ID NOs:85-87 and SEQ ID NOs: 88-90 contain backmutations and other mutations as shown in Table 14. The amino acids at positions in hu6A10-VH_v1, hu6A10-VH_v2, and hu6A10-VH_v3 are listed in Table 15. The amino acids at positions in hu6A10-VL_v1, hu6A10-VL_v2, and hu6A10-VL_v3 are listed in Table 16. The percentage humanness for humanized VH chains hu6A10-VH_v1, hu6A10-VH_v2, and hu6A10-VH_v3, (SEQ ID NOs: 85-87, respectively) with respect to the most similar human germline gene IGHV1-2*02 (SEQ ID NO:82), and for humanized VL chains hu6A10-VL_v1, hu6A10-VL_v2, and hu6A10-VL_v3 (SEQ ID NOs:88-90, respectively) with respect to the most similar human germline gene IGKV2-30*02 (SEQ ID NO:84), is shown in Table 17.

TABLE 12

| Linear residue # | Kabat residue # | FR or CDR | Murine 6A10 VL (SEQ ID NO: 64) | Acceptor Acc. # ABC66863 (SEQ ID NO: 83) | hu6A10-VL_v1 (SEQ ID NO: 88) | hu6A10-VL_v2 (SEQ ID NO: 89) | hu6A10-VL_v3 (SEQ ID NO: 90) |
|---|---|---|---|---|---|---|---|
| 1 | 1 | Fr1 | D | D | D | D | D |
| 2 | 2 | Fr1 | V | I | I | I | I |
| 3 | 3 | Fr1 | V | V | V | V | V |
| 4 | 4 | Fr1 | M | M | M | M | M |
| 5 | 5 | Fr1 | T | T | T | T | T |
| 6 | 6 | Fr1 | Q | Q | Q | Q | Q |
| 7 | 7 | Fr1 | T | S | S | S | S |
| 8 | 8 | Fr1 | P | P | P | P | P |
| 9 | 9 | Fr1 | L | L | L | L | L |
| 10 | 10 | Fr1 | T | S | S | S | S |
| 11 | 11 | Fr1 | L | L | L | L | L |
| 12 | 12 | Fr1 | S | P | P | P | S |
| 13 | 13 | Fr1 | V | V | V | V | V |
| 14 | 14 | Fr1 | T | T | T | T | T |
| 15 | 15 | Fr1 | I | L | L | L | L |
| 16 | 16 | Fr1 | G | G | G | G | G |
| 17 | 17 | Fr1 | Q | Q | Q | Q | E |
| 18 | 18 | Fr1 | P | P | P | P | P |
| 19 | 19 | Fr1 | A | A | A | A | A |
| 20 | 20 | Fr1 | S | S | S | S | S |
| 21 | 21 | Fr1 | I | I | I | I | I |
| 22 | 22 | Fr1 | S | S | S | S | S |
| 23 | 23 | Fr1 | C | C | C | C | C |
| 24 | 24 | CDR-L1 | K | R | K | K | K |
| 25 | 25 | CDR-L1 | S | S | S | S | S |
| 26 | 26 | CDR-L1 | S | S | S | S | S |
| 27 | 27 | CDR-L1 | Q | Q | Q | Q | Q |
| 28 | 27A | CDR-L1 | S | S | S | S | S |
| 29 | 27B | CDR-L1 | L | L | L | L | L |
| 30 | 27C | CDR-L1 | L | V | L | L | L |
| 31 | 27D | CDR-L1 | D | Y | D | D | D |
| 32 | 27E | CDR-L1 | S | S | S | S | S |
| 33 | 27F | CDR-L1 | — | — | — | — | — |

TABLE 12-continued

| Linear residue # | Kabat residue # | FR or CDR | Murine 6A10 VL (SEQ ID NO: 64) | Acceptor Acc. # ABC66863 (SEQ ID NO: 83) | hu6A10-VL_v1 (SEQ ID NO: 88) | hu6A10-VL_v2 (SEQ ID NO: 89) | hu6A10-VL_v3 (SEQ ID NO: 90) |
|---|---|---|---|---|---|---|---|
| 34 | 28 | CDR-L1 | D | D | D | D | D |
| 35 | 29 | CDR-L1 | G | G | G | G | G |
| 36 | 30 | CDR-L1 | K | N | K | K | K |
| 37 | 31 | CDR-L1 | T | T | T | T | T |
| 38 | 32 | CDR-L1 | Y | Y | Y | Y | Y |
| 39 | 33 | CDR-L1 | L | L | L | L | L |
| 40 | 34 | CDR-L1 | N | N | N | N | N |
| 41 | 35 | Fr2 | W | W | W | W | W |
| 42 | 36 | Fr2 | L | F | F | F | F |
| 43 | 37 | Fr2 | L | Q | Q | Q | Q |
| 44 | 38 | Fr2 | Q | Q | Q | Q | Q |
| 45 | 39 | Fr2 | R | R | R | R | R |
| 46 | 40 | Fr2 | P | P | P | P | P |
| 47 | 41 | Fr2 | G | G | G | G | G |
| 48 | 42 | Fr2 | Q | Q | Q | Q | Q |
| 49 | 43 | Fr2 | S | S | S | S | S |
| 50 | 44 | Fr2 | P | P | P | P | P |
| 51 | 45 | Fr2 | K | R | R | R | R |
| 52 | 46 | Fr2 | R | R | R | L | L |
| 53 | 47 | Fr2 | L | L | L | L | L |
| 54 | 48 | Fr2 | I | I | I | I | I |
| 55 | 49 | Fr2 | Y | Y | Y | Y | Y |
| 56 | 50 | CDR-L2 | L | K | L | L | L |
| 57 | 51 | CDR-L2 | V | V | V | V | V |
| 58 | 52 | CDR-L2 | S | S | S | S | S |
| 59 | 53 | CDR-L2 | K | N | K | K | K |
| 60 | 54 | CDR-L2 | L | R | L | L | L |
| 61 | 55 | CDR-L2 | D | D | D | D | D |
| 62 | 56 | CDR-L2 | S | S | S | S | S |
| 63 | 57 | Fr3 | G | G | G | G | G |
| 64 | 58 | Fr3 | V | V | V | V | V |
| 65 | 59 | Fr3 | P | P | P | P | P |
| 66 | 60 | Fr3 | D | D | D | D | D |
| 67 | 61 | Fr3 | R | R | R | R | R |
| 68 | 62 | Fr3 | F | F | F | F | F |
| 69 | 63 | Fr3 | T | S | S | S | S |
| 70 | 64 | Fr3 | G | G | G | G | G |
| 71 | 65 | Fr3 | S | S | S | S | S |
| 72 | 66 | Fr3 | G | G | G | G | G |
| 73 | 67 | Fr3 | S | S | S | S | S |
| 74 | 68 | Fr3 | G | G | G | G | G |
| 75 | 69 | Fr3 | T | T | T | T | T |
| 76 | 70 | Fr3 | D | D | D | D | D |
| 77 | 71 | Fr3 | F | F | F | F | F |
| 78 | 72 | Fr3 | T | T | T | T | T |
| 79 | 73 | Fr3 | L | L | L | L | L |
| 80 | 74 | Fr3 | K | K | K | K | K |
| 81 | 75 | Fr3 | I | I | I | I | I |
| 82 | 76 | Fr3 | S | S | S | S | S |
| 83 | 77 | Fr3 | R | R | R | R | R |
| 84 | 78 | Fr3 | V | V | V | V | V |
| 85 | 79 | Fr3 | E | E | E | E | E |
| 86 | 80 | Fr3 | A | A | A | A | A |
| 87 | 81 | Fr3 | E | E | E | E | E |
| 88 | 82 | Fr3 | D | D | D | D | D |
| 89 | 83 | Fr3 | L | V | V | V | V |
| 90 | 84 | Fr3 | G | G | G | G | G |
| 91 | 85 | Fr3 | V | V | V | V | V |
| 92 | 86 | Fr3 | Y | Y | Y | Y | Y |
| 93 | 87 | Fr3 | Y | Y | Y | Y | Y |
| 94 | 88 | Fr3 | C | C | C | C | C |
| 95 | 89 | CDR-L3 | W | M | W | W | W |
| 96 | 90 | CDR-L3 | Q | Q | Q | Q | Q |
| 97 | 91 | CDR-L3 | G | G | G | G | G |
| 98 | 92 | CDR-L3 | T | T | T | T | T |
| 99 | 93 | CDR-L3 | H | H | H | H | H |
| 100 | 94 | CDR-L3 | F | R | F | F | F |
| 101 | 95 | CDR-L3 | P | P | P | P | P |
| 102 | 95A | CDR-L3 | — | — | — | — | — |
| 103 | 95B | CDR-L3 | — | — | — | — | — |
| 104 | 95C | CDR-L3 | — | — | — | — | — |
| 105 | 95D | CDR-L3 | — | — | — | — | — |
| 106 | 95E | CDR-L3 | — | — | — | — | — |
| 107 | 95F | CDR-L3 | — | — | — | — | — |

TABLE 12-continued

| Linear residue # | Kabat residue # | FR or CDR | Murine 6A10 VL (SEQ ID NO: 64) | Acceptor Acc. # ABC66863 (SEQ ID NO: 83) | hu6A10-VL_v1 (SEQ ID NO: 88) | hu6A10-VL_v2 (SEQ ID NO: 89) | hu6A10-VL_v3 (SEQ ID NO: 90) |
|---|---|---|---|---|---|---|---|
| 108 | 96 | CDR-L3 | Y | L | Y | Y | Y |
| 109 | 97 | CDR-L3 | T | T | T | T | T |
| 110 | 98 | Fr4 | F | F | F | F | F |
| 111 | 99 | Fr4 | G | G | G | G | G |
| 112 | 100 | Fr4 | G | G | G | G | G |
| 113 | 101 | Fr4 | G | G | G | G | G |
| 114 | 102 | Fr4 | T | T | T | T | T |
| 115 | 103 | Fr4 | K | K | K | K | K |
| 116 | 104 | Fr4 | L | V | V | V | V |
| 117 | 105 | Fr4 | E | E | E | E | E |
| 118 | 106 | Fr4 | I | I | I | I | I |
| 119 | 106A | Fr4 | — | — | — | — | — |
| 120 | 107 | Fr4 | K | K | K | K | K |

TABLE 13

| Linear residue # | Kabat residue # | FR or CDR | Murine 6A10 VH (SEQ ID NO: 63) | Acceptor Acc. # ACR16112 (SEQ ID NO: 81) | hu6A10-VH_v1 (SEQ ID NO: 85) | hu6A10-VH_v2 (SEQ ID NO: 86) | hu6A10-VH_v3 (SEQ ID NO: 87) |
|---|---|---|---|---|---|---|---|
| 1 | 1 | Fr1 | E | Q | Q | Q | Q |
| 2 | 2 | Fr1 | V | V | V | V | V |
| 3 | 3 | Fr1 | Q | Q | Q | Q | Q |
| 4 | 4 | Fr1 | L | L | L | L | L |
| 5 | 5 | Fr1 | Q | Q | Q | Q | Q |
| 6 | 6 | Fr1 | Q | E | E | E | E |
| 7 | 7 | Fr1 | S | S | S | S | S |
| 8 | 8 | Fr1 | G | G | G | G | G |
| 9 | 9 | Fr1 | A | A | A | A | A |
| 10 | 10 | Fr1 | E | E | E | E | E |
| 11 | 11 | Fr1 | L | V | V | V | V |
| 12 | 12 | Fr1 | V | K | K | K | K |
| 13 | 13 | Fr1 | R | K | K | K | K |
| 14 | 14 | Fr1 | S | P | P | P | P |
| 15 | 15 | Fr1 | G | G | G | G | G |
| 16 | 16 | Fr1 | A | A | A | A | G |
| 17 | 17 | Fr1 | S | S | S | S | S |
| 18 | 18 | Fr1 | V | V | V | V | V |
| 19 | 19 | Fr1 | K | K | K | K | K |
| 20 | 20 | Fr1 | L | V | V | V | V |
| 21 | 21 | Fr1 | S | S | S | S | S |
| 22 | 22 | Fr1 | C | C | C | C | C |
| 23 | 23 | Fr1 | T | K | K | K | K |
| 24 | 24 | Fr1 | A | A | A | A | A |
| 25 | 25 | Fr1 | S | S | S | S | S |
| 26 | 26 | CDR-H1 | G | G | G | G | G |
| 27 | 27 | CDR-H1 | L | Y | L | L | L |
| 28 | 28 | CDR-H1 | N | T | N | N | N |
| 29 | 29 | CDR-H1 | I | F | I | I | I |
| 30 | 30 | CDR-H1 | K | T | K | K | K |
| 31 | 31 | CDR-H1 | D | G | D | D | D |
| 32 | 32 | CDR-H1 | Y | Y | Y | Y | Y |
| 33 | 33 | CDR-H1 | Y | Y | Y | Y | Y |
| 34 | 34 | CDR-H1 | I | M | I | I | I |
| 35 | 35 | CDR-H1 | H | H | H | H | H |
| 36 | 35A | CDR-H1 | — | — | | | |
| 37 | 35B | CDR-H1 | — | — | | | |
| 38 | 36 | Fr2 | W | W | W | W | W |
| 39 | 37 | Fr2 | V | V | V | V | V |
| 40 | 38 | Fr2 | K | R | R | R | R |
| 41 | 39 | Fr2 | Q | Q | Q | Q | Q |
| 42 | 40 | Fr2 | R | A | A | A | A |
| 43 | 41 | Fr2 | P | P | P | P | P |
| 44 | 42 | Fr2 | E | G | G | G | G |
| 45 | 43 | Fr2 | Q | Q | Q | Q | Q |
| 46 | 44 | Fr2 | G | G | G | G | G |
| 47 | 45 | Fr2 | L | L | L | L | L |
| 48 | 46 | Fr2 | E | E | E | E | E |
| 49 | 47 | Fr2 | W | W | W | W | W |
| 50 | 48 | Fr2 | I | M | M | I | I |
| 51 | 49 | Fr2 | G | G | G | G | G |

TABLE 13-continued

| Linear residue # | Kabat residue # | FR or CDR | Murine 6A10 VH (SEQ ID NO: 63) | Acceptor Acc. # ACR16112 (SEQ ID NO: 81) | hu6A10-VH_v1 (SEQ ID NO: 85) | hu6A10-VH_v2 (SEQ ID NO: 86) | hu6A10-VH_v3 (SEQ ID NO: 87) |
|---|---|---|---|---|---|---|---|
| 52 | 50 | CDR-H2 | W | W | W | W | W |
| 53 | 51 | CDR-H2 | I | I | I | I | I |
| 54 | 52 | CDR-H2 | D | N | D | D | D |
| 55 | 52A | CDR-H2 | P | P | P | P | P |
| 56 | 52B | CDR-H2 | — | — | | | |
| 57 | 52C | CDR-H2 | — | — | | | |
| 58 | 53 | CDR-H2 | E | N | E | E | E |
| 59 | 54 | CDR-H2 | N | S | N | N | N |
| 60 | 55 | CDR-H2 | D | G | D | D | D |
| 61 | 56 | CDR-H2 | D | D | D | D | D |
| 62 | 57 | CDR-H2 | T | T | T | T | T |
| 63 | 58 | CDR-H2 | E | N | E | E | E |
| 64 | 59 | CDR-H2 | Y | Y | Y | Y | Y |
| 65 | 60 | CDR-H2 | A | A | A | A | A |
| 66 | 61 | CDR-H2 | P | Q | P | P | P |
| 67 | 62 | CDR-H2 | K | K | K | K | K |
| 68 | 63 | CDR-H2 | F | F | F | F | F |
| 69 | 64 | CDR-H2 | Q | Q | Q | Q | Q |
| 70 | 65 | CDR-H2 | G | G | G | G | G |
| 71 | 66 | Fr3 | R | R | R | R | R |
| 72 | 67 | Fr3 | A | V | V | V | V |
| 73 | 68 | Fr3 | T | T | T | T | T |
| 74 | 69 | Fr3 | L | T | T | T | I |
| 75 | 70 | Fr3 | T | T | T | T | T |
| 76 | 71 | Fr3 | T | R | R | R | R |
| 77 | 72 | Fr3 | D | D | D | D | D |
| 78 | 73 | Fr3 | T | T | T | T | T |
| 79 | 74 | Fr3 | S | S | S | S | S |
| 80 | 75 | Fr3 | S | I | I | I | I |
| 81 | 76 | Fr3 | N | S | S | S | S |
| 82 | 77 | Fr3 | T | T | T | T | T |
| 83 | 78 | Fr3 | A | A | A | A | A |
| 84 | 79 | Fr3 | Y | Y | Y | Y | Y |
| 85 | 80 | Fr3 | L | M | M | M | L |
| 86 | 81 | Fr3 | Q | E | E | E | E |
| 87 | 82 | Fr3 | L | L | L | L | L |
| 88 | 82A | Fr3 | S | S | S | S | S |
| 89 | 82B | Fr3 | S | R | R | R | R |
| 90 | 82C | Fr3 | L | L | L | L | L |
| 91 | 83 | Fr3 | T | R | R | R | R |
| 92 | 84 | Fr3 | S | S | S | S | S |
| 93 | 85 | Fr3 | E | D | D | D | D |
| 94 | 86 | Fr3 | D | D | D | D | D |
| 95 | 87 | Fr3 | T | T | T | T | T |
| 96 | 88 | Fr3 | A | A | A | A | A |
| 97 | 89 | Fr3 | V | V | V | V | V |
| 98 | 90 | Fr3 | Y | Y | Y | Y | Y |
| 99 | 91 | Fr3 | Y | Y | Y | Y | Y |
| 100 | 92 | Fr3 | C | C | C | C | C |
| 101 | 93 | Fr3 | T | A | A | A | A |
| 102 | 94 | Fr3 | P | R | R | R | R |
| 103 | 95 | CDR-H3 | L | L | L | L | L |
| 104 | 96 | CDR-H3 | — | A | — | — | |
| 105 | 97 | CDR-H3 | — | A | — | — | |
| 106 | 98 | CDR-H3 | — | R | — | — | |
| 107 | 99 | CDR-H3 | — | P | — | — | |
| 108 | 100 | CDR-H3 | — | L | — | — | |
| 109 | 100A | CDR-H3 | — | — | — | — | |
| 110 | 100B | CDR-H3 | — | — | — | — | |
| 111 | 100C | CDR-H3 | — | — | — | — | |
| 112 | 100D | CDR-H3 | — | — | — | — | |
| 113 | 100E | CDR-H3 | — | — | — | | |
| 114 | 100F | CDR-H3 | — | — | — | | |
| 115 | 100G | CDR-H3 | — | — | — | | |
| 116 | 100H | CDR-H3 | — | — | — | | |
| s 117 | 100I | CDR-H3 | — | — | — | | |
| 118 | 100J | CDR-H3 | — | — | — | | |
| 119 | 100K | CDR-H3 | — | — | — | | |
| 120 | 101 | CDR-H3 | D | D | D | D | D |
| 121 | 102 | CDR-H3 | Y | Y | Y | Y | Y |
| 122 | 103 | Fr4 | W | W | W | W | W |
| 123 | 104 | Fr4 | G | G | G | G | G |
| 124 | 105 | Fr4 | Q | Q | Q | Q | Q |
| 125 | 106 | Fr4 | G | G | G | G | G |
| 126 | 107 | Fr4 | T | T | T | T | T |
| 127 | 108 | Fr4 | S | L | L | L | L |

TABLE 13-continued

| Linear residue # | Kabat residue # | FR or CDR | Murine 6A10 VH (SEQ ID NO: 63) | Acceptor Acc. # ACR16112 (SEQ ID NO: 81) | hu6A10-VH_v1 (SEQ ID NO: 85) | hu6A10-VH_v2 (SEQ ID NO: 86) | hu6A10-VH_v3 (SEQ ID NO: 87) |
|---|---|---|---|---|---|---|---|
| 128 | 109 | Fr4 | V | V | V | V | V |
| 129 | 110 | Fr4 | T | T | T | T | T |
| 130 | 111 | Fr4 | V | V | V | V | V |
| 131 | 112 | Fr4 | S | S | S | S | S |
| 132 | 113 | Fr4 | S | S | S | S | S |

TABLE 14

$V_H$, $V_L$ Backmutations and Other Mutations for Humanized 6A10

| $V_H$ or $V_L$ Variant | $V_H$ or $V_L$ Exon Acceptor Sequence | Changes from Acceptor Framework Residues (based on Kabat/Chothia Composite CDRs) |
|---|---|---|
| hu6A10-VH_v1 (SEQ ID NO: 85) | Acceptor Acc. # ACR16112 (SEQ ID NO: 81) | None |
| hu6A10-VH_v2 (SEQ ID NO: 86) | Acceptor Acc. # ACR16112 (SEQ ID NO: 81) | H48 |
| hu6A10-VH_v3 (SEQ ID NO: 87) | Acceptor Acc. # ACR16112 (SEQ ID NO: 81) | H16, H48, H69, H80 |
| hu6A10-VL_v1 (SEQ ID NO: 88) | Acceptor Acc. # ABC66863 (SEQ ID NO: 83) | None |
| hu6A10-VL_v2 (SEQ ID NO: 89) | Acceptor Acc. # ABC66863 (SEQ ID NO: 83) | L46 |
| hu6A10-VL_v3 (SEQ ID NO: 90) | Acceptor Acc. # ABC66863 (SEQ ID NO: 83) | L12, L17, L46 |

TABLE 15

Kabat Numbering of Framework Residues (based on Kabat/Chothia Composite CDRs) for Backmutations and Other Mutations in Heavy Chains of Humanized 6A10 Antibodies

| Kabat Residue # | Acceptor Acc. # ACR16112 (SEQ ID NO: 81) | Murine 6A10 VH (SEQ ID NO: 63) | hu6A10-VH_v1 (SEQ ID NO: 85) | hu6A10-VH_v2 (SEQ ID NO: 86) | hu6A10-VH_v3 (SEQ ID NO: 87) |
|---|---|---|---|---|---|
| H16 | A | A | A | A | G |
| H48 | M | I | M | I | I |
| H69 | T | L | T | T | I |
| H80 | M | L | M | M | L |

TABLE 16

Kabat Numbering of Framework Residues (based on Kabat/Chothia Composite CDRs) for Backmutations and Other Mutations in Light Chains of Humanized 6A10 Antibodies

| Kabat Residue # | Acceptor Acc. # ABC66863 (SEQ ID NO: 83) | Murine 6A10 VL (SEQ ID NO: 64) | hu6A10-VL_v1 (SEQ ID NO: 88) | hu6A10-VL_v2 (SEQ ID NO: 89) | hu6A10-VL_v3 (SEQ ID NO: 90) |
|---|---|---|---|---|---|
| L12 | P | S | P | P | S |
| L17 | Q | Q | Q | Q | E |
| L46 | R | R | R | L | L |

TABLE 17

Percentage Humanness of Heavy and Light Chains of Humanized 6A10 Antibodies

| $V_H$ or $V_L$ Variant | % Humanness |
|---|---|
| hu6A10-VH_v1 (SEQ ID NO: 85) | 83.7% |
| hu6A10-VH_v2 (SEQ ID NO: 86) | 82.7% |
| hu6A10-VH_v3 (SEQ ID NO: 87) | 80.6% |
| hu6A10-VL_v1 (SEQ ID NO: 88) | 90.0% |
| hu6A10-VL_v2 (SEQ ID NO: 89) | 89.0% |
| hu6A10-VL_v3 (SEQ ID NO: 90) | 87.0% |

Positions at which Chothia class canonical, vernier, or interface/packing residues differ between mouse and human acceptor sequences are candidates for substitution. Examples of Chothia class canonical residues include Kabat residues H48 and H93 in Tables 12 and 13. Examples of vernier residues include Kabat residues in Tables 12 and 13. Examples of interface/packing (VH+VL) residues include Kabat residues H35, H37, H39, H45, H47, H91, H93, H95, H103, L34, L36, L38, L44, L46, L87, L89, L91, L96, and L98, in Tables 12 and 13.

The rationales for selection of the positions indicated in Table 12 in the light chain variable region as candidates for substitution are as follows.

R46L: This is interface residue and is typically L
P12S: P is rare in human framework at this position, S is frequent
Q17E: Q is rare in human framework at this position, E is frequent

```
Light chain variable regions:
mature region of m6A10VL amino acid sequence
                                             (SEQ ID NO: 64)
DVVMTQTPLTLSVTIGQPASISCKSSQSLLDSDGKTYLNWLLQRPGQSPKRLIYLVSKLD
SGVPDRFTGSGSGTDFTLKISRVEAEDLGVYYCWQGTHFPYTFGGGTKLEIK 6A10 VL Acceptor accession #ABC66863
                                             (SEQ ID NO: 83)
DIVMTQSPLSLPVTLGQPASISCRSSQSLVYSDGNTYLNWFQQRPGQSPRRLIYKVSNRD
SGVPDRFSGSGSGTDFTLKISRVEAEDVGVYYCMQGTHRPLTFGGGTKVEIK >3F4-VL Accession No. 1CR9_L
                                             (SEQ ID NO: 30)
DVVMTQTPLSLSVTIGQPASISCKSSQSLLDSDGKTYLIWVFQRPGQSPKRLIFLVSKRDS
GVPDRFTGSGSGTDFTLKISRVEAEDVGVYYCWQGTHFPHTVGGGTKLEIA >IGKV2-30*02
                                             (SEQ ID NO: 84)
DVVMTQSPLSLPVTLGQPASICRSSQSLVHSDGNTYLNWFQQRPGQSPRRLIYKVSNRD
SGVPDRFSGSGSGTDFTLKISRVEAEDVGVYYCMQGTHWPLTFGGGTKVEIK >hu6A10-VL_v1
                                             (SEQ ID NO: 88)
DIVMTQSPLSLPVTLGQPASISCKSSQSLLDSDGKTYLNWFQQRPGQSPRRLIYLVSKLDS
GVPDRFSGSGSGTDFTLKISRVEAEDVGVYYCFGGGTKVEIK >hu6A10-VL_v2
                                             (SEQ ID NO: 89)
DIVMTQSPLSLPVTLGQPASISCKSSQSLLDSDGKTYLNWFQQRPGQSPRLLIYLVSKLDS
GVPDRFSGSGSGTDFTLKISRVEAEDVGVYYCFGGGTKVEIK >hu6A10-VL_v3
                                             (SEQ ID NO: 90)
DIVMTQSPLSLSVTLGEPASISCKSSQSLLDSDGKTYLNWFQQRPGQSPRLLIYLVSKLDS
GVPDRFSGSGSGTDFTLKISRVEAEDVGVYYCFGGGTKVEIK
```

The rationales for selection of the positions indicated in Table 13 in the heavy chain variable region as candidates for substitution are as follows.

M48I: This is a canonical/CDR interacting residue, back-mutated to preserve CDR interaction.

A16G: Ala is rare in human framework at this position, Gly is frequent

T69I: Thr is rare at this position, Ile is frequent

M80L: Although Met is frequent, Leu is most frequent at this position

```
Heavy chain variable regions:
mature region of m6A10VH amino acid sequence
                                             (SEQ ID NO: 63)
EVQLQQSGAELVRSGASVKLSCTASGLNIKDYYIHWVKQRPEQGLEWIG
WIDPENDDTEYAPKFQGRATLTTDTSSNTAYLQLSSLTSEDTAVYYCTP
LDYWGQGTSVTSS 6A10 VH Acceptor accession # ACR16112
                                             (SEQ ID NO: 84)
QVQLQESGAEVKKPGASVKVSCKASGYTFTGYYMHWVRQAPGQGLEWMG
WINPNSGDTNYAQKFQGRVTTTRDTSISTAYMELSRLRSDDTAVYYCAR
LAARPLDYWGQGTLVTVSS >3F4-VH Accession No. 1CR9_H
                                             (SEQ ID NO: 27)
KVKLQQSGAELVRSGASVKLSCTASGFNIKDYYIQWVKQRPEQGLEWIG
WIDPENGNSEYAPRFQGKATMTADTLSNTAYLQLSSLTSEDTAVYYCNA
DLHDYWGQGTTLTVSS >IGHV1-2*02
                                             (SEQ ID NO: 82)
QVQLVQSGAEVKKPGASVKVSCKASGYTFTGYYMHWVRQAPGQGLEWMG
WINPNSGGTNYAQKFQGRVTMTRDTSISTAYMELSRLRSDDTAVYYCAR
SRRGYYDFWSGSPEDYWGQGTLVTVSS >hu6A10-VH_v1
                                             (SEQ ID NO: 85)
QVQLQESGAEVKKPGASVKVSCKASGLNIKDYYIHWVRQAPGQGLEWMG
WIDPENDDTEYAPKFQGRVTTTRDTSISTAYMELSRLRSDDTAVYYCAR
LDWGQGTLVTVSS
```

-continued

>hu6A10-VH_v2
(SEQ ID NO: 86)
QVQLQESGAEVKKPGASVKVSCKASGLNIKDYYIHWVRQAPGQGLEWIG
WIDPENDDTEYAPKFQGRVTTTRDTSISTAYMELSRLRSDDTAVYYCAR
LDYWGQGTLVTVSS

>hu6A10-VH_v3
(SEQ ID NO: 87)
QVQLQESGAEVKKPGGSVKVSCKASGLNIKDYYIHWVRQAPGQGLEWIG
WIDPENDDTEYAPKFQGRVTITRDTSISTAYLELSRLRSDDTAVYYCAR
LDYWGQGTLVTVSS

Example 8. Design of Humanized 8A4 Antibodies

The starting point for monoclonal antibody 8A4 humanization is murine antibody 8A4. The heavy chain variable amino acid sequence of mature 8A4 is provided as SEQ ID NO:91. The light chain variable amino acid sequence of mature 8A4 is provided as SEQ ID NO:92. The heavy chain Kabat/Chothia Composite CDR1, CDR2, and CDR3 amino acid sequences are provided as SEQ ID NOs:93-95, respectively. The light chain Kabat CDR1, CDR2, and CDR3 amino acid sequences are provided as SEQ ID NOs:96-98 respectively. Kabat numbering is used throughout.

Alignment of the variable region sequences of 8A4 with the consensus sequences of antibody variable regions from Kabat, et al. (Kabat E A, Wu T T, Foeller C, Perry H M, Gottesman K S. (1991) *Sequences of Proteins of Immunological Interest* (5th edition). Bethesda, MD: National Institutes of Health) indicates that the heavy chain variable region (VH) of 8A4 belongs to mouse VH subgroup 2c, which corresponds to human VH subgroup 1. The kappa light chain variable region (VL) of 8A4 belongs to mouse Vk subgroup 2, which corresponds to human Vk subgroup 2.

The CDRs of 8A4 VH and VL were identified using Martin's sequence-based CDR-identification rules (Martin A C R. (2010) Protein sequence and structure analysis of antibody variable domains. In: Kontermann R and Dubel S (eds). *Antibody Engineering*. Heidelberg, Germany: Springer International Publishing AG.) The CDRs were then assigned to the Chothia canonical classes using the summary of key residues presented in Table 3.5 of Martin:

- CDR-H1 consists of 10 amino acids and is similar to Chothia canonical class 1.
- CDR-H2 consists of 17 amino acids and is similar to Chothia canonical class 2.
- CDR-H3 consists of 3 amino acids; there are no classes for CDR-H3.
- CDR-L1 consists of 16 amino acids and is similar to Chothia canonical class 4.
- CDR-L2 consists of 7 amino acids and is of Chothia canonical class 1.
- CDR-L3 consists of 9 amino acids and is similar to Chothia canonical class 1.

The residues at the interface between the Vk and Vh domains are the ones commonly found, except that 93S in the heavy chain is typically an alanine; therefore, this residue is analyzed as a target for back-mutation. Similarly, 36L in vk is typically Y or F therefore, this residue is also analyzed for back-mutations. Additionally, light chain CRD3 has an unpaired cysteine residue.

A search was made over the protein sequences in the PDB database [Deshpande N. et al., (2005) Nucleic Acids Res. 33: D233-D237.] to find structures, which would provide a rough structural model of 8A4. The crystal structure of antibody fab (pdb code 3JAU; SEQ ID NO:111) [Ye X, et al., (2016) *PLoS Pathog.*] was used for the Vk structure since it had good resolution (4.8 A) and overall sequence similarity to 8A4 Vk retaining the same canonical structures for the loops. Same structure {pdb code 3JAU; SEQ ID NO:109} was also used for the Vh structure since it had good overall sequence similarity and reasonably good resolution (4.8 A). In addition, CDRs-H1 and H2 had the same canonical structures as 8A4 Vh. Bioluminate software was used to model a rough structure of 8A4. This software is licensed from Schrodinger Inc.

A search of the non-redundant protein sequence database from NCBI allowed selection of suitable human frameworks into which to graft the murine CDRs. For Vk, a human kappa light chain variable region with accession #ABA26100 [SEQ ID NO:112; Rabquer, B. J., et al, 2016; Differential variable gene usage between pneumococcal polysaccharide specific B cells isolated 5-10 days and 4-6 weeks post-vaccination. Unpublished] was chosen. This has the same canonical classes for CDR-L1 and L2 as murine 8A4 VL. It is a member of Kabat human kappa subgroup 2. For Vh, human heavy chain variable region with accession #ADU57742 [SEQ ID NO:110; Lantto, J., et al, 2011 *J. Virol.* 85: 1820-1833] was chosen; it has same canonical classes as murine 8A4 VH. It is a member of Kabat human heavy subgroup 1.

3 humanized heavy chain variable region variants and 3 humanized light chain variable region variants were constructed containing different permutations of substitutions, hu8A4-VH_v1, hu8A4-VH_v2, and hu8A4-VH_v3, (SEQ ID NOs: 113-115 respectively) and hu8A4-VL_v1, hu8A4-VL_v2, and hu8A4-VL_v3, (SEQ ID NOs: 116-118, respectively). (Tables 18 and 19). The exemplary humanized VL and VH designs, with backmutations and other mutations based on selected human frameworks, are shown in Tables 18 and 19, respectively. The bolded areas in Tables 18 and 19 indicate the CDRs as defined by Kabat/Chothia Composite. A "-" in the columns in Tables 18 and 19 indicates no residue at the indicated position. SEQ ID NOs:113-115 and SEQ ID NOs: 116-118 contain backmutations and other mutations as shown in Table 20. The amino acids at positions in hu8A4-VH_v1, hu8A4-VH_v2, and hu8A4-VH_v3 are listed in Table 21. The amino acids at positions in hu8A4-VL_v1, hu8A4-VL_v2, and hu8A4-VL_v3 are listed in Table 22. The percentage humanness for humanized VH chains hu8A4-VH_v1, hu8A4-VH_v2, and hu8A4-VH_v3, (SEQ ID NOs: 113-115, respectively) with respect to the most similar human germline gene IGHV1-2*02 (SEQ ID NO:82), and for humanized VL chains hu8A4-VL_v1, hu8A4-VL_v2, and hu8A4-VL_v3 (SEQ ID NOs:116-118, respectively) with respect to the most similar human germline gene IGKV2-30*02 (SEQ ID NO:84), is shown in Table 23.

TABLE 18

| Linear residue # | Kabat residue # | FR or CDR | Murine 8A4 VL (SEQ ID NO: 92) | Acceptor Acc. #ABA26100 (SEQ ID NO: 112) | Hu8A4-VL_v1 (SEQ ID NO: 116) | hu u8A4-VL_v2 (SEQ ID NO: 117) | hu u8A4-VL_v3 (SEQ ID NO: 118) |
|---|---|---|---|---|---|---|---|
| 1 | 1 | Fr1 | D | D | D | D | D |
| 2 | 2 | Fr1 | V | I | I | I | V |

TABLE 18-continued

| Linear residue # | Kabat residue # | FR or CDR | Murine 8A4 VL (SEQ ID NO: 92) | Acceptor Acc. #ABA26100 (SEQ ID NO: 112) | Hu8A4-VL_v1 (SEQ ID NO: 116) | hu u8A4-VL_v2 (SEQ ID NO: 117) | hu u8A4-VL_v3 (SEQ ID NO: 118) |
|---|---|---|---|---|---|---|---|
| 3 | 3 | Fr1 | V | V | V | V | V |
| 4 | 4 | Fr1 | M | M | M | M | M |
| 5 | 5 | Fr1 | T | T | T | T | T |
| 6 | 6 | Fr1 | Q | Q | Q | Q | Q |
| 7 | 7 | Fr1 | T | S | S | S | S |
| 8 | 8 | Fr1 | P | P | P | P | P |
| 9 | 9 | Fr1 | L | L | L | L | L |
| 10 | 10 | Fr1 | T | S | S | S | S |
| 11 | 11 | Fr1 | L | L | L | L | L |
| 12 | 12 | Fr1 | S | S | S | S | S |
| 13 | 13 | Fr1 | V | V | V | V | V |
| 14 | 14 | Fr1 | T | T | T | T | T |
| 15 | 15 | Fr1 | I | L | L | L | L |
| 16 | 16 | Fr1 | G | G | G | G | G |
| 17 | 17 | Fr1 | Q | Q | Q | E | E |
| 18 | 18 | Fr1 | P | P | P | P | P |
| 19 | 19 | Fr1 | A | A | A | A | A |
| 20 | 20 | Fr1 | S | S | S | S | S |
| 21 | 21 | Fr1 | I | I | I | I | I |
| 22 | 22 | Fr1 | S | S | S | S | S |
| 23 | 23 | Fr1 | C | C | C | C | C |
| 24 | 24 | CDR-L1 | K | R | K | K | K |
| 25 | 25 | CDR-L1 | S | S | S | S | S |
| 26 | 26 | CDR-L1 | S | S | S | S | S |
| 27 | 27 | CDR-L1 | Q | Q | Q | Q | Q |
| 28 | 27A | CDR-L1 | S | S | S | S | S |
| 29 | 27B | CDR-L1 | L | L | L | L | L |
| 30 | 27C | CDR-L1 | L | V | L | L | L |
| 31 | 27D | CDR-L1 | D | Y | D | D | D |
| 32 | 27E | CDR-L1 | S | S | S | S | S |
|  | 27F | CDR-L1 | — | — |  |  |  |
| 33 | 28 | CDR-L1 | D | D | D | D | D |
| 34 | 29 | CDR-L1 | G | G | G | G | G |
| 35 | 30 | CDR-L1 | K | S | K | K | K |
| 36 | 31 | CDR-L1 | T | T | T | T | T |
| 37 | 32 | CDR-L1 | Y | W | Y | Y | Y |
| 38 | 33 | CDR-L1 | L | L | L | L | L |
| 39 | 34 | CDR-L1 | N | N | N | N | N |
| 40 | 35 | Fr2 | W | W | W | W | W |
| 41 | 36 | Fr2 | L | F | F | F | L |
| 42 | 37 | Fr2 | L | Q | Q | Q | Q |
| 43 | 38 | Fr2 | Q | Q | Q | Q | Q |
| 44 | 39 | Fr2 | R | R | R | R | R |
| 45 | 40 | Fr2 | P | P | P | P | P |
| 46 | 41 | Fr2 | G | G | G | G | G |
| 47 | 42 | Fr2 | Q | Q | Q | Q | Q |
| 48 | 43 | Fr2 | S | S | S | S | S |
| 49 | 44 | Fr2 | P | P | P | P | P |
| 50 | 45 | Fr2 | K | R | R | R | R |
| 51 | 46 | Fr2 | R | R | R | R | R |
| 52 | 47 | Fr2 | L | L | L | L | L |
| 53 | 48 | Fr2 | I | I | I | I | I |
| 54 | 49 | Fr2 | Y | Y | Y | Y | Y |
| 55 | 50 | CDR-L2 | L | D | L | L | L |
| 56 | 51 | CDR-L2 | V | V | V | V | V |
| 57 | 52 | CDR-L2 | S | S | S | S | S |
| 58 | 53 | CDR-L2 | K | T | K | K | K |
| 59 | 54 | CDR-L2 | L | R | L | L | L |
| 60 | 55 | CDR-L2 | D | D | D | D | D |
| 61 | 56 | CDR-L2 | S | S | S | S | S |
| 62 | 57 | Fr3 | G | G | G | G | G |
| 63 | 58 | Fr3 | V | V | V | V | V |
| 64 | 59 | Fr3 | P | P | P | P | P |
| 65 | 60 | Fr3 | D | D | D | D | D |
| 66 | 61 | Fr3 | R | R | R | R | R |
| 67 | 62 | Fr3 | F | F | F | F | F |
| 68 | 63 | Fr3 | T | S | S | S | S |
| 69 | 64 | Fr3 | G | G | G | G | G |
| 70 | 65 | Fr3 | S | S | S | S | S |
| 71 | 66 | Fr3 | G | G | G | G | G |
| 72 | 67 | Fr3 | S | S | S | S | S |
| 73 | 68 | Fr3 | G | G | G | G | G |
| 74 | 69 | Fr3 | T | T | T | T | T |
| 75 | 70 | Fr3 | D | D | D | D | D |
| 76 | 71 | Fr3 | F | F | F | F | F |
| 77 | 72 | Fr3 | T | T | T | T | T |
| 78 | 73 | Fr3 | L | L | L | L | L |

TABLE 18-continued

| Linear residue # | Kabat residue # | FR or CDR | Murine 8A4 VL (SEQ ID NO: 92) | Acceptor Acc. #ABA26100 (SEQ ID NO: 112) | Hu8A4-VL_v1 (SEQ ID NO: 116) | hu u8A4-VL_v2 (SEQ ID NO: 117) | hu u8A4-VL_v3 (SEQ ID NO: 118) |
|---|---|---|---|---|---|---|---|
| 79 | 74 | Fr3 | K | K | K | K | K |
| 80 | 75 | Fr3 | I | I | I | I | I |
| 81 | 76 | Fr3 | S | S | S | S | S |
| 82 | 77 | Fr3 | R | R | R | R | R |
| 83 | 78 | Fr3 | V | V | V | V | V |
| 84 | 79 | Fr3 | E | E | E | E | E |
| 85 | 80 | Fr3 | A | A | A | A | A |
| 86 | 81 | Fr3 | E | E | E | E | E |
| 87 | 82 | Fr3 | D | D | D | D | D |
| 88 | 83 | Fr3 | L | V | V | V | V |
| 89 | 84 | Fr3 | G | G | G | G | G |
| 90 | 85 | Fr3 | V | V | V | V | V |
| 91 | 86 | Fr3 | Y | Y | Y | Y | Y |
| 92 | 87 | Fr3 | Y | Y | Y | Y | Y |
| 93 | 88 | Fr3 | C | C | C | C | C |
| 94 | 89 | CDR-L3 | W | M | W | W | W |
| 95 | 90 | CDR-L3 | Q | Q | Q | Q | Q |
| 96 | 91 | CDR-L3 | G | F | G | G | G |
| 97 | 92 | CDR-L3 | T | I | T | T | T |
| 98 | 93 | CDR-L3 | H | D | H | H | H |
| 99 | 94 | CDR-L3 | F | W | F | F | F |
| 100 | 95 | CDR-L3 | P | P | P | P | P |
|  | 95A | CDR-L3 | — | — | — | — | — |
|  | 95B | CDR-L3 | — | — | — | — | — |
|  | 95C | CDR-L3 | — | — | — | — | — |
|  | 95D | CDR-L3 | — | — | — | — | — |
|  | 95E | CDR-L3 | — | — | — | — | — |
|  | 95F | CDR-L3 | — | — | — | — | — |
| 101 | 96 | CDR-L3 | C | H | C | C | C |
| 102 | 97 | CDR-L3 | T | T | T | T | T |
| 103 | 98 | Fr4 | F | F | F | F | F |
| 104 | 99 | Fr4 | G | G | G | G | G |
| 105 | 100 | Fr4 | G | Q | Q | Q | Q |
| 106 | 101 | Fr4 | G | G | G | G | G |
| 107 | 102 | Fr4 | T | T | T | T | T |
| 108 | 103 | Fr4 | K | K | K | K | K |
| 109 | 104 | Fr4 | L | L | L | L | L |
| 110 | 105 | Fr4 | E | E | E | E | E |
| 111 | 106 | Fr4 | I | I | I | I | I |
|  | 106A | Fr4 | — | — | — | — | — |
| 112 | 107 | Fr4 | K | K | K | K | K |

TABLE 19

| Linear residue # | Kabat residue # | FR or CDR | Murine 8A4 VH (SEQ ID NO: 91) | Acceptor Acc. # ADU57742 (SEQ ID NO: 110) | hu8A4-VH_v1 (SEQ ID NO: 113) | hu8A4-VH_v2 (SEQ ID NO: 114) | hu8A4-VH_v3 (SEQ ID NO: 115) |
|---|---|---|---|---|---|---|---|
| 1 | 1 | Fr1 | E | Q | Q | Q | Q |
| 2 | 2 | Fr1 | V | V | V | V | V |
| 3 | 3 | Fr1 | Q | Q | Q | Q | Q |
| 4 | 4 | Fr1 | L | L | L | L | L |
| 5 | 5 | Fr1 | Q | Q | Q | Q | Q |
| 6 | 6 | Fr1 | Q | Q | Q | Q | Q |
| 7 | 7 | Fr1 | S | S | S | S | S |
| 8 | 8 | Fr1 | G | G | G | G | G |
| 9 | 9 | Fr1 | A | A | A | A | A |
| 10 | 10 | Fr1 | E | E | E | E | E |
| 11 | 11 | Fr1 | L | V | V | V | V |
| 12 | 12 | Fr1 | V | K | K | V | V |
| 13 | 13 | Fr1 | R | K | K | K | K |
| 14 | 14 | Fr1 | P | P | P | P | P |
| 15 | 15 | Fr1 | G | G | G | G | G |
| 16 | 16 | Fr1 | A | S | S | G | G |
| 17 | 17 | Fr1 | L | S | S | S | S |
| 18 | 18 | Fr1 | V | V | V | V | V |
| 19 | 19 | Fr1 | K | K | K | K | K |
| 20 | 20 | Fr1 | L | V | V | L | L |
| 21 | 21 | Fr1 | S | S | S | S | S |
| 22 | 22 | Fr1 | C | C | C | C | C |
| 23 | 23 | Fr1 | K | K | K | K | K |
| 24 | 24 | Fr1 | A | A | A | A | A |
| 25 | 25 | Fr1 | S | S | S | S | S |
| 26 | 26 | CDR-H1 | G | G | G | G | G |

TABLE 19-continued

| Linear residue # | Kabat residue # | FR or CDR | Murine 8A4 VH (SEQ ID NO: 91) | Acceptor Acc. # ADU57742 (SEQ ID NO: 110) | hu8A4-VH_v1 (SEQ ID NO: 113) | hu8A4-VH_v2 (SEQ ID NO: 114) | hu8A4-VH_v3 (SEQ ID NO: 115) |
|---|---|---|---|---|---|---|---|
| 27 | 27 | CDR-H1 | F | G | F | F | F |
| 28 | 28 | CDR-H1 | N | T | N | N | N |
| 29 | 29 | CDR-H1 | I | F | I | I | I |
| 30 | 30 | CDR-H1 | K | S | K | K | K |
| 31 | 31 | CDR-H1 | D | S | D | D | D |
| 32 | 32 | CDR-H1 | Y | N | Y | Y | Y |
| 33 | 33 | CDR-H1 | Y | P | Y | Y | Y |
| 34 | 34 | CDR-H1 | I | V | I | I | I |
| 35 | 35 | CDR-H1 | H | S | H | H | H |
|  | 35A | CDR-H1 | — | — | — | — | — |
|  | 35B | CDR-H1 | — | — | — | — | — |
| 36 | 36 | Fr2 | W | W | W | W | W |
| 37 | 37 | Fr2 | V | V | V | V | V |
| 38 | 38 | Fr2 | K | R | R | R | R |
| 39 | 39 | Fr2 | Q | Q | Q | Q | Q |
| 40 | 40 | Fr2 | R | A | A | A | A |
| 41 | 41 | Fr2 | P | P | P | P | P |
| 42 | 42 | Fr2 | E | G | G | G | G |
| 43 | 43 | Fr2 | Q | Q | Q | Q | Q |
| 44 | 44 | Fr2 | G | G | G | G | G |
| 45 | 45 | Fr2 | L | L | L | L | L |
| 46 | 46 | Fr2 | E | E | E | E | E |
| 47 | 47 | Fr2 | W | W | W | W | W |
| 48 | 48 | Fr2 | I | M | M | M | I |
| 49 | 49 | Fr2 | G | G | G | G | G |
| 50 | 50 | CDR-H2 | W | G | W | W | W |
| 51 | 51 | CDR-H2 | I | I | I | I | I |
| 52 | 52 | CDR-H2 | D | I | D | D | D |
| 53 | 52A | CDR-H2 | P | P | P | P | P |
|  | 52B | CDR-H2 | — | — | — | — | — |
|  | 52C | CDR-H2 | — | — | — | — | — |
| 54 | 53 | CDR-H2 | E | F | E | E | E |
| 55 | 54 | CDR-H2 | N | A | N | N | N |
| 56 | 55 | CDR-H2 | G | Q | G | G | G |
| 57 | 56 | CDR-H2 | D | K | D | D | D |
| 58 | 57 | CDR-H2 | T | V | T | T | T |
| 59 | 58 | CDR-H2 | V | L | V | V | V |
| 60 | 59 | CDR-H2 | Y | G | Y | Y | Y |
| 61 | 60 | CDR-H2 | D | A | D | D | D |
| 62 | 61 | CDR-H2 | P | Q | P | P | P |
| 63 | 62 | CDR-H2 | Q | R | Q | Q | Q |
| 64 | 63 | CDR-H2 | F | V | F | F | F |
| 65 | 64 | CDR-H2 | Q | R | Q | Q | Q |
| 66 | 65 | CDR-H2 | D | D | D | D | D |
| 67 | 66 | Fr3 | K | R | R | R | R |
| 68 | 67 | Fr3 | A | I | I | I | A |
| 69 | 68 | Fr3 | N | N | N | T | T |
| 70 | 69 | Fr3 | I | I | I | I | I |
| 71 | 70 | Fr3 | T | T | T | T | T |
| 72 | 71 | Fr3 | A | A | A | A | A |
| 73 | 72 | Fr3 | D | D | D | D | D |
| 74 | 73 | Fr3 | T | T | T | T | T |
| 75 | 74 | Fr3 | S | S | S | S | S |
| 76 | 75 | Fr3 | S | T | T | T | T |
| 77 | 76 | Fr3 | N | S | S | S | S |
| 78 | 77 | Fr3 | T | T | T | T | T |
| 79 | 78 | Fr3 | A | A | A | A | A |
| 80 | 79 | Fr3 | Y | Y | Y | Y | Y |
| 81 | 80 | Fr3 | L | M | M | M | M |
| 82 | 81 | Fr3 | Q | E | E | E | E |
| 83 | 82 | Fr3 | L | L | L | L | L |
| 84 | 82A | Fr3 | S | S | S | S | S |
| 85 | 82B | Fr3 | S | G | G | G | G |
| 86 | 82C | Fr3 | L | L | L | L | L |
| 87 | 83 | Fr3 | T | R | R | R | R |
| 88 | 84 | Fr3 | S | S | S | S | S |
| 89 | 85 | Fr3 | E | D | D | D | E |
| 90 | 86 | Fr3 | G | D | D | D | D |
| 91 | 87 | Fr3 | T | T | T | T | T |
| 92 | 88 | Fr3 | A | A | A | A | A |
| 93 | 89 | Fr3 | V | V | V | V | V |
| 94 | 90 | Fr3 | Y | Y | Y | Y | Y |
| 95 | 91 | Fr3 | Y | Y | Y | Y | Y |
| 96 | 92 | Fr3 | C | C | C | C | C |
| 97 | 93 | Fr3 | S | A | S | S | A |
| 98 | 94 | Fr3 | T | T | T | T | T |

TABLE 19-continued

| Linear residue # | Kabat residue # | FR or CDR | Murine 8A4 VH (SEQ ID NO: 91) | Acceptor Acc. # ADU57742 (SEQ ID NO: 110) | hu8A4-VH_v1 (SEQ ID NO: 113) | hu8A4-VH_v2 (SEQ ID NO: 114) | hu8A4-VH_v3 (SEQ ID NO: 115) |
|---|---|---|---|---|---|---|---|
| 99 | 95 | CDR-H3 | L | G | L | L | L |
|  | 96 | CDR-H3 | — | Q | — | — | — |
|  | 97 | CDR-H3 | — | Q | — | — | — |
|  | 98 | CDR-H3 | — | L | — | — | — |
|  | 99 | CDR-H3 | — | Y | — | — | — |
|  | 100 | CDR-H3 | — | S | — | — | — |
|  | 100A | CDR-H3 | — | L | — | — | — |
|  | 100B | CDR-H3 | — | — | — | — | — |
|  | 100C | CDR-H3 | — | — | — | — | — |
|  | 100D | CDR-H3 | — | — | — | — | — |
|  | 100E | CDR-H3 | — | — | — | — | — |
|  | 100F | CDR-H3 | — | — | — | — | — |
|  | 100G | CDR-H3 | — | — | — | — | — |
|  | 100H | CDR-H3 | — | — | — | — | — |
|  | 100I | CDR-H3 | — | — | — | — | — |
|  | 100J | CDR-H3 | — | — | — | — | — |
|  | 100K | CDR-H3 | — | — | — | — | — |
| 100 | 101 | CDR-H3 | D | H | D | D | D |
| 101 | 102 | CDR-H3 | F | Y | F | F | F |
| 102 | 103 | Fr4 | W | W | W | W | W |
| 103 | 104 | Fr4 | G | G | G | G | G |
| 104 | 105 | Fr4 | Q | Q | Q | Q | Q |
| 105 | 106 | Fr4 | G | G | G | G | G |
| 106 | 107 | Fr4 | T | T | T | T | T |
| 107 | 108 | Fr4 | T | L | L | L | L |
| 108 | 109 | Fr4 | L | V | V | V | V |
| 109 | 110 | Fr4 | T | T | T | T | T |
| 110 | 111 | Fr4 | V | V | V | V | V |
| 111 | 112 | Fr4 | S | S | S | S | S |
| 112 | 113 | Fr4 | S | S | S | S | S |

TABLE 20

$V_H$, $V_L$ Backmutations and Other Mutations for Humanized 8A4

| $V_H$ or $V_L$ Variant | $V_H$ or $V_L$ Exon Acceptor Sequence | Changes from Acceptor Framework Residues (based on Kabat/Chothia Composite CDRs) |
|---|---|---|
| hu8A4-VH_v1 (SEQ ID NO: 113) | Acceptor Acc. # ADU57742 (SEQ ID NO: 110) | H93 |
| hu8A4-VH_v2 (SEQ ID NO: 114) | Acceptor Acc. # ADU57742 (SEQ ID NO: 110) | H12, H16, H20, H68, H93 |
| hu8A4-VH_v3 (SEQ ID NO: 115) | Acceptor Acc. # ADU57742 (SEQ ID NO: 110) | H12, H16, H20, H48, H67, H68, H85 |
| hu8A4-VL_v1 (SEQ ID NO: 116) | Acceptor Acc. # ABA26100 (SEQ ID NO: 112) | None |
| hu8A4-VL_v2 (SEQ ID NO: 117) | Acceptor Acc. # ABA26100 (SEQ ID NO: 112) | L17 |
| hu8A4-VL_v3 (SEQ ID NO: 118) | Acceptor Acc. # ABA26100 (SEQ ID NO: 112) | L2, L17, L36 |

TABLE 21

Kabat Numbering of Framework Residues (based on Kabat/Chothia Composite CDRs) for Backmutations and Other Mutations in Heavy Chains of Humanized 8A4 Antibodies

| Kabat Residue # | Acceptor Acc. # ADU57742 (SEQ ID NO: 110) | Murine 8A4 VH (SEQ ID NO: 91) | hu8A4-VH_v1 (SEQ ID NO: 113) | hu8A4-VH_v2 (SEQ ID NO: 114) | hu8A4-VH_v3 (SEQ ID NO: 115) |
|---|---|---|---|---|---|
| H12 | K | V | K | V | V |
| H16 | S | A | S | G | G |
| H20 | V | L | V | L | L |
| H48 | M | I | M | M | I |
| H67 | I | A | I | I | A |

TABLE 21-continued

Kabat Numbering of Framework Residues (based on Kabat/Chothia Composite CDRs) for Backmutations and Other Mutations in Heavy Chains of Humanized 8A4 Antibodies

| Kabat Residue # | Acceptor Acc. # ADU57742 (SEQ ID NO: 110) | Murine 8A4 VH (SEQ ID NO: 91) | hu8A4-VH_v1 (SEQ ID NO: 113) | hu8A4-VH_v2 (SEQ ID NO: 114) | hu8A4-VH_v3 (SEQ ID NO: 115) |
|---|---|---|---|---|---|
| H68 | N | N | N | T | T |
| H85 | D | E | D | D | E |
| H93 | A | S | S | S | A |

TABLE 22

Kabat Numbering of Framework Residues (based on Kabat/Chothia Composite CDRs) for Backmutations and Other Mutations in Light Chains of Humanized 8A4 Antibodies

| Kabat Residue # | Acceptor Acc. # ABA26100 (SEQ ID NO: 112) | Murine 8A4 VL (SEQ ID NO: 92) | hu8A4-VL_v1 (SEQ ID NO: 116) | hu8A4-VL_v2 (SEQ ID NO: 117) | hu8A4-VL_v3 (SEQ ID NO: 118) |
|---|---|---|---|---|---|
| L2  | I | V | I | I | V |
| L17 | Q | Q | Q | E | E |
| L36 | F | L | F | F | L |

TABLE 23

Percentage Humanness of Heavy and Light Chains of Humanized 8A4 Antibodies

| $V_H$ or $V_L$ Variant | % Humanness |
|---|---|
| hu8A4-VH_v1 (SEQ ID NO: 113) | 75.3% |
| hu8A4-VH_v2 (SEQ ID NO: 114) | 75.3% |
| hu8A4-VH_v3 (SEQ ID NO: 115) | 75.3% |
| hu8A4-VL_v1 (SEQ ID NO: 116) | 89% |
| hu8A4-VL_v2 (SEQ ID NO: 117) | 88% |
| hu8A4-VL_v3 (SEQ ID NO: 118) | 88% |

Positions at which Chothia class canonical, vernier, or interface/packing residues differ between mouse and human acceptor sequences are candidates for substitution. Examples of Chothia class canonical residues include Kabat residues H24, H26, H29, H34, H54, H55, H71, H94, L2, L25, L27B, L27C, L29, L33, L34, L71, L90, L94, L95, and L97 in Tables 18 and 19 and y. Examples of vernier residues include Kabat residues H2, H27, H28, H29, H30, H47, H48, H49, H67, H69, H71, H73, H78, H93, H94, H103, L2, L4, L35, L36, L46, L47, L48, L49, L64, L66, L68, L69, L71, and L98, in Tables 18 and 19. Examples of interface/packing (VH+VL) residues include Kabat residues H35, H37, H39, H45, H47, H91, H93, H95, H103, L34, L36, L38, L44, L46, L87, L89, L91, L96, and L98 in Tables 18 and 19.

The rationales for selection of the positions indicated in Table 18 in the light chain variable region as candidates for substitution are as follows.

I2V is a backmutation of a canonical and Vernier residue.
Q17E is a frequency based mutation as Q is rare in human frameworks at this position and E is most frequent.
F36L is a backmutation of an interface and Vernier residue.

```
Light chain variable regions:
mature region of murine 8A4VL
                                           (SEQ ID NO: 92)
DVVMTQTPLTLSVTIGQPASISCKSSQSLLDSDGKTYLNWLLQRPGQSPK
RLIYLVSKLDSGVPDRFTGSGSGTDFTLKISRVEAEDLGVYYCWQGTHFP
CTFGGGTKLEIK 3JAUVL
                                          (SEQ ID NO: 111)
DVLMTQTPLSLPVSLGDQASISCRSSQSIVHSNGNTYLEWYLQKPGQSPK
LLIYKVSNRFSGVPDRFSGSGSGTDFTLKISRVEADDVGVYYCYQGSHVP
YTFGGGTKLEIK ABA26100
                                          (SEQ ID NO: 112)
DVMTSSSVTGASSCRSSSVYSDGSTWNWRGSRRYDVSTRDSGVDRSGSGS
GTDTKSRVADVGVYYCMDWHTGGTKK IGKV2-30*02
                                           (SEQ ID NO: 84)
DIVMTQSPLSLSVTLGQPASISCKSSQSLLDSDGKTYLNWFQQRPGQSPR
RLIYLVSKLDSGVPDRFSGSGSGTDFTLKISRVEAEDVGVYYCWQGTHFP
CTFGQGTKLEIK hu8A4-VL_v1
                                          (SEQ ID NO: 116)
DIVMTQSPLSLSVTLGQPASISCKSSQSLLDSDGKTYLNWFQQRPGQSPR
RLIYLVSKLDSGVPDRFSGSGSGTDFTLKISRVEAEDVGVYYCWQGTHFP
CTFGQGTKLEIK hu8A4-VL_v2
                                          (SEQ ID NO: 117)
DIVMTQSPLSLSVTLGEPASISCKSSQSLLDSDGKTYLNWFQQRPGQSPR
RLIYLVSKLDSGVPDRFSGSGSGTDFTLKISRVEAEDVGVYYCWQGTHFP
CTFGQGTKLEIK hu8A4-VL_v3
                                          (SEQ ID NO: 118)
DVVMTQSPLSLSVTLGEPASISCKSSQSLLDSDGKTYLNWLQQRPGQSPR
RLIYLVSKLDSGVPDRFSGSGSGTDFTLKISRVEAEDVGVYYCWQGTHFP
CTFGQGTKLEIK
```

The rationales for selection of the positions indicated in Table 19 in the heavy chain variable region as candidates for substitution are as follows.

K12V is a backmutation and a frequency-based mutation as V is frequent at this position in human frameworks.
S16G is a frequency-based mutation as G is most frequent at this position.
V20L is a backmutation and a frequency-based mutation as L is most frequent at this position.
M48I is a backmutation of a Vernier residue.
I67A is a backmutation of a Vernier residue.

N68T is a frequency-based mutation as T is most frequent at this position.

D85E is a frequency-based mutation as E is most frequent at this position in human frameworks. A93S is a backmutation in hu8A4-VHv1 and hu8A4VH-v2 of a Vernier and interface residue to preserve CDR packing. In hu8A4VH-v3, Kabat position is A as A is most frequent at this position and S is rare.

```
Heavy chain variable regions:
mature region of murine 8A4VH
                                   (SEQ ID NO: 91)
EVQLQQSGAELVRPGALVKLSCKASGFNIKDYYIHWVKQRPEQGLEWIG
WIDPENGDTVYDPQFQDKANITADTSSNTAYLQLSSLTSEGTAVYYCST
LDFWGQGTTLTVSS 3JAUVH
                                   (SEQ ID NO: 109)
EVQLQQSGAELVKPGASVKLSCTASGFNIKDTYIHWVKQRPEQGLEWIG
KIDPANGNTKYDPKFQDKATITADTSSNTAYLQLSSLTSEDTAVYYCAN
SNYWFDFDYWGQGTTLTVSS ADU57742
                                   (SEQ ID NO: 110)
QVQLQQSGAEVKKPGSSVKVSCKASGGTFSSNPVSWVRQAPGQGLEWMG
GIIPFAQKVLGAQRVRDRINITADTSTSTAYMELSGLRSDDTAVYYCAT
GQQLYSLHYWGQGTLVTVSS IGHV1-2*02
                                   (SEQ ID NO: 82)
QVQLQQSGAEVKKPGSSVKVSCKASGFNIKDYYIHWVRQAPGQGLEWMG
WIDPENGDTVYDPQFQDRINITADTSTSTAYMELSGLRSDDTAVYYCST
LDFWGQGTLVTVSS hu8A4-VH_v1
                                   (SEQ ID NO: 113)
QVQLQQSGAEVKKPGSSVKVSCKASGFNIKDYYIHWVRQAPGQGLEWMG
WIDPENGDTVYDPQFQDRINITADTSTSTAYMELSGLRSDDTAVYYCST
LDFWGQGTLVTVSS hu8A4-VH_v2:
                                   (SEQ ID NO: 114)
QVQLQQSGAEVVKPGGSVKLSCKASGFNIKDYYIHWVRQAPGQGLEWMG
WIDPENGDTVYDPQFQDRITITADTSTSTAYMELSGLRSDDTAVYYCST
LDFWGQGTLVTVSS hu8A4-VH_v3
                                   (SEQ ID NO: 115)
QVQLQQSGAEVVKPGGSVKLSCKASGFNIKDYYIHWVRQAPGQGLEWIG
WIDPENGDTVYDPQFQDRATITADTSTSTAYMELSGLRSEDTAVYYCAT
LDFWGQGTLVTVSS
```

Example 9. Design of Humanized 7G6 Antibodies

The starting point for monoclonal antibody 7G6 humanization is murine antibody 7G6. The heavy chain variable amino acid sequence of mature 7G6 is provided as SEQ ID NO:119 The light chain variable amino acid sequence of mature 7G6 is provided as SEQ ID NO:120. The heavy chain Kabat/Chothia Composite CDR1, CDR2, and CDR3 amino acid sequences are provided as SEQ ID NOs:121-123, respectively. The light chain Kabat CDR1, CDR2, and CDR3 amino acid sequences are provided as SEQ ID NOs:124-126, respectively. Kabat numbering is used throughout.

Alignment of the variable region sequences of 7G6 with the consensus sequences of antibody variable regions from Kabat, et al. [Kabat E A, Wu T T, Perry H, Gottesman K, Foeller C. (1991) Sequences of Proteins of Immunological Interest, Fifth Edition. NIH Publication No. 91-3242] indicates that the heavy chain variable region (VH) of 7G6 belongs to mouse VH subgroup 2c, which corresponds to human VH subgroup 1. The kappa light chain variable region (VL) of 7G6 belongs to mouse Vk subgroup 2, which corresponds to human Vk subgroup 2.

The CDRs of 7G6 VH and VL were identified using Martin's sequence-based CDR-identification rules [Martin A C, Thornton J M. (1996) Structural families in loops of homologous proteins: automatic classification, modeling and application to antibodies. J Mol Biol. 263:800-15.]. The CDRs were then assigned to the Chothia canonical classes using the summary of key residues presented in Table 3.5 of Martin:

CDR-H1 consists of 7 amino acids and is similar to Chothia canonical class 1.

CDR-H2 consists of 6 amino acids and is similar to Chothia canonical class 2.

CDR-H3 consists of 3 amino acids; there are no classes for CDR-H3.

CDR-L1 consists of 16 amino acids and is similar to Chothia canonical class 4.

CDR-L2 consists of 7 amino acids and is of Chothia canonical class 1.

CDR-L3 consists of 9 amino acids and is similar to Chothia canonical class 1.

Humanization Rationale for Immunoglobulin Variable Domain 7G6

The murine antibody Prothena-7G6 (just 7G6 hereafter) was humanized by reference to the acceptor human antibody template denoted as 3U0T [La Porte, S. L., et al., (2012) J. Mol. Biol. 421: 525-536] in the RCSB Protein Data Bank. This antibody template was identified by antibody-specific sequence homology search, restricted to variable domain residues VL (1-110) and VH (1-114). Homology search employed the Schrodinger BioLuminate software, version 3.1, release 2018-1. This software compares the target antibody sequence (7G6) with a Schrodinger-curated database of human and murine variable domain sequences for which high quality protein crystals structures have been published.

Human Antibody Template Selection

Template antibody 3U0T [3U0T_VH SEQ ID NO: 127; 3U0T_VL SEQ ID NO: 138] which has resolution 2.5 Angstrom, was identified within a group several human antibodies that have greater than 80% amino acid identity or similarity to 7G6 in respective variable domains VH and VL and also have crystal structure with resolution below 3.0 Angstroms. Some other antibodies in this group included (by PDB code): 4YVG, 6BOG, 4KY1, 5TZT, 4HCR, and 5K9O. 3U0T was selected because of high sequence homology to 7G6 at the VH/VL interface positions as numbered by Kabat. VH [35,37,39,45,47,89,91,93] and VL[44,45,46,47, 48,49]. Among these interfacial residues 7G6 and 3U0T differ only at VL-45 (R vs K) and VH-93 (T vs A). Overall homology variable domain homology in Chothia-defined framework regions is in Table 24. (The Chothia framework, in contrast to Kabat, terminates CDR-H2 at position 58).

TABLE 24

Sequence homology between 7G6 and 3U0T variable domains

| Domain | Framework Total Residues | Identical | Similar | Distinct |
|---|---|---|---|---|
| VL | 81 | 7 | 6 | 5 |
| VH | 89 | 62 | 13 | 14 |

Similar amino acids are grouped by polarity and charge, aromaticity, hydrophobicity, or volume and shape, for instance (I,L,M,V), (S,T), (F,Y), (E,Q,D,N). VL has greater than 93% identity or similarity in the framework and VH has greater than 84% identity or similarity in the framework. Further inspection identifies the high homology for the very long light chain CDR-1. Among 20 residues, 17 are identical and 2 are distinct, (D,Y) at VL-7D and (G,A) at VL-29. The crystal structure for 3U0T therefore should provide an excellent reference for the shape of CDR L-1.

Exemplary Differences Between 7G6 and 3U0T are:

Residue 89-W in VL of 7G6. This residue is within the VL/VH interface, where it replaces F from 3U0T. Initial structural modeling with BioLuminate Antibody Prediction yielded structures in which W89 had either of two side chain rotamers. Ch1=0 or 90 degrees. The rotamer Chi=0 places W89 perpendicular to the VL/VH interface. In this position W89 contributes to the floor of the antigen binding pocket and has potential for van der Waals contact with both CDR-H3 (especially Leu-95 in VH) and several of the conserved residues that otherwise structure the VL/VH interface. The rotamer Ch1=180 orient the Tryptophan side chain parallel to the VH/VL interface; it then has no contact to CDR-H3 but would have van der Waals contacts with several other conserved residues that structure the VH/VL interface. Exemplary humanized variants of 7G6 VL use the ch1=0 orientation of Trp. The invention also contemplates mutation of other framework amino acids that have van der Waals contact with W89 at ch1=90 but not ch1=0.

The highly conserved cystine at Kabat 92H is nearly ubiquitous in immunoglobulin folds, because it forms a disulfide bridge with the equally conserved Cys 22-Hvy that precedes CDR H1. Nonetheless, in sequence 7G6 this disulfide bridge of VH is broken by the mutation 94 Cys to 94 Ser. Initial structural modeling with BioLuminate shows the framework residues have little distortion derived from the missing disulfide bridge. Nonetheless, the broken disulfide bond does impart greater flexibility to the peptide backbone at Ser-94-hvy. Exemplary humanized variants of 7G6 VH start CDR-H3 at Ser-92 rather than Ser-94.

Even with this extension by two residues, CDR H3 of 7G6 antibody has only 6 amino acid residues: STSLDF. The brevity of CDR H3 opens up the antigen-binding pocket and also creates room for the exemplary W89 ch1=0 rotamer the light chain VL domain to pack against the heavy chain.

The hot spots for mutations of the human acceptor sequence 3U0T are those in which the framework residue differs from the mouse sequence AND such framework residue also has best potential to form van der Waals contacts to rotamers of light chain W89. These positions include: Heavy Chain 50 W at start of CDR2 and exemplary revertant mutations at Light chain 36 (F to L), 37 (Q to L), 45 (R to K) and 100 (Q to G). In an embodiment, the murine residue 50 W is used in the heavy chain because it is part of CDR-H2.

2 humanized heavy chain variable region variants and 8 humanized light chain variable region variants were constructed containing different permutations of substitutions, hu7G6-VH_v1 and hu7G6-VH_v2 (SEQ ID NOs: 139-140, respectively) and hu7G6-VL_v1, hu7G6-VL_v2, hu7G6-VL_v3, hu7G6-VL_v4, hu7G6-VL_v5, hu7G6-VL_v6, hu7G6-VL_v7, and hu7G6-VL_v8, (SEQ ID NOs: 141-148, respectively). (Tables 25 and 26). The exemplary humanized VL and VH designs, with backmutations and other mutations based on selected human frameworks, are shown in Tables 25 and 26, respectively. The bolded areas in Tables 25 and 26 indicate the CDRs as defined by Kabat/Chothia Composite. A "-" in the columns in Tables 25 and 26 indicates no residue at the indicated position. SEQ ID NOs:139-140 and SEQ ID NOs: 141-148 contain backmutations and other mutations as shown in Table 27. The amino acids at positions in hu7G6-VH_v1 and hu7G6-VH_v2 are listed in Table 28. The amino acids at positions in hu7G6-VL_v1, hu7G6-VL_v2, hu7G6-VL_v3, hu7G6-VL_v4, hu7G6-VL_v5, hu7G6-VL_v6, hu7G6-VL_v7, and hu7G6-VL_v8 are listed in Table 29. The percentage humanness for humanized VH chains hu7G6-VH_v1 and hu7G6-VH_v2 (SEQ ID NOs: 139-140, respectively) with respect to the most similar human germline gene IGHV1-69-2*01 (SEQ ID NO:149), and for humanized VL chains hu7G6-VL_v1, hu7G6-VL_v2, hu7G6-VL_v3, hu7G6-VL_v4, hu7G6-VL_v5, hu7G6-VL_v6, hu7G6-VL_v7, and hu7G6-VL_v8 (SEQ ID NOs:141-148, respectively) with respect to the most similar human germline geneIGKV2-30*02 (SEQ ID NO:84), is shown in Table 30.

TABLE 25

| Linear residue # | Kabat residue # | FR or CDR | Murine 7G6 VL (SEQ ID NO: 120) | Acceptor Acc. # PDB 3U0T_VL (SEQ ID NO: 138) | hu7G6-VL_v1 (SEQ ID NO: 141) | hu7G6-VL_v2 (SEQ ID NO: 142) | hu7G6-VL_v3 (SEQ ID NO: 143) | hu7G6-VL_v4 (SEQ ID NO: 144) | hu7G6-VL_v5 (SEQ ID NO: 145) | hu7G6-VL_v6 (SEQ ID NO: 146) | hu7G6-VL_v7 (SEQ ID NO: 147) | hu7G6-VL_v8 (SEQ ID NO: 148) |
|---|---|---|---|---|---|---|---|---|---|---|---|---|
| 1 | 1 | Fr1 | D | D | D | D | D | D | D | D | D | D |
| 2 | 2 | Fr1 | V | V | V | V | V | V | V | V | V | V |
| 3 | 3 | Fr1 | V | V | V | V | V | V | V | V | V | V |
| 4 | 4 | Fr1 | M | M | M | M | M | M | M | M | M | M |
| 5 | 5 | Fr1 | T | T | T | T | T | T | T | T | T | T |
| 6 | 6 | Fr1 | Q | Q | Q | Q | Q | Q | Q | Q | Q | Q |
| 7 | 7 | Fr1 | T | S | S | S | S | S | S | S | S | S |
| 8 | 8 | Fr1 | P | P | P | P | P | P | P | P | P | P |
| 9 | 9 | Fr1 | L | L | L | L | L | L | L | L | L | L |
| 10 | 10 | Fr1 | T | S | S | S | S | S | S | S | S | S |
| 11 | 11 | Fr1 | L | L | L | L | L | L | L | L | L | L |
| 12 | 12 | Fr1 | S | P | S | S | S | S | S | S | S | S |
| 13 | 13 | Fr1 | V | V | V | V | V | V | V | V | V | V |
| 14 | 14 | Fr1 | T | T | T | T | T | T | T | T | T | T |
| 15 | 15 | Fr1 | I | L | L | L | L | L | L | L | L | L |
| 16 | 16 | Fr1 | G | G | G | G | G | G | G | G | G | G |
| 17 | 17 | Fr1 | Q | Q | Q | Q | Q | Q | Q | Q | Q | Q |
| 18 | 18 | Fr1 | P | P | P | P | P | P | P | P | P | P |
| 19 | 19 | Fr1 | A | A | A | A | A | A | A | A | A | A |
| 20 | 20 | Fr1 | S | S | S | S | S | S | S | S | S | S |
| 21 | 21 | Fr1 | I | I | I | I | I | I | I | I | I | I |

TABLE 25-continued

| Linear residue # | Kabat residue # | FR or CDR | Murine 7G6 VL (SEQ ID NO: 120) | Acceptor Acc. # PDB 3U0T_VL (SEQ ID NO: 138) | hu7G6-VL_v1 (SEQ ID NO: 141) | hu7G6-VL_v2 (SEQ ID NO: 142) | hu7G6-VL_v3 (SEQ ID NO: 143) | hu7G6-VL_v4 (SEQ ID NO: 144) | hu7G6-VL_v5 (SEQ ID NO: 145) | hu7G6-VL_v6 (SEQ ID NO: 146) | hu7G6-VL_v7 (SEQ ID NO: 147) | hu7G6-VL_v8 (SEQ ID NO: 148) |
|---|---|---|---|---|---|---|---|---|---|---|---|---|
| 22 | 22 | Fr1 | S | S | S | S | S | S | S | S | S | S |
| 23 | 23 | Fr1 | C | C | C | C | C | C | C | C | C | C |
| 24 | 24 | CDR-L1 | K | K | K | K | K | K | K | K | K | K |
| 25 | 25 | CDR-L1 | S | S | S | S | S | S | S | S | S | S |
| 26 | 26 | CDR-L1 | T | S | T | T | T | T | T | T | T | T |
| 27 | 27 | CDR-L1 | Q | Q | Q | Q | Q | Q | Q | Q | Q | Q |
| 28 | 27A | CDR-L1 | S | S | S | S | S | S | S | S | S | S |
| 29 | 27B | CDR-L1 | L | L | L | L | L | L | L | L | L | L |
| 30 | 27C | CDR-L1 | L | L | L | L | L | L | L | L | L | L |
| 31 | 27D | CDR-L1 | D | Y | D | D | D | D | D | D | D | D |
| 32 | 27E | CDR-L1 | S | S | S | S | S | S | S | S | S | S |
| 33 | 27F | CDR-L1 | — | — | — | — | — | — | — | — | — | — |
| 34 | 28 | CDR-L1 | D | D | D | D | D | D | D | D | D | D |
| 35 | 29 | CDR-L1 | G | A | G | G | G | G | G | G | G | G |
| 36 | 30 | CDR-L1 | K | K | K | K | K | K | K | K | K | K |
| 37 | 31 | CDR-L1 | T | T | T | T | T | T | T | T | T | T |
| 38 | 32 | CDR-L1 | Y | Y | Y | Y | Y | Y | Y | Y | Y | Y |
| 39 | 33 | CDR-L1 | L | L | L | L | L | L | L | L | L | L |
| 40 | 34 | CDR-L1 | N | N | N | N | N | N | N | N | N | N |
| 41 | 35 | Fr2 | W | W | W | W | W | W | W | W | W | W |
| 42 | 36 | Fr2 | L | F | F | F | L | L | F | L | F | L |
| 43 | 37 | Fr2 | L | Q | Q | L | Q | L | Q | L | Q | L |
| 44 | 38 | Fr2 | Q | Q | Q | Q | Q | Q | Q | Q | Q | Q |
| 45 | 39 | Fr2 | R | R | R | R | R | R | R | R | R | R |
| 46 | 40 | Fr2 | P | P | P | P | P | P | P | P | P | P |
| 47 | 41 | Fr2 | G | G | G | G | G | G | G | G | G | G |
| 48 | 42 | Fr2 | Q | Q | Q | Q | Q | Q | Q | Q | Q | Q |
| 49 | 43 | Fr2 | S | S | S | S | S | S | S | S | S | S |
| 50 | 44 | Fr2 | P | P | P | P | P | P | P | P | P | P |
| 51 | 45 | Fr2 | K | R | R | R | R | R | K | K | R | R |
| 52 | 46 | Fr2 | R | R | R | R | R | R | R | R | R | R |
| 53 | 47 | Fr2 | L | L | L | L | L | L | L | L | L | L |
| 54 | 48 | Fr2 | I | I | I | I | I | I | I | I | I | I |
| 55 | 49 | Fr2 | Y | Y | Y | Y | Y | Y | Y | Y | Y | Y |
| 56 | 50 | CDR-L2 | L | Q | L | L | L | L | L | L | L | L |
| 57 | 51 | CDR-L2 | V | I | V | V | V | V | V | V | V | V |
| 58 | 52 | CDR-L2 | S | S | S | S | S | S | S | S | S | S |
| 59 | 53 | CDR-L2 | K | R | K | K | K | K | K | K | K | K |
| 60 | 54 | CDR-L2 | L | L | L | L | L | L | L | L | L | L |
| 61 | 55 | CDR-L2 | D | D | D | D | D | D | D | D | D | D |
| 62 | 56 | CDR-L2 | S | P | S | S | S | S | S | S | S | S |
| 63 | 57 | Fr3 | G | G | G | G | G | G | G | G | G | G |
| 64 | 58 | Fr3 | V | V | V | V | V | V | V | V | V | V |
| 65 | 59 | Fr3 | P | P | P | P | P | P | P | P | P | P |
| 66 | 60 | Fr3 | D | D | D | D | D | D | D | D | D | D |
| 67 | 61 | Fr3 | R | R | R | R | R | R | R | R | R | R |
| 68 | 62 | Fr3 | F | F | F | F | F | F | F | F | F | F |
| 69 | 63 | Fr3 | T | S | S | S | S | S | S | S | S | S |
| 70 | 64 | Fr3 | G | G | G | G | G | G | G | G | G | G |
| 71 | 65 | Fr3 | S | S | S | S | S | S | S | S | S | S |
| 72 | 66 | Fr3 | G | G | G | G | G | G | G | G | G | G |
| 73 | 67 | Fr3 | S | S | S | S | S | S | S | S | S | S |
| 74 | 68 | Fr3 | G | G | G | G | G | G | G | G | G | G |
| 75 | 69 | Fr3 | T | T | T | T | T | T | T | T | T | T |
| 76 | 70 | Fr3 | D | D | D | D | D | D | D | D | D | D |
| 77 | 71 | Fr3 | F | F | F | F | F | F | F | F | F | F |
| 78 | 72 | Fr3 | T | T | T | T | T | T | T | T | T | T |
| 79 | 73 | Fr3 | L | L | L | L | L | L | L | L | L | L |
| 80 | 74 | Fr3 | K | K | K | K | K | K | K | K | K | K |
| 81 | 75 | Fr3 | I | I | I | I | I | I | I | I | I | I |
| 82 | 76 | Fr3 | S | S | S | S | S | S | S | S | S | S |
| 83 | 77 | Fr3 | R | R | R | R | R | R | R | R | R | R |
| 84 | 78 | Fr3 | V | V | V | V | V | V | V | V | V | V |
| 85 | 79 | Fr3 | E | E | E | E | E | E | E | E | E | E |
| 86 | 80 | Fr3 | A | A | A | A | A | A | A | A | A | A |
| 87 | 81 | Fr3 | E | E | E | E | E | E | E | E | E | E |
| 88 | 82 | Fr3 | D | D | D | D | D | D | D | D | D | D |
| 89 | 83 | Fr3 | L | V | V | V | V | V | V | V | V | V |
| 90 | 84 | Fr3 | G | G | G | G | G | G | G | G | G | G |
| 91 | 85 | Fr3 | V | V | V | V | V | V | V | V | V | V |
| 92 | 86 | Fr3 | Y | Y | Y | Y | Y | Y | Y | Y | Y | Y |
| 93 | 87 | Fr3 | Y | Y | Y | Y | Y | Y | Y | Y | Y | Y |
| 94 | 88 | Fr3 | C | C | C | C | C | C | C | C | C | C |

TABLE 25-continued

| Linear residue # | Kabat residue # | FR or CDR | Murine 7G6 VL (SEQ ID NO: 120) | Acceptor Acc. # PDB 3U0T_VL (SEQ ID NO: 138) | hu7G6-VL_v1 (SEQ ID NO: 141) | hu7G6-VL_v2 (SEQ ID NO: 142) | hu7G6-VL_v3 (SEQ ID NO: 143) | hu7G6-VL_v4 (SEQ ID NO: 144) | hu7G6-VL_v5 (SEQ ID NO: 145) | hu7G6-VL_v6 (SEQ ID NO: 146) | hu7G6-VL_v7 (SEQ ID NO: 147) | hu7G6-VL_v8 (SEQ ID NO: 148) |
|---|---|---|---|---|---|---|---|---|---|---|---|---|
| 95 | 89 | CDR-L3 | W | L | W | W | W | W | W | W | W | W |
| 96 | 90 | CDR-L3 | Q | Q | Q | Q | Q | Q | Q | Q | Q | Q |
| 97 | 91 | CDR-L3 | G | G | G | G | G | G | G | G | G | G |
| 98 | 92 | CDR-L3 | T | T | T | T | T | T | T | T | T | T |
| 99 | 93 | CDR-L3 | H | H | H | H | H | H | H | H | H | H |
| 100 | 94 | CDR-L3 | F | Y | F | F | F | F | F | F | F | F |
| 101 | 95 | CDR-L3 | P | P | P | P | P | P | P | P | P | P |
| 102 | 95A | CDR-L3 | — | — | — | — | — | — | — | — | — | — |
| 103 | 95B | CDR-L3 | — | — | — | — | — | — | — | — | — | — |
| 104 | 95C | CDR-L3 | — | — | — | — | — | — | — | — | — | — |
| 105 | 95D | CDR-L3 | — | — | — | — | — | — | — | — | — | — |
| 106 | 95E | CDR-L3 | — | — | — | — | — | — | — | — | — | — |
| 107 | 95F | CDR-L3 | — | — | — | — | — | — | — | — | — | — |
| 108 | 96 | CDR-L3 | Y | V | Y | Y | Y | Y | Y | Y | Y | Y |
| 109 | 97 | CDR-L3 | T | L | T | T | T | T | T | T | T | T |
| 110 | 98 | Fr4 | F | F | F | F | F | F | F | F | F | F |
| 111 | 99 | Fr4 | G | G | G | G | G | G | G | G | G | G |
| 112 | 100 | Fr4 | G | Q | Q | Q | Q | Q | Q | Q | G | G |
| 113 | 101 | Fr4 | G | G | G | G | G | G | G | G | G | G |
| 114 | 102 | Fr4 | T | T | T | T | T | T | T | T | T | T |
| 115 | 103 | Fr4 | K | R | K | K | K | K | K | K | K | K |
| 116 | 104 | Fr4 | L | L | L | L | L | L | L | L | L | L |
| 117 | 105 | Fr4 | E | E | E | E | E | E | E | E | E | E |
| 118 | 106 | Fr4 | I | I | I | I | I | I | I | I | I | I |
| 119 | 106A | Fr4 | K | K | K | K | K | K | K | K | K | K |
| 120 | 107 | Fr4 | R | R | R | R | R | R | R | R | R | R |

TABLE 26

| Linear residue # | Kabat residue # | FR or CDR | Murine 7G6 VH (SEQ ID NO: 119) | Acceptor Acc. # PDB 3U0T_VH (SEQ ID NO: 137) | hu7G6-VH_v1 (SEQ ID NO: 139) | hu7G6-VH_v2 (SEQ ID NO: 140) |
|---|---|---|---|---|---|---|
| 1 | 1 | Fr1 | E | Q | Q | Q |
| 2 | 2 | Fr1 | V | V | V | V |
| 3 | 3 | Fr1 | Q | Q | Q | Q |
| 4 | 4 | Fr1 | L | L | L | L |
| 5 | 5 | Fr1 | Q | V | V | V |
| 6 | 6 | Fr1 | Q | Q | Q | Q |
| 7 | 7 | Fr1 | S | S | S | S |
| 8 | 8 | Fr1 | G | G | G | G |
| 9 | 9 | Fr1 | A | A | A | A |
| 10 | 10 | Fr1 | E | E | E | E |
| 11 | 11 | Fr1 | L | V | V | V |
| 12 | 12 | Fr1 | V | K | V | V |
| 13 | 13 | Fr1 | R | K | K | K |
| 14 | 14 | Fr1 | P | P | P | P |
| 15 | 15 | Fr1 | G | G | G | G |
| 16 | 16 | Fr1 | A | A | A | A |
| 17 | 17 | Fr1 | L | S | S | S |
| 18 | 18 | Fr1 | V | V | V | V |
| 19 | 19 | Fr1 | K | K | K | K |
| 20 | 20 | Fr1 | L | V | L | L |
| 21 | 21 | Fr1 | S | S | S | S |
| 22 | 22 | Fr1 | C | C | C | C |
| 23 | 23 | Fr1 | K | K | K | K |
| 24 | 24 | Fr1 | A | A | A | A |
| 25 | 25 | Fr1 | S | S | S | S |
| 26 | 26 | CDR-H1 | G | G | G | G |
| 27 | 27 | CDR-H1 | F | Y | F | F |
| 28 | 28 | CDR-H1 | N | Y | N | N |
| 29 | 29 | CDR-H1 | I | T | I | I |
| 30 | 30 | CDR-H1 | K | E | K | K |
| 31 | 31 | CDR-H1 | D | A | D | D |
| 32 | 32 | CDR-H1 | Y | Y | Y | Y |
| 33 | 33 | CDR-H1 | Y | Y | Y | Y |
| 34 | 34 | CDR-H1 | I | I | I | I |
| 35 | 35 | CDR-H1 | H | H | H | H |
| 36 | 35A | CDR-H1 | — | — | — | — |
| 37 | 35B | CDR-H1 | — | — | — | — |

TABLE 26-continued

| Linear residue # | Kabat residue # | FR or CDR | Murine 7G6 VH (SEQ ID NO: 119) | Acceptor Acc. # PDB 3U0T_VH (SEQ ID NO: 137) | hu7G6-VH_v1 (SEQ ID NO: 139) | hu7G6-VH_v2 (SEQ ID NO: 140) |
|---|---|---|---|---|---|---|
| 38 | 36 | Fr2 | W | W | W | W |
| 39 | 37 | Fr2 | V | V | V | V |
| 40 | 38 | Fr2 | K | R | R | K |
| 41 | 39 | Fr2 | Q | Q | Q | Q |
| 42 | 40 | Fr2 | R | A | A | A |
| 43 | 41 | Fr2 | P | P | P | P |
| 44 | 42 | Fr2 | E | G | G | G |
| 45 | 43 | Fr2 | Q | Q | Q | Q |
| 46 | 44 | Fr2 | G | G | G | G |
| 47 | 45 | Fr2 | L | L | L | L |
| 48 | 46 | Fr2 | E | E | E | E |
| 49 | 47 | Fr2 | W | W | W | W |
| 50 | 48 | Fr2 | I | M | M | M |
| 51 | 49 | Fr2 | G | G | G | G |
| 52 | 50 | CDR-H2 | W | R | W | W |
| 53 | 51 | CDR-H2 | I | I | I | I |
| 54 | 52 | CDR-H2 | D | D | D | D |
| 55 | 52A | CDR-H2 | P | P | P | P |
| 56 | 52B | CDR-H2 | | | | |
| 57 | 52C | CDR-H2 | | | | |
| 58 | 53 | CDR-H2 | E | A | E | E |
| 59 | 54 | CDR-H2 | N | T | N | N |
| 60 | 55 | CDR-H2 | G | G | G | G |
| 61 | 56 | CDR-H2 | E | N | E | E |
| 62 | 57 | CDR-H2 | T | T | T | T |
| 63 | 58 | CDR-H2 | V | K | V | V |
| 64 | 59 | CDR-H2 | Y | Y | Y | Y |
| 65 | 60 | CDR-H2 | D | A | D | D |
| 66 | 61 | CDR-H2 | P | P | P | P |
| 67 | 62 | CDR-H2 | K | R | K | K |
| 68 | 63 | CDR-H2 | F | L | F | F |
| 69 | 64 | CDR-H2 | Q | Q | Q | Q |
| 70 | 65 | CDR-H2 | G | D | G | G |
| 71 | 66 | Fr3 | K | R | R | R |
| 72 | 67 | Fr3 | A | V | V | V |
| 73 | 68 | Fr3 | S | T | T | T |
| 74 | 69 | Fr3 | I | M | I | I |
| 75 | 70 | Fr3 | T | T | T | T |
| 76 | 71 | Fr3 | S | R | R | R |
| 77 | 72 | Fr3 | D | D | D | D |
| 78 | 73 | Fr3 | T | T | T | T |
| 79 | 74 | Fr3 | S | S | S | S |
| 80 | 75 | Fr3 | S | T | T | T |
| 81 | 76 | Fr3 | N | S | N | N |
| 82 | 77 | Fr3 | T | T | T | T |
| 83 | 78 | Fr3 | A | V | A | A |
| 84 | 79 | Fr3 | Y | Y | Y | Y |
| 85 | 80 | Fr3 | L | M | L | L |
| 86 | 81 | Fr3 | Q | E | Q | Q |
| 87 | 82 | Fr3 | L | L | L | L |
| 88 | 82A | Fr3 | R | S | S | S |
| 89 | 82B | Fr3 | S | S | S | S |
| 90 | 82C | Fr3 | L | L | L | L |
| 91 | 83 | Fr3 | T | R | R | R |
| 92 | 84 | Fr3 | S | S | S | S |
| 93 | 85 | Fr3 | E | E | E | E |
| 94 | 86 | Fr3 | D | D | D | D |
| 95 | 87 | Fr3 | T | T | T | T |
| 96 | 88 | Fr3 | A | A | A | A |
| 97 | 89 | Fr3 | V | V | V | V |
| 98 | 90 | Fr3 | Y | Y | Y | Y |
| 99 | 91 | Fr3 | Y | Y | Y | Y |
| 100 | 92 | Fr3 | S | C | S | S |
| 101 | 93 | Fr3 | T | A | T | T |
| 102 | 94 | Fr3 | S | S | S | S |
| 103 | 95 | CDR-H3 | L | L | L | L |
| 104 | 96 | CDR-H3 | — | Y | — | |
| 105 | 97 | CDR-H3 | — | S | — | |
| 106 | 98 | CDR-H3 | — | L | — | |
| 107 | 99 | CDR-H3 | — | P | — | |
| 108 | 100 | CDR-H3 | — | — | — | |
| 109 | 100A | CDR-H3 | — | — | — | — |
| 110 | 100B | CDR-H3 | — | — | — | — |
| 111 | 100C | CDR-H3 | — | — | — | — |
| 112 | 100D | CDR-H3 | — | — | — | — |
| 113 | 100E | CDR-H3 | — | — | — | — |

TABLE 26-continued

| Linear residue # | Kabat residue # | FR or CDR | Murine 7G6 VH (SEQ ID NO: 119) | Acceptor Acc. # PDB 3U0T_VH (SEQ ID NO: 137) | hu7G6-VH_v1 (SEQ ID NO: 139) | hu7G6-VH_v2 (SEQ ID NO: 140) |
|---|---|---|---|---|---|---|
| 114 | 100F | CDR-H3 | — | — | — | — |
| 115 | 100G | CDR-H3 | — | — | — | — |
| 116 | 100H | CDR-H3 | — | — | — | — |
| s 117 | 100I | CDR-H3 | — | — | — | — |
| 118 | 100J | CDR-H3 | — | — | — | — |
| 119 | 100K | CDR-H3 | — | — | — | — |
| 120 | 101 | CDR-H3 | D | V | D | D |
| 121 | 102 | CDR-H3 | F | Y | F | F |
| 122 | 103 | Fr4 | W | W | W | W |
| 123 | 104 | Fr4 | G | G | G | G |
| 124 | 105 | Fr4 | Q | Q | Q | Q |
| 125 | 106 | Fr4 | G | G | G | G |
| 126 | 107 | Fr4 | T | T | T | T |
| 127 | 108 | Fr4 | S | S | S | S |
| 128 | 109 | Fr4 | V | V | V | V |
| 129 | 110 | Fr4 | T | T | T | T |
| 130 | 111 | Fr4 | V | V | V | V |
| 131 | 112 | Fr4 | S | S | S | S |
| 132 | 113 | Fr4 | S | S | S | S |

TABLE 27

$V_H$, $V_L$ Backmutations and Other Mutations for Humanized 7G6

| $V_H$ or $V_L$ Variant | $V_H$ or $V_L$ Exon Acceptor Sequence | Changes from Acceptor Framework Residues (based on Kabat/Chothia Composite CDRs) |
|---|---|---|
| hu7G6-VH_v1 (SEQ ID NO: 139) | Acceptor Acc. # PDB 3U0T_VH (SEQ ID NO: 137) | H12, H20, H69, H76, H78, H80, H81, H92, H93 |
| hu7G6-VH_v2 (SEQ ID NO: 140) | Acceptor Acc. # PDB 3U0T_VH (SEQ ID NO: 137) | H12, H20, H38, H69, H76, H78, H80, H81, H92, H93 |
| hu7G6-VL_v1 (SEQ ID NO: 141) | Acceptor Acc. # PDB 3U0T_VL (SEQ ID NO: 138) | L12, L103 |
| hu7G6-VL_v2 (SEQ ID NO: 142) | Acceptor Acc. # PDB 3U0T_VL (SEQ ID NO: 138) | L12, L37, L103 |
| hu7G6-VL_v3 (SEQ ID NO: 143) | Acceptor Acc. # PDB 3U0T_VL (SEQ ID NO: 138) | L12, L36, L103 |
| hu7G6-VL_v4 (SEQ ID NO: 144) | Acceptor Acc. # PDB 3U0T_VL (SEQ ID NO: 138) | L12, L36, L37, L103 |
| hu7G6-VL_v5 (SEQ ID NO: 145) | Acceptor Acc. # PDB 3U0T_VL (SEQ ID NO: 138) | L12, L45, L103 |
| hu7G6-VL_v6 (SEQ ID NO: 146) | Acceptor Acc. # PDB 3U0T_VL (SEQ ID NO: 138) | L12, L36, L37, L45, L103 |
| hu7G6-VL_v7 (SEQ ID NO: 147) | Acceptor Acc. # PDB 3U0T_VL (SEQ ID NO: 138) | L12, L100, L103 |
| hu7G6-VL_v8 (SEQ ID NO: 148) | Acceptor Acc. # PDB 3U0T_VL (SEQ ID NO: 138) | L12, L36, L37, L100, L103 |

TABLE 28

Kabat Numbering of Framework Residues (based on Kabat/Chothia Composite CDRs) for Backmutations and Other Mutations in Heavy Chains of Humanized 7G6 Antibodies

| Kabat Residue # | Acceptor Acc. # PDB 3U0T_VH (SEQ ID NO: 137) | Murine 7G6 VH (SEQ ID NO: 119) | hu7G6-VH_v1 (SEQ ID NO: 139) | hu7G6-VH_v2 (SEQ ID NO: 140) |
|---|---|---|---|---|
| H12 | K | V | V | V |
| H20 | V | L | L | L |
| H38 | R | K | R | K |
| H69 | M | I | I | I |
| H76 | S | N | N | N |
| H78 | V | A | A | A |
| H80 | M | L | L | L |
| H81 | E | Q | Q | Q |

TABLE 28-continued

Kabat Numbering of Framework Residues (based on Kabat/Chothia Composite CDRs) for Backmutations and Other Mutations in Heavy Chains of Humanized 7G6 Antibodies

| Kabat Residue # | Acceptor Acc. # PDB 3U0T_VH (SEQ ID NO: 137) | Murine 7G6 VH (SEQ ID NO: 119) | hu7G6-VH_v1 (SEQ ID NO: 139) | hu7G6-VH_v2 (SEQ ID NO: 140) |
|---|---|---|---|---|
| H92 | C | S | S | S |
| H93 | A | T | T | T |

TABLE 29

Kabat Numbering of Framework Residues (based on Kabat/Chothia Composite CDRs) for Backmutations and Other Mutations in Light Chains of Humanized 7G6 Antibodies

| Kabat Residue # | Acceptor Acc. # PDB 3U0T VL (SEQ ID NO: 137) | Murine 7G6 VL (SEQ ID NO: 119) | hu7G6-VL_v1 (SEQ ID NO: 141) | hu7G6-VL_v2 (SEQ ID NO: 142) | hu7G6-VL_v3 (SEQ ID NO: 143) | hu7G6-VL_v4 (SEQ ID NO: 144) | hu7G6-VL_v5 (SEQ ID NO: 145) | hu7G6-VL_v6 (SEQ ID NO: 146) | hu7G6-VL_v7 (SEQ ID NO: 147) | hu7G6-VL_v8 (SEQ ID NO: 148) |
|---|---|---|---|---|---|---|---|---|---|---|
| L12 | P | S | S | S | S | S | S | S | S | S |
| L36 | F | L | F | F | L | L | F | L | F | L |
| L37 | Q | L | Q | L | Q | L | Q | L | Q | L |
| L45 | R | K | R | R | R | R | K | K | R | R |
| L100 | Q | G | Q | Q | Q | Q | Q | Q | G | G |
| L103 | R | K | K | K | K | K | K | K | K | K |

TABLE 30

Percentage Humanness of Heavy and Light Chains of Humanized 7G6 Antibodies

| $V_H$ or $V_L$ Variant | % Humanness |
|---|---|
| hu7G6-VH_v1 (SEQ ID NO: 139) | 77.9% |
| hu7G6-VH_v2 (SEQ ID NO: 140) | 76.8% |
| hu7G6-VL_v1 (SEQ ID NO: 141) | 89.0% |
| hu7G6-VL_v2 (SEQ ID NO: 142) | 88.0% |
| hu7G6-VL_v3 (SEQ ID NO: 143) | 88.0% |
| hu7G6-VL_v4 (SEQ ID NO: 144) | 87.0% |
| hu7G6-VL_v5 (SEQ ID NO: 145) | 88.0% |
| hu7G6-VL_v6 (SEQ ID NO: 146) | 86.0% |
| hu7G6-VL_v7 (SEQ ID NO: 147) | 89.0% |
| hu7G6-VL_v8 (SEQ ID NO: 148) | 87.0% |

Positions at which Chothia class canonical, vernier, or interface/packing residues differ between mouse and human acceptor sequences are candidates for substitution. Examples of Chothia class canonical residues include Kabat residue L2 in Tables 25 and 26. Examples of vernier residues include Kabat residues H66, H67, H69, and L49 in Tables 25 and 26. Examples of interface/packing (VH+VL) residues include Kabat residues H35, H37, H39, H45, H47, H93, H95, H97, H103, L34, L36, L39, L44, L45, L46, L87, L89, L91, L96, and L98, in Tables 25 and 26.

The rationales for selection of the positions indicated in Table 25 in the light chain variable region as candidates for substitution are as follows.

P12S is a frequency based mutation as P is rare in human frameworks at this position.

F36L is a backmutation of an interface residue.

Q37L: Based upon structure model Leu potentially could interfere with W89 (VL) and VH CDR-H3 95Leu, therefore a backmutation is tested.

R45K is a backmutation of an interface residue.

Q100G: Q potentially can interfere with W89 (VL), therefore, Q100G backmutation is tested.

R103K is a frequency-based mutation as R is rare in human frameworks at this position.

```
Light chain variable regions:
murine mAb7G6 VL
                                                  (SEQ ID NO: 120)
DVVMTQTPLTLSVTIGQPASISCKSTQSLLDSDGKTYLNWLLQRPGQSPKRLIYLVSKLD
SGVPDRFTGSGSGTDFTLKISRVEAEDLGVYYCWQGTHFPYTFGGGTKLEIKR Human VL Acceptor PDB 3U0T_VL
                                                  (SEQ ID NO: 138)
DVVMTQSPLSLPVTLGQPASISCKSSQSLLYSDAKTYLNWFQQRPGQSPRRLIYQISRLDP
GVPDRFSGSGSGTDFTLKISRVEAEDVGVYYCLQGTHYPVLFGQGTRLEIKR human germline sequence IGKV2-30*02
                                                  (SEQ ID NO: 84)
DVVMTQSPLSLPVTLGQPASISCRSSQSLVHSDGNTYLNWFQQRPGQSPRRLIYKVSNRD
SGVPDRFSGSGSGTDFTLKISRVEAEDVGVYYCMQGTHWPLTFGGGTKVEIK hu7G6-VL_v1
                                                  (SEQ ID NO: 141)
DVVMTQSPLSLSVTLGQPASISCKSTQSLLDSDGKTYLNWFQQRPGQSPRRLIYLVSKLD
SGVPDRFSGSGSGTDFTLKISRVEAEDVGVYYCWQGTHFPYTFGQGTKLEIKR
``` hu7G6-VL_v2

(SEQ ID NO: 142)
DVVMTQSPLSLSVTLGQPASISCKSTQSLLDSDGKTYLNWFLQRPGQSPRRLIYLVSKLD
SGVPDRFSGSGSGTDFTLKISRVEAEDVGVYYCWQGTHFPYTFGQGTKLEIKR hu7G6-VL_v3

(SEQ ID NO: 143)
DVVMTQSPLSLSVTLGQPASISCKSTQSLLDSDGKTYLNWLQQRPGQSPRRLIYLVSKLD
SGVPDRFSGSGSGTDFTLKISRVEAEDVGVYYCWQGTHFPYTFGQGTKLEIKR hu7G6-VL_v4

(SEQ ID NO: 144)
DVVMTQSPLSLSVTLGQPASISCKSTQSLLDSDGKTYLNWLLQRPGQSPRRLIYLVSKLD
SGVPDRFSGSGSGTDFTLKISRVEAEDVGVYYCWQGTHFPYTFGQGTKLEIKR hu7G6-VL_v5

(SEQ ID NO: 145)
DVVMTQSPLSLSVTLGQPASISCKSTQSLLDSDGKTYLNWFQQRPGQSPKRLIYLVSKLD
SGVPDRFSGSGSGTDFTLKISRVEAEDVGVYYCWQGTHFPYTFGQGTKLEIKR hu7G6-VL_v6

(SEQ ID NO: 146)
DVVMTQSPLSLSVTLGQPASISCKSTQSLLDSDGKTYLNWLLQRPGQSPKRLIYLVSKLD
SGVPDRFSGSGSGTDFTLKISRVEAEDVGVYYCWQGTHFPYTFGQGTKLEIKR hu7G6-VL_v7:

(SEQ ID NO: 147)
DVVMTQSPLSLSVTLGQPASISCKSTQSLLDSDGKTYLNWFQQRPGQSPRRLIYLVSKLD
SGVPDRFSGSGSGTDFTLKISRVEAEDVGVYYCWQGTHFPYTFGGGTKLEIKR hu7G6-VL_v8

(SEQ ID NO: 148)
DVVMTQSPLSLSVTLGQPASISCKSTQSLLDSDGKTYLNWLLQRPGQSPRRLIYLVSKLD
SGVPDRFSGSGSGTDFTLKISRVEAEDVGVYYCWQGTHFPYTFGGGTKLEIKR

The rationales for selection of the positions indicated in Table 26 in the heavy chain variable region as candidates for substitution are as follows.

- K12V is a frequency-based backmutation as V is found more often than K at this position.
- V20L is a frequency-based backmutation as L is found more often than V at this position.
- R38K: structure model predicts that Arg could interfere with Tyr91 and could potentially be stabilizing residue, but will also test Lys as backmutation.
- M69I is a frequency-based backmutation as I is found more often than M at this position in human frameworks and is in proximity to CDR-H2.
- S76N is a frequency-based backmutation as N is found more often than S at this position in human frameworks.
- V78A is a frequency-based backmutation as A is found more often than V at this position in human frameworks.
- M80L is a frequency-based backmutation as L is found more often than M at this position in human frameworks.
- E81Q is a frequency-based backmutation as Q is found more often than E at this position in human frameworks.
- C92S: In the murine sequence Ser is present. Normally Cys at this position forms a disulfide bond but that bond is broken in murine potentially implying flexibility. In order to conserve CDR loop flexibility, conserve Ser at this position by making C92S backmutation.
- A93T is a backmutation of an interface residue Heavy chain variable regions:
murine mAb7G6 VH (SEQ ID NO: 119)
EVQLQQSGAELVRPGALVKLSCKASGFNIKDYYIHWVKQRPEQGLEWIG
WIDPENGETVYDPKFQGKASITSDTSSNTAYLQLRSLTSEDTAVYYSTS
LDFWGQGTSVTVSS Human VH Acceptor DB 3UOT_VH (SEQ ID NO: 137)
QVQLVQSGAEVKKPGASVKVSCKASGYYTEAYYIHWVRQAPGQGLEWMG
RIDPATGNTKYAPRLQDRVTMTRDTSTSTVYMELSSLRSEDTAVYYCAS
LYSLPVYWGQGTTVTVSS human germline sequence IGHV1-69-2*01

(SEQ ID NO: 149)
EVQLQQSGAEVRPGALVKLSCKASGFNIKDYYIHWVKQRPEQGLEWIG
WIDPENGETVYDPKFQGKASITSDTSSNTAYLQLRSLTSEDTAVYYSTS
LDFWGQGTSVTVSS hu7G6-VH_v1

(SEQ ID NO: 139)
QVQLVQSGAEVVKPGASVKLSCKASGFNIKDYYIHWVRQAPGQGLEWMG
WIDPENGETVYDPKFQGRVTITRDTSTNTAYLQLSSLRSEDTAVYYSTS
LDFWGQGTTVTVSS hu7G6-VH_v2

(SEQ ID NO: 140)
QVQLVQSGAEVVKPGASVKLSCKASGFNIKDYYIHWVKQAPGQGLEWMG
WIDPENGETVYDPKFQGRVTITRDTSTNTAYLQLSSLRSEDTAVYYSTS
LDFWGQGTTVTVSS

Example 10 Epitope Mapping of 5G8, 6A10, 8A4, 7G6 and 3D6

Overlapping biotinylated peptides spanning the length of the 4R0N isoform of tau (383 amino acids) were bound to wells of a streptavidin-coated ELISA plate. The plate was washed and blocked, and murine forms of antibodies 5G8, 6A10, 8A4, 7G6 and 3D6 were applied. After washing, a horseradish peroxidase-conjugated anti-mouse antibody was applied to the plate, followed by treatment with OPD (o-phenylenediamine dihydrochloride) to allow color development. The plate was read at 450 nm absorbance, with background from wells omitting primary antibody used as a blank subtraction. For antibodies 5G8, 6A10, 8A4, 7G6 and 3D6, positive binding was detected with peptides spanning amino acids 199-213 and 262-276 of SEQ ID NO:3. These peptides correspond to amino acids 257-271 and 315-329 in the full-length 4R2N human tau protein.

Listing of Sequences

```
P10636-8 (SEQ ID NO: 1)
MAEPRQEFEVMEDHAGTYGLGDRKDQGGYTMHQDQEGDTDAGLKESPLQTPTEDGSE
EPGSETSDAKSTPTAEDVTAPLVDEGAPGKQAAAQPHTEIPEGTTAEEAGIGDTPSLEDE
AAGHVTQARMVSKSKDGTGSDDKKAKGADGKTKIATPRGAAPPGQKGQANATRIPAK
TPPAPKTPPSSGEPPKSGDRSGYSSPGSPGTPGSRSRTPSLPTPPTREPKKVAVVRTPPKSP
SSAKSRLQTAPVPMPDLKNVKSKIGSTENLKHQPGGGKVQIINKKLDLSNVQSKCGSKD
NIKHVPGGGSVQIVYKPVDLSKVTSKCGSLGNIHHKPGGGQVEVKSEKLDFKDRVQSKI
GSLDNITHVPGGGNKKIETHKLTFRENAKAKTDHGAEIVYKSPVVSGDTSPRHLSNVSST
GSIDMVDSPQLATLADEVSASLAKQGL

P10636-7 (SEQ ID NO: 2)
MAEPRQEFEVMEDHAGTYGLGDRKDQGGYTMHQDQEGDTDAGLKESPLQTPTEDGSE
EPGSETSDAKSTPTAEAEEEAGIGDTPSLEDEAAGHVTQARMVSKSKDGTGSDDKKAKG
ADGKTKIATPRGAAPPGQKGQANATRIPAKTPPAPKTPPSSGEPPKSGDRSGYSSPGSPG
TPGSRSRTPSLPTPPTREPKKVAVVRTPPKSPSSAKSRLQTAPVPMPDLKNVKSKIGSTEN
LKHQPGGGKVQIINKKLDLSNVQSKCGSKDNIKHVPGGGSVQIVYKPVDLSKVTSKCGS
LGNIHHKPGGGQVEVKSEKLDFKDRVQSKIGSLDNITHVPGGGNKKIETHKLTFRENAK
AKTDHGAEIVYKSPVVSGDTSPRHLSNVSSTGSIDMVDSPQLATLADEVSASLAKQGL

P10636-6 (4R0N human tau) (SEQ ID NO: 3)
MAEPRQEFEVMEDHAGTYGLGDRKDQGGYTMHQDQEGDTDAGLKAEEEAGIGDTPSLE
DEAAGHVTQARMVSKSKDGTGSDDKKAKGADGKTKIATPRGAAPPGQKGQANATRIP
AKTPPAPKTPPSSGEPPKSGDRSGYSSPGSPGTPGSRSRTPSLPTPPTREPKKVAVVRTPPK
SPSSAKSRLQTAPVPMPDLKNVKSKIGSTENLKHQPGGGKVQIINKKLDLSNVQSKCGS
KDNIKHVPGGGSVQIVYKPVDLSKVTSKCGSLGNIHHKPGGGQVEVKSEKLDFKDRVQ
SKIGSLDNITHVPGGGNKKIETHKLTFRENAKAKTDHGAEIVYKSPVVSGDTSPRHLSNV
SSTGSIDMVDSPQLATLADEVSASLAKQGL P10636-5 (SEQ ID NO: 4)
MAEPRQEFEVMEDHAGTYGLGDRKDQGGYTMHQDQEGDTDAGLKESPLQTPTEDGSE
EPGSETSDAKSTPTAEDVTAPLVDEGAPGKQAAAQPHTEIPEGTTAEEAGIGDTPSLEDE
AAGHVTQARMVSKSKDGTGSDDKKAKGADGKTKIATPRGAAPPGQKGQANATRIPAK
TPPAPKTPPSSGEPPKSGDRSGYSSPGSPGTPGSRSRTPSLPTPPTREPKKVAVVRTPPKSP
SSAKSRLQTAPVPMPDLKNVKSKIGSTENLKHQPGGGKVQIVYKPVDLSKVTSKCGSLG
NIFIFIKPGGGQVEVKSEKLDFKDRVQSKIGSLDNITHVPGGGNKKIETHKLTFRENAKAK
TDHGAEIVYKSPVVSGDTSPRHLSNVSSTGSIDMVDSPQLATLADEVSASLAKQGL P10636-4 (SEQ ID NO: 5)
MAEPRQEFEVMEDHAGTYGLGDRKDQGGYTMHQDQEGDTDAGLKESPLQTPTEDGSE
EPGSETSDAKSTPTAEAEEAGIGDTPSLEDEAAGHVTQARMVSKSKDGTGSDDKKAKG
ADGKTKIATPRGAAPPGQKGQANATRIPAKTPPAPKTPPSSGEPPKSGDRSGYSSPGSPG
TPGSRSRTPSLPTPPTREPKKVAVVRTPPKSPSSAKSRLQTAPVPMPDLKNVKSKIGSTEN
LKHQPGGGKVQIVYKPVDLSKVTSKCGSLGNIHHKPGGGQVEVKSEKLDFKDRVQSKI
GSLDNITHVPGGGNKKIETHKLTFRENAKAKTDHGAEIVYKSPVVSGDTSPRHLSNVSST
GSIDMVDSPQLATLADEVSASLAKQGL P10636-2 (SEQ ID NO: 6)
MAEPRQEFEVMEDHAGTYGLGDRKDQGGYTMHQDQEGDTDAGLKAEEEAGIGDTPSLE
DEAAGHVTQARMVSKSKDGTGSDDKKAKGADGKTKIATPRGAAPPGQKGQANATRIP
AKTPPAPKTPPSSGEPPKSGDRSGYSSPGSPGTPGSRSRTPSLPTPPTREPKKVAVVRTPPK
SPSSAKSRLQTAPVPMPDLKNVKSKIGSTENLKHQPGGGKVQIVYKPVDLSKVTSKCGS
LGNIFIFIKPGGGQVEVKSEKLDFKDRVQSKIGSLDNITHVPGGGNKKIETHKLTFRENAK
AKTDHGAEIVYKSPVVSGDTSPRHLSNVSSTGSIDMVDSPQLATLADEVSASLAKQGL SEQ ID NO: 7; Murine 5G8 VH amino acid sequence without signal peptide
EVQLQQSGAELVRSGASVRLSCTASGFNIKDYYMHWVRQRPEQGLEWIGWIDPENGDT
VYAPKFQGKATMTSDTSSNTAYLHLSSLTSEDTAVYYCSPLDFWGQGTTLTVSS SEQ ID NO: 8; Murine 5G8 VL amino acid sequence without signal peptide
DVVMTQTPLTLSVTIGQPASISCKSSQSLLDSDGKTYLNWLLQRPGQSPKRLIYLVSKLD
SGVPDRFTGSGSGTDFTLKIRRVEAEDLGVYYCWQGTLFPYTFGGGTKLEIKR SEQ ID NO: 9; Nucleotide sequence encoding murine 5G8 VH amino acid sequence with
signal peptide
ATGAAATGCAGCTGGGTCATCTTCTTCCTGATGGCAGTGGTTATAGGAATCAATTCA
GAGGTTCAGCTGCAGCAGTCTGGGGCAGAGCTTGTGAGGTCAGGGGCCTCAGTCAG
GTTGTCCTGCACAGCTTCTGGCTTCAACATTAAGGACTACTATATGCACTGGGTGAG
GCAGAGGCCTGAACAGGGCCTGGAGTGGATTGGATGGATTGATCCTGAGAATGGTG
ATACTGTATATGCCCCGAAGTTCCAGGGCAAGGCCACTATGACTTCAGACACATCCT
CCAACACAGCCTACCTGCACCTCAGCAGCCTGACATCTGAAGACACTGCCGTCTATT
ACTGTAGCCCCCTTGACTTCTGGGGCCAAGGCACCACTCTCACAGTCTCCTCA
```

SEQ ID NO: 10: Nucleotide sequence encoding murine 5G8 VL amino acid sequence with signal peptide:
ATGATGAGTCCTGCCCAGTTCCTGTTTCTGTTAGTACTCTGGATTCGGGAAACCAAC
GGTGATGTTGTGATGACCCAGACTCCACTCACTTTGTCGGTTACCATTGGACAACCA
GCCTCCATCTCTTGCAAGTCAAGTCAGAGCCTCTTAGATAGTGATGGAAAGACATAT
TTGAATTGGTTGTTACAGAGGCCAGGCCAGTCTCCAAAGCGCCTAATCTATCTGGTG
TCTAAACTGGACTCTGGAGTCCCTGACAGGTTCACTGGCAGTGGATCAGGGACAGAT
TTCACACTGAAAATCCGCAGAGTGGAGGCTGAGGATTTGGGAGTTTATTATTGCTGG
CAAGGTACACTTTTTCCGTACACGTTCGGAGGGGGGACCAAGCTGGAAATAAAACG
G SEQ ID NO: 11: Murine 5G8 Kabat/Chothia Composite HCDR-1
GFNIKDYYMH SEQ ID NO: 12: Murine 5G8 Kabat HCDR-2
WIDPENGDTVYAPKFQG SEQ ID NO: 13: Murine 5G8 Kabat HCDR-3
LDF SEQ ID NO: 14: Murine 5G8 Kabat LCDR-1
KSSQSLLDSDGKTYLN SEQ ID NO: 15: Murine 5G8 Kabat LCDR-2
LVSKLDS SEQ ID NO: 16: Murine 5G8 Kabat LCDR-3
WQGTLFPYT SEQ ID NO: 17 Murine 5G8 Kabat HCDR-1
DYYMH SEQ ID NO: 18 Murine 5G8 Chothia HCDR-1
GFNIKDY SEQ ID NO: 19 Murine 5G8 Contact HCDR-1
KDYYMH SEQ ID NO: 20 Murine 5G8 Chothia HCDR-2
DPENGD SEQ ID NO: 21 Murine 5G8 AbM HCDR-2
WIDPENGDTV EQ ID NO: 22 Murine 5G8 Contact HCDR-2
WIGWIDPENGDTV SEQ ID NO: 23 Murine 5G8 Contact HCDR-3
SPLD SEQ ID NO: 24 Murine 5G8 Contact LCDR-1
KTYLNWL SEQ ID NO: 25 Murine 5G8 Contact LCDR-2
RLIYLVSKLD SEQ ID NO: 26 Murine 5G8 Contact LCDR-3
WQGTLFPY SEQ ID NO: 27 >3F4-VH
KVKLQQSGAELVRSGASVKLSCTASGFNIKDYYIQWVKQRPEQGLEWIGWIDPENGNSE
YAPRFQGKATMTADTLSNTAYLQLSSLTSEDTAVYYCNADLHDYWGQGTTLTVSS SEQ ID NO: 28 >aDabi-Fab2b-VH
QVQLVQSGAEVKKPGASVKVSCKASGYTFTDYYMHWVRQAPGQGLEWMGETNPRNG
GTTYNEKFKGKATMTRDTSTSTAYMELSSLRSEDTAVYYCTIGTSGYDYFDYWGQGTL
VTVSS SEQ ID NO: 29 >IGHV1-46
QVQLVQSGAEVKKPGASVKVSCKASGYTFTSYYMHWVRQAPGQGLEWMGIINPSGGS
TSYAQKFQGRVTMTRDTSTSTVYMELSSLRSEDTAVYYCAR SEQ ID NO: 30 >3F4-VL
DVVMTQTPLSLSVTIGQPASISCKSSQSLLDSDGKTYLIWVFQRPGQSPKRLIFLVSKRDS
GVPDRFTGSGSGTDFTLKISRVEAEDVGVYYCWQGTHFPHTVGGGTKLEIA

```
SEQ ID NO: 31 >aDabi-Fab2b-VL
DIVMTQTPLSLSVTPGQPASISCRSSQSIVHSDGNIYLEWYLQKPGQSPKLLIYKVSYRFS
GVPDRFSGSGSGTGFTLKISRVEAEDVGVYYCFQASHVPYTFGGGTKLEIK SEQ ID NO: 32 >IGKV2-29
DIVMTQTPLSLSVTPGQPASICKSSQSLLHSDGKTYLYWYLQKPGQSPQLLIYEVSSRFS
GVPDRFSGSGSGTDFTLKISRVEAEDVGVYYCMQGIHLP SEQ ID NO: 33 >hu5G8-VH_v1
QVQLVQSGAEVKKPGASVKVSCKASGFNIKDYYMHWVRQAPGQGLEWMGWIDPENG
DTVYAPKFQGKATMTRDTSTSTAYMELSSLRSEDTAVYYCTILDFWGQGTLVTVSS SEQ ID NO: 34 >hu5G8-VH_v2
QVQLVQSGAEVKKPGASVKVSCKASGFNIKDYYMHWVRQAPGQGLEWIGWIDPENGD
TVYAPKFQGKATMTSDTSTSTAYMELSSLRSEDTAVYYCSPLDFWGQGTLVTVSS SEQ ID NO: 35 hu5G8-VH_v3
EVQLVQSGAEVKKPGASVKVSCKASGFNIKDYYMHWVRQAPGQGLEWIGWIDPENGD
TVYAPKFQGKATMTSDTSTSTAYMELSSLRSEDTAVYYCSPLDFWGQGTLVTVSS SEQ ID NO: 36 >hu5G8-VH_v4
EVQLVQSGAEVKKPGASVKVSCKASGFNIKDYYMHWVRQAPGQGLDWIGWIDPENGD
TVYAPKFQGKATMTSDTSTSTAYMELSSLRSEDTAVYYCSPLDFWGQGTLVTVSS SEQ ID NO: 37 >hu5G8-VH_v5
EVQLVQSGAELVKPGASVRLSCKASGFNIKDYYMHWVRQAPGQGLDWIGWIDPENGD
TVYAPKFQGKATMTSDTSTNTAYLELSSLRSEDTAVYYCSPLDFWGQGTLVTVSS SEQ ID NO: 38 >hu5G8-VH_v6
EVQLVQSGAELVKPGASVRLSCAASGFNIKDYYMHWVRQAPGQGLDWIGWIDPENGD
TVYAPKFQGKATMTSDTSTNTAYLELSSLRSEDTAVYYCSPLDFWGQGTLVTVSS SEQ ID NO: 39 >hu5G8-VH_v7
QVQLVQSGAEVKKPGASVKVSCKASGFNIKDYYMHWVRQAPGQGLEWMGWIDPENG
DTVYAPKFQGRVTMTRDTSTSTVYMELSSLRSEDTAVYYCARLDFWGQGTLVTVSS SEQ ID NO: 40 >hu5G8-VH_v8
EVQLVQSGAEVKKPGASVKVSCKASGFNIKDYYMHWVRQAPGQGLDWIGWIDPENGD
TVYAPKFQGRVTMTSDTSTSTVYMELSSLRSEDTAVYYCSPLDFWGQGTLVTVSS SEQ ID NO: 41 >hu5G8-VL_v1
DIVMTQTPLSLSVTPGQPASISCKSSQSLLDSDGKTYLNWYLQKPGQSPKLLIYLVSKLD
SGVPDRFSGSGSGTGFTLKISRVEAEDVGVYYCWQGTLFPYTFGGGTKLEIK SEQ ID NO: 42 >hu5G8-VL_v2
DVVMTQTPLSLSVTPGQPASISCKSSQSLLDSDGKTYLNWLLQKPGQSPKRLIYLVSKLD
SGVPDRFSGSGSGTGFTLKISRVEAEDVGVYYCWQGTLFPYTFGGGTKLEIK SEQ ID NO: 43 >hu5G8-VL_v3
DVVMTQTPLSLSVTPGQPASISCKSSQSLLDSDGKTYLNWLLQKPGQSPKRLIYLVSKLD
SGVPDRFSGSGSGTDFTLKISRVEAEDVGVYYCWQGTLFPYTFGGGTKLEIK SEQ ID NO: 44 >hu5G8-VL_v4
DVVMTQSPLSLSVTPGEPASISCKSSQSLLDSDGKTYLNWLLQKPGQSPKRLIYLVSKLD
SGVPDRFSGSGSGTDFTLKISRVEAEDVGVYYCWQGTLFPYTFGGGTKLEIK SEQ ID NO: 45 >hu5G8-VL_v5
DIVMTQTPLSLSVTPGQPASISCKSSQSLLDSDGKTYLNWYLQKPGQSPQLLIYLVSKLD
SGVPDRFSGSGSGTDFTLKISRVEAEDVGVYYCWQGTLFPYTFGGGTKLEIK SEQ ID NO: 46 >hu5G8-VL_v6
DVVMTQTPLSLSVTPGQPASISCKSSQSLLDSDGKTYLNWLLQKPGQSPQRLIYLVSKLD
SGVPDRFSGSGSGTDFTLKISRVEAEDVGVYYCWQGTLFPYTFGGGTKLEIK SEQ ID NO: 47 >Murine 5G8 VH amino acid sequence with signal peptide
MKCSWVIFFLMAVVIGINSEVQLQQSGAELVRSGASVRLSCTASGFNIKDYYMHWVRQ
RPEQGLEWIGWIDPENGDTVYAPKFQGKATMTSDTSSNTAYLHLSSLTSEDTAVYYCSP
LDFWGQGTTLTVSS SEQ ID NO: 48 >Murine 5G8 VL amino acid sequence with signal peptide
MMSPAQFLFLLVLWIRETNGDVVMTQTPLTLSVTIGQPASICKSSQSLLDSDGKTYLN
WLLQRPGQSPKRLIYLVSKLDSGVPDRFTGSGSGTDFTLKIRRVEAEDLGVYYCWQGTL
FPYTFGGGTKLEIK SEQ ID NO: 49 >:m6A10VH amino acid sequence:
MKCSWVIFFLMAVVIGINSEVQLQQSGAELVRSGASVKLSCTASGLNIKDYYIEWVKQR
PEQGLEWIGWIDPENDDTEYAPKFQGRATLTTDTSSNTAYLQLSSLTSEDTAVYYCTPLD
YWGQGTSVTVSS
```

SEQ ID NO: 50 :m6A10VL amino acid sequence:
MMSPAQFLFLLVLWIRETNGDVVMTQTPLTLSVTIGQPASISCKSSQSLLDSDGKTYLN
WLLQRPGQSPKRLIYLVSKLDSGVPDRFTGSGSGTDFTLKISRVEAEDLGVYYCWQGTH
FPYTFGGGTKLEIKR SEQ ID NO: 51 :m7G6VH amino acid sequence:
MKCSWVIFFLMAVVTGVNSEVQLQQSGAELVRPGALVKLSCKASGFNIKDYYIHWVKQ
RPEQGLEWIGWIDPENGETVYDPKFQGKASITSDTSSNTAYLQLRSLTSEDTAVYYSTSL
DFWGQGTSVTVSS SEQ ID NO: 52 m7G6VL amino acid sequence:
MMSPAQFLFLLVLWIRETNGDVVMTQTPLTLSVTIGQPASISCKSTQSLLDSDGKTYLN
WLLQRPGQSPKRLIYLVSKLDSGVPDRFTGSGSGTDFTLKISRVEAEDLGVYYCWQGTH
FPYTFGGGTKLEIKR SEQ ID NO: 53 m8A4VH amino acid sequence:
MKCSWVIFFLMAVVTGVNSEVQLQQSGAELVRPGALVKLSCKASGFNIKDYYIHWVKQ
RPEQGLEWIGWIDPENGDTVYDPQFQDKANITADTSSNTAYLQLSSLTSEGTAVYYCST
LDFWGQGTTLTVSS SEQ ID NO: 54 m8A4VL amino acid sequence:
MMSPAQFLFLLVLWNRETNGDVVMTQTPLTLSVTIGQPASISCKSSQSLLDSDGKTYLN
WLLQRPGQSPKRLIYLVSKLDSGVPDRFTGSGSGTDFTLKISRVEAEDLGVYYCWQGTH
FPCTFGGGTKLEIKR SEQ ID NO: 55; Murine 3D6 VH amino acid sequence:
EVQLQQSGADLVRPGALVKLSCKASGFNIKDYYLHWVRQRPEQGLEWIGWIDPENGDT
VYDPKFQGKATITADTSSNTAYLQLGSLTSEDTAVYFCSTLDFWGQGTTLTVSS SEQ ID NO: 56; Murine 3D6 Kabat/Chothia HCDR1:
GFNIKDYYLH SEQ ID NO: 57; Murine 3D6 Kabat HCDR2:
WIDPENGDTVYDPKFQG SEQ ID NO: 58; Murine 3D6 Kabat HCDR3:
LDF SEQ ID NO: 59; Murine 3D6 VL amino acid sequence:
DVVMTQTPLTLSVTIGQPASISCKSSQSLLDSDGKTYLNWLLQRPGQSPKRLIYLVSKLD
SGVPDRFTGSGSGTDFTLKISRVEAEDLGVYYCWQGTHFPYTFGGGTKLEIKR SEQ ID NO: 60; Murine 3D6 Kabat LCDR1:
KSSQSLLDSDGKTYLN SEQ ID NO: 61; Murine 3D6 Kabat LCDR2:
LVSKLDS SEQ ID NO: 62; Murine 3D6 Kabat LCDR3:
WQGTHFPYT SEQ ID NO: 63 mature region of m6A10VH amino acid sequence:
EVQLQQSGAELVRSGASVKLSCTASGLNIKDYYIHWVKQRPEQGLEWIGWIDPENDDTE
YAPKFQGRATLTTDTSSNTAYLQLSSLTSEDTAVYYCTPLDYWGQGTSVTVSS SEQ ID NO: 64 :mature region of m6A10VL amino acid sequence:
DVVMTQTPLTLSVTIGQPASISCKSSQSLLDSDGKTYLNWLLQRPGQSPKRLIYLVSKLD
SGVPDRFTGSGSGTDFTLKISRVEAEDLGVYYCWQGTHFPYTFGGGTKLEIK SEQ ID NO: 65 Murine 6A10 Kabat/Chothia composite CDR-H1:
GLNIKDYYIH SEQ ID NO: 66 Murine 6A10 Kabat CDR-H2:
WIDPENDDTEYAPKFQG SEQ ID NO: 67 Murine 6A10 Kabat CDR-H3:
LDY SEQ ID NO: 68 Murine 6A10 Kabat CDR-L1:
KSSQSLLDSDGKTYLN SEQ ID NO: 69 Murine 6A10 Kabat CDR-L2:
LVSKLDS SEQ ID NO: 70 Murine 6A10 Kabat CDR-L3:
WQGTHFPYT SEQ ID NO: 71 Murine 6A10 Kabat CDR-H1:
DYYIH SEQ ID NO: 72 Murine 6A10 Chothia CDR-H1:
GLNIKDY SEQ ID NO: 73 Murine 6A10 Contact CDR-H1:
KDYYIH SEQ ID NO:74 Murine 6A10 Chothia CDR-H2:
DPENDD SEQ ID NO:75 Murine 6A10 AbM CDR-H2:
WIDPENDDTE SEQ ID NO:76 Murine 6A10 Contact CDR-H2:
WIGWIDPENDDTE SEQ ID NO:77 Murine 6A10 Contact CDR-H3:
TPLD SEQ ID NO: 78 Murine 6A10 Contact CDR-L1:
KTYLNWL SEQ ID NO: 79 Murine 6A10 Contact CDR-L2:
RLIYLVSKLD SEQ ID NO: 80 Murine 6A10 Contact CDR-L3:
WQGTHFPY SEQ ID NO: 81 6A10 VH Acceptor accession # ACR16112:
QVQLQESGAEVKKPGASVKVSCKASGYTFTGYYMEIWVRQAPGQGLEWMGWINPNSG
DTNYAQKFQGRVTTTRDTSISTAYMELSRLRSDDTAVYYCARLAARPLDWGQGTLVT
VSS SEQ ID NO: 82 human germline sequence IGHV1-2*02:
QVQLVQSGAEVKKPGASVKVSCKASGYTFTGYYMHWVRQAPGQGLEWMGWINPNSG
GTNYAQKFQGRVTMTRDTSISTAYMELSRLRSDDTAVYYCARSRRGYYDFWSGSPEDY
WGQGTLVTVSS SEQ ID NO: 83 6A10 VL Acceptor accession #ABC66863:
DIVMTQSPLSLPVTLGQPASISCRSSQSLVYSDGNTYLNWFQQRPGQSPRRLIYKVSNRD
SGVPDRFSGSGSGTDFTLKISRVEAEDVGVYYCMQGTHRPLTFGGGTKVEIK SEQ ID NO: 84 human germline sequence IGKV2-30*02:
DVVMTQSPLSLPVTLGQPASISCRSSQSLVHSDGNTYLNWFQQRPGQSPRRLIYKVSNRD
SGVPDRFSGSGSGTDFTLKISRVEAEDVGVYYCMQGTHWPLTFGGGTKVEIK SEQ ID NO: 85 hu6A10-VH_v1:
QVQLQESGAEVKKPGASVKVSCKASGLNIKDYYIEWVRQAPGQGLEWMGWIDPENDD
TEYAPKFQGRVTTTRDTSISTAYMELSRLRSDDTAVYYCARLDWGQGTLVTVSS SEQ ID NO: 86 hu6A10-VH_v2:
QVQLQESGAEVKKPGASVKVSCKASGLNIKDYYIHWVRQAPGQGLEWIGWIDPENDDT
EYAPKFQGRVTTTRDTSISTAYMELSRLRSDDTAVYYCARLDYWGQGTLVTVSS SEQ ID NO: 87 hu6A10-VH_v3:
QVQLQESGAEVKKPGGSVKVSCKASGLNIKDYYIHWVRQAPGQGLEWIGWIDPENDDT
EYAPKFQGRVTITRDTSISTAYLELSRLRSDDTAVYYCARLDYWGQGTLVTVSS SEQ ID NO: 88 hu6A10-VL_v1:
DIVMTQSPLSLPVTLGQPASISCKSSQSLLDSDGKTYLNWFQQRPGQSPRRLIYLVSKLDS
GVPDRFSGSGSGTDFTLKISRVEAEDVGVYYCWQGTHFPYTFGGGTKVEIK SEQ ID NO: 89 hu6A10-VL_v2:
DIVMTQSPLSLPVTLGQPASISCKSSQSLLDSDGKTYLNWFQQRPGQSPRLLIYLVSKLDS
GVPDRFSGSGSGTDFTLKISRVEAEDVGVYYCWQGTHFPYTFGGGTKVEIK SEQ ID NO: 90 hu6A10-VL_v3:
DIVMTQSPLSLSVTLGEPASISCKSSQSLLDSDGKTYLNWFQQRPGQSPRLLIYLVSKLDS
GVPDRFSGSGSGTDFTLKISRVEAEDVGVYYCWQGTHFPYTFGGGTKVEIK SEQ ID NO: 91 mature region of murine 8A4VH:
EVQLQQSGAELVRPGALVKLSCKASGFNIKDYYIHWVKQRPEQGLEWIGWIDPENGDT
VYDPQFQDKANITADTSSNTAYLQLSSLTSEGTAVYYCSTLDFWGQGTTLTVSS SEQ ID NO: 92 mature region of murine 8A4VL:
DVVMTQTPLTLSVTIGQPASISCKSSQSLLDSDGKTYLNWLLQRPGQSPKRLIYLVSKLD
SGVPDRFTGSGSGTDFTLKISRVEAEDLGVYYCWQGTHFPCTFGGGTKLEIK

```
SEQ ID NO: 93 murine 8A4 Kabat/Chothia composite CDR-H1:
GFNIKDYYIH

SEQ ID NO: 94 murine 8A4 Kabat CDR-H2:
WIDPENGDTVYDPQFQD

SEQ ID NO: 95 murine 8A4 Kabat CDR-H3:
LDF

SEQ ID NO: 96 murine 8A4 Kabat CDR-L1:
KSSQSLLDSDGKTYLN

SEQ ID NO: 97 murine 8A4 Kabat CDR-L2:
LVSKLDS

SEQ ID NO: 98 murine 8A4 Kabat CDR-L3:
WQGTHFPCT

SEQ ID NO: 99 murine 8A4 Kabat CDR-H1:
DYYIH

SEQ ID NO: 100 murine 8A4 Chothia CDR-H1:
GFNIKDY

SEQ ID NO: 101 murine 8A4 Contact CDR-H1:
KDYYIH

SEQ ID NO: 102 murine 8A4 Chothia CDR-H2:
DPENGD

SEQ ID NO: 103 murine 8A4 AbM CDR-H2:
WIDPENGDTV

SEQ ID NO: 104 murine 8A4 Contact CDR-H2:
WIGWIDPENGDTV

SEQ ID NO: 105 murine 8A4 Contact CDR-H3:
STLD

SEQ ID NO: 106 murine 8A4 Contact CDR-L1:
KTYLNWL

SEQ ID NO: 107 murine 8A4 Contact CDR-L2:
RLIYLVSKLD

SEQ ID NO: 108 murine 8A4 Contact CDR-L3:
WQGTHFPC

SEQ ID NO: 109 3JAUVH:
EVQLQQSGAELVKPGASVKLSCTASGFNIKDTYIHWVKQRPEQGLEWIGKIDPANGNTK
YDPKFQDKATITADTSSNTAYLQLSSLTSEDTAVYYCANSNYWFDFDYWGQGTTLTVS
S

SEQ ID NO: 110 ADU57742:
QVQLQQSGAEVKKPGSSVKVSCKASGGTFSSNPVSWVRQAPGQGLEWMGGIIPFAQKV
LGAQRVRDRINITADTSTSTAYMELSGLRSDDTAVYYCATGQQLYSLHYWGQGTLVTV
SS

SEQ ID NO: 111 3JAUVL:
DVLMTQTPLSLPVSLGDQASISCRSSQSIVHSNGNTYLEWYLQKPGQSPKLLIYKVSNRF
SGVPDRFSGSGSGTDFTLKISRVEADDVGVYYCYQGSHVPYTFGGGTKLEIK

SEQ ID NO: 112 ABA26100:
DVMTSSSVTGASSCRSSSVYSDGSTWNWRGSRRYDVSTRDSGVDRSGSGSGTDTKSRV
ADVGVYYCMDWHTGGTKK

SEQ ID NO: 113 hu8A4-VH v1:
QVQLQQSGAEVKKPGSSVKVSCKASGFNIKDYYIHWVRQAPGQGLEWMGWIDPENGD
TVYDPQFQDRINITADTSTSTAYMELSGLRSDDTAVYYCSTLDFWGQGTLVTVSS

SEQ ID NO: 114 hu8A4-VH v2:
QVQLQQSGAEVVKPGGSVKLSCKASGFNIKDYYIHWVRQAPGQGLEWMGWIDPENGD
TVYDPQFQDRITITADTSTSTAYMELSGLRSDDTAVYYCSTLDFWGQGTLVTVSS

SEQ ID NO: 115 hu8A4-VH v3:
QVQLQQSGAEVVKPGGSVKLSCKASGFNIKDYYIHWVRQAPGQGLEWIGWIDPENGDT
VYDPQFQDRATITADTSTSTAYMELSGLRSEDTAVYYCATLDFWGQGTLVTVSS
```

SEQ ID NO: 116 hu8A4-VL v1:
DIVMTQSPLSLSVTLGQPASISCKSSQSLLDSDGKTYLNWFQQRPGQSPRRLIYLVSKLDS
GVPDRFSGSGSGTDFTLKISRVEAEDVGVYYCWQGTHFPCTFGQGTKLEIK

SEQ ID NO: 117 hu8A4-VL v2:
DIVMTQSPLSLSVTLGEPASISCKSSQSLLDSDGKTYLNWFQQRPGQSPRRLIYLVSKLDS
GVPDRFSGSGSGTDFTLKISRVEAEDVGVYYCWQGTHFPCTFGQGTKLEIK

SEQ ID NO: 118 hu8A4-VL v3:
DVVMTQSPLSLSVTLGEPASISCKSSQSLLDSDGKTYLNWLQQRPGQSPRRLIYLVSKLD
SGVPDRFSGSGSGTDFTLKISRVEAEDVGVYYCWQGTHFPCTFGQGTKLEIK

SEQ ID NO: 119 murine mAb7G6 VH:
EVQLQQSGAELVRPGALVKLSCKASGFNIKDYYIHWVKQRPEQGLEWIGWIDPENGET
VYDPKFQGKASITSDTSSNTAYLQLRSLTSEDTAVYYSTSLDFWGQGTSVTVSS SEQ ID NO: 120 murine mAb7G6 VL:
DVVMTQTPLTLSVTIGQPASISCKSTQSLLDSDGKTYLNWLLQRPGQSPKRLIYLVSKLD
SGVPDRFTGSGSGTDFTLKISRVEAEDLGVYYCWQGTHFPYTFGGGTKLEIKR SEQ ID NO: 121 murine 7G6 Kabat/Chothia composite CDR-H1:
GFNIKDYYIH SEQ ID NO: 122 murine 7G6 Kabat CDR-H2:
WIDPENGETVYDPKFQG SEQ ID NO: 123 murine 7G6 Kabat CDR-H3:
LDF SEQ ID NO: 124 murine 7G6 Kabat CDR-L1:
KSTQSLLDSDGKTYLN SEQ ID NO: 125 murine 7G6 Kabat CDR-L2:
LVSKLDS SEQ ID NO: 126 murine 7G6 Kabat CDR-L3:
WQGTHFPYT SEQ ID NO: 127 murine 7G6 Kabat CDR-H1:
DYYIH SEQ ID NO: 128 murine 7G6 Chothia CDR-H1:
GFNIKDY SEQ ID NO: 129 murine 7G6 Contact CDR-H1:
KDYYH SEQ ID NO: 130 murine 7G6 Chothia CDR-H2:
DPENGE SEQ ID NO: 131 murine 7G6 AbM CDR-H2:
WIDPENGETV SEQ ID NO: 132 murine 7G6 Contact CDR-H2:
WIGWIDPENGETV SEQ ID NO: 133 murine 7G6 Contact CDR-H3:
TSLD SEQ ID NO: 134 murine 7G6 Contact CDR-L1:
KTYLNWL SEQ ID NO: 135 murine 7G6 Contact CDR-L2:
RLIYLVSKLD SEQ ID NO: 136 murine 7G6 Contact CDR-L3:
WQGTHFPY SEQ ID NO: 137 Human VH Acceptor DB 3U0T_VH:
QVQLVQSGAEVKKPGASVKVSCKASGYYTEAYYIEWVRQAPGQGLEWMGRIDPATGN
TKYAPRLQDRVTMTRDTSTSTVYMELSSLRSEDTAVYYCASLYSLPVYWGQGTTVTVS
S SEQ ID NO: 138 Human VL Acceptor PDB 3U0T_VL:
DVVMTQSPLSLPVTLGQPASISCKSSQSLLYSDAKTYLNWFQQRPGQSPRRLIYQISRLDP
GVPDRFSGSGSGTDFTLKISRVEAEDVGVYYCLQGTHYPVLFGQGTRLEIKR SEQ ID NO: 139 hu7G6-VH_v1:
QVQLVQSGAEVVKPGASVKLSCKASGFNIKDYYIHWVRQAPGQGLEWMGWIDPENGE
TVYDPKFQGRVTITRDTSTNTAYLQLSSLRSEDTAVYYSTSLDFWGQGTTVTVSS SEQ ID NO: 140 hu7G6-VH_v2:
QVQLVQSGAEVVKPGASVKLSCKASGFNIKDYYIHWVKQAPGQGLEWMGWIDPENGE
TVYDPKFQGRVTITRDTSTNTAYLQLSSLRSEDTAVYYSTSLDFWGQGTTVTVSS SEQ ID NO: 141 hu7G6-VL_v1:
DVVMTQSPLSLSVTLGQPASISCKSTQSLLDSDGKTYLNWFQQRPGQSPRRLIYLVSKLD
SGVPDRFSGSGSGTDFTLKISRVEAEDVGVYYCWQGTHFPYTFGQGTKLEIKR SEQ ID NO: 142 hu7G6-VL_v2:
DVVMTQSPLSLSVTLGQPASISCKSTQSLLDSDGKTYLNWFLQRPGQSPRRLIYLVSKLD
SGVPDRFSGSGSGTDFTLKISRVEAEDVGVYYCWQGTHFPYTFGQGTKLEIKR SEQ ID NO: 143 hu7G6-VL_v3:
DVVMTQSPLSLSVTLGQPASISCKSTQSLLDSDGKTYLNWLQQRPGQSPRRLIYLVSKLD
SGVPDRFSGSGSGTDFTLKISRVEAEDVGVYYCWQGTHFPYTFGQGTKLEIKR SEQ ID NO: 144 hu7G6-VL_v4:
DVVMTQSPLSLSVTLGQPASISCKSTQSLLDSDGKTYLNWLLQRPGQSPRRLIYLVSKLD
SGVPDRFSGSGSGTDFTLKISRVEAEDVGVYYCWQGTHFPYTFGQGTKLEIKR SEQ ID NO: 145 hu7G6-VL_v5:
DVVMTQSPLSLSVTLGQPASISCKSTQSLLDSDGKTYLNWFQQRPGQSPKRLIYLVSKLD
SGVPDRFSGSGSGTDFTLKISRVEAEDVGVYYCWQGTHFPYTFGQGTKLEIKR SEQ ID NO: 146 hu7G6-VL_v6:
DVVMTQSPLSLSVTLGQPASISCKSTQSLLDSDGKTYLNWLLQRPGQSPKRLIYLVSKLD
SGVPDRFSGSGSGTDFTLKISRVEAEDVGVYYCWQGTHFPYTFGQGTKLEIKR SEQ ID NO: 147 hu7G6-VL_v7:
DVVMTQSPLSLSVTLGQPASISCKSTQSLLDSDGKTYLNWFQQRPGQSPRRLIYLVSKLD
SGVPDRFSGSGSGTDFTLKISRVEAEDVGVYYCWQGTHFPYTFGGGTKLEIKR SEQ ID NO: 148 hu7G6-VL_v8:
DVVMTQSPLSLSVTLGQPASISCKSTQSLLDSDGKTYLNWLLQRPGQSPRRLIYLVSKLD
SGVPDRFSGSGSGTDFTLKISRVEAEDVGVYYCWQGTHFPYTFGGGTKLEIKR SEQ ID NO: 149 human germline sequence IGHV1-69-2*01
EVQLQQSGAELVRPGALVKLSCKASGFNIKDYYIHWVKQRPEQGLEWIGWIDPENGET
VYDPKFQGKASITSDTSSNTAYLQLRSLTSEDTAVYYSTSLDFWGQGTSVTVSS

SEQUENCE LISTING

<160> NUMBER OF SEQ ID NOS: 149

<210> SEQ ID NO 1
<211> LENGTH: 441
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
                195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
            290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
            370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
                420                 425                 430

Ser Ala Ser Leu Ala Lys Gln Gly Leu
            435                 440

<210> SEQ ID NO 2
<211> LENGTH: 412
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu

```
            35                  40                  45
Gln Thr Pro Thr Glu Asp Gly Ser Glu Pro Gly Ser Glu Thr Ser
 50                  55                  60
Asp Ala Lys Ser Thr Pro Thr Ala Glu Ala Glu Glu Ala Gly Ile Gly
 65                  70                  75                  80
Asp Thr Pro Ser Leu Glu Asp Glu Ala Ala Gly His Val Thr Gln Ala
                 85                  90                  95
Arg Met Val Ser Lys Ser Lys Asp Gly Thr Gly Ser Asp Asp Lys Lys
                100                 105                 110
Ala Lys Gly Ala Asp Gly Lys Thr Lys Ile Ala Thr Pro Arg Gly Ala
            115                 120                 125
Ala Pro Pro Gly Gln Lys Gly Gln Ala Asn Ala Thr Arg Ile Pro Ala
        130                 135                 140
Lys Thr Pro Pro Ala Pro Lys Thr Pro Pro Ser Ser Gly Glu Pro Pro
145                 150                 155                 160
Lys Ser Gly Asp Arg Ser Gly Tyr Ser Ser Pro Gly Ser Pro Gly Thr
                165                 170                 175
Pro Gly Ser Arg Ser Arg Thr Pro Ser Leu Pro Thr Pro Pro Thr Arg
            180                 185                 190
Glu Pro Lys Lys Val Ala Val Val Arg Thr Pro Pro Lys Ser Pro Ser
        195                 200                 205
Ser Ala Lys Ser Arg Leu Gln Thr Ala Pro Val Pro Met Pro Asp Leu
210                 215                 220
Lys Asn Val Lys Ser Lys Ile Gly Ser Thr Glu Asn Leu Lys His Gln
225                 230                 235                 240
Pro Gly Gly Gly Lys Val Gln Ile Ile Asn Lys Lys Leu Asp Leu Ser
                245                 250                 255
Asn Val Gln Ser Lys Cys Gly Ser Lys Asp Asn Ile Lys His Val Pro
            260                 265                 270
Gly Gly Gly Ser Val Gln Ile Val Tyr Lys Pro Val Asp Leu Ser Lys
        275                 280                 285
Val Thr Ser Lys Cys Gly Ser Leu Gly Asn Ile His His Lys Pro Gly
290                 295                 300
Gly Gly Gln Val Glu Val Lys Ser Glu Lys Leu Asp Phe Lys Asp Arg
305                 310                 315                 320
Val Gln Ser Lys Ile Gly Ser Leu Asp Asn Ile Thr His Val Pro Gly
                325                 330                 335
Gly Gly Asn Lys Lys Ile Glu Thr His Lys Leu Thr Phe Arg Glu Asn
            340                 345                 350
Ala Lys Ala Lys Thr Asp His Gly Ala Glu Ile Val Tyr Lys Ser Pro
        355                 360                 365
Val Val Ser Gly Asp Thr Ser Pro Arg His Leu Ser Asn Val Ser Ser
    370                 375                 380
Thr Gly Ser Ile Asp Met Val Asp Ser Pro Gln Leu Ala Thr Leu Ala
385                 390                 395                 400
Asp Glu Val Ser Ala Ser Leu Ala Lys Gln Gly Leu
                405                 410

<210> SEQ ID NO 3
<211> LENGTH: 383
<212> TYPE: PRT
<213> ORGANISM: Homo sapiens

<400> SEQUENCE: 3
```

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
            85                  90                  95

Arg Gly Ala Ala Pro Pro Gly Gln Lys Gly Gln Ala Asn Ala Thr Arg
        100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
            165                 170                 175

Ser Pro Ser Ser Ala Lys Ser Arg Leu Gln Thr Ala Pro Val Pro Met
        180                 185                 190

Pro Asp Leu Lys Asn Val Lys Ser Lys Ile Gly Ser Thr Glu Asn Leu
    195                 200                 205

Lys His Gln Pro Gly Gly Gly Lys Val Gln Ile Ile Asn Lys Lys Leu
210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
            245                 250                 255

Leu Ser Lys Val Thr Ser Lys Cys Gly Ser Leu Gly Asn Ile His His
        260                 265                 270

Lys Pro Gly Gly Gly Gln Val Glu Val Lys Ser Glu Lys Leu Asp Phe
    275                 280                 285

Lys Asp Arg Val Gln Ser Lys Ile Gly Ser Leu Asp Asn Ile Thr His
290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
            325                 330                 335

Lys Ser Pro Val Val Ser Gly Asp Thr Ser Pro Arg His Leu Ser Asn
        340                 345                 350

Val Ser Ser Thr Gly Ser Ile Asp Met Val Asp Ser Pro Gln Leu Ala
    355                 360                 365

Thr Leu Ala Asp Glu Val Ser Ala Ser Leu Ala Lys Gln Gly Leu
370                 375                 380

<210> SEQ ID NO 4
<211> LENGTH: 410
<212> TYPE: PRT
<213> ORGANISM: Homo sapiens

<400> SEQUENCE: 4
```

-continued

```
Met Ala Glu Pro Arg Gln Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
    195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Val Tyr Lys Pro Val Asp Leu Ser Lys Val Thr
    275                 280                 285

Ser Lys Cys Gly Ser Leu Gly Asn Ile His His Lys Pro Gly Gly Gly
290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
                325                 330                 335

Asn Lys Lys Ile Glu Thr His Lys Leu Thr Phe Arg Glu Asn Ala Lys
            340                 345                 350

Ala Lys Thr Asp His Gly Ala Glu Ile Val Tyr Lys Ser Pro Val Val
    355                 360                 365

Ser Gly Asp Thr Ser Pro Arg His Leu Ser Asn Val Ser Ser Thr Gly
370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410
```

```
<210> SEQ ID NO 5
<211> LENGTH: 381
<212> TYPE: PRT
<213> ORGANISM: Homo sapiens

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
                245                 250                 255

Lys Val Thr Ser Lys Cys Gly Ser Leu Gly Asn Ile His His Lys Pro
            260                 265                 270

Gly Gly Gly Gln Val Glu Val Lys Ser Glu Lys Leu Asp Phe Lys Asp
        275                 280                 285

Arg Val Gln Ser Lys Ile Gly Ser Leu Asp Asn Ile Thr His Val Pro
    290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
            340                 345                 350

Ser Thr Gly Ser Ile Asp Met Val Asp Ser Pro Gln Leu Ala Thr Leu
        355                 360                 365

Ala Asp Glu Val Ser Ala Ser Leu Ala Lys Gln Gly Leu
    370                 375                 380
```

<210> SEQ ID NO 6
<211> LENGTH: 352
<212> TYPE: PRT
<213> ORGANISM: Homo sapiens

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
        275                 280                 285

Phe Arg Glu Asn Ala Lys Ala Lys Thr Asp His Gly Ala Glu Ile Val
    290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 7
<211> LENGTH: 112
<212> TYPE: PRT

<213> ORGANISM: Artificial
<220> FEATURE:
<223> OTHER INFORMATION: Synthesized

<400> SEQUENCE: 7

```
Glu Val Gln Leu Gln Gln Ser Gly Ala Glu Leu Val Arg Ser Gly Ala
1               5                   10                  15
Ser Val Arg Leu Ser Cys Thr Ala Ser Gly Phe Asn Ile Lys Asp Tyr
            20                  25                  30
Tyr Met His Trp Val Arg Gln Arg Pro Glu Gln Gly Leu Glu Trp Ile
        35                  40                  45
Gly Trp Ile Asp Pro Glu Asn Gly Asp Thr Val Tyr Ala Pro Lys Phe
    50                  55                  60
Gln Gly Lys Ala Thr Met Thr Ser Asp Thr Ser Ser Asn Thr Ala Tyr
65                  70                  75                  80
Leu His Leu Ser Ser Leu Thr Ser Glu Asp Thr Ala Val Tyr Tyr Cys
                85                  90                  95
Ser Pro Leu Asp Phe Trp Gly Gln Gly Thr Thr Leu Thr Val Ser Ser
            100                 105                 110
```

<210> SEQ ID NO 8
<211> LENGTH: 113
<212> TYPE: PRT
<213> ORGANISM: Artificial
<220> FEATURE:
<223> OTHER INFORMATION: Synthesized

<400> SEQUENCE: 8

```
Asp Val Val Met Thr Gln Thr Pro Leu Thr Leu Ser Val Thr Ile Gly
1               5                   10                  15
Gln Pro Ala Ser Ile Ser Cys Lys Ser Ser Gln Ser Leu Leu Asp Ser
            20                  25                  30
Asp Gly Lys Thr Tyr Leu Asn Trp Leu Leu Gln Arg Pro Gly Gln Ser
        35                  40                  45
Pro Lys Arg Leu Ile Tyr Leu Val Ser Lys Leu Asp Ser Gly Val Pro
    50                  55                  60
Asp Arg Phe Thr Gly Ser Gly Ser Gly Thr Asp Phe Thr Leu Lys Ile
65                  70                  75                  80
Arg Arg Val Glu Ala Glu Asp Leu Gly Val Tyr Tyr Cys Trp Gln Gly
                85                  90                  95
Thr Leu Phe Pro Tyr Thr Phe Gly Gly Gly Thr Lys Leu Glu Ile Lys
            100                 105                 110
Arg
```

<210> SEQ ID NO 9
<211> LENGTH: 393
<212> TYPE: DNA
<213> ORGANISM: Artificial
<220> FEATURE:
<223> OTHER INFORMATION: Synthesized

<400> SEQUENCE: 9

```
atgaaatgca gctgggtcat cttcttcctg atggcagtgg ttataggaat caattcagag      60
gttcagctgc agcagtctgg ggcagagctt gtgaggtcag ggcctcagt caggttgtcc      120
tgcacagctt ctggcttcaa cattaaggac tactatatgc actgggtgag gcagaggcct      180
gaacagggcc tggagtggat tggatggatt gatcctgaga atggtgatac tgtatatgcc      240
ccgaagttcc agggcaaggc cactatgact tcagacacat cctccaacac agcctacctg      300
```

```
cacctcagca gcctgacatc tgaagacact gccgtctatt actgtagccc ccttgacttc    360
tggggccaag gcaccactct cacagtctcc tca                                 393

<210> SEQ ID NO 10
<211> LENGTH: 399
<212> TYPE: DNA
<213> ORGANISM: Artificial
<220> FEATURE:
<223> OTHER INFORMATION: Synthesized

<400> SEQUENCE: 10
atgatgagtc ctgcccagtt cctgtttctg ttagtactct ggattcggga aaccaacggt    60
gatgttgtga tgacccagac tccactcact tgtcggtta ccattggaca accagcctcc    120
atctcttgca agtcaagtca gagcctctta gatagtgatg aaagacata tttgaattgg    180 ttgttacaga ggccaggcca gtctccaaag cgcctaatct atctggtgtc taaactggac    240
tctggagtcc ctgacaggtt cactggcagt ggatcaggga cagatttcac actgaaaatc    300
cgcagagtgg aggctgagga tttgggagtt tattattgct ggcaaggtac acttttccg    360 tacacgttcg gagggggac caagctggaa ataaaacgg                            399

<210> SEQ ID NO 11
<211> LENGTH: 10
<212> TYPE: PRT
<213> ORGANISM: Artificial
<220> FEATURE:
<223> OTHER INFORMATION: Synthesized

<400> SEQUENCE: 11

Gly Phe Asn Ile Lys Asp Tyr Tyr Met His
1               5                   10

<210> SEQ ID NO 12
<211> LENGTH: 17
<212> TYPE: PRT
<213> ORGANISM: Artificial
<220> FEATURE:
<223> OTHER INFORMATION: Synthesized

<400> SEQUENCE: 12

Trp Ile Asp Pro Glu Asn Gly Asp Thr Val Tyr Ala Pro Lys Phe Gln
1               5                   10                  15

Gly

<210> SEQ ID NO 13
<211> LENGTH: 3
<212> TYPE: PRT
<213> ORGANISM: Artificial Sequence
<220> FEATURE:
<223> OTHER INFORMATION: Synthesized

<400> SEQUENCE: 13

Leu Asp Phe
1

<210> SEQ ID NO 14
<211> LENGTH: 16
<212> TYPE: PRT
<213> ORGANISM: Artificial
<220> FEATURE:
<223> OTHER INFORMATION: Synthesized

<400> SEQUENCE: 14
```

```
Lys Ser Ser Gln Ser Leu Leu Asp Ser Asp Gly Lys Thr Tyr Leu Asn
1               5                   10                  15

<210> SEQ ID NO 15
<211> LENGTH: 7
<212> TYPE: PRT
<213> ORGANISM: Artificial
<220> FEATURE:
<223> OTHER INFORMATION: Synthesized

<400> SEQUENCE: 15

Leu Val Ser Lys Leu Asp Ser
1               5

<210> SEQ ID NO 16
<211> LENGTH: 9
<212> TYPE: PRT
<213> ORGANISM: Artificial
<220> FEATURE:
<223> OTHER INFORMATION: Synthesized

<400> SEQUENCE: 16

Trp Gln Gly Thr Leu Phe Pro Tyr Thr
1               5

<210> SEQ ID NO 17
<211> LENGTH: 5
<212> TYPE: PRT
<213> ORGANISM: Artificial
<220> FEATURE:
<223> OTHER INFORMATION: Synthesized

<400> SEQUENCE: 17

Asp Tyr Tyr Met His
1               5

<210> SEQ ID NO 18
<211> LENGTH: 7
<212> TYPE: PRT
<213> ORGANISM: Artificial
<220> FEATURE:
<223> OTHER INFORMATION: Synthesized

<400> SEQUENCE: 18

Gly Phe Asn Ile Lys Asp Tyr
1               5

<210> SEQ ID NO 19
<211> LENGTH: 6
<212> TYPE: PRT
<213> ORGANISM: Artificial
<220> FEATURE:
<223> OTHER INFORMATION: Synthesized

<400> SEQUENCE: 19

Lys Asp Tyr Tyr Met His
1               5

<210> SEQ ID NO 20
<211> LENGTH: 6
<212> TYPE: PRT
<213> ORGANISM: Artificial
<220> FEATURE:
<223> OTHER INFORMATION: Synthesized

<400> SEQUENCE: 20
```

```
Asp Pro Glu Asn Gly Asp
1               5

<210> SEQ ID NO 21
<211> LENGTH: 10
<212> TYPE: PRT
<213> ORGANISM: Artificial
<220> FEATURE:
<223> OTHER INFORMATION: Synthesized

<400> SEQUENCE: 21

Trp Ile Asp Pro Glu Asn Gly Asp Thr Val
1               5                   10

<210> SEQ ID NO 22
<211> LENGTH: 13
<212> TYPE: PRT
<213> ORGANISM: Artificial
<220> FEATURE:
<223> OTHER INFORMATION: Synthesized

<400> SEQUENCE: 22

Trp Ile Gly Trp Ile Asp Pro Glu Asn Gly Asp Thr Val
1               5                   10

<210> SEQ ID NO 23
<211> LENGTH: 4
<212> TYPE: PRT
<213> ORGANISM: Artificial
<220> FEATURE:
<223> OTHER INFORMATION: Synthesized

<400> SEQUENCE: 23

Ser Pro Leu Asp
1

<210> SEQ ID NO 24
<211> LENGTH: 7
<212> TYPE: PRT
<213> ORGANISM: Artificial
<220> FEATURE:
<223> OTHER INFORMATION: Synthesized

<400> SEQUENCE: 24

Lys Thr Tyr Leu Asn Trp Leu
1               5

<210> SEQ ID NO 25
<211> LENGTH: 10
<212> TYPE: PRT
<213> ORGANISM: Artificial
<220> FEATURE:
<223> OTHER INFORMATION: Synthesized

<400> SEQUENCE: 25

Arg Leu Ile Tyr Leu Val Ser Lys Leu Asp
1               5                   10

<210> SEQ ID NO 26
<211> LENGTH: 8
<212> TYPE: PRT
<213> ORGANISM: Artificial
<220> FEATURE:
<223> OTHER INFORMATION: Synthesized

<400> SEQUENCE: 26

Trp Gln Gly Thr Leu Phe Pro Tyr
```

<210> SEQ ID NO 27
<211> LENGTH: 114
<212> TYPE: PRT
<213> ORGANISM: Mus musculus

<400> SEQUENCE: 27

```
Lys Val Lys Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Ile Gln Trp Val Lys Gln Arg Pro Glu Gln Gly Leu Glu Trp Ile
        35                  40                  45

Gly Trp Ile Asp Pro Glu Asn Gly Asn Ser Gly Tyr Ala Pro Arg Phe
    50                  55                  60

Gln Gly Lys Ala Thr Met Thr Ala Asp Thr Leu Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ala Asp Leu His Asp Tyr Trp Gly Gln Gly Thr Thr Leu Thr Val
            100                 105                 110

Ser Ser
```

<210> SEQ ID NO 28
<211> LENGTH: 119
<212> TYPE: PRT
<213> ORGANISM: Homo sapiens

<400> SEQUENCE: 28

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Glu Thr Asn Pro Arg Asn Gly Gly Thr Thr Tyr Asn Glu Lys Phe
    50                  55                  60

Lys Gly Lys Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ile Gly Thr Ser Gly Tyr Asp Tyr Phe Asp Tyr Trp Gly Gln Gly
            100                 105                 110

Thr Leu Val Thr Val Ser Ser
        115
```

<210> SEQ ID NO 29
<211> LENGTH: 98
<212> TYPE: PRT
<213> ORGANISM: Homo sapiens

<400> SEQUENCE: 29

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 30
<211> LENGTH: 112
<212> TYPE: PRT
<213> ORGANISM: Mus musculus

<400> SEQUENCE: 30

Asp Val Val Met Thr Gln Thr Pro Leu Ser Leu Ser Val Thr Ile Gly
 1               5                  10                  15

Gln Pro Ala Ser Ile Ser Cys Lys Ser Ser Gln Ser Leu Leu Asp Ser
             20                  25                  30

Asp Gly Lys Thr Tyr Leu Ile Trp Val Phe Gln Arg Pro Gly Gln Ser
         35                  40                  45

Pro Lys Arg Leu Ile Phe Leu Val Ser Lys Arg Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro His Thr Val Gly Gly Gly Thr Lys Leu Glu Ile Ala
            100                 105                 110

<210> SEQ ID NO 31
<211> LENGTH: 112
<212> TYPE: PRT
<213> ORGANISM: Homo sapiens

<400> SEQUENCE: 31

Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Ser Ile Val His Ser
             20                  25                  30

Asp Gly Asn Ile Tyr Leu Glu Trp Tyr Leu Gln Lys Pro Gly Gln Ser
         35                  40                  45

Pro Lys Leu Leu Ile Tyr Lys Val Ser Tyr Arg Phe Ser Gly Val Pro
 50                  55                  60

Asp Arg Phe Ser Gly Ser Gly Ser Gly Thr Gly Phe Thr Leu Lys Ile
 65                  70                  75                  80

Ser Arg Val Glu Ala Glu Asp Val Gly Val Tyr Tyr Cys Phe Gln Ala
                 85                  90                  95

Ser His Val Pro Tyr Thr Phe Gly Gly Gly Thr Lys Leu Glu Ile Lys
            100                 105                 110

<210> SEQ ID NO 32
<211> LENGTH: 100
<212> TYPE: PRT
<213> ORGANISM: Homo sapiens

<400> SEQUENCE: 32
```

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro
            100

<210> SEQ ID NO 33
<211> LENGTH: 112
<212> TYPE: PRT
<213> ORGANISM: Artificial
<220> FEATURE:
<223> OTHER INFORMATION: Synthesized

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Val Tyr Ala Pro Lys Phe
    50                  55                  60

Gln Gly Lys Ala Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Ile Leu Asp Phe Trp Gly Gln Gly Thr Leu Val Thr Val Ser Ser
            100                 105                 110

<210> SEQ ID NO 34
<211> LENGTH: 112
<212> TYPE: PRT
<213> ORGANISM: Artificial
<220> FEATURE:
<223> OTHER INFORMATION: Synthesized

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Glu Trp Ile
        35                  40                  45

Gly Trp Ile Asp Pro Glu Asn Gly Asp Thr Val Tyr Ala Pro Lys Phe
    50                  55                  60

Gln Gly Lys Ala Thr Met Thr Ser Asp Thr Ser Thr Ser Thr Ala Tyr
65                  70                  75                  80

Met Glu Leu Ser Ser Leu Arg Ser Glu Asp Thr Ala Val Tyr Tyr Cys

```
                85                  90                  95

Ser Pro Leu Asp Phe Trp Gly Gln Gly Thr Leu Val Thr Val Ser Ser
            100                 105                 110

<210> SEQ ID NO 35
<211> LENGTH: 112
<212> TYPE: PRT
<213> ORGANISM: Artificial
<220> FEATURE:
<223> OTHER INFORMATION: Synthesized

<400> SEQUENCE: 35

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Glu Trp Ile
        35                  40                  45

Gly Trp Ile Asp Pro Glu Asn Gly Asp Thr Val Tyr Ala Pro Lys Phe
    50                  55                  60

Gln Gly Lys Ala Thr Met Thr Ser Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Pro Leu Asp Phe Trp Gly Gln Gly Thr Leu Val Thr Val Ser Ser
            100                 105                 110

<210> SEQ ID NO 36
<211> LENGTH: 112
<212> TYPE: PRT
<213> ORGANISM: Artificial
<220> FEATURE:
<223> OTHER INFORMATION: Synthesized

<400> SEQUENCE: 36

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Asp Trp Ile
        35                  40                  45

Gly Trp Ile Asp Pro Glu Asn Gly Asp Thr Val Tyr Ala Pro Lys Phe
    50                  55                  60

Gln Gly Lys Ala Thr Met Thr Ser Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Pro Leu Asp Phe Trp Gly Gln Gly Thr Leu Val Thr Val Ser Ser
            100                 105                 110

<210> SEQ ID NO 37
<211> LENGTH: 112
<212> TYPE: PRT
<213> ORGANISM: Artificial
<220> FEATURE:
<223> OTHER INFORMATION: Synthesized

<400> SEQUENCE: 37

Glu Val Gln Leu Val Gln Ser Gly Ala Glu Leu Val Lys Pro Gly Ala
1               5                   10                  15
```

```
Ser Val Arg Leu Ser Cys Lys Ala Ser Gly Phe Asn Ile Lys Asp Tyr
            20                  25                  30

Tyr Met His Trp Val Arg Gln Ala Pro Gly Gln Gly Leu Asp Trp Ile
        35                  40                  45

Gly Trp Ile Asp Pro Glu Asn Gly Asp Thr Val Tyr Ala Pro Lys Phe
50                      55                  60

Gln Gly Lys Ala Thr Met Thr Ser Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Ser Pro Leu Asp Phe Trp Gly Gln Gly Thr Leu Val Thr Val Ser Ser
            100                 105                 110

<210> SEQ ID NO 38
<211> LENGTH: 112
<212> TYPE: PRT
<213> ORGANISM: Artificial
<220> FEATURE:
<223> OTHER INFORMATION: Synthesized

<400> SEQUENCE: 38

Glu Val Gln Leu Val Gln Ser Gly Ala Glu Leu Val Lys Pro Gly Ala
1               5                   10                  15

Ser Val Arg Leu Ser Cys Ala Ser Gly Phe Asn Ile Lys Asp Tyr
            20                  25                  30

Tyr Met His Trp Val Arg Gln Ala Pro Gly Gln Gly Leu Asp Trp Ile
        35                  40                  45

Gly Trp Ile Asp Pro Glu Asn Gly Asp Thr Val Tyr Ala Pro Lys Phe
50                      55                  60

Gln Gly Lys Ala Thr Met Thr Ser Asp Thr Ser Thr Asn Thr Ala Tyr
65                  70                  75                  80

Leu Glu Leu Ser Ser Leu Arg Ser Glu Asp Thr Ala Val Tyr Tyr Cys
                85                  90                  95

Ser Pro Leu Asp Phe Trp Gly Gln Gly Thr Leu Val Thr Val Ser Ser
            100                 105                 110

<210> SEQ ID NO 39
<211> LENGTH: 112
<212> TYPE: PRT
<213> ORGANISM: Artificial
<220> FEATURE:
<223> OTHER INFORMATION: Synthesized

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Val Tyr Ala Pro Lys Phe
50                      55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Asp Phe Trp Gly Gln Gly Thr Leu Val Thr Val Ser Ser
```

```
<210> SEQ ID NO 40
<211> LENGTH: 112
<212> TYPE: PRT
<213> ORGANISM: Artificial
<220> FEATURE:
<223> OTHER INFORMATION: Synthesized

<400> SEQUENCE: 40

Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Asp Trp Ile
        35                  40                  45

Gly Trp Ile Asp Pro Glu Asn Gly Asp Thr Val Tyr Ala Pro Lys Phe
    50                  55                  60

Gln Gly Arg Val Thr Met Thr Ser Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ser Pro Leu Asp Phe Trp Gly Gln Gly Thr Leu Val Thr Val Ser Ser
            100                 105                 110

<210> SEQ ID NO 41
<211> LENGTH: 112
<212> TYPE: PRT
<213> ORGANISM: Artificial
<220> FEATURE:
<223> OTHER INFORMATION: Synthesized

<400> SEQUENCE: 41

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Tyr Leu Gln Lys Pro Gly Gln Ser
        35                  40                  45

Pro Lys Leu Leu Ile Tyr Leu Val Ser Lys Leu Asp Ser Gly Val Pro
    50                  55                  60

Asp Arg Phe Ser Gly Ser Gly Ser Gly Thr Gly Phe Thr Leu Lys Ile
65                  70                  75                  80

Ser Arg Val Glu Ala Glu Asp Val Gly Val Tyr Tyr Cys Trp Gln Gly
                85                  90                  95

Thr Leu Phe Pro Tyr Thr Phe Gly Gly Gly Thr Lys Leu Glu Ile Lys
            100                 105                 110

<210> SEQ ID NO 42
<211> LENGTH: 112
<212> TYPE: PRT
<213> ORGANISM: Artificial
<220> FEATURE:
<223> OTHER INFORMATION: Synthesized

<400> SEQUENCE: 42

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30
```

```
Asp Gly Lys Thr Tyr Leu Asn Trp Leu Leu Gln Lys Pro Gly Gln Ser
            35                  40                  45

Pro Lys Arg Leu Ile Tyr Leu Val Ser Lys Leu Asp Ser Gly Val Pro
 50                  55                  60

Asp Arg Phe Ser Gly Ser Gly Ser Gly Thr Gly Phe Thr Leu Lys Ile
 65                  70                  75                  80

Ser Arg Val Glu Ala Glu Asp Val Gly Val Tyr Tyr Cys Trp Gln Gly
                 85                  90                  95

Thr Leu Phe Pro Tyr Thr Phe Gly Gly Gly Thr Lys Leu Glu Ile Lys
            100                 105                 110
```

<210> SEQ ID NO 43
<211> LENGTH: 112
<212> TYPE: PRT
<213> ORGANISM: Artificial
<220> FEATURE:
<223> OTHER INFORMATION: Synthesized

<400> SEQUENCE: 43

```
Asp Val Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
            35                  40                  45

Pro Lys Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr Leu Phe Pro Tyr Thr Phe Gly Gly Gly Thr Lys Leu Glu Ile Lys
            100                 105                 110
```

<210> SEQ ID NO 44
<211> LENGTH: 112
<212> TYPE: PRT
<213> ORGANISM: Artificial
<220> FEATURE:
<223> OTHER INFORMATION: Synthesized

<400> SEQUENCE: 44

```
Asp Val Val Met Thr Gln Ser Pro Leu Ser Leu Ser Val Thr Pro Gly
 1               5                  10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
            35                  40                  45

Pro Lys Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr Leu Phe Pro Tyr Thr Phe Gly Gly Gly Thr Lys Leu Glu Ile Lys
            100                 105                 110
```

-continued

```
<210> SEQ ID NO 45
<211> LENGTH: 112
<212> TYPE: PRT
<213> ORGANISM: Artificial
<220> FEATURE:
<223> OTHER INFORMATION: Synthesized

<400> SEQUENCE: 45

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr Leu Phe Pro Tyr Thr Phe Gly Gly Gly Thr Lys Leu Glu Ile Lys
            100                 105                 110

<210> SEQ ID NO 46
<211> LENGTH: 112
<212> TYPE: PRT
<213> ORGANISM: Artificial
<220> FEATURE:
<223> OTHER INFORMATION: Synthesized

<400> SEQUENCE: 46

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr Leu Phe Pro Tyr Thr Phe Gly Gly Gly Thr Lys Leu Glu Ile Lys
            100                 105                 110

<210> SEQ ID NO 47
<211> LENGTH: 131
<212> TYPE: PRT
<213> ORGANISM: Artificial
<220> FEATURE:
<223> OTHER INFORMATION: Synthesized

<400> SEQUENCE: 47

Met Lys Cys Ser Trp Val Ile Phe Phe Leu Met Ala Val Val Ile Gly
1               5                   10                  15

Ile Asn Ser Glu Val Gln Leu Gln Gln Ser Gly Ala Glu Leu Val Arg
            20                  25                  30

Ser Gly Ala Ser Val Arg Leu Ser Cys Thr Ala Ser Gly Phe Asn Ile
        35                  40                  45
```

```
Lys Asp Tyr Tyr Met His Trp Val Arg Gln Arg Pro Glu Gln Gly Leu
     50                   55                   60

Glu Trp Ile Gly Trp Ile Asp Pro Glu Asn Gly Asp Thr Val Tyr Ala
 65                   70                   75                   80

Pro Lys Phe Gln Gly Lys Ala Thr Met Thr Ser Asp Thr Ser Ser Asn
                 85                   90                   95

Thr Ala Tyr Leu His Leu Ser Ser Leu Thr Ser Glu Asp Thr Ala Val
                100                  105                  110

Tyr Tyr Cys Ser Pro Leu Asp Phe Trp Gly Gln Gly Thr Thr Leu Thr
                115                  120                  125

Val Ser Ser
    130
```

<210> SEQ ID NO 48
<211> LENGTH: 132
<212> TYPE: PRT
<213> ORGANISM: Artificial
<220> FEATURE:
<223> OTHER INFORMATION: Synthesized

<400> SEQUENCE: 48

```
Met Met Ser Pro Ala Gln Phe Leu Phe Leu Leu Val Leu Trp Ile Arg
  1               5                  10                  15

Glu Thr Asn Gly Asp Val Val Met Thr Gln Thr Pro Leu Thr Leu Ser
                 20                  25                  30

Val Thr Ile Gly Gln Pro Ala Ser Ile Ser Cys Lys Ser Ser Gln Ser
             35                  40                  45

Leu Leu Asp Ser Asp Gly Lys Thr Tyr Leu Asn Trp Leu Leu Gln Arg
 50                  55                  60

Pro Gly Gln Ser Pro Lys Arg Leu Ile Tyr Leu Val Ser Lys Leu Asp
 65                  70                  75                  80

Ser Gly Val Pro Asp Arg Phe Thr Gly Ser Gly Ser Gly Thr Asp Phe
                 85                  90                  95

Thr Leu Lys Ile Arg Arg Val Glu Ala Glu Asp Leu Gly Val Tyr Tyr
                100                  105                  110

Cys Trp Gln Gly Thr Leu Phe Pro Tyr Thr Phe Gly Gly Gly Thr Lys
                115                  120                  125

Leu Glu Ile Lys
    130
```

<210> SEQ ID NO 49
<211> LENGTH: 131
<212> TYPE: PRT
<213> ORGANISM: Artificial
<220> FEATURE:
<223> OTHER INFORMATION: Synthesized

<400> SEQUENCE: 49

```
Met Lys Cys Ser Trp Val Ile Phe Phe Leu Met Ala Val Val Ile Gly
  1               5                  10                  15

Ile Asn Ser Glu Val Gln Leu Gln Gln Ser Gly Ala Glu Leu Val Arg
                 20                  25                  30

Ser Gly Ala Ser Val Lys Leu Ser Cys Thr Ala Ser Gly Leu Asn Ile
             35                  40                  45

Lys Asp Tyr Tyr Ile His Trp Val Lys Gln Arg Pro Glu Gln Gly Leu
 50                  55                  60

Glu Trp Ile Gly Trp Ile Asp Pro Glu Asn Asp Asp Thr Glu Tyr Ala
```

```
            65                  70                  75                  80
Pro Lys Phe Gln Gly Arg Ala Thr Leu Thr Thr Asp Thr Ser Ser Asn
                    85                  90                  95

Thr Ala Tyr Leu Gln Leu Ser Ser Leu Thr Ser Glu Asp Thr Ala Val
                100                 105                 110

Tyr Tyr Cys Thr Pro Leu Asp Tyr Trp Gly Gln Gly Thr Ser Val Thr
                115                 120                 125

Val Ser Ser
    130

<210> SEQ ID NO 50
<211> LENGTH: 133
<212> TYPE: PRT
<213> ORGANISM: Artificial
<220> FEATURE:
<223> OTHER INFORMATION: Synthesized

<400> SEQUENCE: 50

Met Met Ser Pro Ala Gln Phe Leu Phe Leu Leu Val Leu Trp Ile Arg
1               5                   10                  15

Glu Thr Asn Gly Asp Val Val Met Thr Gln Thr Pro Leu Thr Leu Ser
                20                  25                  30

Val Thr Ile Gly Gln Pro Ala Ser Ile Ser Cys Lys Ser Ser Gln Ser
            35                  40                  45

Leu Leu Asp Ser Asp Gly Lys Thr Tyr Leu Asn Trp Leu Leu Gln Arg
        50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
                100                 105                 110

Cys Trp Gln Gly Thr His Phe Pro Tyr Thr Phe Gly Gly Gly Thr Lys
            115                 120                 125

Leu Glu Ile Lys Arg
    130

<210> SEQ ID NO 51
<211> LENGTH: 131
<212> TYPE: PRT
<213> ORGANISM: Artificial
<220> FEATURE:
<223> OTHER INFORMATION: Synthesized

<400> SEQUENCE: 51

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Arg
                20                  25                  30

Pro Gly Ala Leu Val Lys Leu Ser Cys Lys Ala Ser Gly Phe Asn Ile
            35                  40                  45

Lys Asp Tyr Tyr Ile His Trp Val Lys Gln Arg Pro Glu Gln Gly Leu
        50                  55                  60

Glu Trp Ile Gly Trp Ile Asp Pro Glu Asn Gly Glu Thr Val Tyr Asp
65                  70                  75                  80

Pro Lys Phe Gln Gly Lys Ala Ser Ile Thr Ser Asp Thr Ser Ser Asn
                85                  90                  95
```

```
Thr Ala Tyr Leu Gln Leu Arg Ser Leu Thr Ser Glu Asp Thr Ala Val
            100                 105                 110

Tyr Tyr Ser Thr Ser Leu Asp Phe Trp Gly Gln Gly Thr Ser Val Thr
        115                 120                 125

Val Ser Ser
    130

<210> SEQ ID NO 52
<211> LENGTH: 133
<212> TYPE: PRT
<213> ORGANISM: Artificial
<220> FEATURE:
<223> OTHER INFORMATION: Synthesized

<400> SEQUENCE: 52

Met Met Ser Pro Ala Gln Phe Leu Phe Leu Leu Val Leu Trp Ile Arg
1               5                   10                  15

Glu Thr Asn Gly Asp Val Val Met Thr Gln Thr Pro Leu Thr Leu Ser
            20                  25                  30

Val Thr Ile Gly Gln Pro Ala Ser Ile Ser Cys Lys Ser Thr Gln Ser
        35                  40                  45

Leu Leu Asp Ser Asp Gly Lys Thr Tyr Leu Asn Trp Leu Leu Gln Arg
50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Trp Gln Gly Thr His Phe Pro Tyr Thr Phe Gly Gly Gly Thr Lys
        115                 120                 125

Leu Glu Ile Lys Arg
    130

<210> SEQ ID NO 53
<211> LENGTH: 131
<212> TYPE: PRT
<213> ORGANISM: Artificial
<220> FEATURE:
<223> OTHER INFORMATION: Synthesized

<400> SEQUENCE: 53

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Arg
            20                  25                  30

Pro Gly Ala Leu Val Lys Leu Ser Cys Lys Ala Ser Gly Phe Asn Ile
        35                  40                  45

Lys Asp Tyr Tyr Ile His Trp Val Lys Gln Arg Pro Glu Gln Gly Leu
50                  55                  60

Glu Trp Ile Gly Trp Ile Asp Pro Glu Asn Gly Asp Thr Val Tyr Asp
65                  70                  75                  80

Pro Gln Phe Gln Asp Lys Ala Asn Ile Thr Ala Asp Thr Ser Ser Asn
                85                  90                  95

Thr Ala Tyr Leu Gln Leu Ser Ser Leu Thr Ser Glu Gly Thr Ala Val
            100                 105                 110

Tyr Tyr Cys Ser Thr Leu Asp Phe Trp Gly Gln Gly Thr Thr Leu Thr
        115                 120                 125
```

Val Ser Ser
    130

<210> SEQ ID NO 54
<211> LENGTH: 133
<212> TYPE: PRT
<213> ORGANISM: Artificial
<220> FEATURE:
<223> OTHER INFORMATION: Synthesized

<400> SEQUENCE: 54

Met Met Ser Pro Ala Gln Phe Leu Phe Leu Leu Val Leu Trp Asn Arg
1               5                   10                  15

Glu Thr Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Asp Ser Asp Gly Lys Thr Tyr Leu Asn Trp Leu Leu Gln Arg
    50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Trp Gln Gly Thr His Phe Pro Cys Thr Phe Gly Gly Gly Thr Lys
        115                 120                 125

Leu Glu Ile Lys Arg
    130

<210> SEQ ID NO 55
<211> LENGTH: 112
<212> TYPE: PRT
<213> ORGANISM: Artificial
<220> FEATURE:
<223> OTHER INFORMATION: Synthesized

<400> SEQUENCE: 55

Glu Val Gln Leu Gln Gln Ser Gly Ala Asp Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Leu His Trp Val Arg Gln Arg Pro Glu Gln Gly Leu Glu Trp Ile
        35                  40                  45

Gly Trp Ile Asp Pro Glu Asn Gly Asp Thr Val Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Gly Ser Leu Thr Ser Glu Asp Thr Ala Val Tyr Phe Cys
                85                  90                  95

Ser Thr Leu Asp Phe Trp Gly Gln Gly Thr Thr Leu Thr Val Ser Ser
            100                 105                 110

<210> SEQ ID NO 56
<211> LENGTH: 10
<212> TYPE: PRT
<213> ORGANISM: Artificial
<220> FEATURE:
<223> OTHER INFORMATION: Synthesized

<400> SEQUENCE: 56

Gly Phe Asn Ile Lys Asp Tyr Tyr Leu His
1               5                   10

<210> SEQ ID NO 57
<211> LENGTH: 17
<212> TYPE: PRT
<213> ORGANISM: Artificial
<220> FEATURE:
<223> OTHER INFORMATION: Synthesized

<400> SEQUENCE: 57

Trp Ile Asp Pro Glu Asn Gly Asp Thr Val Tyr Asp Pro Lys Phe Gln
1               5                   10                  15

Gly

<210> SEQ ID NO 58
<211> LENGTH: 3
<212> TYPE: PRT
<213> ORGANISM: Artificial Sequence
<220> FEATURE:
<223> OTHER INFORMATION: Synthesized

<400> SEQUENCE: 58

Leu Asp Phe
1

<210> SEQ ID NO 59
<211> LENGTH: 113
<212> TYPE: PRT
<213> ORGANISM: Artificial
<220> FEATURE:
<223> OTHER INFORMATION: Synthesized

<400> SEQUENCE: 59

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

Arg

<210> SEQ ID NO 60
<211> LENGTH: 16
<212> TYPE: PRT
<213> ORGANISM: Artificial
<220> FEATURE:
<223> OTHER INFORMATION: Synthesized

<400> SEQUENCE: 60

Lys Ser Ser Gln Ser Leu Leu Asp Ser Asp Gly Lys Thr Tyr Leu Asn
1               5                   10                  15

<210> SEQ ID NO 61
<211> LENGTH: 7
<212> TYPE: PRT
<213> ORGANISM: Artificial
<220> FEATURE:
<223> OTHER INFORMATION: Synthesized

<400> SEQUENCE: 61

Leu Val Ser Lys Leu Asp Ser
1               5

<210> SEQ ID NO 62
<211> LENGTH: 9
<212> TYPE: PRT
<213> ORGANISM: Artificial
<220> FEATURE:
<223> OTHER INFORMATION: Synthesized

<400> SEQUENCE: 62

Trp Gln Gly Thr His Phe Pro Tyr Thr
1               5

<210> SEQ ID NO 63
<211> LENGTH: 112
<212> TYPE: PRT
<213> ORGANISM: Artificial
<220> FEATURE:
<223> OTHER INFORMATION: Synthesized

<400> SEQUENCE: 63

Glu Val Gln Leu Gln Gln Ser Gly Ala Glu Leu Val Arg Ser Gly Ala
1               5                   10                  15

Ser Val Lys Leu Ser Cys Thr Ala Ser Gly Leu Asn Ile Lys Asp Tyr
            20                  25                  30

Tyr Ile His Trp Val Lys Gln Arg Pro Glu Gln Gly Leu Glu Trp Ile
        35                  40                  45

Gly Trp Ile Asp Pro Glu Asn Asp Asp Thr Glu Tyr Ala Pro Lys Phe
    50                  55                  60

Gln Gly Arg Ala Thr Leu Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Pro Leu Asp Tyr Trp Gly Gln Gly Thr Ser Val Thr Val Ser Ser
            100                 105                 110

<210> SEQ ID NO 64
<211> LENGTH: 112
<212> TYPE: PRT
<213> ORGANISM: Artificial
<220> FEATURE:
<223> OTHER INFORMATION: Synthesized

<400> SEQUENCE: 64

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

```
Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr His Phe Pro Tyr Thr Phe Gly Gly Gly Thr Lys Leu Glu Ile Lys
            100                 105                 110

<210> SEQ ID NO 65
<211> LENGTH: 10
<212> TYPE: PRT
<213> ORGANISM: Artificial
<220> FEATURE:
<223> OTHER INFORMATION: Synthesized

<400> SEQUENCE: 65

Gly Leu Asn Ile Lys Asp Tyr Tyr Ile His
1               5                   10

<210> SEQ ID NO 66
<211> LENGTH: 17
<212> TYPE: PRT
<213> ORGANISM: Artificial
<220> FEATURE:
<223> OTHER INFORMATION: Synthesized

<400> SEQUENCE: 66

Trp Ile Asp Pro Glu Asn Asp Asp Thr Glu Tyr Ala Pro Lys Phe Gln
1               5                   10                  15

Gly

<210> SEQ ID NO 67
<211> LENGTH: 3
<212> TYPE: PRT
<213> ORGANISM: Artificial Sequence
<220> FEATURE:
<223> OTHER INFORMATION: Synthesized

<400> SEQUENCE: 67

Leu Asp Tyr
1

<210> SEQ ID NO 68
<211> LENGTH: 16
<212> TYPE: PRT
<213> ORGANISM: Artificial
<220> FEATURE:
<223> OTHER INFORMATION: Synthesized

<400> SEQUENCE: 68

Lys Ser Ser Gln Ser Leu Leu Asp Ser Asp Gly Lys Thr Tyr Leu Asn
1               5                   10                  15

<210> SEQ ID NO 69
<211> LENGTH: 7
<212> TYPE: PRT
<213> ORGANISM: Artificial
<220> FEATURE:
<223> OTHER INFORMATION: Synthesized

<400> SEQUENCE: 69

Leu Val Ser Lys Leu Asp Ser
1               5

<210> SEQ ID NO 70
```

```
<211> LENGTH: 9
<212> TYPE: PRT
<213> ORGANISM: Artificial
<220> FEATURE:
<223> OTHER INFORMATION: Synthesized

<400> SEQUENCE: 70

Trp Gln Gly Thr His Phe Pro Tyr Thr
 1               5

<210> SEQ ID NO 71
<211> LENGTH: 5
<212> TYPE: PRT
<213> ORGANISM: Artificial
<220> FEATURE:
<223> OTHER INFORMATION: Synthesized

<400> SEQUENCE: 71

Asp Tyr Tyr Ile His
 1               5

<210> SEQ ID NO 72
<211> LENGTH: 7
<212> TYPE: PRT
<213> ORGANISM: Artificial
<220> FEATURE:
<223> OTHER INFORMATION: Synthesized

<400> SEQUENCE: 72

Gly Leu Asn Ile Lys Asp Tyr
 1               5

<210> SEQ ID NO 73
<211> LENGTH: 6
<212> TYPE: PRT
<213> ORGANISM: Artificial
<220> FEATURE:
<223> OTHER INFORMATION: Synthesized

<400> SEQUENCE: 73

Lys Asp Tyr Tyr Ile His
 1               5

<210> SEQ ID NO 74
<211> LENGTH: 6
<212> TYPE: PRT
<213> ORGANISM: Artificial
<220> FEATURE:
<223> OTHER INFORMATION: Synthesized

<400> SEQUENCE: 74

Asp Pro Glu Asn Asp Asp
 1               5

<210> SEQ ID NO 75
<211> LENGTH: 10
<212> TYPE: PRT
<213> ORGANISM: Artificial
<220> FEATURE:
<223> OTHER INFORMATION: Synthesized

<400> SEQUENCE: 75

Trp Ile Asp Pro Glu Asn Asp Asp Thr Glu
 1               5                  10

<210> SEQ ID NO 76
<211> LENGTH: 13
```

```
<212> TYPE: PRT
<213> ORGANISM: Artificial
<220> FEATURE:
<223> OTHER INFORMATION: Synthesized

<400> SEQUENCE: 76

Trp Ile Gly Trp Ile Asp Pro Glu Asn Asp Asp Thr Glu
1               5                   10

<210> SEQ ID NO 77
<211> LENGTH: 4
<212> TYPE: PRT
<213> ORGANISM: Artificial
<220> FEATURE:
<223> OTHER INFORMATION: Synthesized

<400> SEQUENCE: 77

Thr Pro Leu Asp
1

<210> SEQ ID NO 78
<211> LENGTH: 7
<212> TYPE: PRT
<213> ORGANISM: Artificial
<220> FEATURE:
<223> OTHER INFORMATION: Synthesized

<400> SEQUENCE: 78

Lys Thr Tyr Leu Asn Trp Leu
1               5

<210> SEQ ID NO 79
<211> LENGTH: 10
<212> TYPE: PRT
<213> ORGANISM: Artificial
<220> FEATURE:
<223> OTHER INFORMATION: Synthesized

<400> SEQUENCE: 79

Arg Leu Ile Tyr Leu Val Ser Lys Leu Asp
1               5                   10

<210> SEQ ID NO 80
<211> LENGTH: 8
<212> TYPE: PRT
<213> ORGANISM: Artificial
<220> FEATURE:
<223> OTHER INFORMATION: Synthesized

<400> SEQUENCE: 80

Trp Gln Gly Thr His Phe Pro Tyr
1               5

<210> SEQ ID NO 81
<211> LENGTH: 117
<212> TYPE: PRT
<213> ORGANISM: Homo sapiens

<400> SEQUENCE: 81

Gln Val Gln Leu Gln Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45
```

Gly Trp Ile Asn Pro Asn Ser Gly Asp Thr Asn Tyr Ala Gln Lys Phe
            50                  55                  60

Gln Gly Arg Val Thr Thr Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Ala Ala Arg Pro Leu Asp Tyr Trp Gly Gln Gly Thr Leu
            100                 105                 110

Val Thr Val Ser Ser
            115

<210> SEQ ID NO 82
<211> LENGTH: 125
<212> TYPE: PRT
<213> ORGANISM: Homo sapiens

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Arg Arg Gly Tyr Tyr Asp Phe Trp Ser Gly Ser Pro Glu
            100                 105                 110

Asp Tyr Trp Gly Gln Gly Thr Leu Val Thr Val Ser Ser
            115                 120                 125

<210> SEQ ID NO 83
<211> LENGTH: 112
<212> TYPE: PRT
<213> ORGANISM: Homo sapiens

<400> SEQUENCE: 83

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Arg Pro Leu Thr Phe Gly Gly Gly Thr Lys Val Glu Ile Lys
            100                 105                 110

<210> SEQ ID NO 84
<211> LENGTH: 112

<212> TYPE: PRT
<213> ORGANISM: Homo sapiens

<400> SEQUENCE: 84

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gly Gly Thr Lys Val Glu Ile Lys
            100                 105                 110
```

<210> SEQ ID NO 85
<211> LENGTH: 112
<212> TYPE: PRT
<213> ORGANISM: Artificial
<220> FEATURE:
<223> OTHER INFORMATION: Synthesized

<400> SEQUENCE: 85

```
Gln Val Gln Leu Gln Glu Ser Gly Ala Glu Val Lys Lys Pro Gly Ala
1               5                   10                  15

Ser Val Lys Val Ser Cys Lys Ala Ser Gly Leu Asn Ile Lys Asp Tyr
            20                  25                  30

Tyr Ile His Trp Val Arg Gln Ala Pro Gly Gln Gly Leu Glu Trp Met
        35                  40                  45

Gly Trp Ile Asp Pro Glu Asn Asp Asp Thr Glu Tyr Ala Pro Lys Phe
    50                  55                  60

Gln Gly Arg Val Thr Thr Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Leu Asp Tyr Trp Gly Gln Gly Thr Leu Val Thr Val Ser Ser
            100                 105                 110
```

<210> SEQ ID NO 86
<211> LENGTH: 112
<212> TYPE: PRT
<213> ORGANISM: Artificial
<220> FEATURE:
<223> OTHER INFORMATION: Synthesized

<400> SEQUENCE: 86

```
Gln Val Gln Leu Gln Glu Ser Gly Ala Glu Val Lys Lys Pro Gly Ala
1               5                   10                  15

Ser Val Lys Val Ser Cys Lys Ala Ser Gly Leu Asn Ile Lys Asp Tyr
            20                  25                  30

Tyr Ile His Trp Val Arg Gln Ala Pro Gly Gln Gly Leu Glu Trp Ile
        35                  40                  45

Gly Trp Ile Asp Pro Glu Asn Asp Asp Thr Glu Tyr Ala Pro Lys Phe
    50                  55                  60
```

```
Gln Gly Arg Val Thr Thr Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Leu Asp Tyr Trp Gly Gln Gly Thr Leu Val Thr Val Ser Ser
            100                 105                 110
```

<210> SEQ ID NO 87
<211> LENGTH: 112
<212> TYPE: PRT
<213> ORGANISM: Artificial
<220> FEATURE:
<223> OTHER INFORMATION: Synthesized

<400> SEQUENCE: 87

```
Gln Val Gln Leu Gln Glu Ser Gly Ala Glu Val Lys Lys Pro Gly Gly
1               5                   10                  15

Ser Val Lys Val Ser Cys Lys Ala Ser Gly Leu Asn Ile Lys Asp Tyr
                20                  25                  30

Tyr Ile His Trp Val Arg Gln Ala Pro Gly Gln Gly Leu Glu Trp Ile
            35                  40                  45

Gly Trp Ile Asp Pro Glu Asn Asp Asp Thr Glu Tyr Ala Pro Lys Phe
50                  55                  60

Gln Gly Arg Val Thr Ile Thr Arg Asp Thr Ser Ile Ser Thr Ala Tyr
65                  70                  75                  80

Leu Glu Leu Ser Arg Leu Arg Ser Asp Thr Ala Val Tyr Tyr Cys
                85                  90                  95

Ala Arg Leu Asp Tyr Trp Gly Gln Gly Thr Leu Val Thr Val Ser Ser
            100                 105                 110
```

<210> SEQ ID NO 88
<211> LENGTH: 112
<212> TYPE: PRT
<213> ORGANISM: Artificial
<220> FEATURE:
<223> OTHER INFORMATION: Synthesized

<400> SEQUENCE: 88

```
Asp Ile Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
                20                  25                  30

Asp Gly Lys Thr Tyr Leu Asn Trp Phe Gln Gln Arg Pro Gly Gln Ser
            35                  40                  45

Pro Arg Arg Leu Ile Tyr Leu Val Ser Lys Leu Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Val Glu Ile Lys
            100                 105                 110
```

<210> SEQ ID NO 89
<211> LENGTH: 112
<212> TYPE: PRT
<213> ORGANISM: Artificial
<220> FEATURE:
<223> OTHER INFORMATION: Synthesized

<400> SEQUENCE: 89

Asp Ile Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Leu Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Val Glu Ile Lys
            100                 105                 110

<210> SEQ ID NO 90
<211> LENGTH: 112
<212> TYPE: PRT
<213> ORGANISM: Artificial
<220> FEATURE:
<223> OTHER INFORMATION: Synthesized

<400> SEQUENCE: 90

Asp Ile Val Met Thr Gln Ser Pro Leu Ser Val Thr Leu Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Leu Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Val Glu Ile Lys
            100                 105                 110

<210> SEQ ID NO 91
<211> LENGTH: 112
<212> TYPE: PRT
<213> ORGANISM: Artificial
<220> FEATURE:
<223> OTHER INFORMATION: Synthesized

<400> SEQUENCE: 91

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Ile His Trp Val Lys Gln Arg Pro Glu Gln Gly Leu Glu Trp Ile
        35                  40                  45

Gly Trp Ile Asp Pro Glu Asn Gly Asp Thr Val Tyr Asp Pro Gln Phe
    50                  55                  60

Gln Asp Lys Ala Asn Ile Thr Ala Asp Thr Ser Ser Asn Thr Ala Tyr
65                  70                  75                  80

```
Leu Gln Leu Ser Ser Leu Thr Ser Glu Gly Thr Ala Val Tyr Tyr Cys
                85                  90                  95

Ser Thr Leu Asp Phe Trp Gly Gln Gly Thr Thr Leu Thr Val Ser Ser
            100                 105                 110
```

<210> SEQ ID NO 92
<211> LENGTH: 112
<212> TYPE: PRT
<213> ORGANISM: Artificial
<220> FEATURE:
<223> OTHER INFORMATION: Synthesized

<400> SEQUENCE: 92

```
Asp Val Val Met Thr Gln Thr Pro Leu Thr Leu Ser Val Thr Ile Gly
1               5                  10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Cys Thr Phe Gly Gly Gly Thr Lys Leu Glu Ile Lys
            100                 105                 110
```

<210> SEQ ID NO 93
<211> LENGTH: 10
<212> TYPE: PRT
<213> ORGANISM: Artificial
<220> FEATURE:
<223> OTHER INFORMATION: Synthesized

<400> SEQUENCE: 93

```
Gly Phe Asn Ile Lys Asp Tyr Tyr Ile His
1               5                   10
```

<210> SEQ ID NO 94
<211> LENGTH: 17
<212> TYPE: PRT
<213> ORGANISM: Artificial
<220> FEATURE:
<223> OTHER INFORMATION: Synthesized

<400> SEQUENCE: 94

```
Trp Ile Asp Pro Glu Asn Gly Asp Thr Val Tyr Asp Pro Gln Phe Gln
1               5                   10                  15

Asp
```

<210> SEQ ID NO 95
<211> LENGTH: 3
<212> TYPE: PRT
<213> ORGANISM: Artificial Sequence
<220> FEATURE:
<223> OTHER INFORMATION: Synthesized

<400> SEQUENCE: 95

```
Leu Asp Phe
1
```

```
<210> SEQ ID NO 96
<211> LENGTH: 16
<212> TYPE: PRT
<213> ORGANISM: Artificial
<220> FEATURE:
<223> OTHER INFORMATION: Synthesized

<400> SEQUENCE: 96

Lys Ser Ser Gln Ser Leu Leu Asp Ser Asp Gly Lys Thr Tyr Leu Asn
1               5                   10                  15

<210> SEQ ID NO 97
<211> LENGTH: 7
<212> TYPE: PRT
<213> ORGANISM: Artificial
<220> FEATURE:
<223> OTHER INFORMATION: Synthesized

<400> SEQUENCE: 97

Leu Val Ser Lys Leu Asp Ser
1               5

<210> SEQ ID NO 98
<211> LENGTH: 9
<212> TYPE: PRT
<213> ORGANISM: Artificial
<220> FEATURE:
<223> OTHER INFORMATION: Synthesized

<400> SEQUENCE: 98

Trp Gln Gly Thr His Phe Pro Cys Thr
1               5

<210> SEQ ID NO 99
<211> LENGTH: 5
<212> TYPE: PRT
<213> ORGANISM: Artificial
<220> FEATURE:
<223> OTHER INFORMATION: Synthesized

<400> SEQUENCE: 99

Asp Tyr Tyr Ile His
1               5

<210> SEQ ID NO 100
<211> LENGTH: 7
<212> TYPE: PRT
<213> ORGANISM: Artificial
<220> FEATURE:
<223> OTHER INFORMATION: Synthesized

<400> SEQUENCE: 100

Gly Phe Asn Ile Lys Asp Tyr
1               5

<210> SEQ ID NO 101
<211> LENGTH: 6
<212> TYPE: PRT
<213> ORGANISM: Artificial
<220> FEATURE:
<223> OTHER INFORMATION: Synthesized

<400> SEQUENCE: 101

Lys Asp Tyr Tyr Ile His
1               5

<210> SEQ ID NO 102
```

```
<211> LENGTH: 6
<212> TYPE: PRT
<213> ORGANISM: Artificial
<220> FEATURE:
<223> OTHER INFORMATION: Synthesized

<400> SEQUENCE: 102

Asp Pro Glu Asn Gly Asp
1               5

<210> SEQ ID NO 103
<211> LENGTH: 10
<212> TYPE: PRT
<213> ORGANISM: Artificial
<220> FEATURE:
<223> OTHER INFORMATION: Synthesized

<400> SEQUENCE: 103

Trp Ile Asp Pro Glu Asn Gly Asp Thr Val
1               5                   10

<210> SEQ ID NO 104
<211> LENGTH: 13
<212> TYPE: PRT
<213> ORGANISM: Artificial
<220> FEATURE:
<223> OTHER INFORMATION: Synthesized

<400> SEQUENCE: 104

Trp Ile Gly Trp Ile Asp Pro Glu Asn Gly Asp Thr Val
1               5                   10

<210> SEQ ID NO 105
<211> LENGTH: 4
<212> TYPE: PRT
<213> ORGANISM: Artificial
<220> FEATURE:
<223> OTHER INFORMATION: Synthesized

<400> SEQUENCE: 105

Ser Thr Leu Asp
1

<210> SEQ ID NO 106
<211> LENGTH: 7
<212> TYPE: PRT
<213> ORGANISM: Artificial
<220> FEATURE:
<223> OTHER INFORMATION: Synthesized

<400> SEQUENCE: 106

Lys Thr Tyr Leu Asn Trp Leu
1               5

<210> SEQ ID NO 107
<211> LENGTH: 10
<212> TYPE: PRT
<213> ORGANISM: Artificial
<220> FEATURE:
<223> OTHER INFORMATION: Synthesized

<400> SEQUENCE: 107

Arg Leu Ile Tyr Leu Val Ser Lys Leu Asp
1               5                   10

<210> SEQ ID NO 108
<211> LENGTH: 8
```

```
<212> TYPE: PRT
<213> ORGANISM: Artificial
<220> FEATURE:
<223> OTHER INFORMATION: Synthesized

<400> SEQUENCE: 108

Trp Gln Gly Thr His Phe Pro Cys
1               5

<210> SEQ ID NO 109
<211> LENGTH: 118
<212> TYPE: PRT
<213> ORGANISM: Mus musculus

<400> SEQUENCE: 109

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Lys Ile Asp Pro Ala Asn Gly Asn Thr Lys Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Asn Ser Asn Tyr Trp Phe Asp Phe Asp Tyr Trp Gly Gln Gly Thr
            100                 105                 110

Thr Leu Thr Val Ser Ser
        115

<210> SEQ ID NO 110
<211> LENGTH: 118
<212> TYPE: PRT
<213> ORGANISM: Homo sapiens

<400> SEQUENCE: 110

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Asn
            20                  25                  30

Pro Val Ser Trp Val Arg Gln Ala Pro Gly Gln Gly Leu Glu Trp Met
        35                  40                  45

Gly Gly Ile Ile Pro Phe Ala Gln Lys Val Leu Gly Ala Gln Arg Val
    50                  55                  60

Arg Asp Arg Ile Asn Ile Thr Ala Asp Thr Ser Thr Ser Thr Ala Tyr
65                  70                  75                  80

Met Glu Leu Ser Gly Leu Arg Ser Asp Asp Thr Ala Val Tyr Tyr Cys
                85                  90                  95

Ala Thr Gly Gln Gln Leu Tyr Ser Leu His Tyr Trp Gly Gln Gly Thr
            100                 105                 110

Leu Val Thr Val Ser Ser
        115

<210> SEQ ID NO 111
<211> LENGTH: 112
<212> TYPE: PRT
<213> ORGANISM: Mus musculus
```

<400> SEQUENCE: 111

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Tyr Gln Gly
                85                  90                  95

Ser His Val Pro Tyr Thr Phe Gly Gly Gly Thr Lys Leu Glu Ile Lys
            100                 105                 110

<210> SEQ ID NO 112
<211> LENGTH: 76
<212> TYPE: PRT
<213> ORGANISM: Homo sapiens

<400> SEQUENCE: 112

Asp Val Met Thr Ser Ser Val Thr Gly Ala Ser Ser Cys Arg Ser
1               5                   10                  15

Ser Ser Val Tyr Ser Asp Gly Ser Thr Trp Asn Trp Arg Gly Ser Arg
            20                  25                  30

Arg Tyr Asp Val Ser Thr Arg Asp Ser Gly Val Asp Arg Ser Gly Ser
        35                  40                  45

Gly Ser Gly Thr Asp Thr Lys Ser Arg Val Ala Asp Val Gly Val Tyr
    50                  55                  60

Tyr Cys Met Asp Trp His Thr Gly Gly Thr Lys Lys
65                  70                  75

<210> SEQ ID NO 113
<211> LENGTH: 112
<212> TYPE: PRT
<213> ORGANISM: Artificial
<220> FEATURE:
<223> OTHER INFORMATION: Synthesized

<400> SEQUENCE: 113

Gln Val Gln Leu Gln Gln Ser Gly Ala Glu Val Lys Lys Pro Gly Ser
1               5                   10                  15

Ser Val Lys Val Ser Cys Lys Ala Ser Gly Phe Asn Ile Lys Asp Tyr
            20                  25                  30

Tyr Ile His Trp Val Arg Gln Ala Pro Gly Gln Gly Leu Glu Trp Met
        35                  40                  45

Gly Trp Ile Asp Pro Glu Asn Gly Asp Thr Val Tyr Asp Pro Gln Phe
    50                  55                  60

Gln Asp Arg Ile Asn Ile Thr Ala Asp Thr Ser Thr Ser Thr Ala Tyr
65                  70                  75                  80

Met Glu Leu Ser Gly Leu Arg Ser Asp Asp Thr Ala Val Tyr Tyr Cys
                85                  90                  95

Ser Thr Leu Asp Phe Trp Gly Gln Gly Thr Leu Val Thr Val Ser Ser
            100                 105                 110

<210> SEQ ID NO 114
<211> LENGTH: 112
<212> TYPE: PRT
<213> ORGANISM: Artificial
<220> FEATURE:
<223> OTHER INFORMATION: Synthesized

<400> SEQUENCE: 114

Gln Val Gln Leu Gln Gln Ser Gly Ala Glu Val Val Lys Pro Gly Gly
1               5                   10                  15

Ser Val Lys Leu Ser Cys Lys Ala Ser Gly Phe Asn Ile Lys Asp Tyr
            20                  25                  30

Tyr Ile His Trp Val Arg Gln Ala Pro Gly Gln Gly Leu Glu Trp Met
        35                  40                  45

Gly Trp Ile Asp Pro Glu Asn Gly Asp Thr Val Tyr Asp Pro Gln Phe
    50                  55                  60

Gln Asp Arg Ile Thr Ile Thr Ala Asp Thr Ser Ser Thr Ala Tyr
65                  70                  75                  80

Met Glu Leu Ser Gly Leu Arg Ser Asp Thr Ala Val Tyr Tyr Cys
                85                  90                  95

Ser Thr Leu Asp Phe Trp Gly Gln Gly Thr Leu Val Thr Val Ser Ser
            100                 105                 110

<210> SEQ ID NO 115
<211> LENGTH: 112
<212> TYPE: PRT
<213> ORGANISM: Artificial
<220> FEATURE:
<223> OTHER INFORMATION: Synthesized

<400> SEQUENCE: 115

Gln Val Gln Leu Gln Gln Ser Gly Ala Glu Val Val Lys Pro Gly Gly
1               5                   10                  15

Ser Val Lys Leu Ser Cys Lys Ala Ser Gly Phe Asn Ile Lys Asp Tyr
            20                  25                  30

Tyr Ile His Trp Val Arg Gln Ala Pro Gly Gln Gly Leu Glu Trp Ile
        35                  40                  45

Gly Trp Ile Asp Pro Glu Asn Gly Asp Thr Val Tyr Asp Pro Gln Phe
    50                  55                  60

Gln Asp Arg Ala Thr Ile Thr Ala Asp Thr Ser Thr Ser Thr Ala Tyr
65                  70                  75                  80

Met Glu Leu Ser Gly Leu Arg Ser Glu Asp Thr Ala Val Tyr Tyr Cys
                85                  90                  95

Ala Thr Leu Asp Phe Trp Gly Gln Gly Thr Leu Val Thr Val Ser Ser
            100                 105                 110

<210> SEQ ID NO 116
<211> LENGTH: 112
<212> TYPE: PRT
<213> ORGANISM: Artificial
<220> FEATURE:
<223> OTHER INFORMATION: Synthesized

<400> SEQUENCE: 116

Asp Ile Val Met Thr Gln Ser Pro Leu Ser Leu Ser Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
            50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Cys Thr Phe Gly Gln Gly Thr Lys Leu Glu Ile Lys
            100                 105                 110

<210> SEQ ID NO 117
<211> LENGTH: 112
<212> TYPE: PRT
<213> ORGANISM: Artificial
<220> FEATURE:
<223> OTHER INFORMATION: Synthesized

<400> SEQUENCE: 117

Asp Ile Val Met Thr Gln Ser Pro Leu Ser Leu Ser Val Thr Leu Gly
 1               5                  10                  15

Glu Pro Ala Ser Ile Ser Cys Lys Ser Ser Gln Ser Leu Leu Asp Ser
             20                  25                  30

Asp Gly Lys Thr Tyr Leu Asn Trp Phe Gln Gln Arg Pro Gly Gln Ser
         35                  40                  45

Pro Arg Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Cys Thr Phe Gly Gln Gly Thr Lys Leu Glu Ile Lys
            100                 105                 110

<210> SEQ ID NO 118
<211> LENGTH: 112
<212> TYPE: PRT
<213> ORGANISM: Artificial
<220> FEATURE:
<223> OTHER INFORMATION: Synthesized

<400> SEQUENCE: 118

Asp Val Val Met Thr Gln Ser Pro Leu Ser Leu Ser Val Thr Leu Gly
 1               5                  10                  15

Glu Pro Ala Ser Ile Ser Cys Lys Ser Ser Gln Ser Leu Leu Asp Ser
             20                  25                  30

Asp Gly Lys Thr Tyr Leu Asn Trp Leu Gln Gln Arg Pro Gly Gln Ser
         35                  40                  45

Pro Arg Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Cys Thr Phe Gly Gln Gly Thr Lys Leu Glu Ile Lys
            100                 105                 110

<210> SEQ ID NO 119
<211> LENGTH: 112
<212> TYPE: PRT

<213> ORGANISM: Artificial
<220> FEATURE:
<223> OTHER INFORMATION: Synthesized

<400> SEQUENCE: 119

Glu Val Gln Leu Gln Gln Ser Gly Ala Glu Leu Val Arg Pro Gly Ala
1               5                   10                  15
Leu Val Lys Leu Ser Cys Lys Ala Ser Gly Phe Asn Ile Lys Asp Tyr
            20                  25                  30
Tyr Ile His Trp Val Lys Gln Arg Pro Glu Gln Gly Leu Glu Trp Ile
        35                  40                  45
Gly Trp Ile Asp Pro Glu Asn Gly Glu Thr Val Tyr Asp Pro Lys Phe
    50                  55                  60
Gln Gly Lys Ala Ser Ile Thr Ser Asp Thr Ser Ser Asn Thr Ala Tyr
65                  70                  75                  80
Leu Gln Leu Arg Ser Leu Thr Ser Glu Asp Thr Ala Val Tyr Tyr Ser
                85                  90                  95
Thr Ser Leu Asp Phe Trp Gly Gln Gly Thr Ser Val Thr Val Ser Ser
            100                 105                 110

<210> SEQ ID NO 120
<211> LENGTH: 113
<212> TYPE: PRT
<213> ORGANISM: Artificial
<220> FEATURE:
<223> OTHER INFORMATION: Synthesized

<400> SEQUENCE: 120

Asp Val Val Met Thr Gln Thr Pro Leu Thr Leu Ser Val Thr Ile Gly
1               5                   10                  15
Gln Pro Ala Ser Ile Ser Cys Lys Ser Thr Gln Ser Leu Leu Asp Ser
            20                  25                  30
Asp Gly Lys Thr Tyr Leu Asn Trp Leu Leu Gln Arg Pro Gly Gln Ser
        35                  40                  45
Pro Lys Arg Leu Ile Tyr Leu Val Ser Lys Leu Asp Ser Gly Val Pro
    50                  55                  60
Asp Arg Phe Thr Gly Ser Gly Ser Gly Thr Asp Phe Thr Leu Lys Ile
65                  70                  75                  80
Ser Arg Val Glu Ala Glu Asp Leu Gly Val Tyr Tyr Cys Trp Gln Gly
                85                  90                  95
Thr His Phe Pro Tyr Thr Phe Gly Gly Gly Thr Lys Leu Glu Ile Lys
            100                 105                 110
Arg

<210> SEQ ID NO 121
<211> LENGTH: 10
<212> TYPE: PRT
<213> ORGANISM: Artificial
<220> FEATURE:
<223> OTHER INFORMATION: Synthesized

<400> SEQUENCE: 121

Gly Phe Asn Ile Lys Asp Tyr Tyr Ile His
1               5                   10

<210> SEQ ID NO 122
<211> LENGTH: 17
<212> TYPE: PRT
<213> ORGANISM: Artificial
<220> FEATURE:

<223> OTHER INFORMATION: Synthesized

<400> SEQUENCE: 122

Trp Ile Asp Pro Glu Asn Gly Glu Thr Val Tyr Asp Pro Lys Phe Gln
1               5                   10                  15
Gly

<210> SEQ ID NO 123
<211> LENGTH: 3
<212> TYPE: PRT
<213> ORGANISM: Artificial Sequence
<220> FEATURE:
<223> OTHER INFORMATION: Synthesized

<400> SEQUENCE: 123

Leu Asp Phe
1

<210> SEQ ID NO 124
<211> LENGTH: 16
<212> TYPE: PRT
<213> ORGANISM: Artificial
<220> FEATURE:
<223> OTHER INFORMATION: Synthesized

<400> SEQUENCE: 124

Lys Ser Thr Gln Ser Leu Leu Asp Ser Asp Gly Lys Thr Tyr Leu Asn
1               5                   10                  15

<210> SEQ ID NO 125
<211> LENGTH: 7
<212> TYPE: PRT
<213> ORGANISM: Artificial
<220> FEATURE:
<223> OTHER INFORMATION: Synthesized

<400> SEQUENCE: 125

Leu Val Ser Lys Leu Asp Ser
1               5

<210> SEQ ID NO 126
<211> LENGTH: 9
<212> TYPE: PRT
<213> ORGANISM: Artificial
<220> FEATURE:
<223> OTHER INFORMATION: Synthesized

<400> SEQUENCE: 126

Trp Gln Gly Thr His Phe Pro Tyr Thr
1               5

<210> SEQ ID NO 127
<211> LENGTH: 5
<212> TYPE: PRT
<213> ORGANISM: Artificial
<220> FEATURE:
<223> OTHER INFORMATION: Synthesized

<400> SEQUENCE: 127

Asp Tyr Tyr Ile His
1               5

<210> SEQ ID NO 128
<211> LENGTH: 7
<212> TYPE: PRT
<213> ORGANISM: Artificial

```
<220> FEATURE:
<223> OTHER INFORMATION: Synthesized

<400> SEQUENCE: 128

Gly Phe Asn Ile Lys Asp Tyr
1               5

<210> SEQ ID NO 129
<211> LENGTH: 6
<212> TYPE: PRT
<213> ORGANISM: Artificial
<220> FEATURE:
<223> OTHER INFORMATION: Synthesized

<400> SEQUENCE: 129

Lys Asp Tyr Tyr Ile His
1               5

<210> SEQ ID NO 130
<211> LENGTH: 6
<212> TYPE: PRT
<213> ORGANISM: Artificial
<220> FEATURE:
<223> OTHER INFORMATION: Synthesized

<400> SEQUENCE: 130

Asp Pro Glu Asn Gly Glu
1               5

<210> SEQ ID NO 131
<211> LENGTH: 10
<212> TYPE: PRT
<213> ORGANISM: Artificial
<220> FEATURE:
<223> OTHER INFORMATION: Synthesized

<400> SEQUENCE: 131

Trp Ile Asp Pro Glu Asn Gly Glu Thr Val
1               5                   10

<210> SEQ ID NO 132
<211> LENGTH: 13
<212> TYPE: PRT
<213> ORGANISM: Artificial
<220> FEATURE:
<223> OTHER INFORMATION: Synthesized

<400> SEQUENCE: 132

Trp Ile Gly Trp Ile Asp Pro Glu Asn Gly Glu Thr Val
1               5                   10

<210> SEQ ID NO 133
<211> LENGTH: 4
<212> TYPE: PRT
<213> ORGANISM: Artificial
<220> FEATURE:
<223> OTHER INFORMATION: Synthesized

<400> SEQUENCE: 133

Thr Ser Leu Asp
1

<210> SEQ ID NO 134
<211> LENGTH: 7
<212> TYPE: PRT
<213> ORGANISM: Artificial
<220> FEATURE:
```

```
<223> OTHER INFORMATION: Synthesized

<400> SEQUENCE: 134

Lys Thr Tyr Leu Asn Trp Leu
1               5

<210> SEQ ID NO 135
<211> LENGTH: 10
<212> TYPE: PRT
<213> ORGANISM: Artificial
<220> FEATURE:
<223> OTHER INFORMATION: Synthesized

<400> SEQUENCE: 135

Arg Leu Ile Tyr Leu Val Ser Lys Leu Asp
1               5                   10

<210> SEQ ID NO 136
<211> LENGTH: 8
<212> TYPE: PRT
<213> ORGANISM: Artificial
<220> FEATURE:
<223> OTHER INFORMATION: Synthesized

<400> SEQUENCE: 136

Trp Gln Gly Thr His Phe Pro Tyr
1               5

<210> SEQ ID NO 137
<211> LENGTH: 116
<212> TYPE: PRT
<213> ORGANISM: Homo sapiens

<400> SEQUENCE: 137

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Tyr Thr Glu Ala Tyr
                20                  25                  30

Tyr Ile His Trp Val Arg Gln Ala Pro Gly Gln Gly Leu Glu Trp Met
            35                  40                  45

Gly Arg Ile Asp Pro Ala Thr Gly Asn Thr Lys Tyr Ala Pro Arg Leu
        50                  55                  60

Gln Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Leu Tyr Ser Leu Pro Val Tyr Trp Gly Gln Gly Thr Thr Val
            100                 105                 110

Thr Val Ser Ser
        115

<210> SEQ ID NO 138
<211> LENGTH: 113
<212> TYPE: PRT
<213> ORGANISM: Homo sapiens

<400> SEQUENCE: 138

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
                20                  25                  30
```

```
Asp Ala Lys Thr Tyr Leu Asn Trp Phe Gln Gln Arg Pro Gly Gln Ser
            35                  40                  45

Pro Arg Arg Leu Ile Tyr Gln Ile Ser Arg Leu Asp Pro Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Leu Gln Gly
                85                  90                  95

Thr His Tyr Pro Val Leu Phe Gly Gln Gly Thr Arg Leu Glu Ile Lys
                100                 105                 110

Arg
```

<210> SEQ ID NO 139
<211> LENGTH: 112
<212> TYPE: PRT
<213> ORGANISM: Artificial
<220> FEATURE:
<223> OTHER INFORMATION: Synthesized

<400> SEQUENCE: 139

```
Gln Val Gln Leu Val Gln Ser Gly Ala Glu Val Val Lys Pro Gly Ala
 1               5                  10                  15

Ser Val Lys Leu Ser Cys Lys Ala Ser Gly Phe Asn Ile Lys Asp Tyr
                20                  25                  30

Tyr Ile His Trp Val Arg Gln Ala Pro Gly Gln Gly Leu Glu Trp Met
            35                  40                  45

Gly Trp Ile Asp Pro Glu Asn Gly Glu Thr Val Tyr Asp Pro Lys Phe
 50                  55                  60

Gln Gly Arg Val Thr Ile Thr Arg Asp Thr Ser Thr Asn Thr Ala Tyr
 65                  70                  75                  80

Leu Gln Leu Ser Ser Leu Arg Ser Glu Asp Thr Ala Val Tyr Tyr Ser
                85                  90                  95

Thr Ser Leu Asp Phe Trp Gly Gln Gly Thr Thr Val Thr Val Ser Ser
                100                 105                 110
```

<210> SEQ ID NO 140
<211> LENGTH: 112
<212> TYPE: PRT
<213> ORGANISM: Artificial
<220> FEATURE:
<223> OTHER INFORMATION: Synthesized

<400> SEQUENCE: 140

```
Gln Val Gln Leu Val Gln Ser Gly Ala Glu Val Val Lys Pro Gly Ala
 1               5                  10                  15

Ser Val Lys Leu Ser Cys Lys Ala Ser Gly Phe Asn Ile Lys Asp Tyr
                20                  25                  30

Tyr Ile His Trp Val Lys Gln Ala Pro Gly Gln Gly Leu Glu Trp Met
            35                  40                  45

Gly Trp Ile Asp Pro Glu Asn Gly Glu Thr Val Tyr Asp Pro Lys Phe
 50                  55                  60

Gln Gly Arg Val Thr Ile Thr Arg Asp Thr Ser Thr Asn Thr Ala Tyr
 65                  70                  75                  80

Leu Gln Leu Ser Ser Leu Arg Ser Glu Asp Thr Ala Val Tyr Tyr Ser
                85                  90                  95

Thr Ser Leu Asp Phe Trp Gly Gln Gly Thr Thr Val Thr Val Ser Ser
                100                 105                 110
```

<210> SEQ ID NO 141
<211> LENGTH: 113
<212> TYPE: PRT
<213> ORGANISM: Artificial
<220> FEATURE:
<223> OTHER INFORMATION: Synthesized

<400> SEQUENCE: 141

Asp Val Val Met Thr Gln Ser Pro Leu Ser Leu Ser Val Thr Leu Gly
1               5                   10                  15
Gln Pro Ala Ser Ile Ser Cys Lys Ser Thr Gln Ser Leu Leu Asp Ser
            20                  25                  30
Asp Gly Lys Thr Tyr Leu Asn Trp Phe Gln Gln Arg Pro Gly Gln Ser
        35                  40                  45
Pro Arg Arg Leu Ile Tyr Leu Val Ser Lys Leu Asp Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Trp Gln Gly
                85                  90                  95
Thr His Phe Pro Tyr Thr Phe Gly Gln Gly Thr Lys Leu Glu Ile Lys
            100                 105                 110
Arg

<210> SEQ ID NO 142
<211> LENGTH: 113
<212> TYPE: PRT
<213> ORGANISM: Artificial
<220> FEATURE:
<223> OTHER INFORMATION: Synthesized

<400> SEQUENCE: 142

Asp Val Val Met Thr Gln Ser Pro Leu Ser Leu Ser Val Thr Leu Gly
1               5                   10                  15
Gln Pro Ala Ser Ile Ser Cys Lys Ser Thr Gln Ser Leu Leu Asp Ser
            20                  25                  30
Asp Gly Lys Thr Tyr Leu Asn Trp Phe Leu Gln Arg Pro Gly Gln Ser
        35                  40                  45
Pro Arg Arg Leu Ile Tyr Leu Val Ser Lys Leu Asp Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Trp Gln Gly
                85                  90                  95
Thr His Phe Pro Tyr Thr Phe Gly Gln Gly Thr Lys Leu Glu Ile Lys
            100                 105                 110
Arg

<210> SEQ ID NO 143
<211> LENGTH: 113
<212> TYPE: PRT
<213> ORGANISM: Artificial
<220> FEATURE:
<223> OTHER INFORMATION: Synthesized

<400> SEQUENCE: 143

Asp Val Val Met Thr Gln Ser Pro Leu Ser Leu Ser Val Thr Leu Gly
1               5                   10                  15

Gln Pro Ala Ser Ile Ser Cys Lys Ser Thr Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Lys Leu Glu Ile Lys
                100                 105                 110

Arg

<210> SEQ ID NO 144
<211> LENGTH: 113
<212> TYPE: PRT
<213> ORGANISM: Artificial
<220> FEATURE:
<223> OTHER INFORMATION: Synthesized

<400> SEQUENCE: 144

Asp Val Val Met Thr Gln Ser Pro Leu Ser Leu Ser Val Thr Leu Gly
1               5                   10                  15

Gln Pro Ala Ser Ile Ser Cys Lys Ser Thr Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Lys Leu Glu Ile Lys
                100                 105                 110

Arg

<210> SEQ ID NO 145
<211> LENGTH: 113
<212> TYPE: PRT
<213> ORGANISM: Artificial
<220> FEATURE:
<223> OTHER INFORMATION: Synthesized

<400> SEQUENCE: 145

Asp Val Val Met Thr Gln Ser Pro Leu Ser Leu Ser Val Thr Leu Gly
1               5                   10                  15

Gln Pro Ala Ser Ile Ser Cys Lys Ser Thr Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly

Thr His Phe Pro Tyr Thr Phe Gly Gln Gly Thr Lys Leu Glu Ile Lys
                100                 105                 110
Arg

<210> SEQ ID NO 146
<211> LENGTH: 113
<212> TYPE: PRT
<213> ORGANISM: Artificial
<220> FEATURE:
<223> OTHER INFORMATION: Synthesized

<400> SEQUENCE: 146

Asp Val Val Met Thr Gln Ser Pro Leu Ser Leu Ser Val Thr Leu Gly
1               5                   10                  15

Gln Pro Ala Ser Ile Ser Cys Lys Ser Thr Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gln Gly Thr Lys Leu Glu Ile Lys
                100                 105                 110
Arg

<210> SEQ ID NO 147
<211> LENGTH: 113
<212> TYPE: PRT
<213> ORGANISM: Artificial
<220> FEATURE:
<223> OTHER INFORMATION: Synthesized

<400> SEQUENCE: 147

Asp Val Val Met Thr Gln Ser Pro Leu Ser Leu Ser Val Thr Leu Gly
1               5                   10                  15

Gln Pro Ala Ser Ile Ser Cys Lys Ser Thr Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Leu Glu Ile Lys
                100                 105                 110
Arg

<210> SEQ ID NO 148
<211> LENGTH: 113
<212> TYPE: PRT
<213> ORGANISM: Artificial
<220> FEATURE:

<223> OTHER INFORMATION: Synthesized

<400> SEQUENCE: 148

```
Asp Val Val Met Thr Gln Ser Pro Leu Ser Leu Ser Val Thr Leu Gly
1               5                   10                  15

Gln Pro Ala Ser Ile Ser Cys Lys Ser Thr Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Tyr Thr Phe Gly Gly Gly Thr Lys Leu Glu Ile Lys
                100                 105                 110

Arg
```

<210> SEQ ID NO 149
<211> LENGTH: 112
<212> TYPE: PRT
<213> ORGANISM: Homo sapiens

<400> SEQUENCE: 149

```
Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Ile His Trp Val Lys Gln Arg Pro Glu Gln Gly Leu Glu Trp Ile
        35                  40                  45

Gly Trp Ile Asp Pro Glu Asn Gly Glu Thr Val Tyr Asp Pro Lys Phe
    50                  55                  60

Gln Gly Lys Ala Ser Ile Thr Ser Asp Thr Ser Ser Asn Thr Ala Tyr
65                  70                  75                  80

Leu Gln Leu Arg Ser Leu Thr Ser Glu Asp Thr Ala Val Tyr Tyr Ser
                85                  90                  95

Thr Ser Leu Asp Phe Trp Gly Gln Gly Thr Ser Val Thr Val Ser Ser
                100                 105                 110
```

What is claimed is:

1. An antibody that binds human tau, comprising three heavy chain CDRs and three light chain CDRs of a mouse antibody characterized by a heavy chain variable region having an amino acid sequence comprising SEQ ID NO: 7 and a light chain variable region having an amino acid sequence comprising SEQ ID NO:8.

2. The antibody of claim 1, wherein the antibody is a humanized antibody.

3. A humanized antibody, wherein the humanized antibody comprises a humanized mature heavy chain variable region comprising the three Kabat heavy chain CDRs of SEQ ID NO: 17, SEQ ID NO: 12, and SEQ ID NO: 13 and a humanized mature light chain variable region comprising the three Kabat light chain CDRs of SEQ ID NOs: 14-16.

4. The humanized antibody of claim 3 comprising a humanized mature heavy chain variable region having an amino acid sequence at least 90% identical to any one of SEQ ID NOs: 33-40 and a humanized mature light chain variable region having an amino acid sequence at least 90% identical to any one of SEQ ID NOs: 41-46.

5. The humanized antibody of claim 4 wherein at least one of the following positions is occupied by the amino acid as specified: Kabat position H1 is occupied by Q or E, Kabat position H11 is occupied by V or L, Kabat position H12 is occupied by K or V, Kabat position H19 is occupied by K or R, Kabat position H20 is occupied by V or L, Kabat position H23 is occupied by K or A, Kabat position H46 is occupied E or D, Kabat position H48 is occupied by M or I, Kabat position H66 is occupied by K or R, Kabat position H67 is occupied by A or V, Kabat position H71 is occupied by R or S, Kabat position H76 is occupied by S or N, Kabat position H78 is occupied by A or V, Kabat position H80 is occupied by M or L, Kabat position H93 is occupied by T, S, or A, and Kabat position H94 is occupied by I, P, or R.

6. The humanized antibody of claim 5, provided positions H1, H11, H12, H19, H20, H23, H46, H48, H71, H76, H80, H93, and H94 in the VH region are occupied by E, L, V, R, L, A, D, I, S, N, L, S, and P, respectively.

7. The humanized antibody of claim 4 wherein at least one of the following positions is occupied by the amino acid as specified: Kabat position L2 is occupied by I or V, Kabat position L7 is occupied by T or S, Kabat position L17 is occupied by Q or E, Kabat position L36 is occupied by Y or L, Kabat position L45 is occupied by K or Q, Kabat position L46 is occupied by L or R, and Kabat position L70 is occupied by G or D.

8. The humanized antibody of claim 7, provided positions L2, L7, L17, L36, L46, and L70 in the VL region are occupied by V, S, E, L, R, and D, respectively.

9. The humanized antibody of claim 4 wherein the mature heavy chain variable region has an amino acid sequence of any of SEQ ID NOs: 33-40 and the mature light chain variable region has an amino acid sequence of any one of SEQ ID NOs: 41-46.

10. The antibody of claim 1 that is an intact antibody.

11. The antibody of claim 1 that is a binding fragment.

12. The antibody of claim 1, wherein the isotype is human IgG1.

13. The antibody of claim 1, wherein the mature light chain variable region is fused to a light chain constant region and the mature heavy chain variable region is fused to a heavy chain constant region.

14. The antibody of claim 13, wherein the heavy chain constant region is a mutant form of a natural human heavy chain constant region which has reduced binding to a Fcγ receptor relative to the natural human heavy chain constant region.

15. The antibody of claim 1 wherein the isotype is of human IgG2 or IgG4 isotype.

16. A pharmaceutical composition comprising the antibody of claim 1 and a pharmaceutically-acceptable carrier.

17. A nucleic acid encoding the heavy chain and/or light chain of the antibody of claim 1.

18. A method of humanizing a mouse antibody, the method comprising:
(a) selecting one or more acceptor antibody sequences;
(b) identifying amino acid residues of the mouse antibody to be retained;
(c) synthesizing a nucleic acid encoding a humanized heavy chain comprising CDRs of the mouse antibody heavy chain and a nucleic acid encoding a humanized light chain comprising CDRs of the mouse antibody light chain; and
(d) expressing the nucleic acids in a host cell to produce a humanized antibody;
wherein the mouse antibody is characterized by a mature heavy chain variable region of SEQ ID NO: 7 and a mature light chain variable region of SEQ ID NO:8.

19. A method of inhibiting or reducing aggregation of tau in a subject having a disease or disorder associated with tau aggregation or deposition, comprising administering to the subject an effective regime of the antibody of claim 1 thereby inhibiting or reducing aggregation of tau in the subject.

20. A method of detecting tau protein deposits in a subject having a disease or disorder associated with tau aggregation or deposition, comprising administering to a subject the antibody of claim 1, and detecting the antibody bound to tau in the subject,
wherein:
(i) the antibody is labeled for detection; or
(ii) the antibody is unlabeled and a second labeling agent that binds to the antibody is used for detection.

21. The method of claim 19, wherein the disease or disorder associated with tau aggregation or deposition is Alzheimer's disease.

22. The method of claim 20, wherein the disease or disorder associated with tau aggregation or deposition is Alzheimer's disease.

* * * * *

UNITED STATES PATENT AND TRADEMARK OFFICE
CERTIFICATE OF CORRECTION

PATENT NO. : 11,958,896 B2  
APPLICATION NO. : 16/500251  
DATED : April 16, 2024  
INVENTOR(S) : Barbour et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 626 days.

Signed and Sealed this
Eighth Day of October, 2024

Katherine Kelly Vidal
*Director of the United States Patent and Trademark Office*